US008753364B2

(12) United States Patent
McCormack et al.

(10) Patent No.: US 8,753,364 B2
(45) Date of Patent: Jun. 17, 2014

(54) SYSTEMS AND METHODS FOR TREATMENT OF COMPRESSED NERVES

(75) Inventors: Bruce M. McCormack, San Francisco, CA (US); Edward Fletcher Eyster, St. Helena, CA (US); Jeffrey D. Smith, Clayton, CA (US); Edward Liou, Mountain View, CA (US); Jonathan Carver, Sausalito, CA (US); Peter How, Sunnyvale, CA (US); Joshua Druker, Redwood City, CA (US); Martin Leugers, San Francisco, CA (US); Shigeru Tanaka, Half Moon Bay, CA (US); Joseph G. McCormack, Jackson Hole, WY (US)

(73) Assignee: Thayer Intellectual Property, Inc., Lafayette, CA (US)

( * ) Notice: Subject to any disclaimer, the term of this patent is extended or adjusted under 35 U.S.C. 154(b) by 0 days.

(21) Appl. No.: 13/170,112

(22) Filed: Jun. 27, 2011

(65) Prior Publication Data
US 2011/0306996 A1 Dec. 15, 2011

Related U.S. Application Data

(63) Continuation-in-part of application No. 12/852,348, filed on Aug. 6, 2010, now Pat. No. 8,348,966.

(60) Provisional application No. 61/266,903, filed on Dec. 4, 2009, provisional application No. 61/232,325, filed on Aug. 7, 2009.

(51) Int. Cl.
*A61B 17/32* (2006.01)
*A61B 8/00* (2006.01)

(52) U.S. Cl.
USPC ............................................ 606/167; 600/439

(58) Field of Classification Search
USPC ............ 606/167, 83, 86 A, 90, 108, 279, 170, 606/53, 171, 176, 177, 178; 600/439
See application file for complete search history.

(56) References Cited

U.S. PATENT DOCUMENTS

| 173,777 A | 2/1876 | Dugan et al. |
| 184,804 A | 11/1876 | Stohlmann |
| 2,342,695 A | 2/1944 | Rinaldy |
| D188,788 S | 9/1960 | Lamb |

(Continued)

FOREIGN PATENT DOCUMENTS

| WO | WO 98-36696 A1 | 8/1998 |
| WO | WO 99-30624 A1 | 6/1999 |

OTHER PUBLICATIONS

U.S. Appl. No. 13/475,745, filed May 18, 2012, McCormack et al.

(Continued)

*Primary Examiner* — Tuan V Nguyen
*Assistant Examiner* — Tin Nguyen
(74) *Attorney, Agent, or Firm* — Polsinelli PC

(57) ABSTRACT

Disclosed herein is a system for releasing a ligament. In one embodiment, the system includes a proximal handle, a tubular body, and a flexible body. The tubular body includes a proximal end and a distal end. The handle is coupled to the proximal end. The flexible body extends through the tubular body and includes a tissue cutting portion. The flexible body or tubular body is longitudinally displaceable to move the tissue cutting portion between a non-deployed state and a deployed state.

32 Claims, 124 Drawing Sheets

(56) References Cited

U.S. PATENT DOCUMENTS

| | | | |
|---|---|---|---|
| 3,765,420 A | 10/1973 | Felczak | |
| 3,835,859 A | 9/1974 | Roberts et al. | |
| 3,929,123 A * | 12/1975 | Jamshidi | 600/567 |
| 4,041,941 A | 8/1977 | Driver | |
| D283,840 S | 5/1986 | Matsutani | |
| 4,963,147 A * | 10/1990 | Agee et al. | 606/170 |
| 5,029,573 A | 7/1991 | Chow | |
| 5,122,137 A * | 6/1992 | Lennox | 606/40 |
| 5,215,100 A | 6/1993 | Spitz et al. | |
| 5,224,488 A * | 7/1993 | Neuffer | 600/564 |
| 5,301,684 A * | 4/1994 | Ogirala | 600/567 |
| 5,323,765 A | 6/1994 | Brown | |
| 5,507,800 A | 4/1996 | Strickland | |
| 5,554,163 A * | 9/1996 | Shturman | 606/159 |
| 5,617,634 A | 4/1997 | Moesmann | |
| 5,730,749 A * | 3/1998 | Battenfield | 606/167 |
| 5,928,158 A | 7/1999 | Aristides | |
| 6,019,774 A | 2/2000 | Weiss et al. | |
| 6,027,514 A * | 2/2000 | Stine et al. | 606/159 |
| 6,096,022 A * | 8/2000 | Laymon et al. | 604/523 |
| D449,771 S | 10/2001 | Douglas et al. | |
| 6,440,138 B1 | 8/2002 | Reiley et al. | |
| D466,388 S | 12/2002 | Chemtob | |
| 6,494,882 B1 | 12/2002 | Lebouitz et al. | |
| 6,685,717 B1 | 2/2004 | Ilic | |
| 6,863,672 B2 | 3/2005 | Reiley et al. | |
| 6,887,271 B2 | 5/2005 | Justin et al. | |
| 6,986,781 B2 | 1/2006 | Smith | |
| 7,058,438 B2 | 6/2006 | Grace et al. | |
| 7,090,690 B2 | 8/2006 | Foerster et al. | |
| 7,189,240 B1 | 3/2007 | Dekel | |
| D546,448 S | 7/2007 | Oi | |
| 7,322,978 B2 | 1/2008 | West, Jr. | |
| D573,867 S | 7/2008 | Laurino et al. | |
| D578,645 S | 10/2008 | Shumer et al. | |
| D585,987 S | 2/2009 | Aparici et al. | |
| D589,614 S | 3/2009 | Cook | |
| 7,553,307 B2 | 6/2009 | Bleich et al. | |
| 7,555,343 B2 | 6/2009 | Bleich | |
| D598,543 S | 8/2009 | Vogel et al. | |
| 7,578,819 B2 | 8/2009 | Bleich et al. | |
| 7,738,968 B2 | 6/2010 | Bleich | |
| 7,738,969 B2 | 6/2010 | Bleich | |
| 7,740,631 B2 | 6/2010 | Bleich et al. | |
| 7,785,332 B2 | 8/2010 | Zannis et al. | |
| D628,694 S | 12/2010 | Donnez | |
| 7,846,165 B2 | 12/2010 | Aram et al. | |
| 7,857,813 B2 | 12/2010 | Schmitz et al. | |
| 7,879,038 B2 | 2/2011 | Reiley et al. | |
| 7,887,538 B2 | 2/2011 | Bleich et al. | |
| 7,918,849 B2 | 4/2011 | Bleich et al. | |
| 7,938,830 B2 | 5/2011 | Saadat et al. | |
| 7,959,577 B2 | 6/2011 | Schmitz et al. | |
| 7,963,915 B2 | 6/2011 | Bleich | |
| D641,870 S | 7/2011 | Anglay et al. | |
| 8,048,080 B2 | 11/2011 | Bleich et al. | |
| 8,062,298 B2 | 11/2011 | Schmitz et al. | |
| 8,062,300 B2 | 11/2011 | Schmitz et al. | |
| 8,092,456 B2 | 1/2012 | Bleich et al. | |
| D666,725 S | 9/2012 | McCormack et al. | |
| 8,273,098 B2 | 9/2012 | Strickland | |
| D674,489 S | 1/2013 | McCormack et al. | |
| 2003/0225412 A1 | 12/2003 | Shiraishi | |
| 2004/0162572 A1 | 8/2004 | Sauer | |
| 2004/0267243 A1 | 12/2004 | Kotz et al. | |
| 2005/0038439 A1* | 2/2005 | Eckman | 606/79 |
| 2005/0159676 A1* | 7/2005 | Taylor et al. | 600/567 |
| 2005/0192564 A1 | 9/2005 | Cosman et al. | |
| 2005/0209530 A1 | 9/2005 | Pflueger | |
| 2006/0030854 A1 | 2/2006 | Haines | |
| 2006/0089633 A1 | 4/2006 | Bleich et al. | |
| 2006/0095028 A1 | 5/2006 | Bleich | |
| 2006/0095059 A1* | 5/2006 | Bleich et al. | 606/170 |
| 2006/0100630 A1 | 5/2006 | West, Jr. | |
| 2006/0122458 A1 | 6/2006 | Bleich | |
| 2006/0276782 A1 | 12/2006 | Gedebou | |
| 2007/0055262 A1 | 3/2007 | Tomita et al. | |
| 2007/0198020 A1 | 8/2007 | Reiley et al. | |
| 2007/0213733 A1 | 9/2007 | Bleich et al. | |
| 2007/0213734 A1 | 9/2007 | Bleich et al. | |
| 2007/0225703 A1 | 9/2007 | Schmitz et al. | |
| 2007/0225740 A1* | 9/2007 | Suddaby | 606/170 |
| 2007/0250057 A1 | 10/2007 | Nobis et al. | |
| 2007/0260252 A1 | 11/2007 | Schmitz et al. | |
| 2007/0270865 A1 | 11/2007 | Arnin et al. | |
| 2007/0288043 A1 | 12/2007 | Rehnke | |
| 2008/0033465 A1 | 2/2008 | Schmitz et al. | |
| 2008/0045860 A1* | 2/2008 | Miller et al. | 600/567 |
| 2008/0051812 A1 | 2/2008 | Schmitz et al. | |
| 2008/0065129 A1 | 3/2008 | Batchelor et al. | |
| 2008/0086034 A1 | 4/2008 | Schmitz et al. | |
| 2008/0086114 A1 | 4/2008 | Schmitz et al. | |
| 2008/0086125 A1 | 4/2008 | Molz et al. | |
| 2008/0091227 A1 | 4/2008 | Schmitz et al. | |
| 2008/0103504 A1 | 5/2008 | Schmitz et al. | |
| 2008/0147084 A1 | 6/2008 | Bleich et al. | |
| 2008/0161809 A1 | 7/2008 | Schmitz et al. | |
| 2008/0183068 A1 | 7/2008 | Carls et al. | |
| 2008/0255624 A1 | 10/2008 | Arcenio et al. | |
| 2008/0275458 A1 | 11/2008 | Bleich et al. | |
| 2008/0312660 A1 | 12/2008 | Bleich et al. | |
| 2009/0018507 A1 | 1/2009 | Schmitz et al. | |
| 2009/0048620 A1 | 2/2009 | Weiss et al. | |
| 2009/0062802 A1 | 3/2009 | Palmer et al. | |
| 2009/0082773 A1 | 3/2009 | Haines | |
| 2009/0149865 A1 | 6/2009 | Schmitz et al. | |
| 2009/0171381 A1 | 7/2009 | Schmitz et al. | |
| 2009/0177241 A1 | 7/2009 | Bleich et al. | |
| 2009/0204119 A1 | 8/2009 | Bleich et al. | |
| 2010/0004654 A1 | 1/2010 | Schmitz et al. | |
| 2010/0010334 A1 | 1/2010 | Bleich et al. | |
| 2010/0069936 A1 | 3/2010 | Palmer et al. | |
| 2010/0094231 A1 | 4/2010 | Bleich et al. | |
| 2010/0161060 A1 | 6/2010 | Schaller et al. | |
| 2010/0274250 A1 | 10/2010 | Wallace et al. | |
| 2010/0331883 A1 | 12/2010 | Schmitz et al. | |
| 2010/0331900 A1 | 12/2010 | Garabedian et al. | |
| 2011/0004207 A1 | 1/2011 | Wallace et al. | |
| 2011/0046613 A1 | 2/2011 | Schmitz et al. | |
| 2011/0060314 A1 | 3/2011 | Wallace et al. | |
| 2011/0087255 A1 | 4/2011 | McCormack et al. | |
| 2011/0112539 A1 | 5/2011 | Wallace et al. | |
| 2011/0160731 A1 | 6/2011 | Bleich et al. | |
| 2011/0160772 A1 | 6/2011 | Arcenio et al. | |
| 2011/0190772 A1 | 8/2011 | Saadat et al. | |
| 2011/0196257 A1 | 8/2011 | Schmitz et al. | |
| 2011/0196373 A1 | 8/2011 | Jacob et al. | |
| 2011/0224709 A1 | 9/2011 | Bleich | |
| 2011/0224710 A1 | 9/2011 | Bleich | |
| 2012/0016368 A1 | 1/2012 | Bleich et al. | |
| 2012/0065639 A1 | 3/2012 | Schmitz et al. | |
| 2012/0078253 A9 | 3/2012 | Bleich et al. | |

OTHER PUBLICATIONS

International Search Report and Written Opinion, PCT/US2010/044784, dated Apr. 21, 2011, 9 pages.
Restriction Requirement, U.S. Appl. No. 12/852,348, dated Aug. 30, 2011, 10 pages.
Response to Restriction, U.S. Appl. No. 12/852,348, filed Sep. 23, 2011, 8 pages.
Non-Final Office Action, U.S. Appl. No. 12/852,348, dated Oct. 28, 2011, 20 pages.
International Search Report and Written Opinion, PCT/US2011/043556, dated Feb. 23, 2012, 10 pages.
Non-Final Office Action, U.S. Appl. No. 29/369,905, mailed Apr. 23, 2012, 20 pages.
Non-Final Office Action, U.S. Appl. No. 29/369,901, mailed Apr. 24, 2012, 19 pages.
Notice of Allowance, U.S. Appl. No. 29/369,897, mailed Apr. 25, 2012, 17 pages.
U.S. Appl. No. 29/369,897, filed Sep. 15, 2010, McCormack.
U.S. Appl. No. 29/369,901, filed Sep. 15, 2010, McCormack.

(56) References Cited

OTHER PUBLICATIONS

U.S. Appl. No. 29/369,905, filed Sep. 15, 2010, McCormack.
Response to Non-Final Office Action, U.S. Appl. No. 12/852,348, dated Feb. 24, 2012, 17 pages.
Final Office Action, U.S. Appl. No. 12/852,348, dated Mar. 16, 2012, 22 pages.
Response to Final Office Action, U.S. Appl. No. 12/852,348, filed Jun. 15, 2012, 19 pages.
Response to Non-Final Office Action, U.S. Appl. No. 29/369,905, filed Jul. 23, 2012, 7 pages.
Response to Non-Final Office Action, U.S. Appl. No. 29/369,901, filed Jul. 24, 2012, 5 pages.
Notice of Allowance, U.S. Appl. No. 29/369,905, mailed Aug. 15, 2012, 8 pages.
Notice of Allowance, U.S. Appl. No. 29/369,901, mailed Aug. 24, 2012, 8 pages.
Notice of Allowance, U.S. Appl. No. 12/852,348, mailed Sep. 20, 2012, 14 pages.
U.S. Appl. No. 13/718,232, filed Dec. 18, 2012, McCormack et al.
International Search Report and Written Opinion, PCT Application No. PCT/US2012/044261, mailed Mar. 25, 2013, 9 pages.
Response to Restriction Requirement, U.S. Appl. No. 13/718,232, filed Mar. 20, 2013, 8 pages.
Restriction Requirement, U.S. Appl. No. 13/475,745, mailed Apr. 12, 2013, 12 pages.
Restriction Requirement, U.S. Appl. No. 13/718,232, mailed Feb. 25, 2013, 11 pages.
Non-Final Office Action, U.S. Appl. No. 13/475,745, mailed Jun. 10, 2013, 24 pages.
Non-Final Office Action, U.S. Appl. No. 13/718,232, mailed May 15, 2013, 21 pages.
Response to Non-Final Office Action, U.S. Appl. No. 13/718,232, filed Aug. 14, 2013, 13 pages.
Response to Restriction Requirement, U.S. Appl. No. 13/475,745, filed May 10, 2013, 8 pages.
Response to Non-Final Office Action, U.S. Appl. No. 13/475,745, filed Sep. 6, 2013, 15 pages.
Final Office Action, U.S. Appl. No. 13/718,232, mailed Sep. 11, 2013, 30 pages.
Notice of Allowance, U.S. Appl. No. 13/475,745, dated Oct. 7, 2013, 24 pages.
European Examination Report, EP10807261.2, dated Feb. 14, 2014, 4 pages.
Supplementary European Search Report, EP 11814976.4, dated Mar. 11, 2014, 8 pages.

* cited by examiner

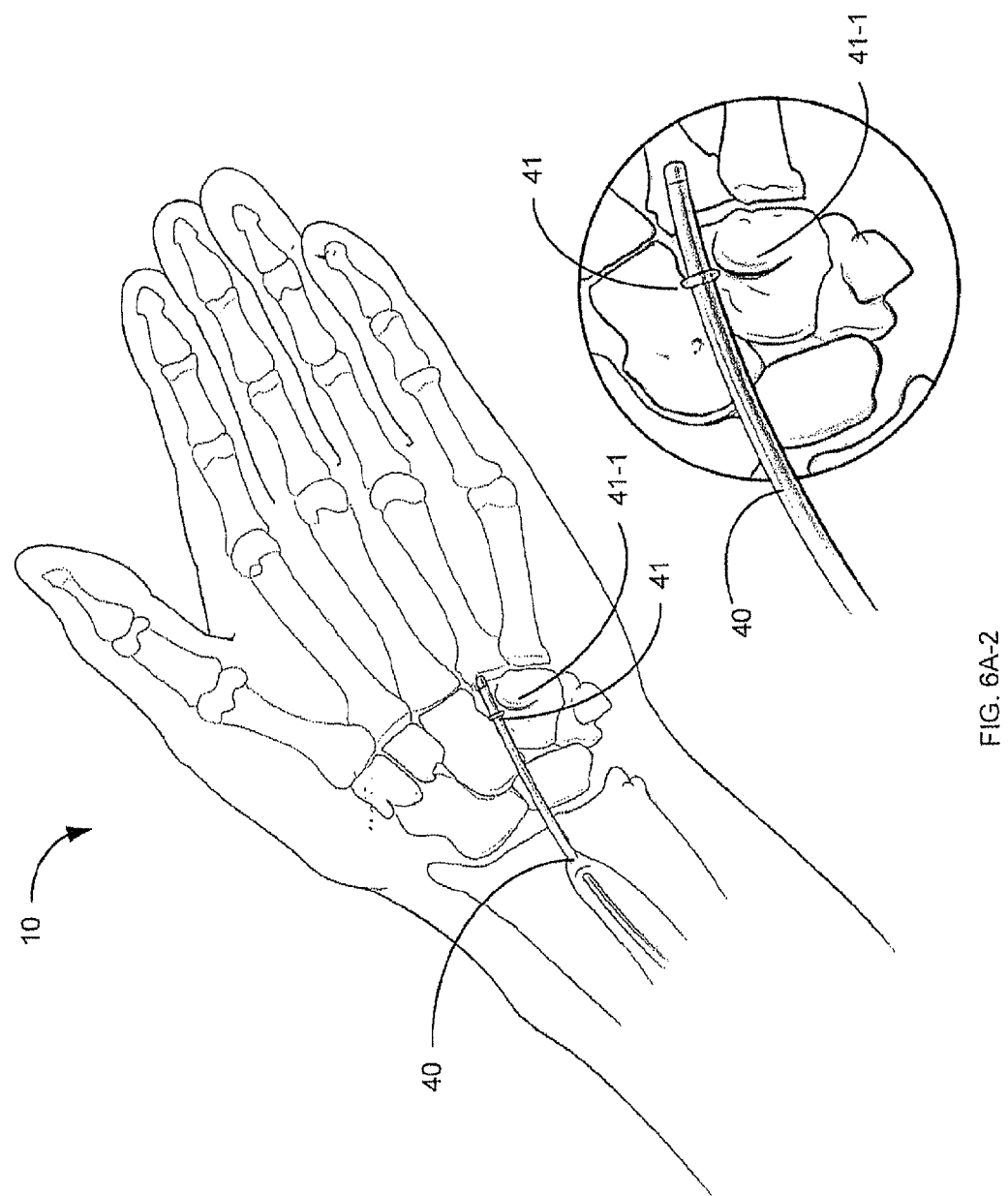

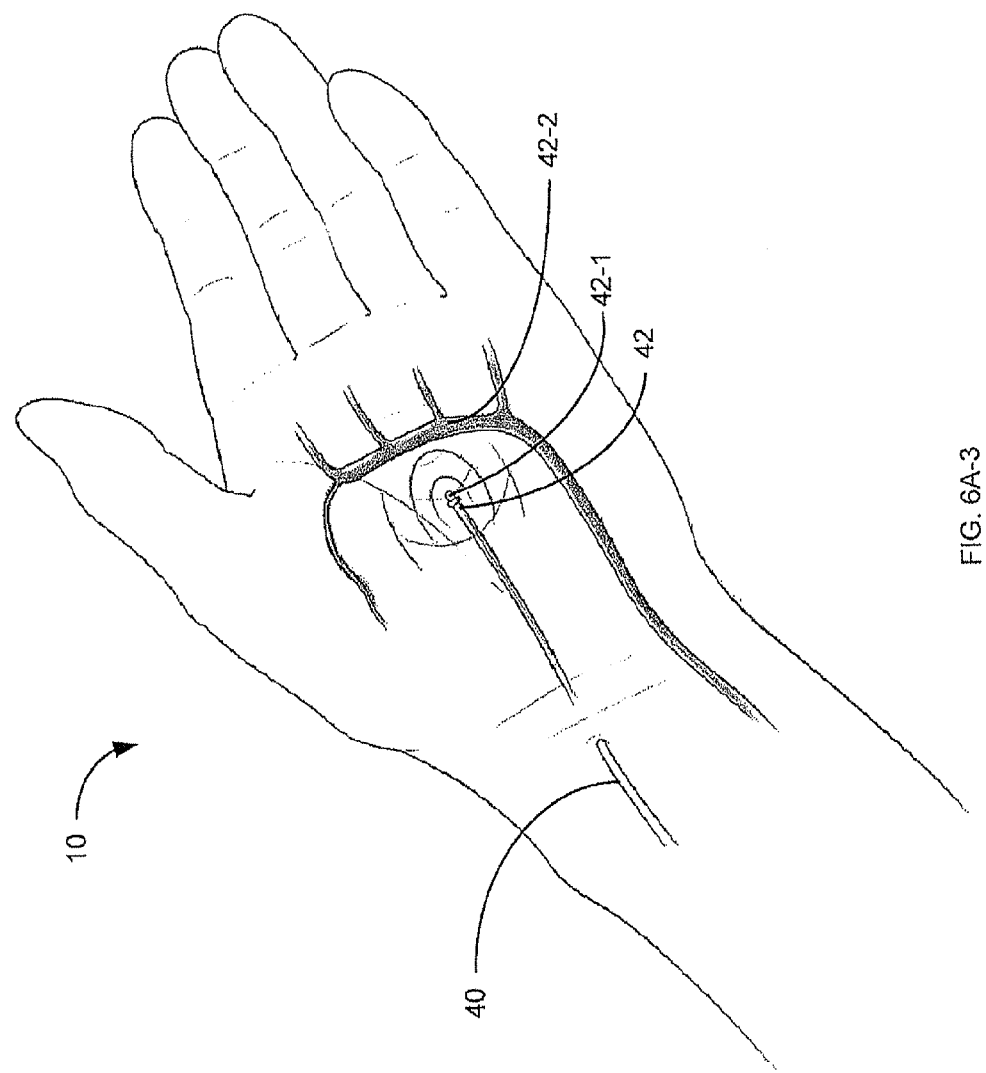

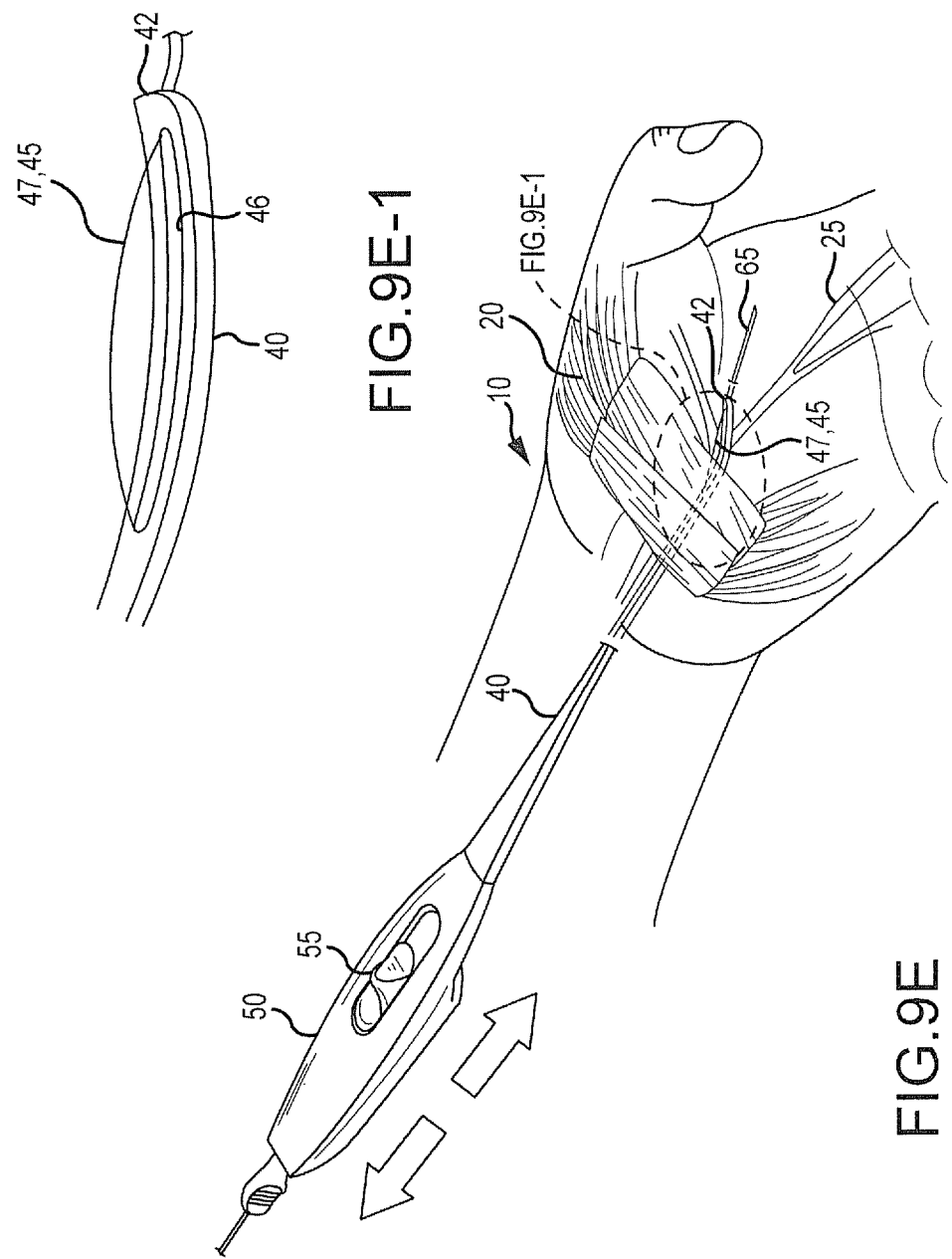

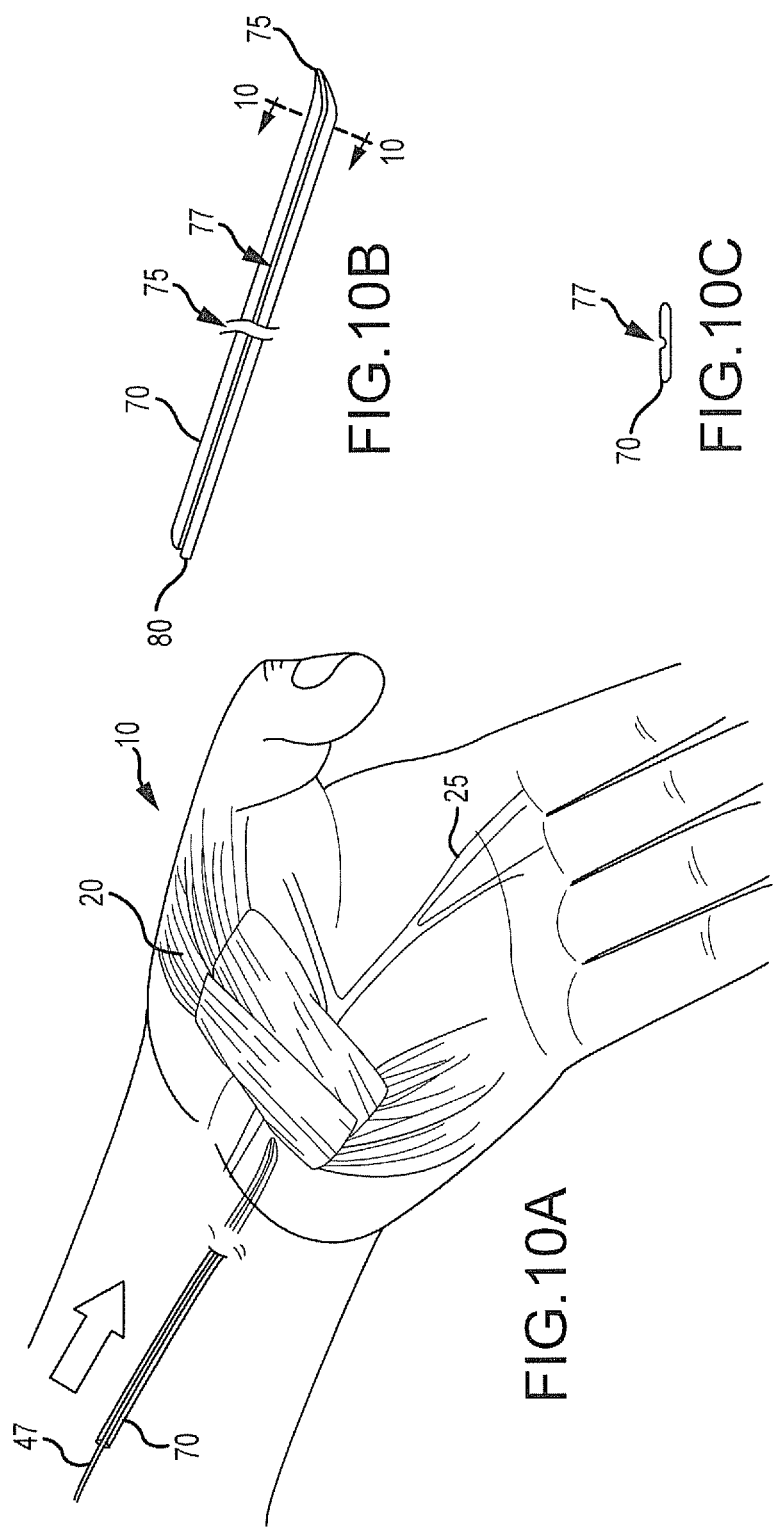

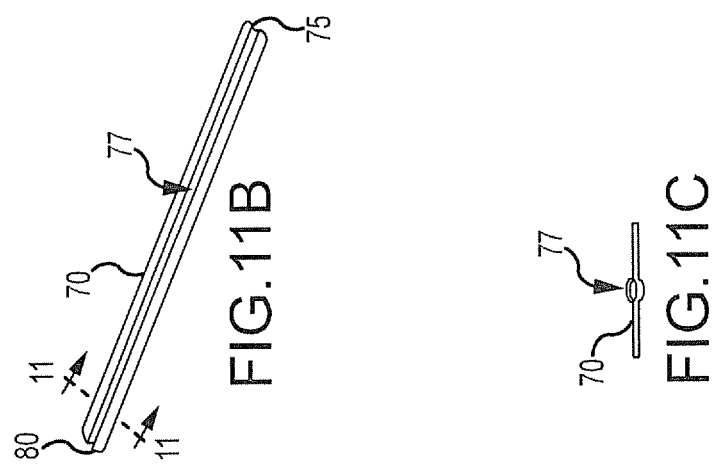
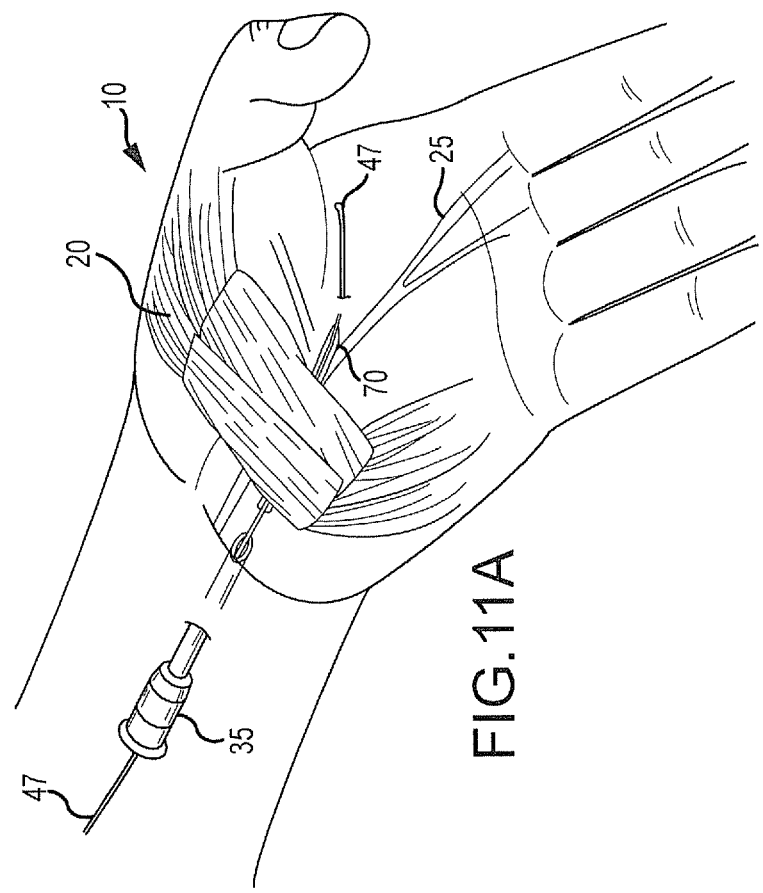

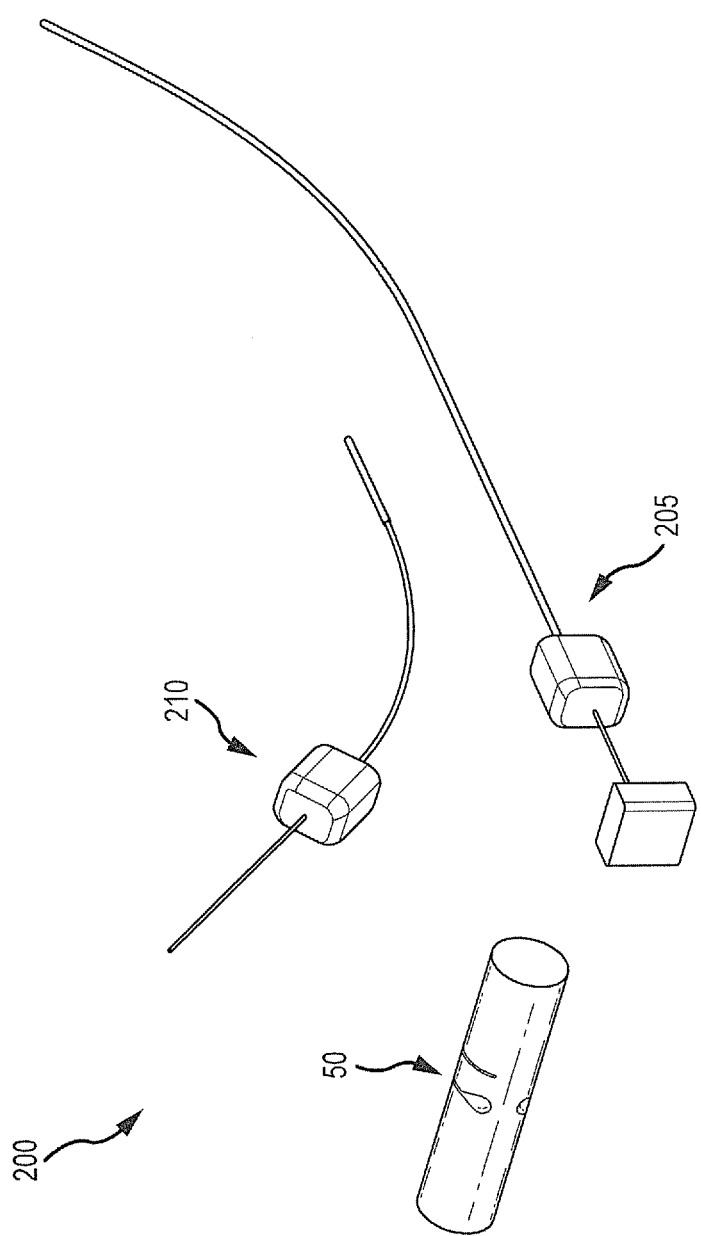

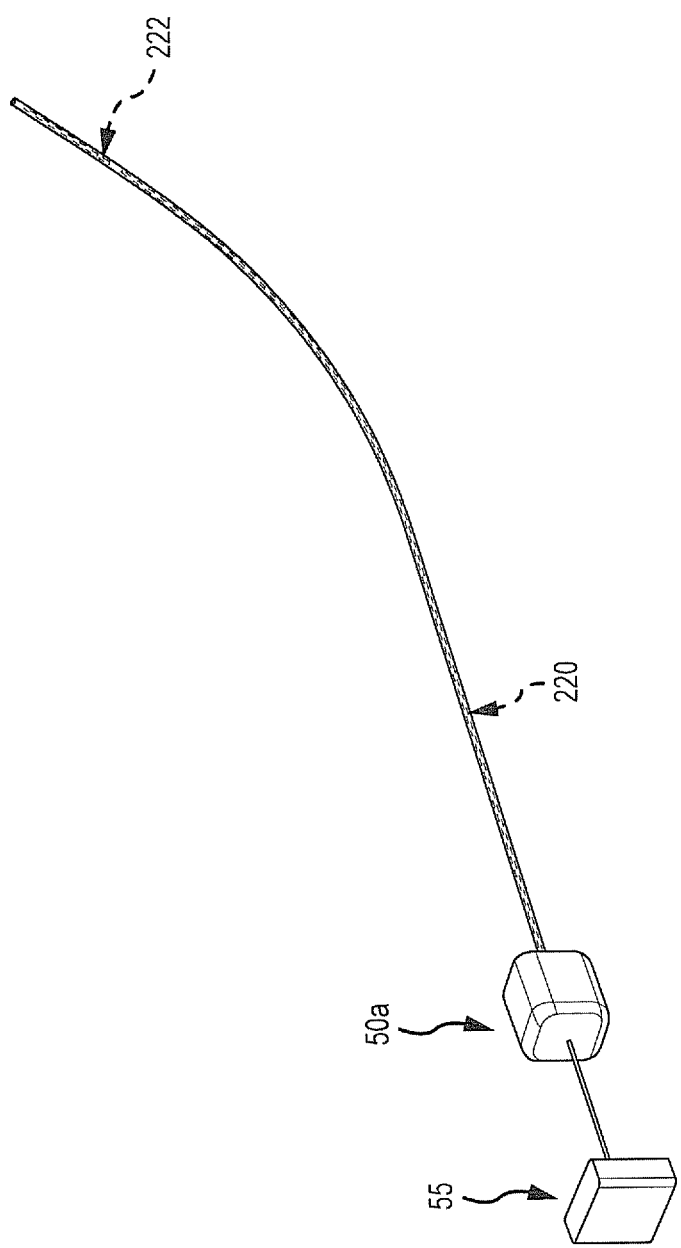

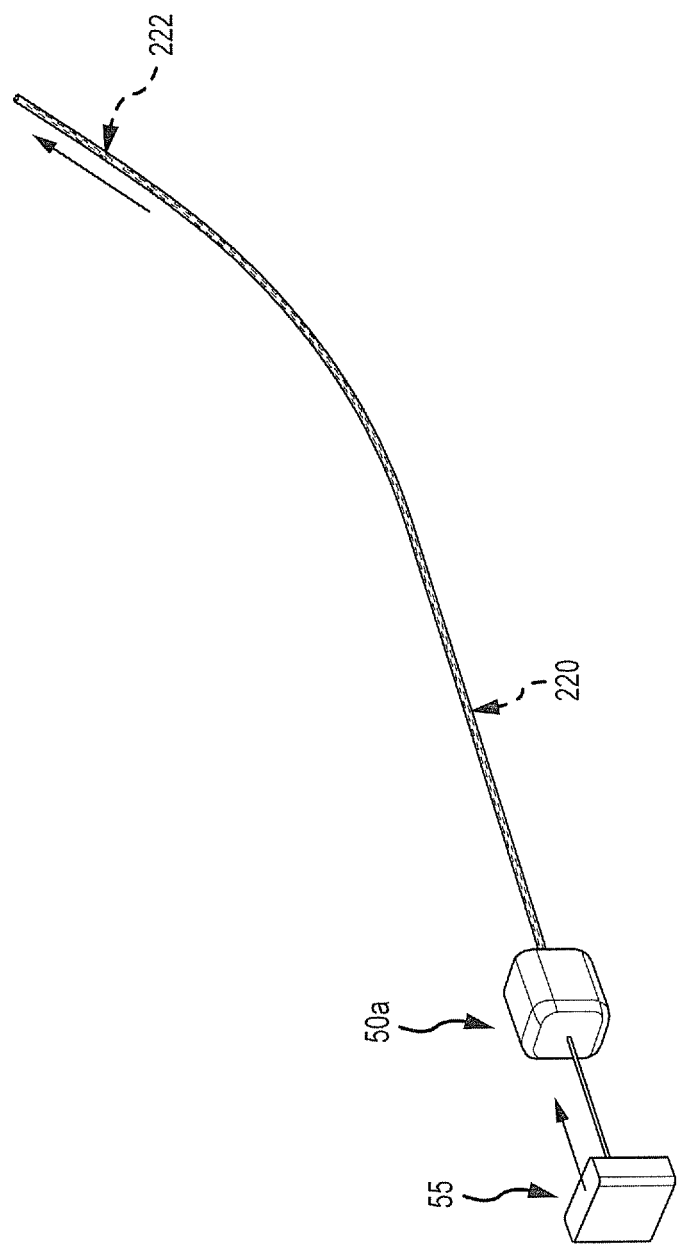

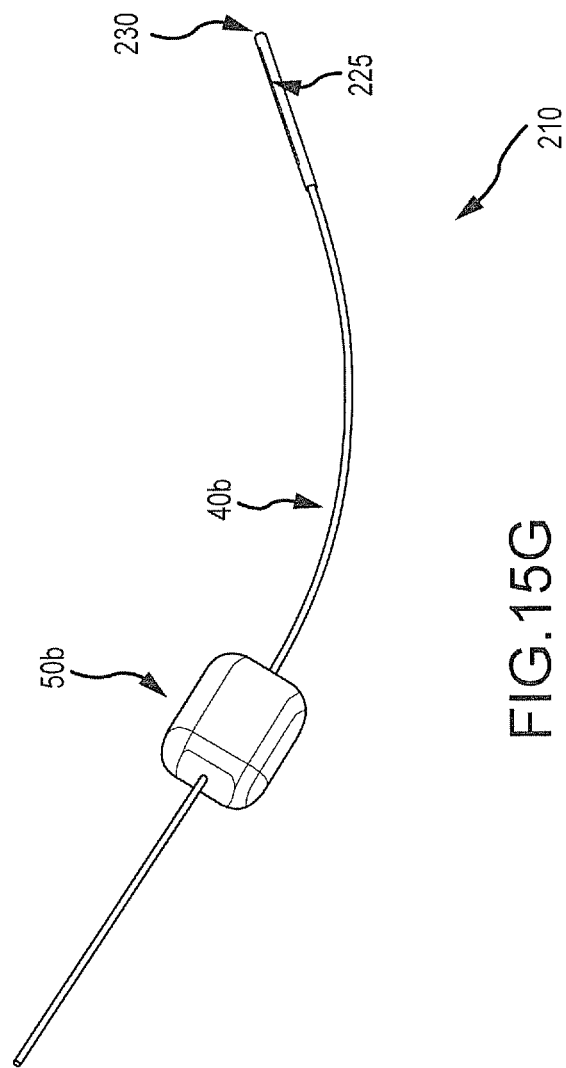

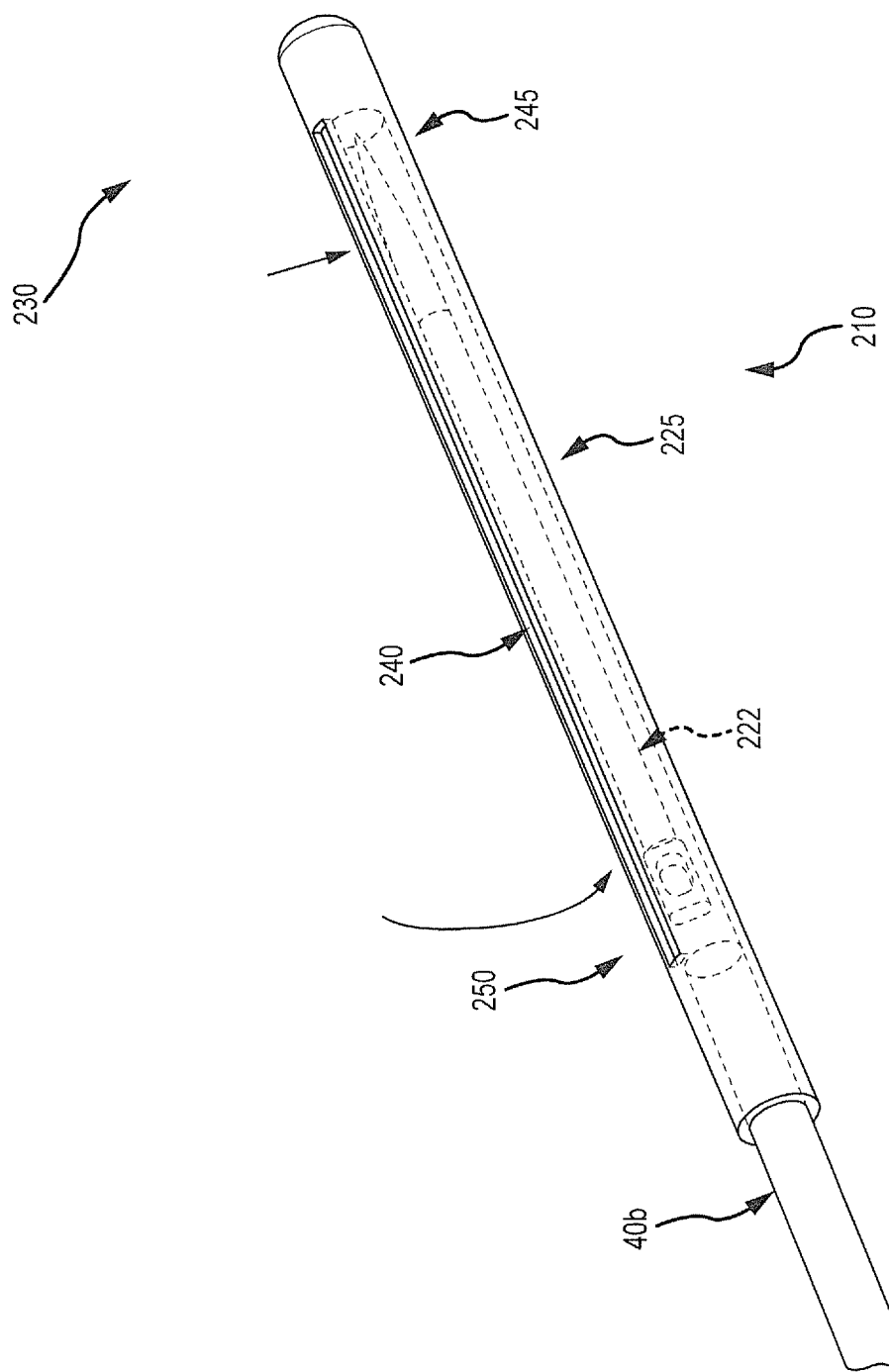

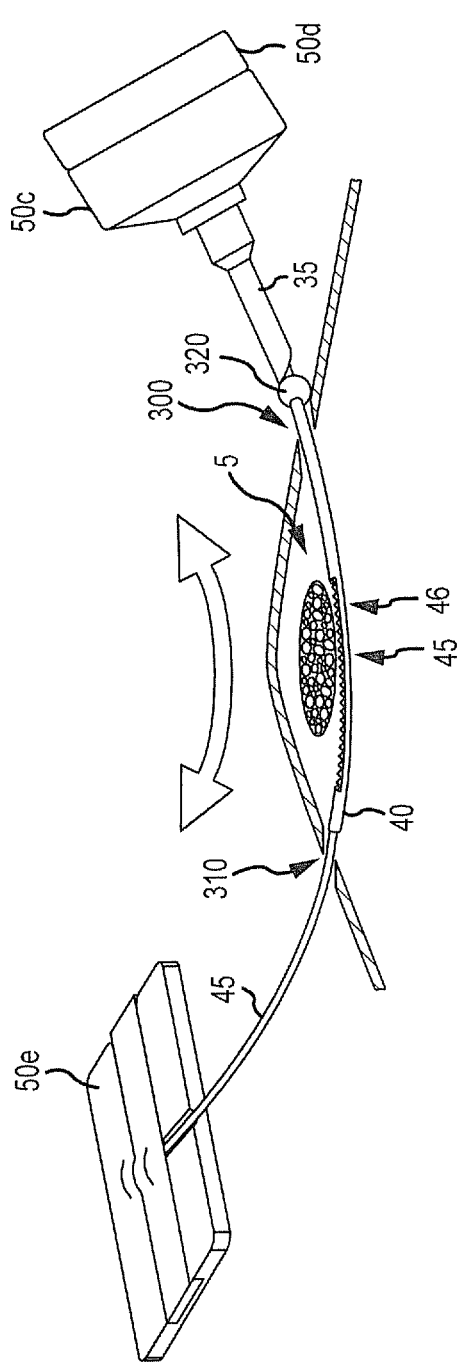
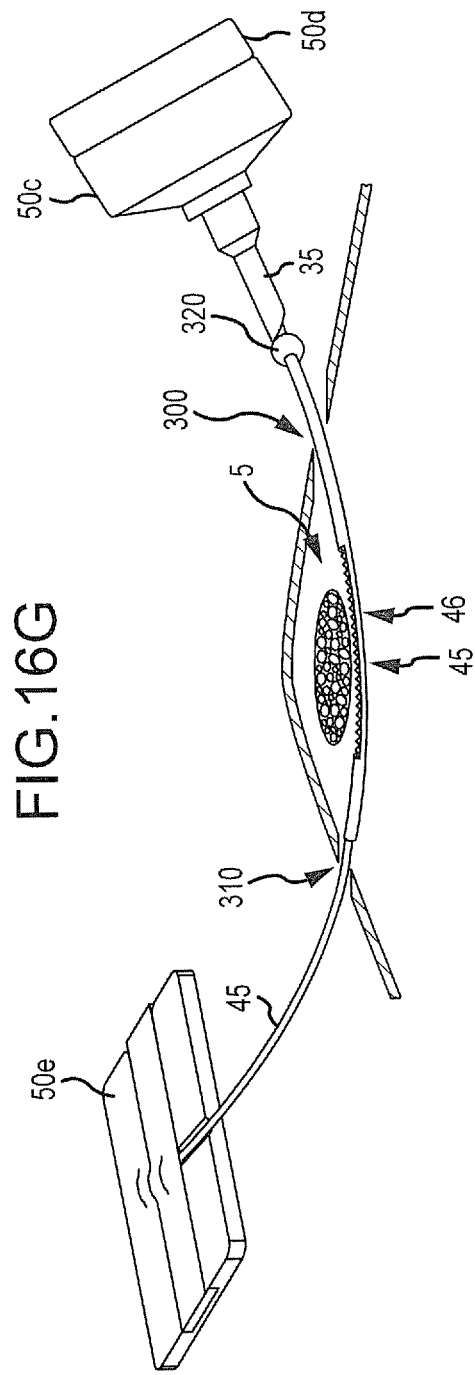
FIG.16G
FIG.16H

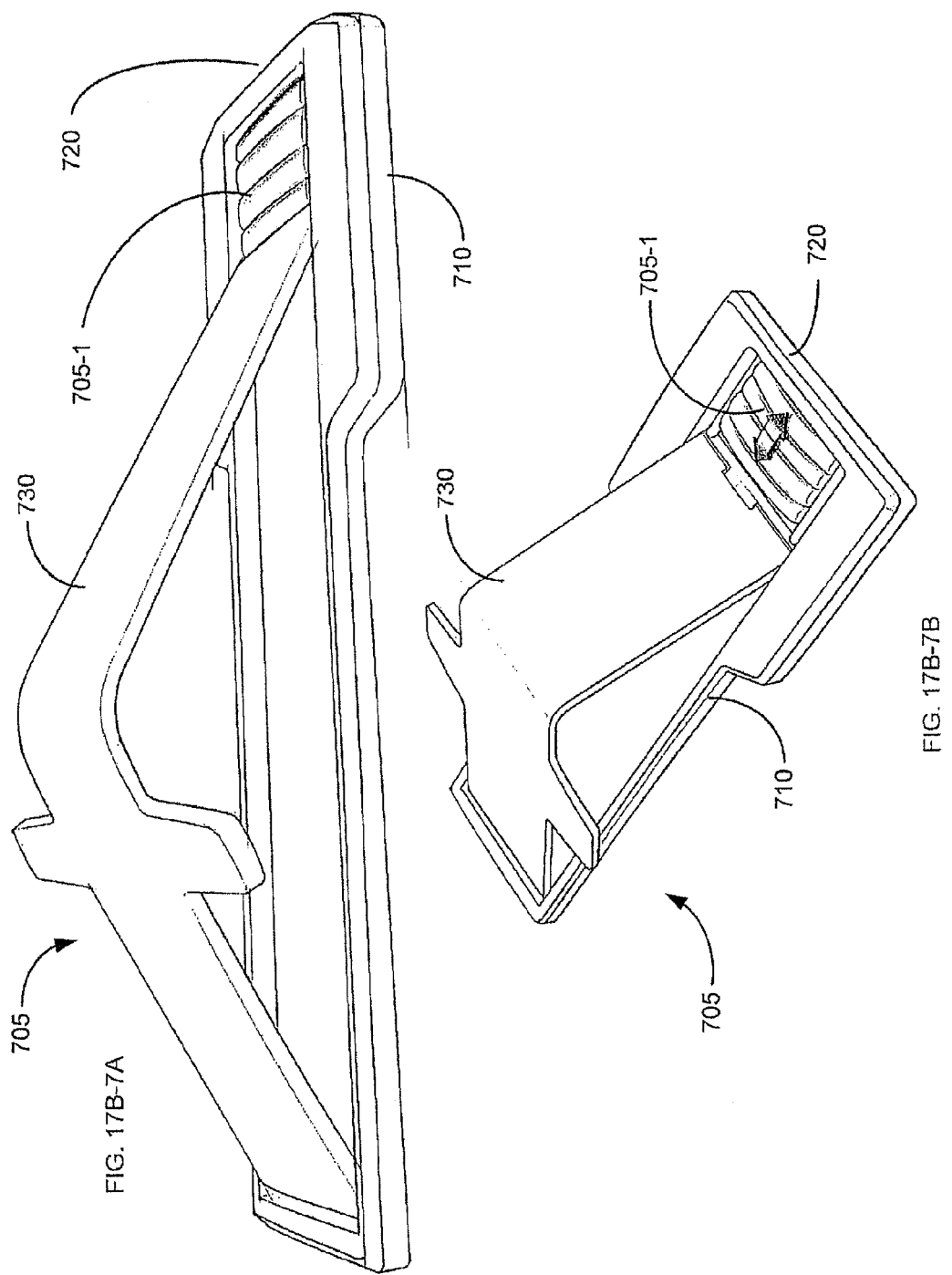

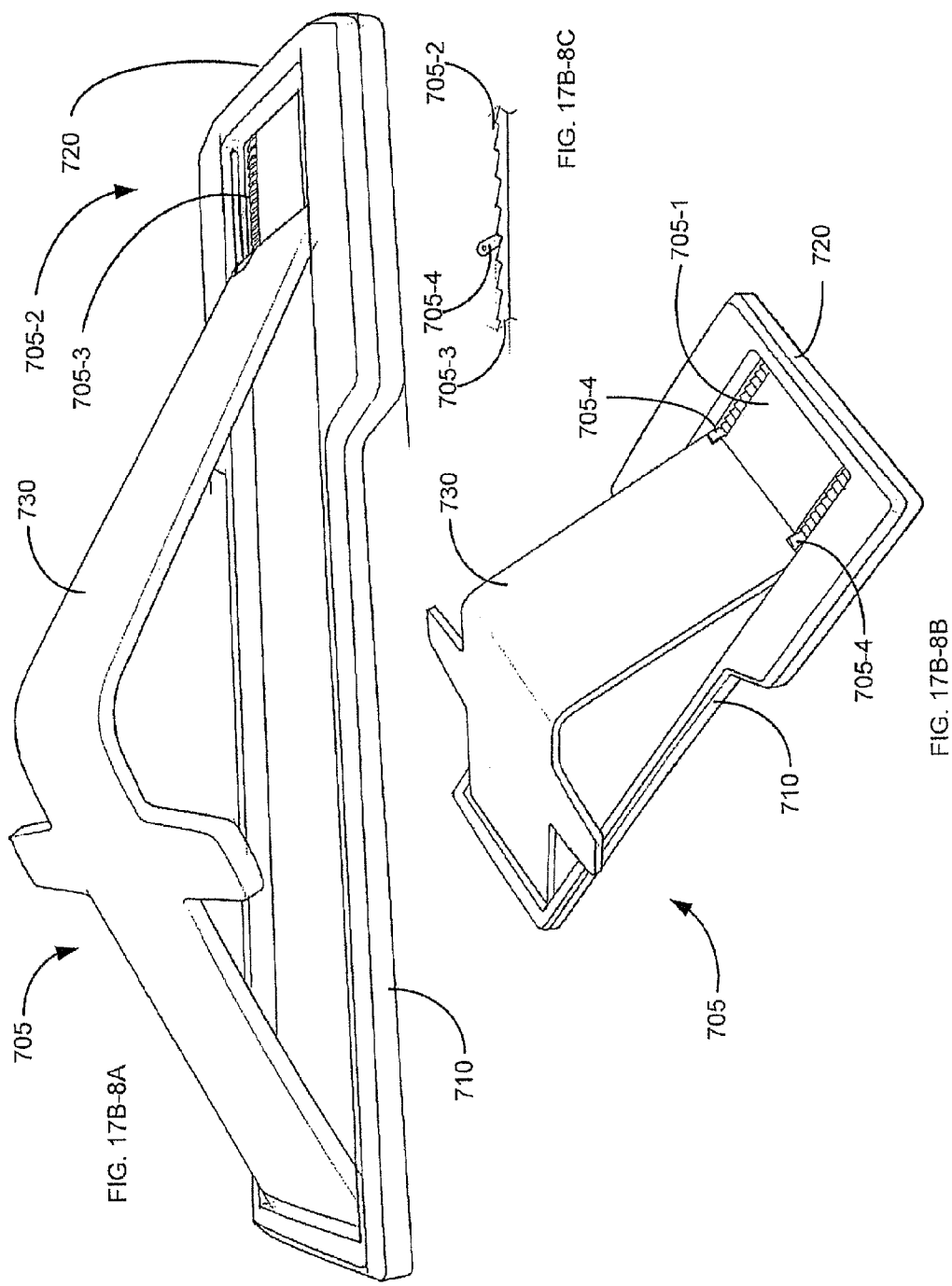

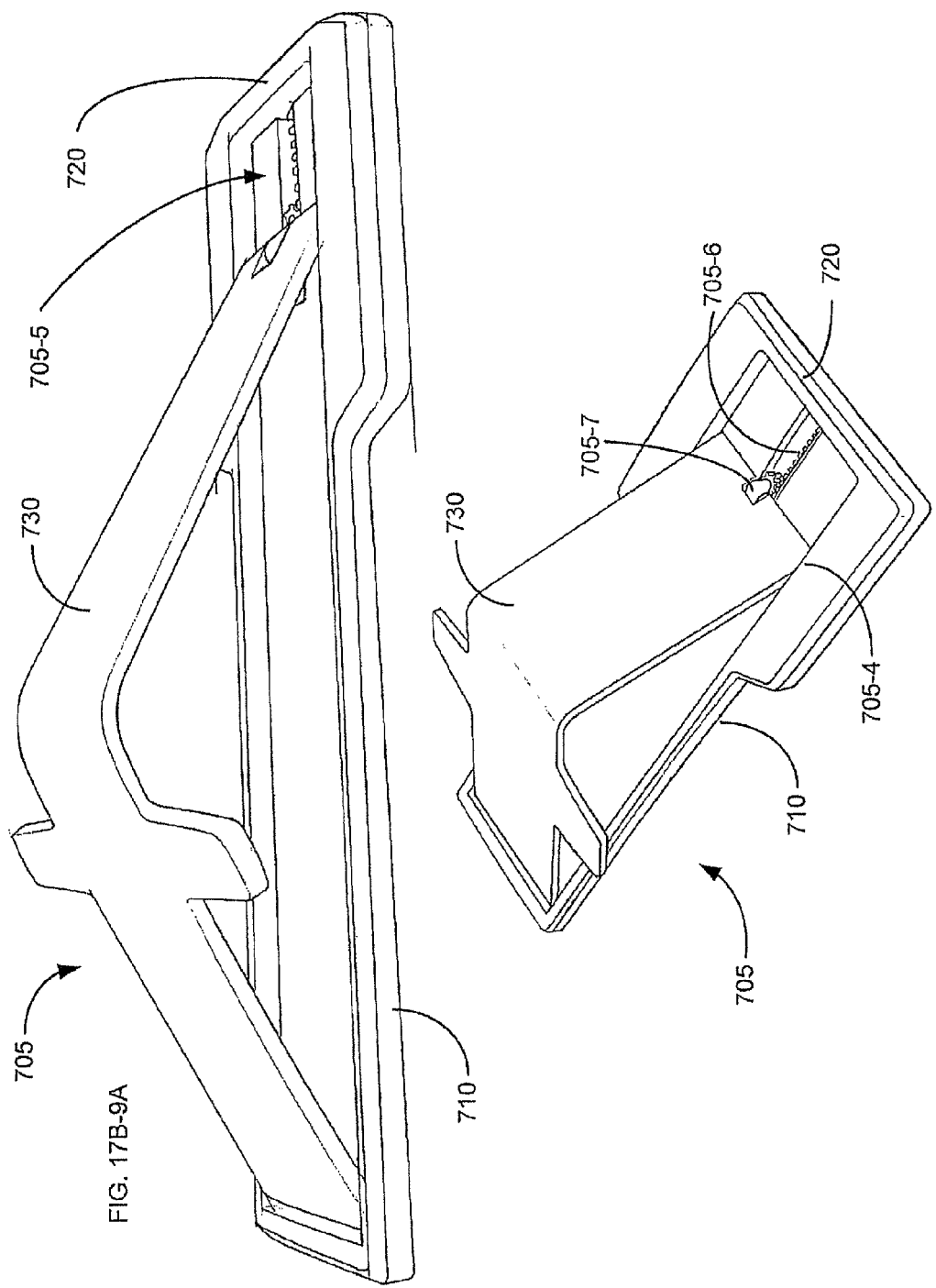

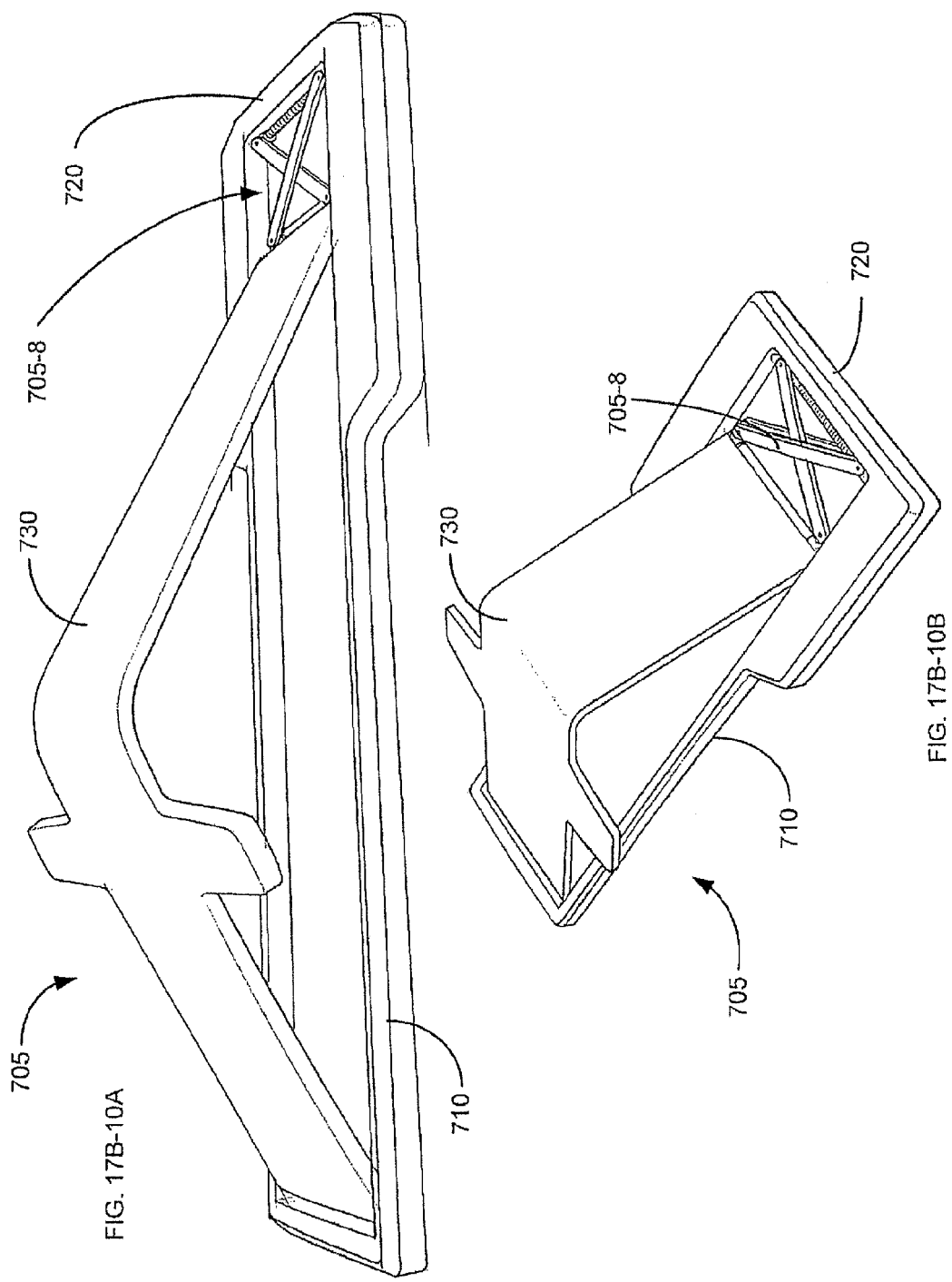

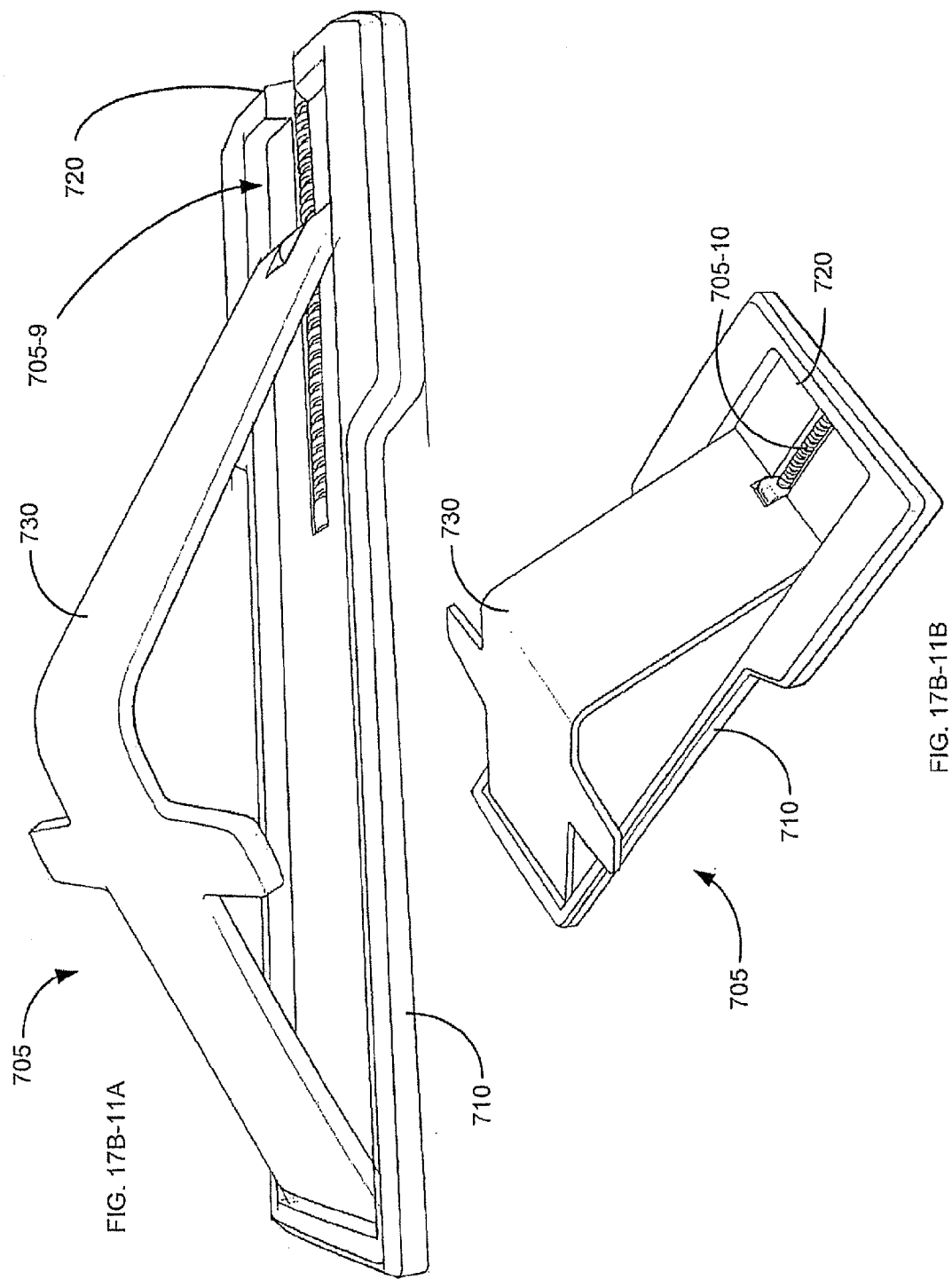

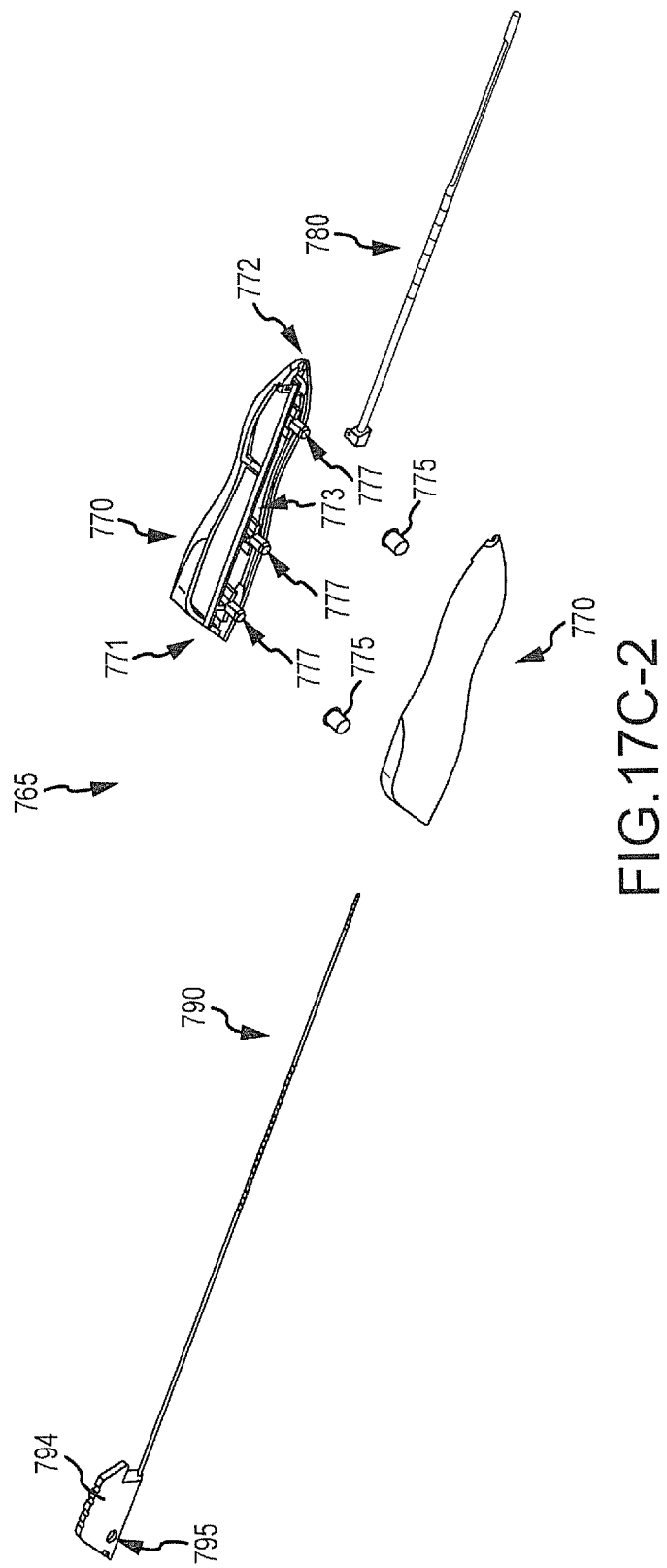

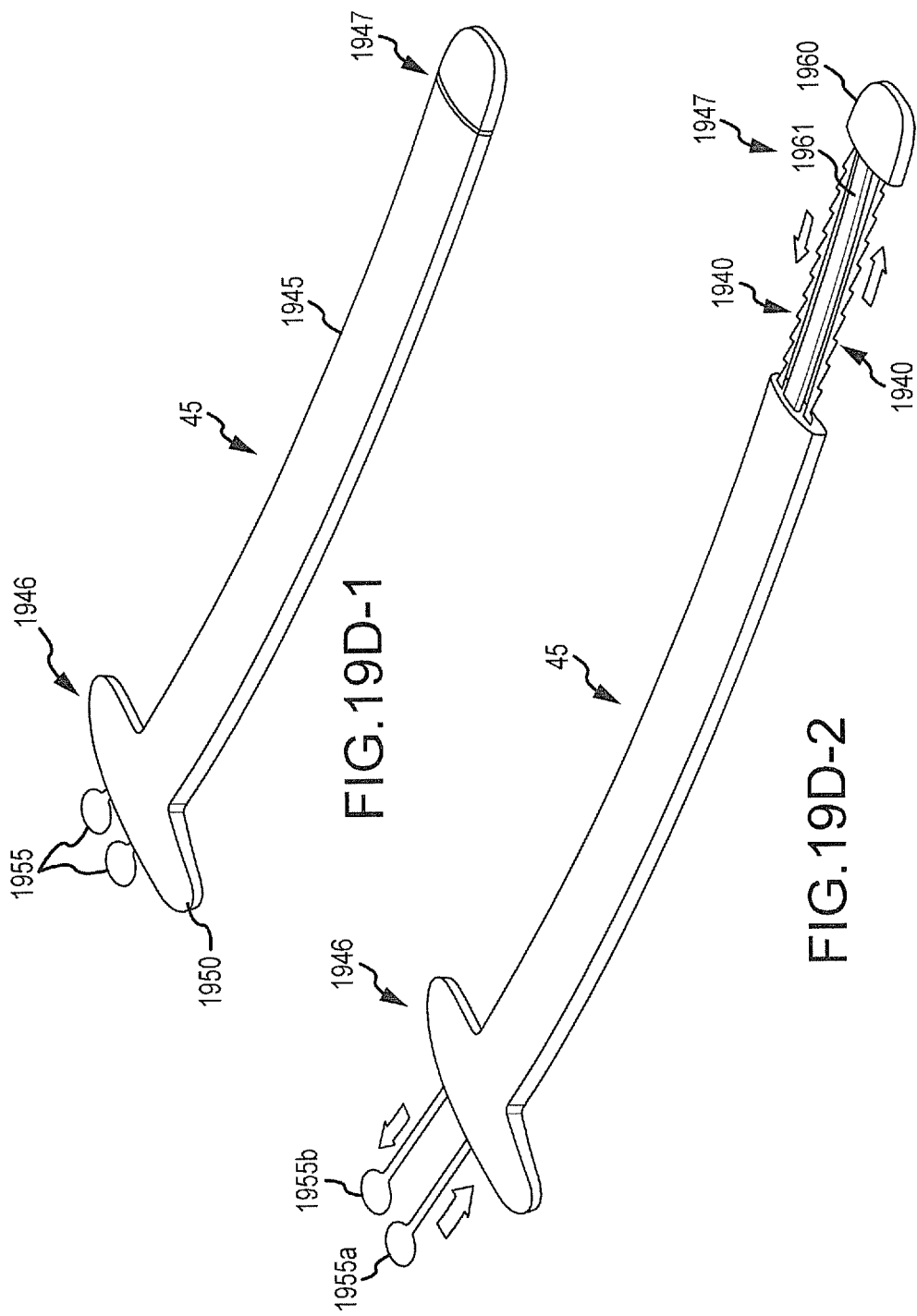

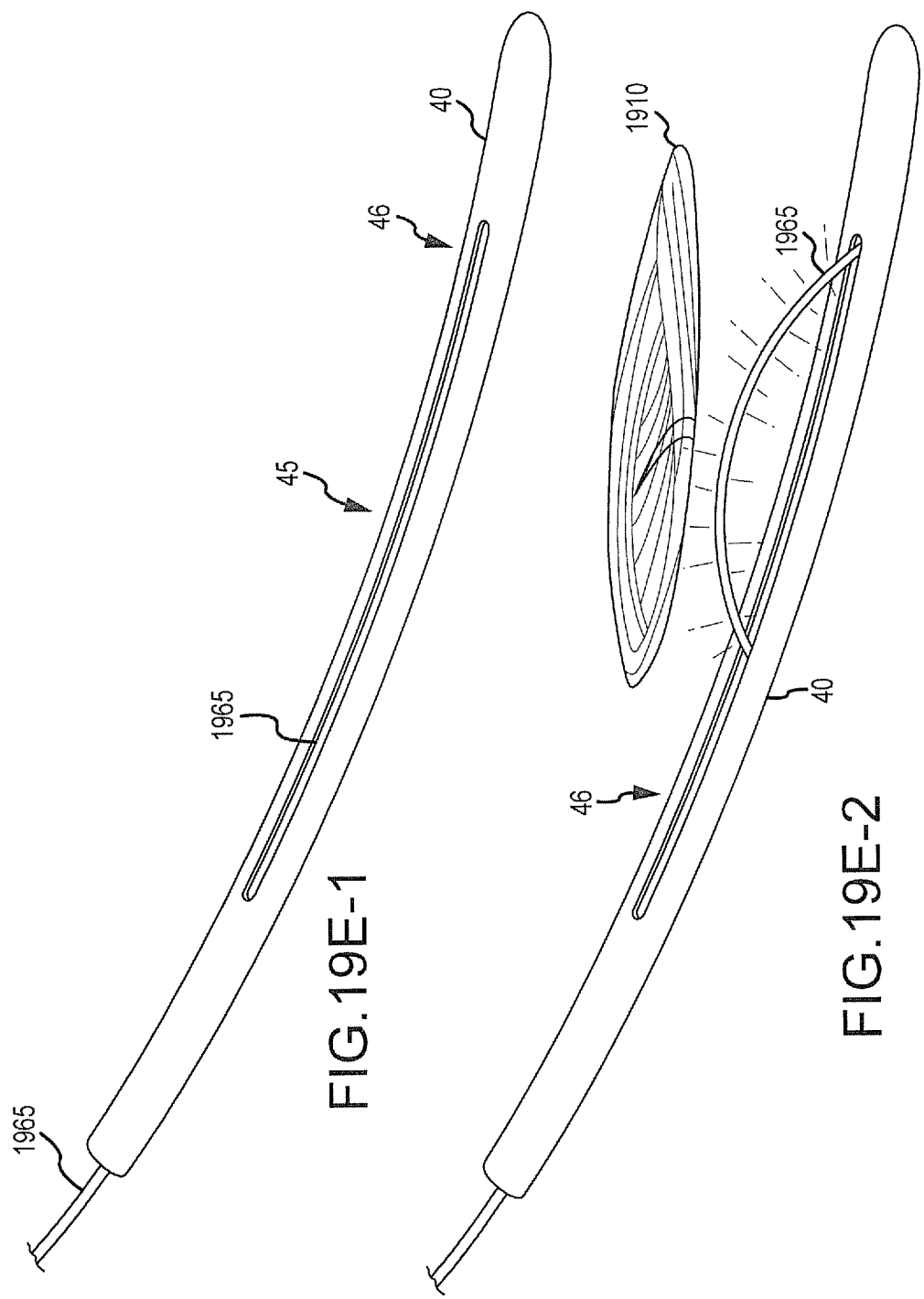

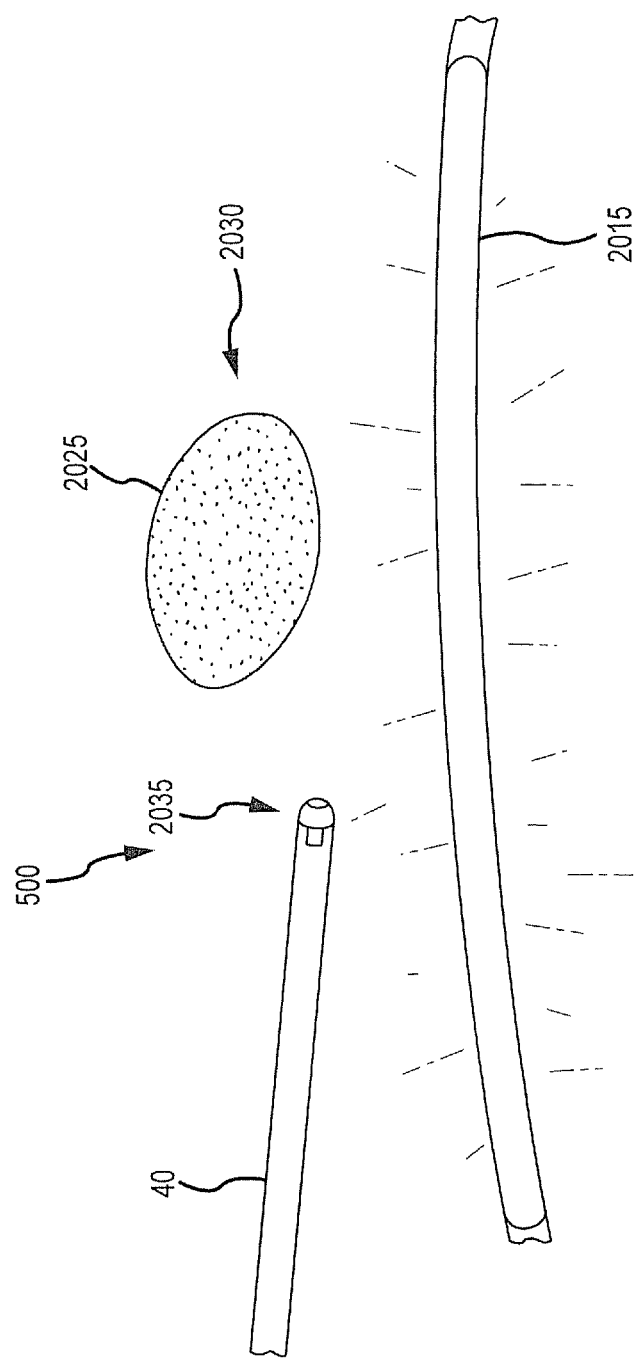

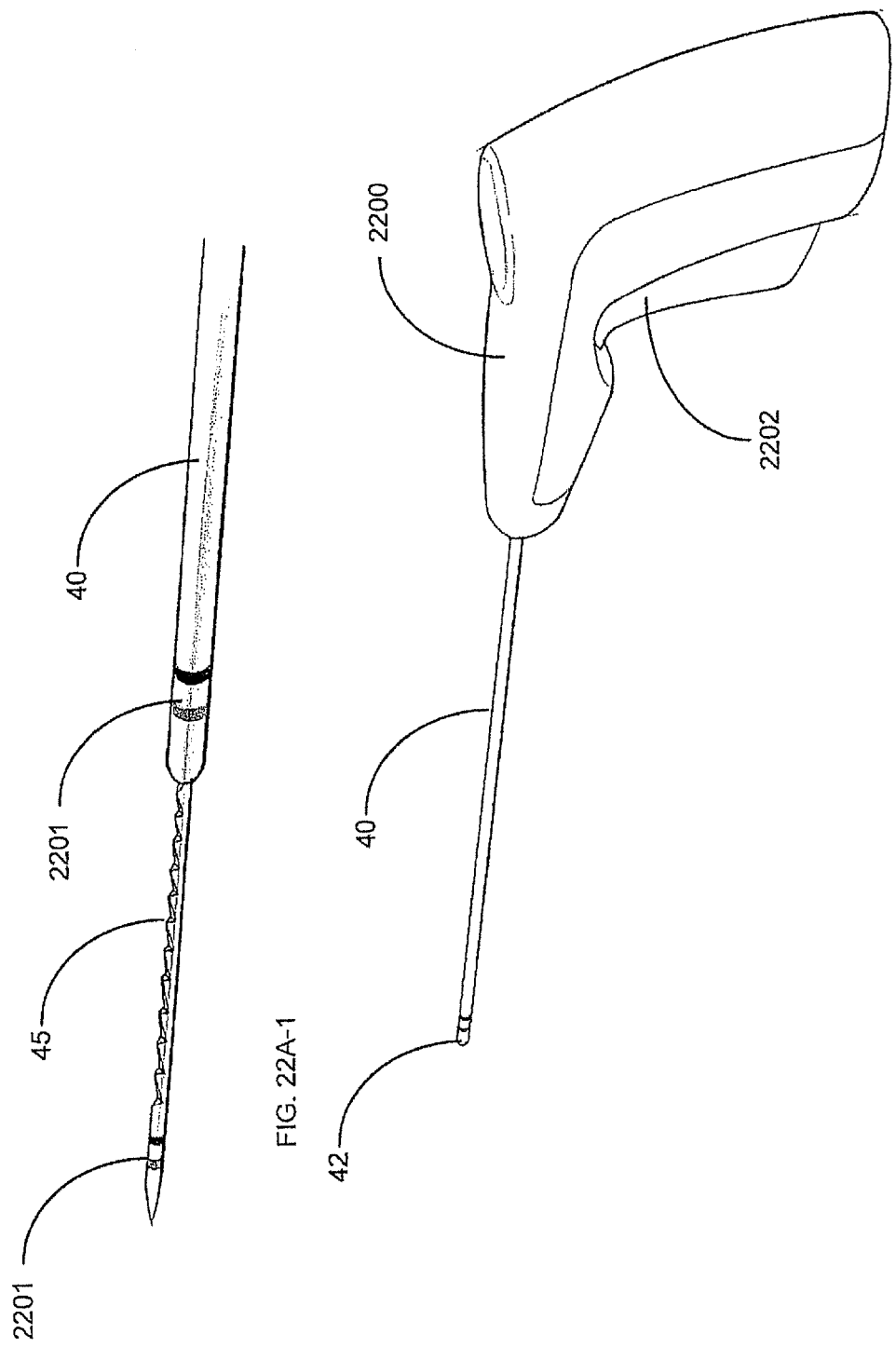

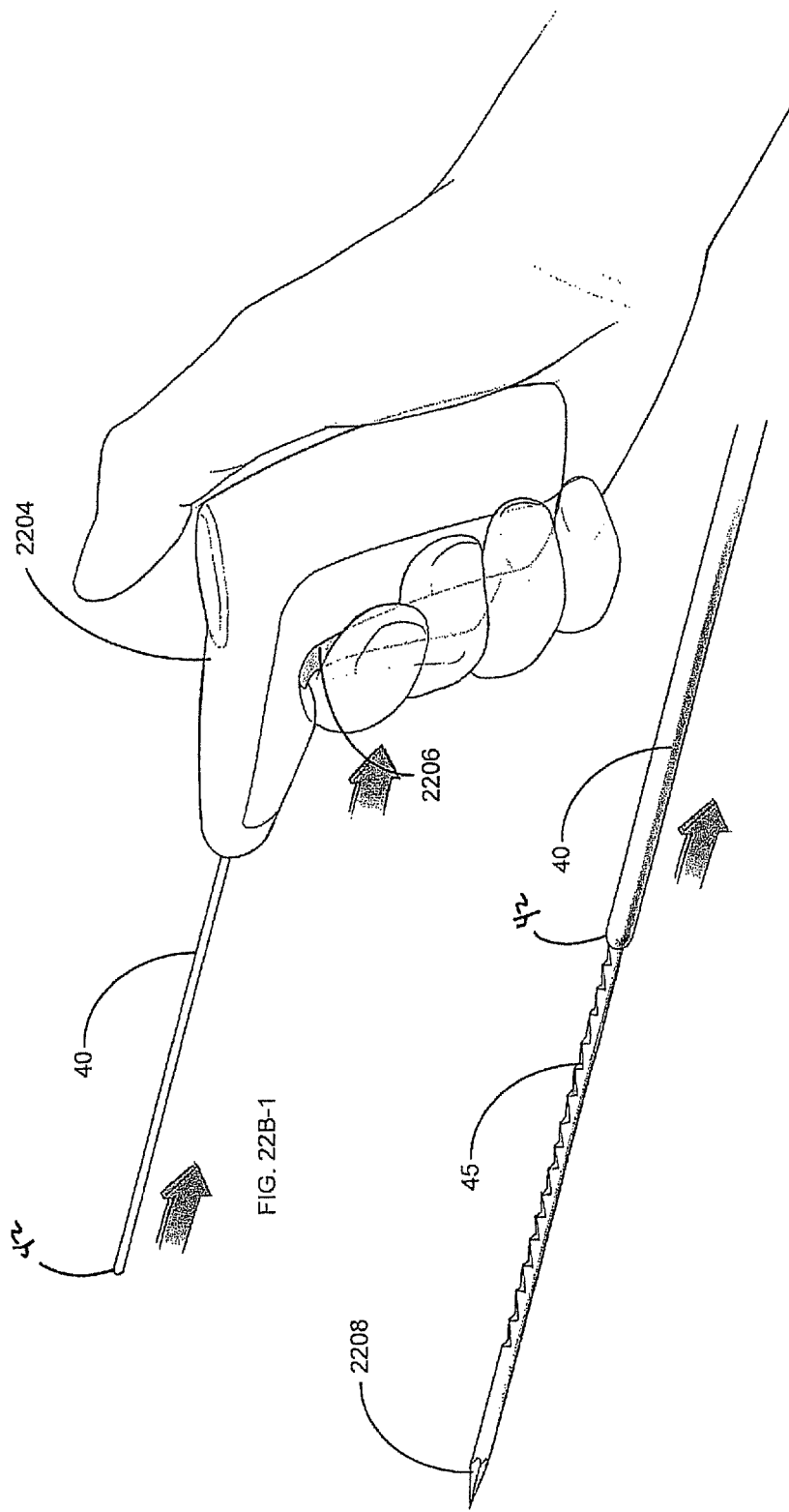

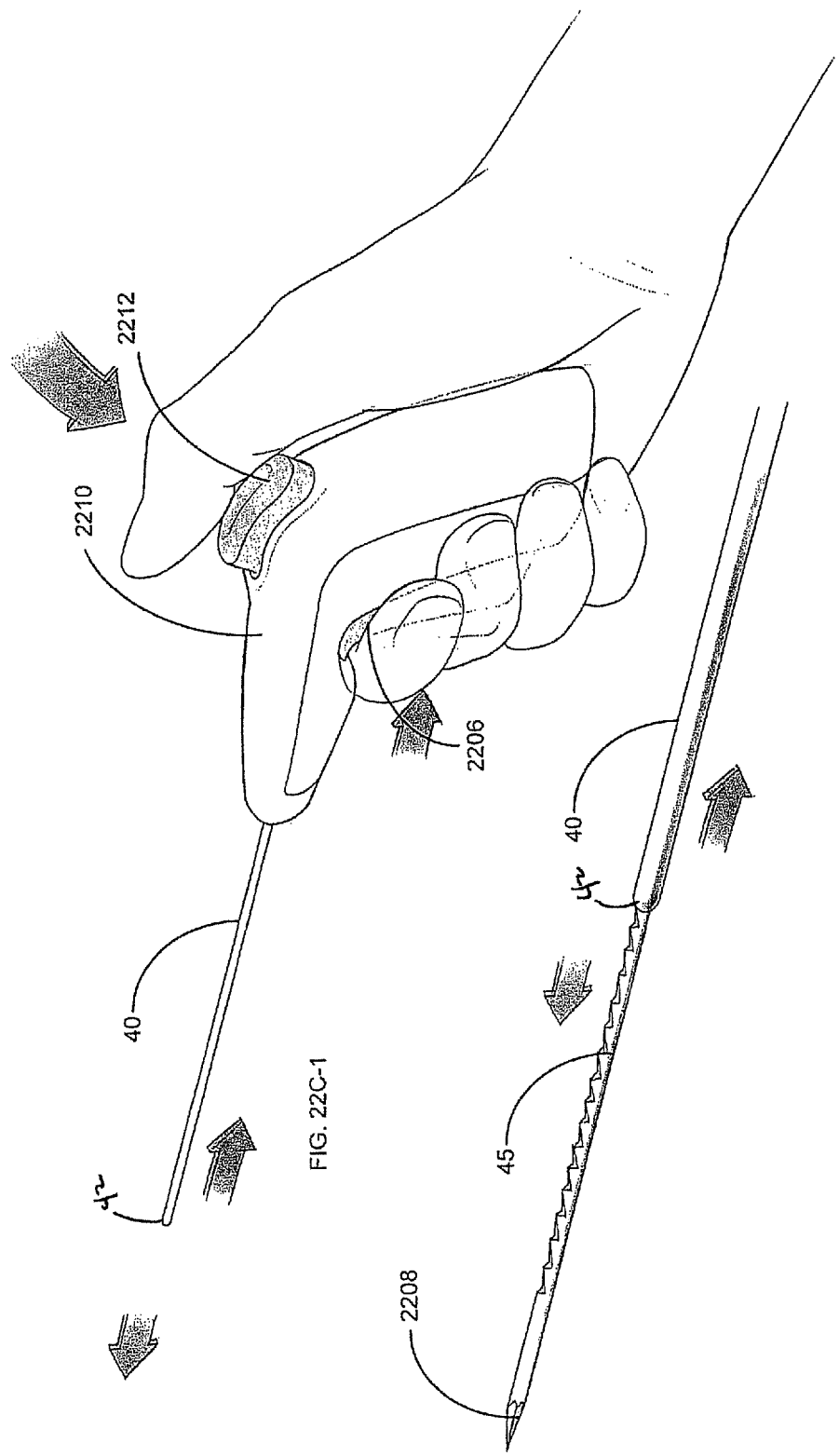

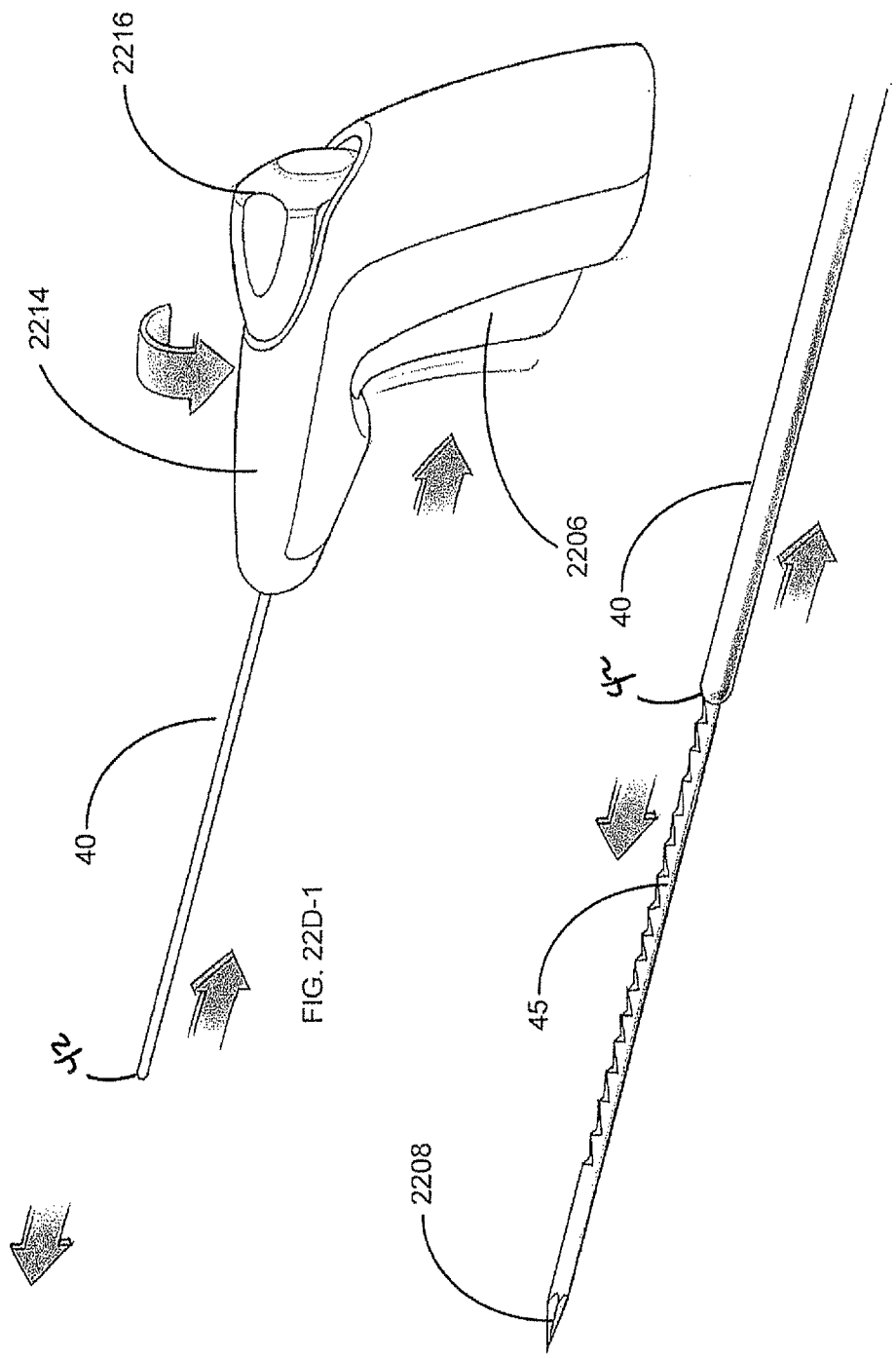

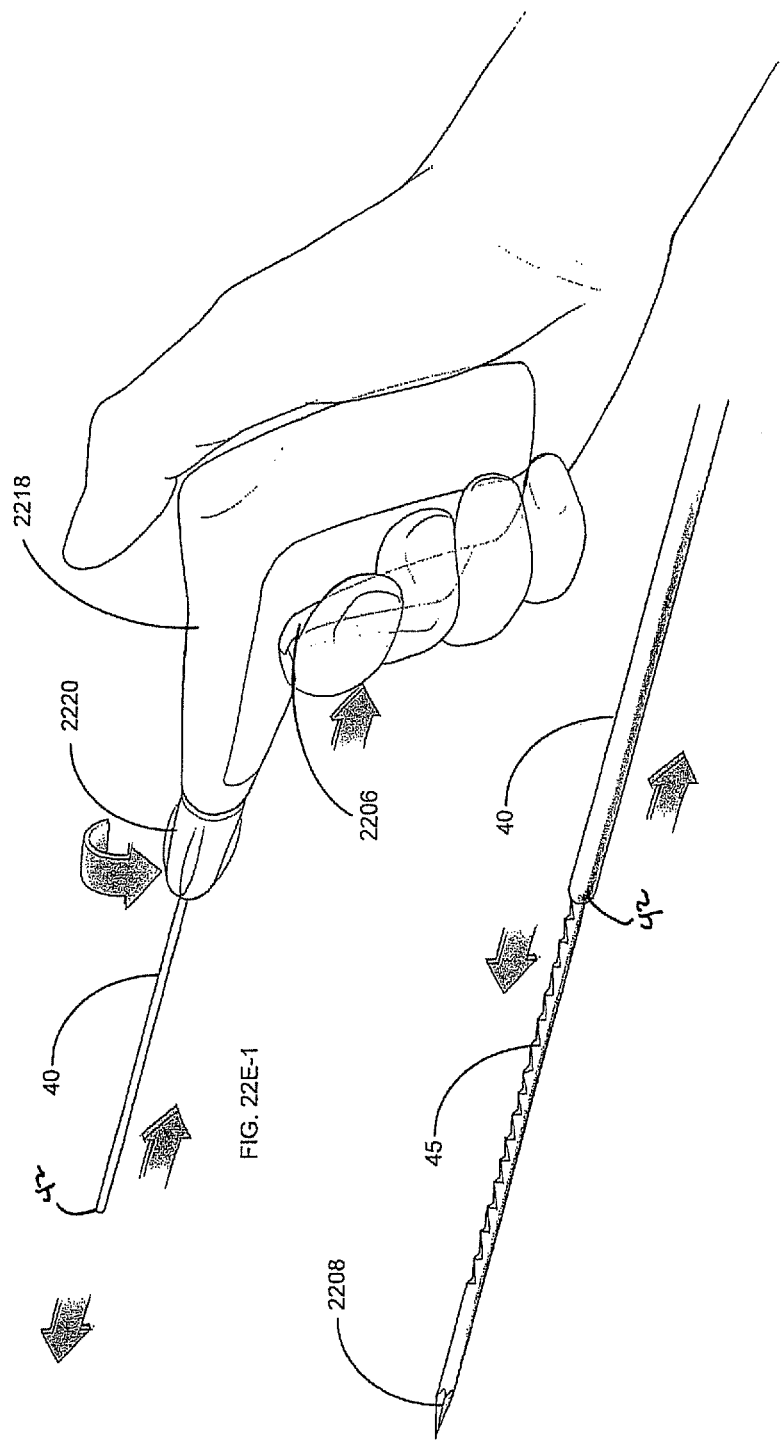

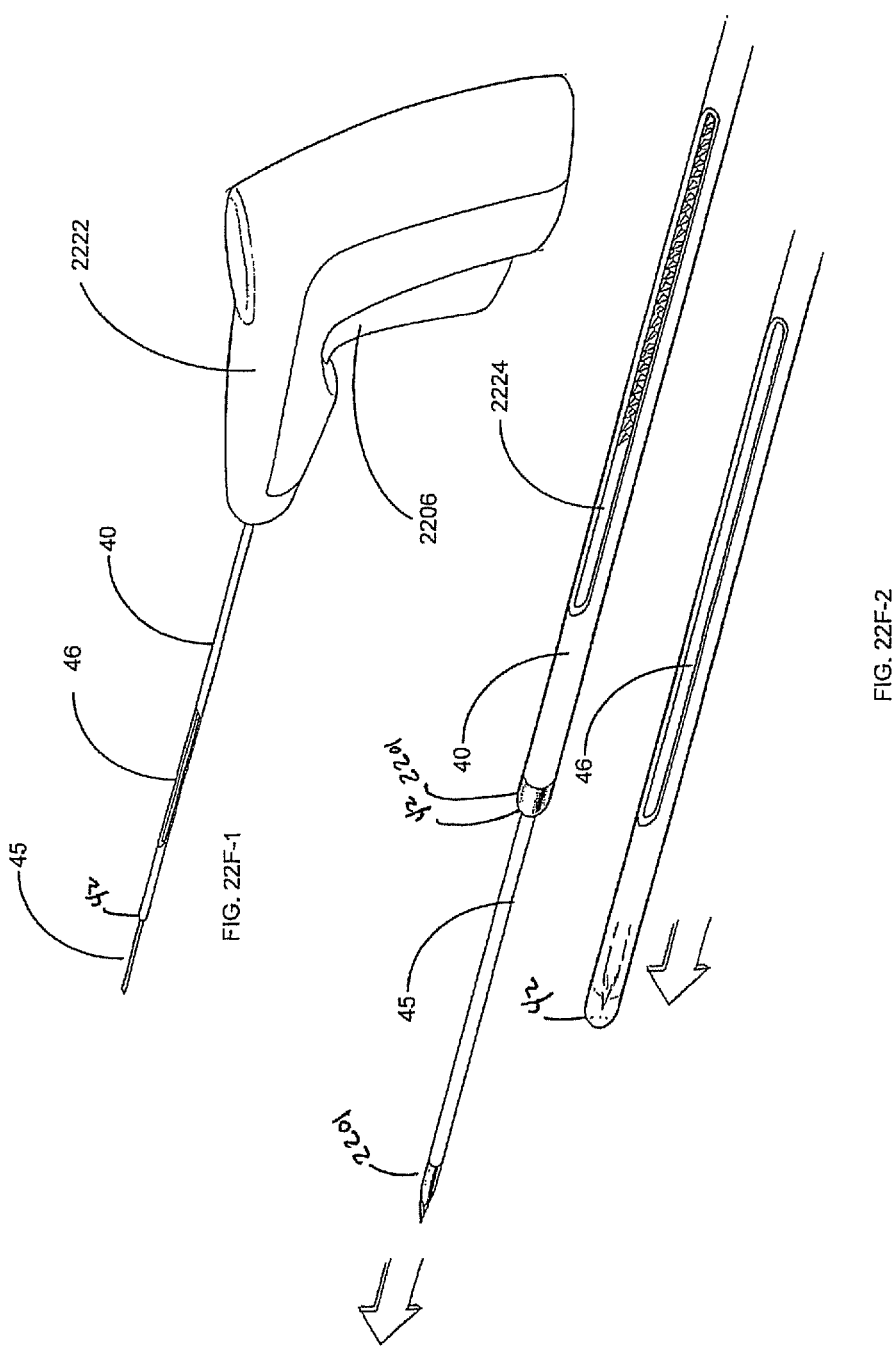

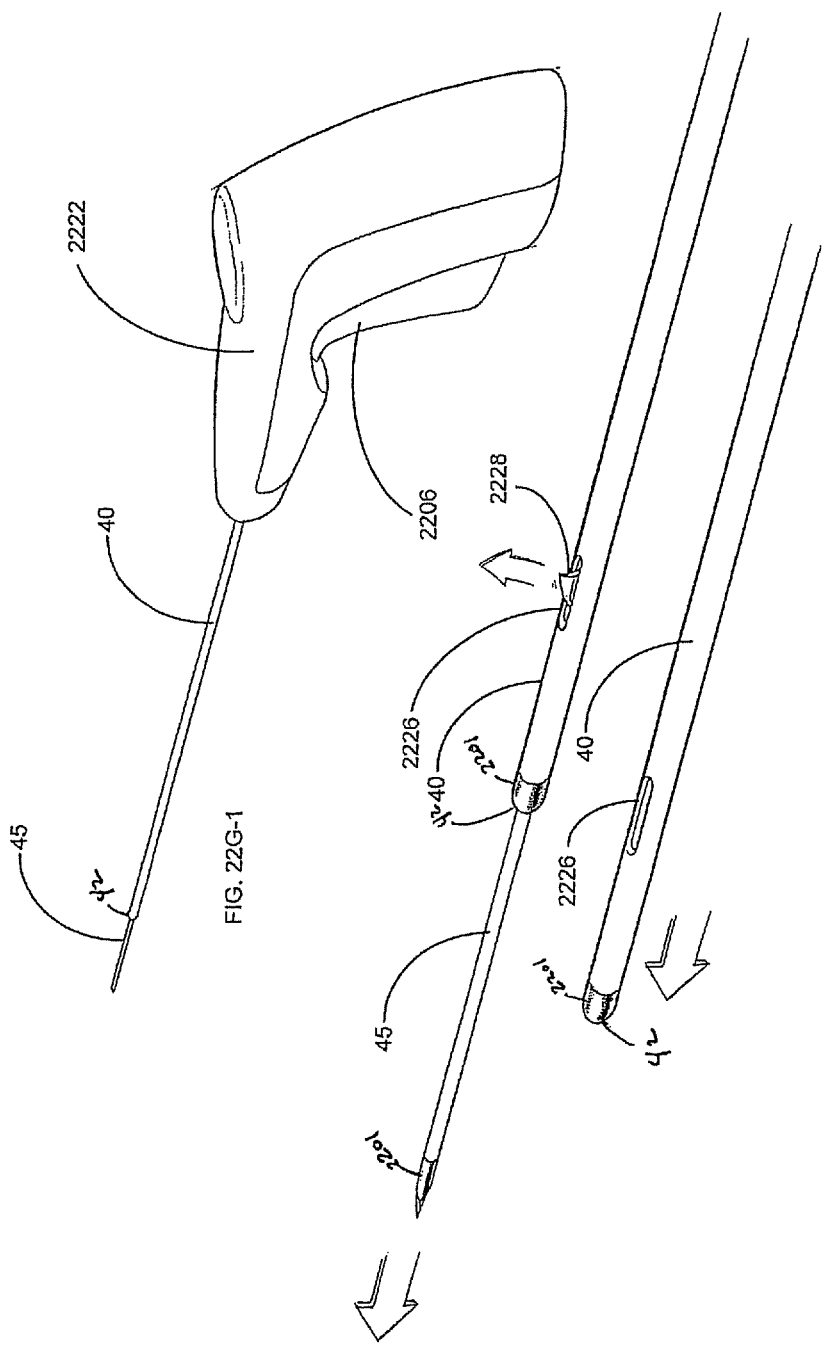

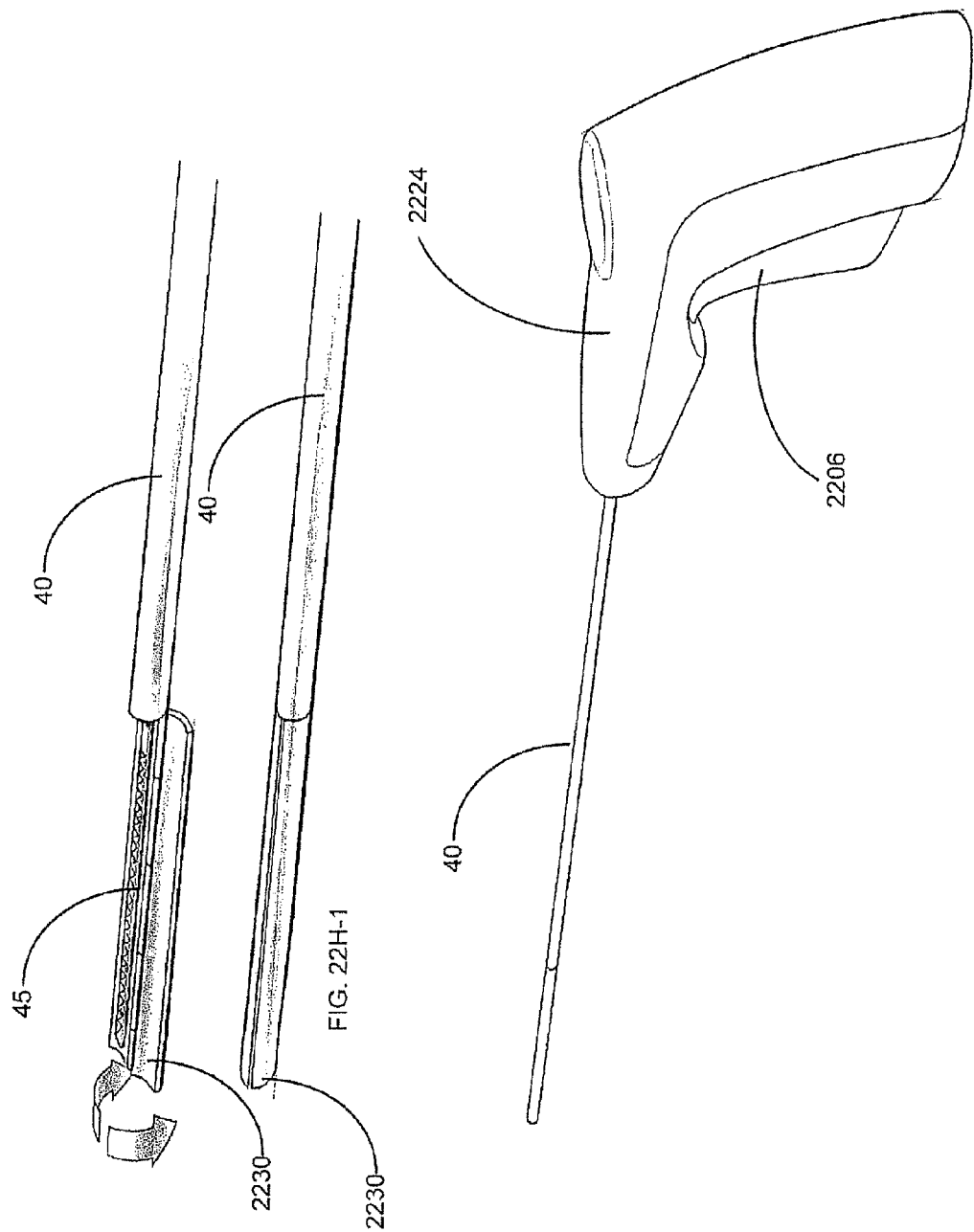

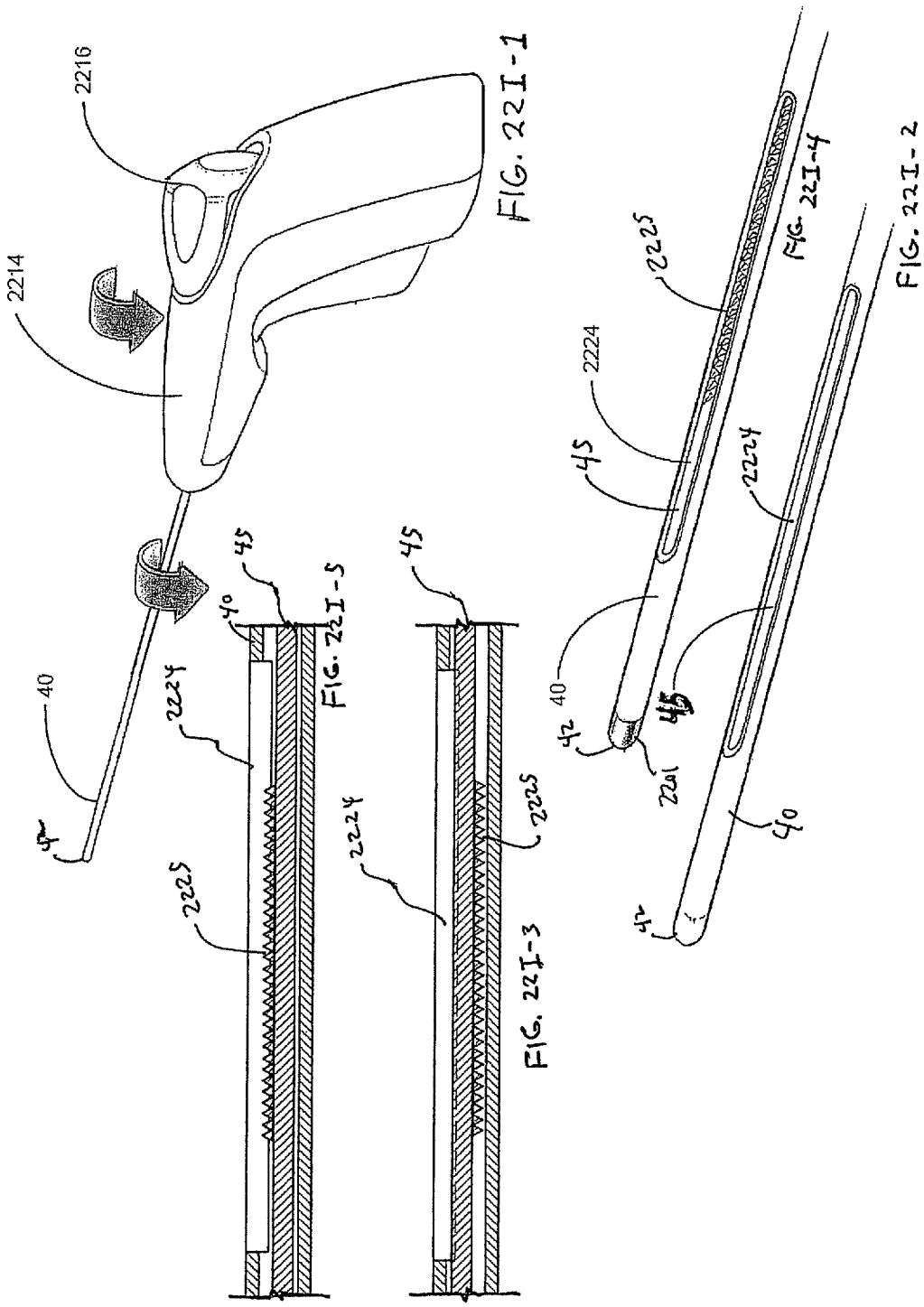

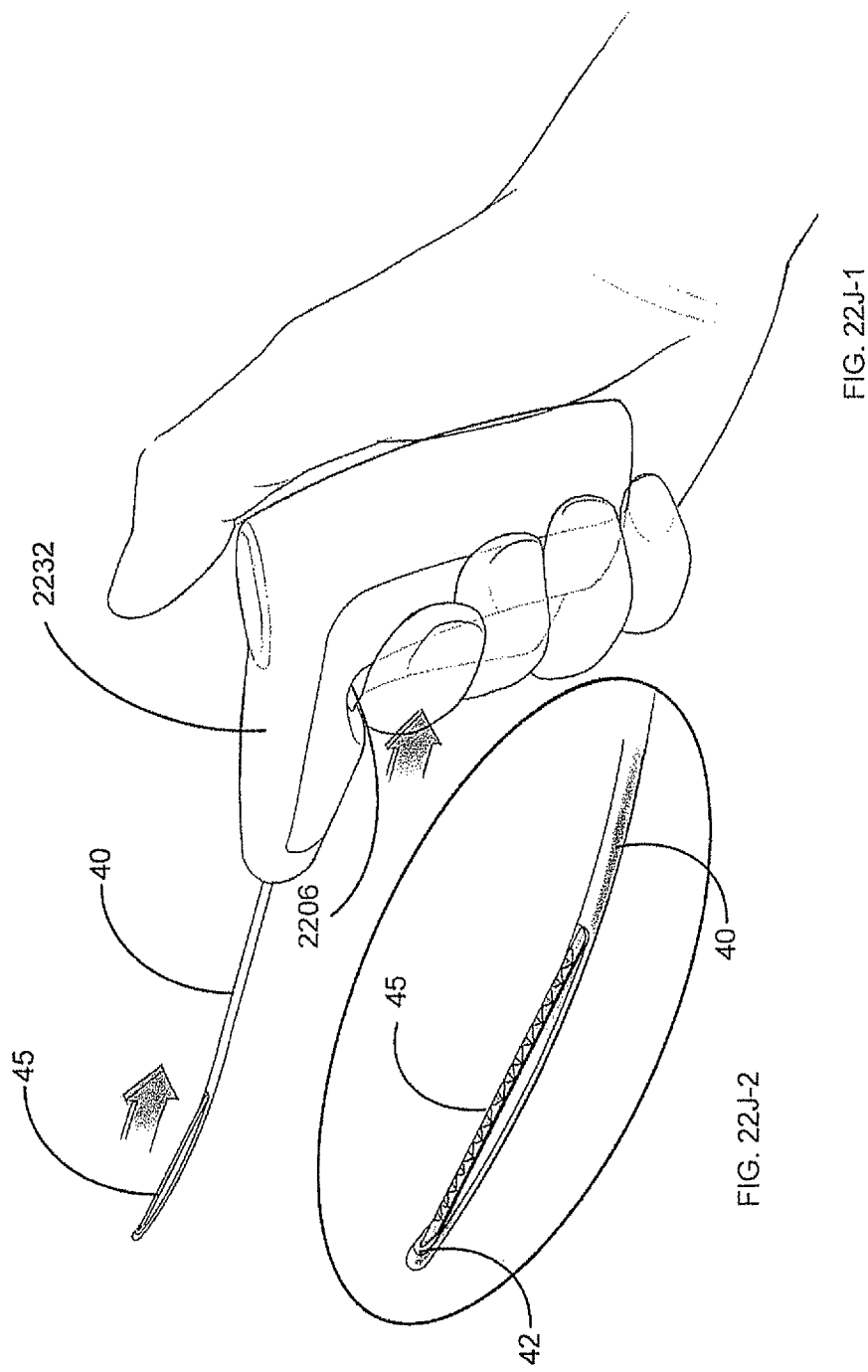

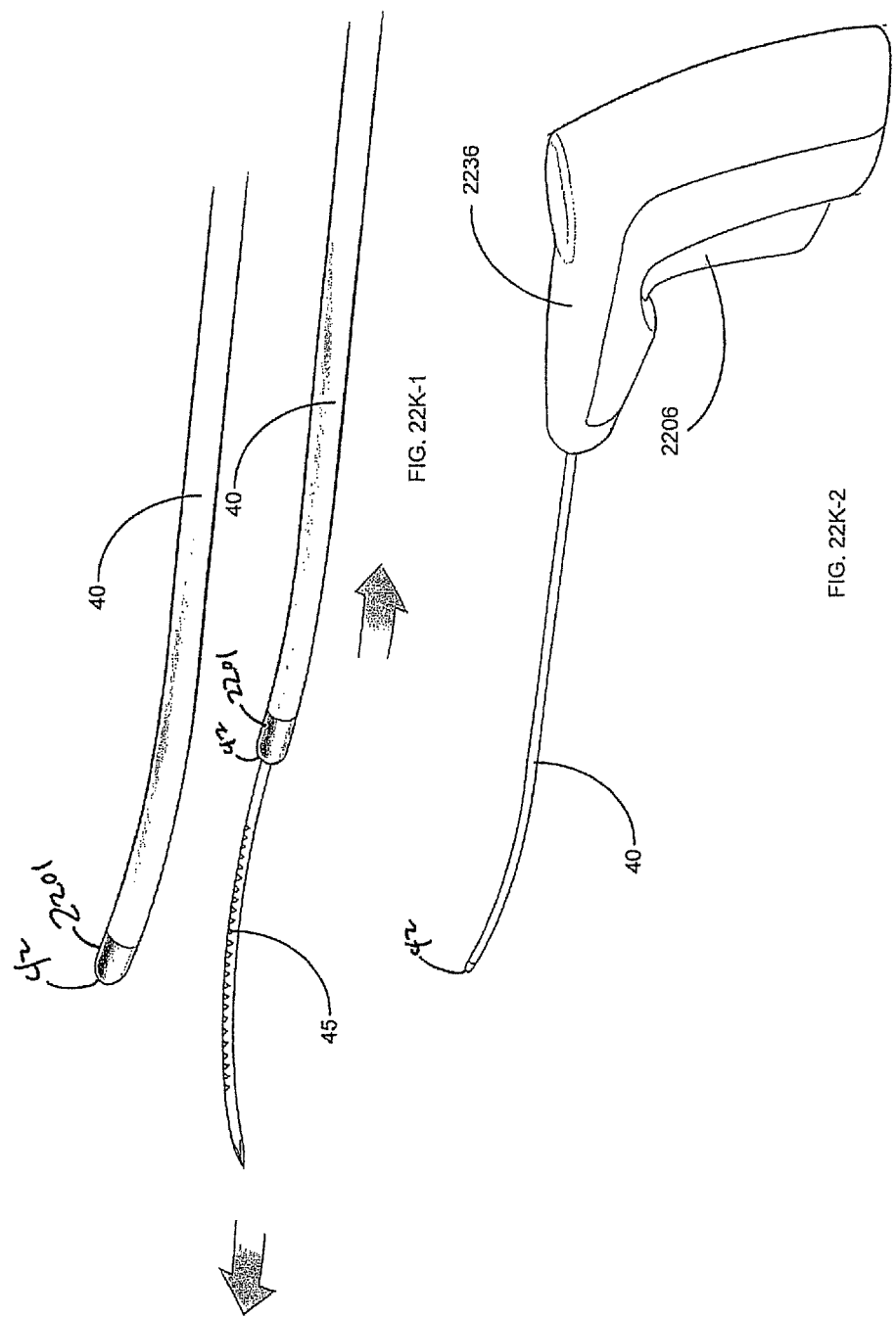

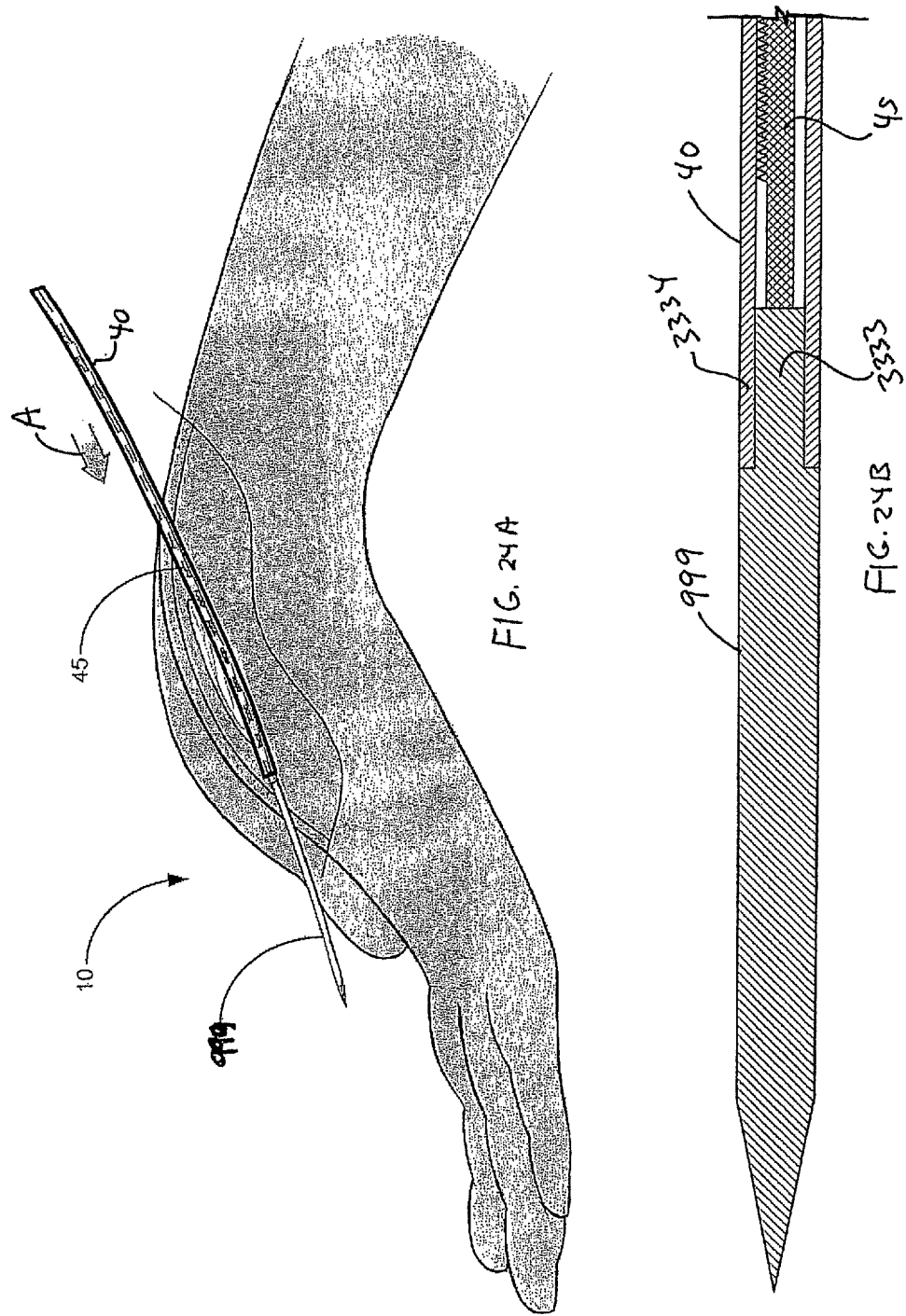

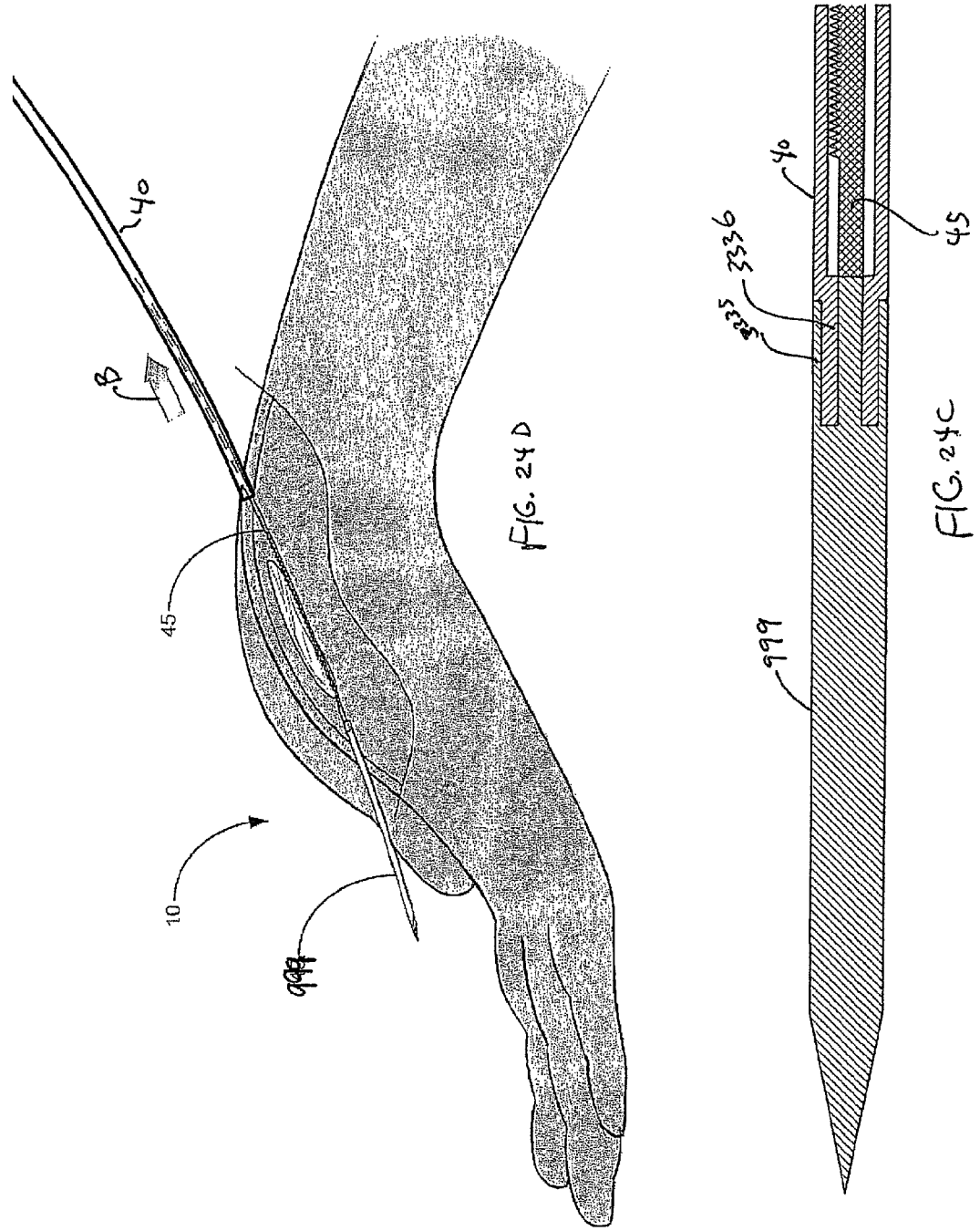

SYSTEMS AND METHODS FOR TREATMENT OF COMPRESSED NERVES

CROSS REFERENCE TO RELATED APPLICATIONS

The present application is a continuation-in-part (CIP) of U.S. patent application Ser. No. 12/852,348, which was entitled "Systems and Methods for Treatment of Compressed Nerves" and filed Aug. 6, 2010. The '348 application claims the benefit of priority under 35 USC §119(e) to: (1) U.S. Patent Application No. 61/266,903, which was entitled "Systems and Methods for Treatment of Carpal Tunnel Syndrome and Plantar Fasciitis" and filed Dec. 4, 2009; and (2) U.S. Patent Application No. 61/232,325, which was entitled "Systems and Methods for Treatment of Carpal Tunnel Syndrome" and filed Aug. 7, 2009. All of these aforementioned applications are hereby incorporated by reference in their entireties into the present application.

FIELD

The present disclosure relates to systems and methods for treatment of compressed nerves.

BACKGROUND

Carpal tunnel syndrome (CTS) is a painful condition of the hand characterized by tingling and numbness and loss of grip strength. CTS is caused by the compression of the median nerve at the carpal tunnel and it is one of the common nerve entrapment syndromes.

As shown in FIG. 1, which illustrates a normal or non-compressed carpal tunnel, the carpal tunnel 5 is the area of the wrist and palm of the hand 10 formed by a U-shaped cluster of bones 15 that form a hard floor and two walls of the tunnel 5. The roof of the tunnel is formed by the transverse carpal ligament (TCL) 20 which attaches to the wrist bones. Within the confines of the tunnel 5 is the median nerve 25 and the flexor tendons 30 of the thumb and fingers.

As indicated in FIG. 2, which depicts a compressed carpal tunnel, a thickening of the TCL 20 and a corresponding narrowing of the size of the carpal tunnel 5 may precipitate CTS. This thickening causes compression of the flexor tendons 30 and median nerve 25 which leads to CTS symptoms.

A number of factors may contribute to the thickening of the TCL. Normal wear and tear and repetitive wrist movements may cause thickening of the TCL. Wrist fracture may cause bony narrowing of the tunnel. Pregnancy, obesity, diabetes, thyroid dysfunction and chronic renal failure may predispose a patient to CTS. CTS generally occurs in people between the ages of 30 and 60 and it is more common in females.

Diagnosis of CTS may be established by history and examination. Symptoms may include nocturnal hand pain. Positive examination findings include nerve irritation signs, such as positive Phalen's wrist flexion test, and Tinel's sign, and weakness and numbness in the median nerve distribution. Electrical studies show prolongation of about 3.5 milliseconds is present in many surgically confirmed cases.

Medical management may be by splinting, anti-inflammatories, and steroid injections in the wrist. If unsuccessful, surgical intervention to decompress or release the TCL may be indicated.

FIG. 3 depicts one type of surgical technique, known as an open release surgery. Open surgical decompression by cutting the TCL was first described in 1930 by Learmonth. The open technique involves creation of an incision beginning in the palm and extending to the wrist. Through this open incision, a surgeon may directly visualize the TCL and may use a scalpel to cut completely through the TCL and release the compression of the median nerve. Angling the incision towards the ulnar aspect of the wrist helps to avoid cutting the palmar sensory cutaneous branch of the median nerve. The skin incision can vary in length from one to five inches depending upon training and experience but should be sufficient to allow full sectioning of the TCL.

After surgery, the hand is wrapped. The stitches are removed 10 to 14 days after surgery. Patients may be directed to wear a splint for several weeks. The pain and numbness may go away right after surgery or may take several months to subside.

However, open incisions require significant time to heal. Also, the skin in the palm is thick and prone to cracking and hand immobilization is necessary for wound healing. Patients are often advised to avoid heavy use of their hand for up to 3 months. When a patient's return to work is dependent on the operated hand, rehabilitative physical therapy is commonly prescribed. Therapy is often prescribed for the resultant symptomatic scar tissue.

FIG. 4 depicts another type of surgical technique known as an endoscopic release surgery. Endoscopic carpal tunnel release is a technical procedure that requires microscopic techniques and the correct endoscopic equipment with the necessary back up equipment.

To perform the procedure, anesthetic is administered and an incision is marked out on the wrist just proximal to the palm. The superficial tendon and small veins are retracted to prevent nerve injury. An 'L' or 'U' shaped incision is made in the first layer called the flexor retinaculum. This layer is lifted up as a flap that forms a doorway into the carpal tunnel.

A spoon shaped device (such as a synovial elevatoris) is used to clean the under surface of the ligament to provide visualization with an endoscope. Dilators help to compress the tissues in the carpal canal to make it possible to insert the endoscopic device with minimal pressure. The endoscopic device is inserted carefully so that the ligament can be seen along its entire length. Often the device is warmed to prevent fogging. Once the ligament is clearly seen, the small blade in the device is used to release the ligament in stages, after making sure that important nerves and arteries are protected.

Once the ligament is completely released, the rest of the flexor retinaculum in the wrist is released with a special type of scissors. Local anesthetic is injected for post-operative pain relief and the incision is sutured. A soft bandage is applied for the patient to keep on for two days to reduce swelling. After two days they can remove the larger dressing and apply a Band-Aid.

This method requires specialized training and a long learning curve. Surgery is longer than the open release procedures and significant injuries have been reported.

Plantar fasciitis is a painful inflammatory process of the plantar fascia. The plantar fascia is a thick fibrous band of tissue originating at the bottom surface of the calcaneus (heel bone) and extending along the sole of the foot towards the toes. According to one study, plantar fasciitis occurs in two million Americans a year and will occur in 10% of the population over a lifetime. Plantar fasciitis is commonly associated with long periods of work-related weight bearing activity, and among non-athletic populations, it is associated with a high body mass index. Typically, pain is felt on the underside of the heel and one may suffer from decreased dorsiflexion of the ankle in addition to knee pain. Generally, treatment is non-surgical, although surgical treatment may be used. One type of surgical technique may include use of an ultrasound guided needle. The needle is inserted into the plantar fascia and moved back and forth to disrupt the fibrous tissue. Another surgical technique is a coblation surgery (also known as a Topaz procedure). This technique has been used in the treatment of recalcitrant plantar fasciitis and utilizes radiofrequency ablation.

However, known surgical techniques may cause injury to the nerve, infection and may fail to relieve the pain.

There is a need in the art for improved systems and methods for surgical treatment of carpal tunnel syndrome and plantar fasciitis with increased efficiency and reduced surgical complications.

SUMMARY

Disclosed herein is a system for releasing the transverse carpal ligament to decompress the median nerve. In one embodiment, the system includes an introducer, an elongated body including a blunt tip and a cutting member for cutting the transverse carpal ligament to decompress the median nerve, a neuro-monitoring system operably connected to the elongated body for aiding a surgeon in navigating the elongated body under the transverse carpal ligament, and handle members respectively operably attached to a distal end and a proximal end of the elongated body, wherein the handle members are operably attached to the respective distal and proximal ends of the elongated body after the elongated body is navigated under the transverse carpal ligament and wherein the handle members at the distal end and the proximal end of the elongated body are used to guide the cutting member of the elongated body to release the transverse carpal ligament to decompress the median nerve. In one embodiment, the system may further include a hand immobilizing system.

Disclosed herein is a method for releasing the transverse carpal ligament to decompress the median nerve. In one embodiment, the method includes providing an introducer into the deep wrist of a patient's hand, introducing an elongated body into the introducer, the elongated body including a blunt tip, a cutting member, a distal end and a proximal end, providing a neuro-monitoring system operably attached to the elongated body, navigating the elongated body under the transverse carpal ligament to an exit point at a surface of the patient's hand via input received from the neuro-monitoring system, extending at least a portion of the elongated body through the exit point such that the distal end of the elongated body is external to the hand, removing the introducer, providing handle members and operably attaching one handle member to the distal end and another handle member to the proximal end of the elongated body, and using the handle members to displace the cutting member of the elongated body along the transverse carpal ligament to release the transverse carpal ligament thereby decompressing the median nerve. In one embodiment, the method may further include providing a hand immobilizer system to immobilize the patient's hand while using the handle members to displace the cutting member of the elongated body along the transverse carpal ligament to release the transverse carpal ligament thereby decompressing the median nerve.

Disclosed herein is a system for releasing the transverse carpal ligament to decompress the median nerve. In one embodiment the system includes an introducer, a first elongated body including a blunt tip and a cutting member for cutting the transverse carpal ligament to decompress the median nerve, a second elongated body including a proximal end and a distal end having a hook, a neuro-monitoring system operably connected to the elongated body for aiding a surgeon in navigating the elongated body under the transverse carpal tunnel ligament; and handle members respectively operably attached to a distal and proximal end of the first elongated body, wherein the handle members are operably attached to the respective proximal and distal ends of the first elongated body after the first elongated body is navigated under the transverse carpal ligament and the second elongated body is navigated through subcutaneous tissue above the transverse carpal ligament and the second elongated body is operably attached to the first elongated body such that when the second elongated body is withdrawn, the first elongated body creates a loop structure about the transverse carpal ligament and wherein the handle members at the distal end and the proximal end of the first elongated body are used to guide the cutting member of the first elongated body to release the transverse carpal ligament to decompress the median nerve.

Disclosed herein is a system for releasing the plantar fascia to treat plantar fasciitis in a plantar fascia release procedure. In one embodiment, the system may include an introducer, an elongated body including a blunt tip and a cutting member for cutting the plantar fascia in a plantar fascia release procedure, a neuro-monitoring system operably connected to the elongated body for aiding a surgeon in navigating the elongated body under the plantar fascia, and handle members respectively operably attached to a distal and proximal end of the elongated body, wherein the handle members are operably attached to the respective proximal and distal ends of the elongated body after the elongated body is navigated under the plantar fascia and wherein the handle members at the distal end and the proximal end of the elongated body are used to guide the cutting member of the elongated body to release the plantar fascia to treat plantar fasciitis in a plantar fascia release procedure.

Disclosed herein is a system for releasing the transverse carpal ligament to decompress the median nerve. In one embodiment, the system includes an elongated body including a blunt tip and a cutting member for cutting the transverse carpal ligament to decompress the median nerve, a neuro-monitoring system operably connected to the elongated body for aiding a surgeon in navigating the elongated body under the transverse carpal tunnel ligament, a securing member that is operably attached to a distal end of the cutting member after the elongated body is navigated under the transverse carpal ligament and the cutting member exits a distal end of the elongated body and then exits the hand at an exit point in the palm, and a handle member including an actuator operably attached to a proximal end of the elongated body wherein the actuator of handle member at the proximal end of the elongated body is used to guide the cutting member of the elongated body to release the transverse carpal ligament to decompress the median nerve.

Disclosed herein is a system for releasing the transverse carpal tunnel ligament to decompress the median nerve. In one embodiment, the system includes an introducer, an elongated body including a proximal end and a distal end, a blunt tip and a cutting member for cutting the transverse carpal ligament to decompress the median nerve, a neuro-monitoring system operably connected to the elongated body for aiding a surgeon in navigating the elongated body under the transverse carpal tunnel ligament, a piercing member that is operably attached to a distal end of the cutting member to pierce the palm at an exit point in the palm of the hand as the cutting member exits the distal end of the elongated body and then exits the hand at the exit point in the palm, a motion limiting feature operably connected to the proximal end of the elongated body, the motion limiting feature configured to prevent the introducer from re-entering an entry point in the palm after withdrawal and configured to prevent the elongated body from exiting at the exit point in the palm, a first handle member operably attached to a proximal end of the elongated body, and a second handle member operably attached to the piercing member at the distal end of the cutting member after the piercing member and the cutting member exit the palm of the hand, wherein the first and second handle members are used to guide the cutting member of the elongated body to release the transverse carpal ligament to decompress the median nerve. In some embodiments, the first handle member may further include an actuator. In some embodiments, this system may be used to release the plantar fascia to treat plantar fasciitis.

Disclosed herein is a system for releasing a ligament. In one embodiment, the system includes a proximal handle, a tubular body, and a flexible body. The tubular body includes a proximal end and a distal end. The handle is coupled to the proximal end. The flexible body extends through the tubular body and includes a tissue cutting portion. The flexible body is longitudinally displaceable relative to the tubular body to move the tissue cutting portion between a non-deployed state and a deployed state.

In one version of the embodiment, the tissue cutting portion includes a plurality of teeth or an abrasive surface. In another version of the embodiment, the tissue cutting portion includes an RF energy cutter or a water jet.

In one version of the embodiment, the flexible body is longitudinally displaced relative to the tubular body during a tissue cutting motion. In another version of the embodiment, the flexible body and tubular body are moved together during a tissue cutting motion. In yet another version of the embodiment, the flexible body is axially rotationally displaced relative to the tubular body during a tissue cutting motion.

In another version of the embodiment, the tubular body is longitudinally displaced relative to the flexible body to expose the tissue cutting portion of the flexible body. In one version of the embodiment, the longitudinal displacement of the tubular body is displaced through one or more actuators on a handle member attached to the proximal end of the tubular body. In one version of this embodiment, the actuator utilizes a spring device to retract the tubular body. In another version of this embodiment, the actuator rotates to retract the tubular body. In yet another version of this embodiment, the handle member includes a plurality of actuators for coinciding longitudinal displacement of the tubular body and the flexible body. In still another version of this embodiment, the tubular body includes a curved portion at the distal end. The flexible body includes a curved bias opposing the curved portion of the tubular body such that, when in the deployed state, the flexible body curves away from the curved portion of the tubular body.

In one version of the embodiment, the tubular body further includes a window, wherein, when the flexible body is longitudinally displaced relative to the tubular body to move the tissue cutting portion from the non-deployed state to the deployed state, the cutting portion moves from being generally hidden within the tubular body to being generally exposed in the window.

In another version of the embodiment, the tubular body further includes a window, wherein, when the flexible body is longitudinally displaced relative to the tubular body to move the tissue cutting portion from the non-deployed state to the deployed state, the cutting portion moves from being generally recessed within the tubular body to being generally exposed in the window. For example, in such a version, when the cutting portion is in the deployed state, the cutting portion assumes a bow-like arrangement with the tubular body. In another version of the embodiment, the window is appropriately sized to allow a hook blade tooth to be exposed within the window in the deployed state. The hook blade tooth is curved such that, when the flexible body is moved into the non-deployed state, the hook blade tooth is generally recessed within the tubular body.

In one version of the embodiment, the system further includes an actuator near the proximal end of the tubular body that causes the cutting portion to move between the non-deployed state and the non-deployed state. The handle may include the actuator.

In another version of the embodiment, the tubular body includes a hinged flap that opens to expose a tissue cutting portion of the flexible body. The hinged flap is opened through an actuator on a handle member attached to the tubular body at the proximate end. In another version of the embodiment, the tubular body includes an inner tube with an inner window and an outer tube with an outer window. The inner tube and the outer tube rotate in opposing directions into a position wherein the inner window and the outer window align. Alignment of the inner window and the outer window coincides with a deployed state such that the tissue cutting portion of the flexible body is exposed for cutting of the tissue. The rotation of the inner tube and the outer tube of the tubular body is engaged by one or more actuators on a handle member attached to the tubular body at the proximate end.

In one version of the embodiment, the system further includes a distal handle configured to operably couple to the distal end of the tubular body. The flexible body may further include a distal end including a tissue penetration tip that moves from a recessed state to a tissue penetration state when the flexible body is longitudinally displace relative to the tubular body. When the penetration tip is in the recessed state, the tissue cutting portion is in the non-deployed state. When the penetration tip is in the tissue penetration state, the tissue cutting portion is in the deployed state. In some versions, the distal handle is configured to operably couple to the distal end of the tubular body by being directly connected to the distal end of the flexible body when the penetration tip is in the penetration state.

In one version of the embodiment, the system further includes an adjustable lock supported on the tubular body that limits a distal cutting stroke displacement of the system. The distal cutting stroke displacement of the system may be limited by the adjustable lock such that the tubular body will extend through an exit hole created in the palm by the penetration tip.

In one version of the embodiment, the system further includes a nerve sensing system electrically coupled to the tubular body or flexible body. The nerve sensing system may be configured to sense nerve impulses or action potentials. The nerve sensing system may include an ultrasound probe operably coupled to the tubular body. The nerve sensing system may include a hardness sensor operably coupled to the tubular body.

Also disclosed herein is a method of releasing a ligament. In one embodiment, the method includes: percutaneously penetrating at a first location with a tubular body; positioning the tubular body adjacent the ligament; employing a nerve sensing system to position a tissue cutting portion away from a nerve, the tissue cutting portion being part of a flexible body longitudinally displaceable relative to the tubular body between a non-deployed state and a deployed state of the tissue cutting portion; causing the tissue cutting portion to longitudinally displace from the non-deployed state to the deployed state; and releasing the ligament with the tissue cutting portion.

Disclosed herein is a system for releasing a ligament. In one embodiment, the system includes: an introducer including a distal end and a proximal end; a flexible body including a first end, a second end and a length extending between the first end and the second end, the length forming a loop distally extending from the distal end of the introducer and configured to have the ligament in the loop, the length comprising a tissue cutting portion, the first end and the second end proximally extending from the proximal end of the introducer. The tissue cutting portion may include a plurality of teeth or an abrasive surface.

In one version of the embodiment, the system further includes an elongated body configured to be extended through the introducer proximal to distal and engage the first end and pull the first end around the ligament and through the introducer to form the loop such that the first end is adjacent the second end extending proximally from the proximal end of the introducer, the elongated body including a first engagement feature configured to engage a second engagement feature on the first end. The first engagement feature may include a hook and the second engagement feature may include a ball. The elongated body may include forceps.

In one version of the embodiment, the system further includes a first handle operably coupled to the first end and a second handle operably coupled to the second end.

In one version of the embodiment, the system further includes a nerve detection system coupled to the flexible body.

Disclosed herein is an apparatus for releasing a ligament. In one embodiment, the apparatus includes a proximal handle, a tubular handle, and an inner body. The tubular body includes a proximal end and a distal end. The handle is coupled to the proximal end. The inner body extends through the tubular body and includes a tissue cutting portion. A flap on the tubular body is transversely displaceable relative to the tubular body to expose the tissue cutting portion.

Another apparatus for releasing a ligament is also disclosed herein. In one embodiment, the apparatus includes a proximal handle, a tubular body, and an inner body. The tubular body includes a proximal end and a distal end. The handle is coupled to the proximal end. The inner body extends through the tubular body and includes a tissue cutting portion. At least one of: the tubular body is axially rotationally displaced relative to the inner body; or the inner body is axially rotationally displaced relative to the tubular body to transition the tissue cutting portion between a non-deployed state and a deployed state.

Also disclosed herein is a system for releasing a ligament. In one embodiment, the system includes a proximal handle, a tubular body and an inner body. The tubular includes a proximal end and a distal end. The handle is coupled to the proximal end. The inner body extends through the tubular body and includes a tissue cutting portion. A distal region of the inner body, when retracted within the tubular body such that the tissue cutting portion is hidden within the tubular body, has a first shape generally the same as the shape of the a distal region of the tubular body. The distal region of the inner body, when extended distally out of the tubular body such that the tissue cutting portion is outside the tubular body, has a second shape different from the first shape.

Yet another system for releasing a ligament is disclosed herein. In one embodiment, the system includes a tubular body and an inner body. The tubular body includes a proximal end and a distal end. The inner body extends through the tubular body. The inner body includes a tissue penetrating portion and a tissue cutting portion. The tissue penetrating portion is at a distal end of the inner body. The tissue cutting portion is proximal the distal end of the inner body. The distal end of the tubular body is configured to engage a proximal end of the tissue penetrating portion such that the tubular body can be used to drive the tissue penetration portion distally and yet be withdrawn proximally from about the inner body.

Disclosed herein is a method for releasing a ligament. In one embodiment, the method includes: percutaneously penetrating at a first location with an introducer including a distal end and a proximal end; providing a flexible body including a first end, a second end and a length extending between the first end and the second end and including a tissue cutting portion; routing the first end distally through the introducer, around the ligament and proximally back through the introducer such that the length forms a loop around the ligament, the loop distally extending from the distal end of the introducer, the first end and the second end proximally extending from the proximal end of the introducer; and employing the tissue cutting portion to release the ligament. The tissue cutting portion may include a plurality of teeth or an abrasive surface.

In one version of the embodiment, the method further includes employing an elongated body configured to be extended through the introducer proximal to distal to engage the first end and pull the first end around the ligament and through the introducer to form the loop.

In one version of the embodiment, the method further includes securing a handle to at least one of the first end or second end. In one version of the embodiment, the method further includes employing a nerve sensing system to position the tissue cutting portion away from a nerve.

Disclosed herein is a handboard assembly for securing a hand and forearm of a patient undergoing a carpal tunnel surgery. In one embodiment, the assembly includes: a chassis base including a first end and a second end; and a flex board including a third end, a fourth end, a first planar region adjacent the third end, a second planar region adjacent the fourth end and a flex region between the first planar region and the second planar region, the third end operably coupled to the first end and the fourth end operably coupled to the second end, the flex region configured to result in a bend in the flex board when the first planar region and the second planar region are each caused to assume an incline relative to the chassis base. The first planar region may be adapted to receive the hand and the second planar region is adapted to receive the forearm. The first planar region may include a finger receiving portion with a finger securing mechanism and a thumb receiving portion with a thumb securing mechanism, and the second planar region includes a forearm securing mechanism. At least one of the finger securing mechanism, thumb securing mechanism, or the forearm securing mechanism may include a strap arrangement. The strap arrangement may include hook and loop regions.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 6A-1 depicts a plurality of embodiments of the elongated bodies of FIG. 6A.

FIG. 6A-2 depicts one embodiment of the elongated body of FIG. 6A with an hamate bone indicator notch.

FIG. 6A-3 depicts one embodiment of the elongated body of FIG. 6A with a Doppler probe to identify structures within the hand.

FIG. 6B-1 depicts the release system of FIG. 6A with a skin grommet at the introduction point on the skin.

FIG. 9E depicts the embodiment of FIG. 9D wherein the cutting member is shown releasing a transverse carpal ligament (TCL).

FIG. 9E-1 depicts an enlarged view of the cutting member releasing the TCL of FIG. 9E.

FIG. 10A depicts another embodiment of the release system, wherein a cutting wire is being introduced into the carpal tunnel area of FIG. 2, and wherein one embodiment of a sled member is shown but an introducer is not shown for clarity purposes.

FIG. 10B is an enlarged view of the sled member of FIG. 10A.

FIG. 10C is a cross-section view of the sled member about section line 10-10 of FIG. 10B.

FIG. 11A depicts another embodiment of the release system, wherein a cutting wire is being introduced into the carpal tunnel area of FIG. 2, and wherein another embodiment of a sled member is shown.

FIG. 11B is an enlarged view of the sled member of FIG. 11A.

FIG. 11C is a cross-section view of the sled member about section line 11-11 of FIG. 11B.

FIG. 15A depicts still another embodiment of a release system having a delivery or deployment instrument, a handle member and a return shaft member.

FIG. 15C is the same view as FIG. 15B except a cutting member delivery device is also shown.

FIG. 15D is the same view as FIG. 15C except the cutting member delivery device is being deployed.

FIG. 15G depicts the return shaft member of FIG. 15A.

FIG. 15I is a transparent view of the return shaft member of FIG. 15H.

FIGS. 16G and 16H are the same view as FIG. 16F wherein the cutting member is positioned in the carpal tunnel region to release the TCL.

FIG. 17B-1 depicts an exploded view of the handboard assembly of FIG. 17A.

FIG. 17B-2 is a top isometric view of a baseplate chassis of the handboard assembly of FIG. 17A.

FIG. 17B-3 is a bottom elevation view of the baseplate chassis of FIG. 17B-2.

FIG. 17B-4 is a top elevation view of a flexboard of the handboard assembly of FIG. 17A.

FIG. 17B-5 is an isometric view looking from the bottom and side of a drape assembly of the handboard assembly of FIG. 17A.

FIG. 17B-6 is an exploded top elevation view of the drape assembly of FIG. 17B-5.

FIG. 17B-7A is a side isometric view of a handboard assembly with a balloon adjustment mechanism.

FIG. 17B-7B is a top isometric view of the handboard assembly of FIG. 17B-7A with the balloon adjustment mechanism.

FIG. 17B-8A is a side isometric view of a handboard assembly with a ratchet adjustment mechanism.

FIG. 17B-8B is a top isometric view of the handboard assembly of FIG. 17B-8A with the ratchet adjustment mechanism.

FIG. 17B-8C is a side view of the ratchet adjustment mechanism of the handboard assembly of FIG. 17B-8A.

FIG. 17B-9A is a side isometric view of a handboard assembly with a rack and pinion adjustment mechanism.

FIG. 17B-9B is a top isometric view of the handboard assembly of FIG. 17B-9A with the rack and pinion adjustment mechanism.

FIG. 17B-10A is a side isometric view of a handboard assembly with a scissor adjustment mechanism.

FIG. 17B-10B is a top isometric view of the handboard assembly of FIG. 17B-10A with the scissor adjustment mechanism.

FIG. 17B-11A is a side isometric view of a handboard assembly with a screw adjustment mechanism.

FIG. 17B-11B is a top isometric view of the handboard assembly of FIG. 17B-11A with the screw adjustment mechanism.

FIG. 17B-12A is a side isometric view of a handboard assembly with a drape glove over the assembly.

FIG. 17B-12B is a top isometric view of the handboard assembly of FIG. 17B-12A with the drape glove over the assembly.

FIG. 17B-13 is a top isometric view of a handboard assembly including a thumb girdle.

FIG. 17C-1 is an isometric view of a proximal handle assembly of the system of FIG. 17A.

FIG. 17C-2 is an exploded view of a first side of the proximal handle assembly of FIG. 17C-1.

FIG. 17C-3 is an exploded view of a second side of the proximal handle assembly of FIG. 17C-1.

FIG. 17C-4 is an isometric view of a distal end of a cutting wire assembly of the proximal handle assembly of FIG. 17C-1.

FIG. 17C-5 is an isometric view of a probe wire assembly of the proximal handle assembly of FIG. 17C-1.

FIG. 17D-1 is an isometric view of a first embodiment of an introducer assembly of the system of FIG. 17A.

FIG. 17D-2 is an isometric view of a second embodiment of an introducer assembly of the system of FIG. 17A.

FIG. 17E-1 is an isometric view of a shaft lock assembly of the system of FIG. 17A.

FIG. 17E-2 is a side view of the shaft lock assembly of FIG. 17E-2.

FIG. 17E-3 is a cross-sectional elevation of the shaft lock assembly taken about section line A-A of FIG. 17E-2.

FIG. 17F-1 is an isometric view from the front of a distal handle assembly of the system of FIG. 17A.

FIG. 17F-2 is an isometric view from the back of a distal handle assembly of the system of FIG. 17A.

FIG. 17F-3 is an exploded view of the distal handle assembly of FIG. 17F-1.

FIG. 17F-4 is an exploded view of the distal handle assembly of FIG. 17F-2.

FIG. 17G-1 is a side view of a distal end of a nerve wire assembly of the system of FIG. 17A.

FIG. 17G-2 is an exploded view of the distal end of the nerve wire assembly of FIG. 17G-1.

FIGS. 19A-19E-2 illustrate various additional embodiments of a cutting member which may be used with a release system according to the present disclosure.

FIGS. 20A-20F illustrate various embodiments of a nerve detection system which may be used with a release system according to the present disclosure.

FIGS. 22A-1 & 22A-2 depict another embodiment of the release system, wherein a tubular body is shown connected to one embodiment of a handle member and the tubular body including a nerve detector.

FIGS. 22B-1 & 22B-2 depict another embodiment of the release system, wherein a tubular body is longitudinally displaced to expose a cutting member within the tubular body.

FIGS. 22C-1 & 22C-2 depict an embodiment of the release system with a handle member wherein a tubular body and cutting member are longitudinally displaced to expose the cutting member within the tubular body.

FIGS. 22D-1 & 22D-2 depict a first embodiment of the release system wherein the tubular body is rotatably and/or longitudinally displaced.

FIGS. 22E-1 & 22E-2 depict a second embodiment of the release system wherein the tubular body is rotatably and/or longitudinally displaced.

FIGS. 22F-1 & 22F-2 depict an embodiment of the release system wherein the tubular body is longitudinally displaced to expose a tissue cutting surface of the cutting member within a window in the tubular body.

FIGS. 22G-1 & 22G-2 depict an embodiment of the release system wherein the tubular body is longitudinally displaced to expose a tissue cutting tooth of the cutting member within a window in the tubular body.

FIGS. 22H-1 & 22H-2 depict an embodiment of the release system wherein the tubular body includes a hinged flap.

FIG. 22I-1 is an isometric view of an embodiment of the release system wherein the tubular body may be rotatable about its longitudinal axis relative to the cutting member and/or the cutting member may be rotatable about its longitudinal axis relative to the tubular body so as to expose the cutting features of the cutting member within a window of the tubular body.

FIG. 22I-2 is an enlarged isometric view of the tubular body of FIG. 22I-1 wherein the tubular body and cutting member are rotated relative to each other such that the cutting features are not exposed in the window of the tubular body.

FIG. 22I-3 is a longitudinal cross section of the tubular body in the condition depicted in FIG. 22I-2.

FIG. 22I-4 is the same view as FIG. 22I-2 except the tubular body and cutting member are rotated relative to each other such that the cutting features are exposed in the window of the tubular body.

FIG. 22I-5 is a longitudinal cross section of the tubular body in the condition depicted in FIG. 22I-4.

FIGS. 22J-1 & 22J-2 depict an embodiment of the release system wherein the flexible body is longitudinally displaced to create a bowstring effect.

FIGS. 22K-1 & 22K-2 depict an embodiment of the release system with a handle member wherein a tubular body and/or a cutting member are longitudinally displaced to expose a cutting surface of the cutting member and the tubular body and cutting member have a curved opposing shape.

FIG. 23 depicts an embodiment of the release system conducted with a single puncture.

FIG. 24A is a distal-proximal cross section of a patient's wrist wherein another embodiment of the release system is being employed, the release system having a cutting member distally terminating in a penetrating element, the penetrating element being pushed through the wrist tissue via a tubular body.

FIGS. 24B and 24C are longitudinal cross sections of the penetrating member and tubular body and illustrating two embodiments of a coupling arrangement between the penetrating member and the tubular body.

FIG. 24D is the same view as FIG. 24A, except the tubular body is being withdrawn from about the cutting member, which has been properly located for severing the TCL.

FIG. 24E is the same view as FIG. 24D, except the cutting member is being displaced to sever the TCL.

DETAILED DESCRIPTION

Figure 1:
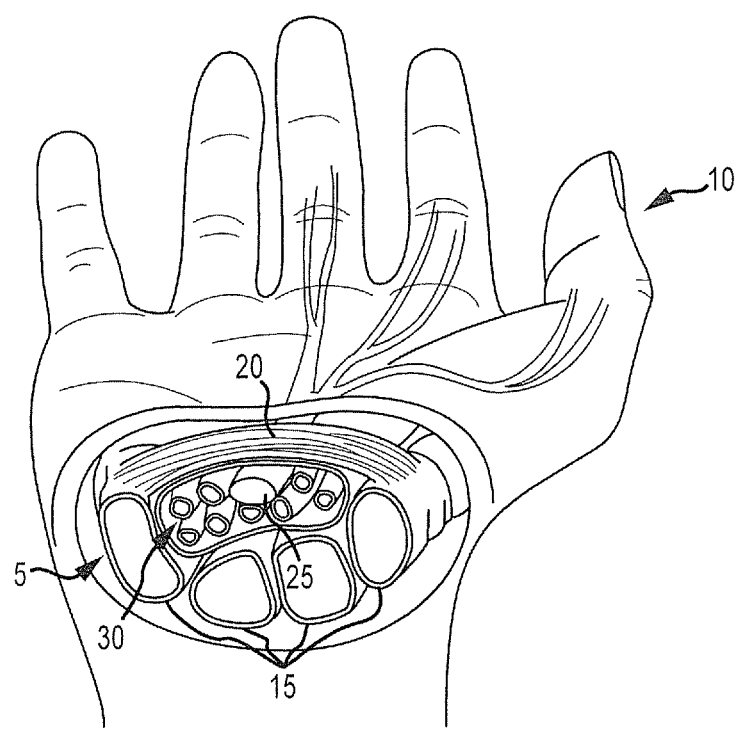
FIG. 1 illustrates a non-compressed carpal tunnel area of a wrist and palm of a hand.

Disclosed herein is an incisionless method and system for releasing the transverse carpal ligament (TCL) to decompress the median nerve. In some embodiments, the method (technique) or system includes needle stick introducer access into the general carpal tunnel area. An elongated or tubular body, such as a hollow wire or cannula, may be introduced into the carpal tunnel area through the introducer and a surgeon may safely guide the elongated body through the compressed carpal tunnel area to an exit point at, near or in the palm of the hand. The elongated body may include cutting members and may include a probe member or the probe member may be a separate instrument. The elongated body may be operably connected to a neuro-monitoring device to help the surgeon guide the elongated body into proper placement under the TCL without injuring the median nerve. An internal cutting wire may be introduced into the elongated body and extended to the exit point where it will exit the palm such that the distal end of the elongated body can be retrieved and be operably connected to a handle member. The cutting member(s) or internal cutting wire may be a flexible body and may include tissue cutting portions. In some embodiments, the cutting members may also be the tissue cutting portions. In other embodiments, the internal cutting wire may exit the palm such that the distal end of the wire can be retrieved and be operably connected to a handle member. In some embodiments, the internal cutting wire may include cutting members or tissue cutting portions and a penetration tip. In still other embodiments, the internal cutting wire may not exit the palm and may be operably coupled to a second elongated body introduced into the carpal tunnel area. In still other embodiments, an abrasive suture material may be introduced into the elongated body via a cutting member delivery device, such as a needle. The abrasive suture material and the cutting member delivery device may be extended to an exit point or opening in the palm where both will exit the palm. The abrasive suture material may be operably connected to a handle member.

The hand may be immobilized. In some embodiments, a distal end of an abrasive suture or other cutting member or flexible body may be stabilized or immobilized at the palm of the hand or may be coupled to a handle member. A proximal end of the abrasive suture or other cutting member may also be operably connected to a handle member. The surgeon may then use the handle member(s) to displace the cutting member (e.g. abrasive suture, internal cutting wire with cutting member or cutting member of the elongated body) along the TCL, such that the cutting member can release the TCL, such as by cutting, flossing, or sawing through the TCL, thereby decompressing the median nerve. Thus, the presently disclosed system and method do not require a large incision, as required for the open surgery technique, and the specialized equipment and knowledge required for the endoscopic release surgery are also unnecessary. This may increase the efficiency of the surgery and reduce surgical complications that may result from, for example, a large open incision. As explained below in more detail with respect to FIGS. 14A-14C, the systems and methods disclosed herein may also be used to release the plantar fascia in the foot. The systems and methods disclosed herein may also be used to decompress the ulnar nerve to treat cubital tunnel syndrome or Guyon's canal syndrome. With cubital tunnel syndrome, the ulnar nerve is compressed by the humerus bone. The system as disclosed herein may shave down this bone to relieve compression on the nerve. Guyon's canal syndrome is compression of the ulnar nerve, by, for example, a cyst or a ligament, e.g. the volnar radio-ulnar ligament. The systems and methods disclosed herein may be used to release that ligament which is compressing the ulnar nerve.

Figure 5:
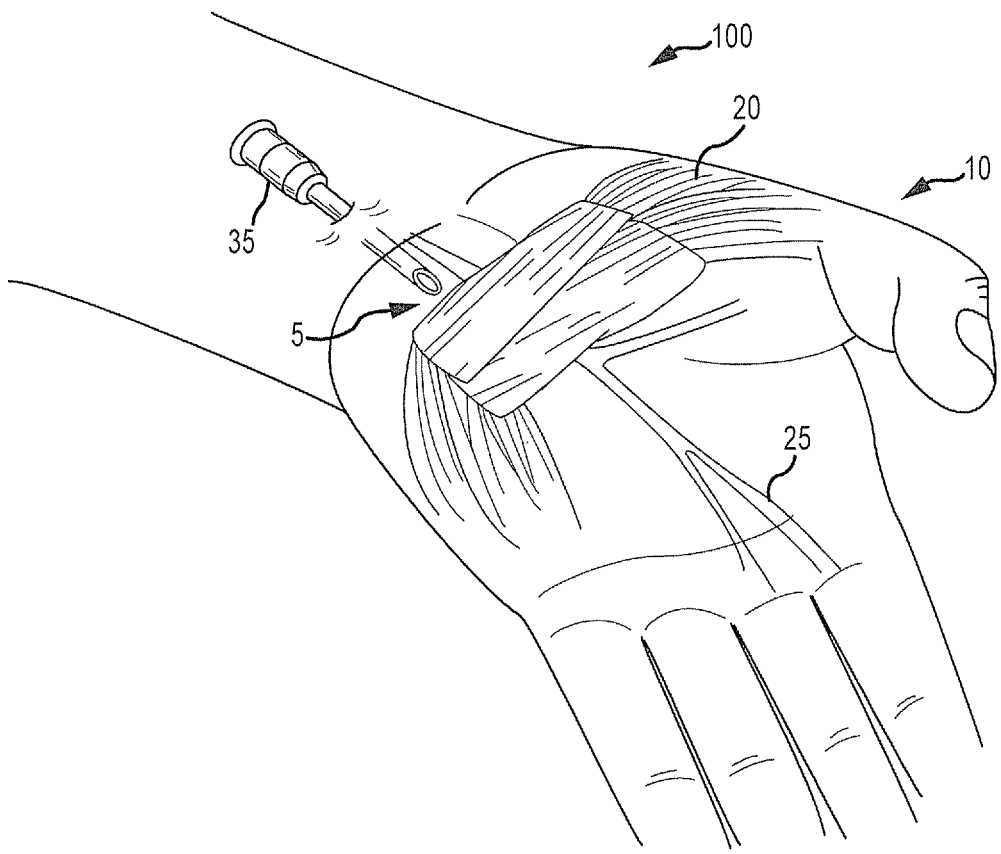
FIG. 5 illustrates placement of an introducer into the carpal tunnel area of FIG. 2.
Figure 6A:
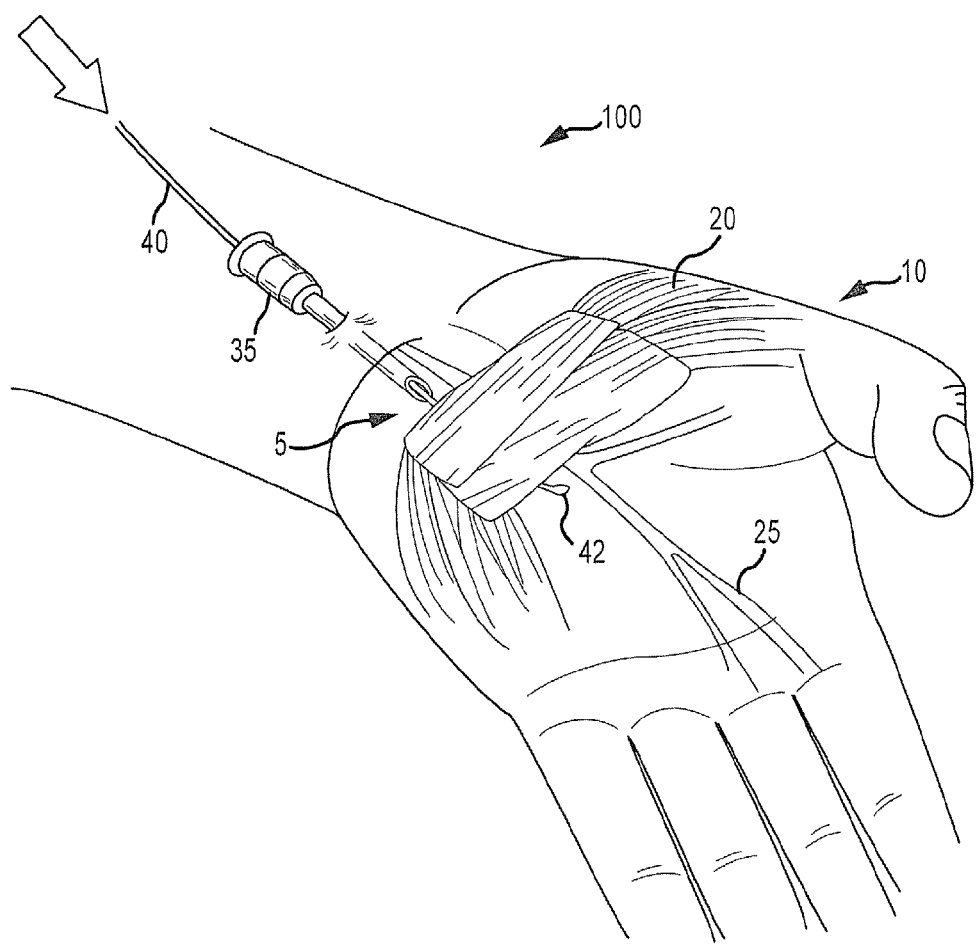
FIG. 6A depicts one embodiment of a release system showing introduction of an elongated body through the introducer into the carpal tunnel area of FIG. 2.
Figures 1, 6A:
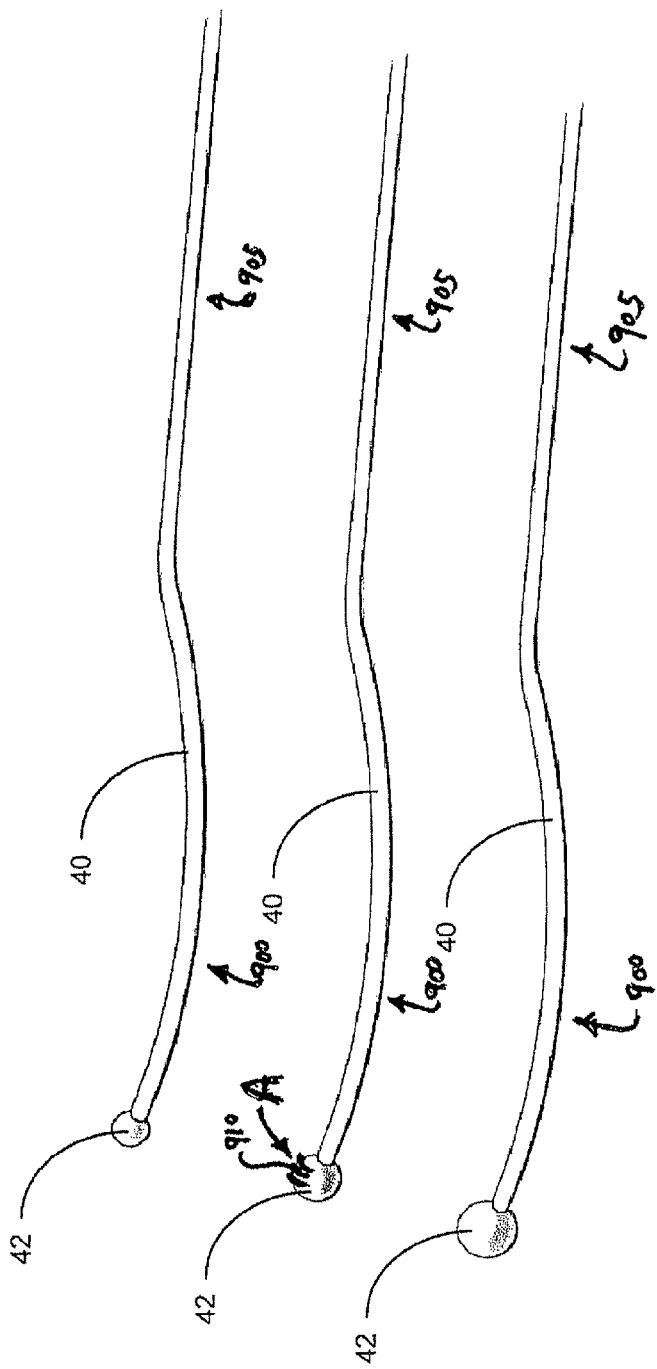
Figure 6B:
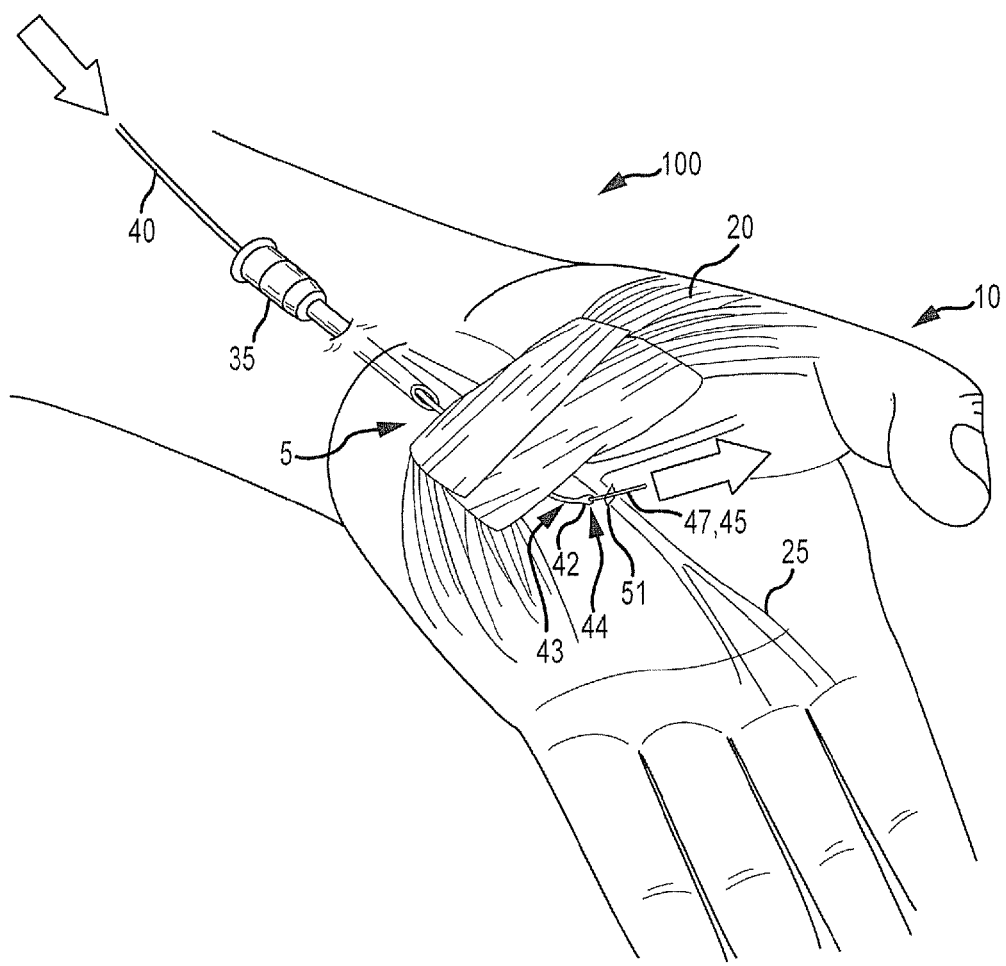
FIG. 6B illustrates the release system of FIG. 6A, wherein an internal cutting wire or other cutting member is being introduced through the elongated body.
Figures 1, 6B:
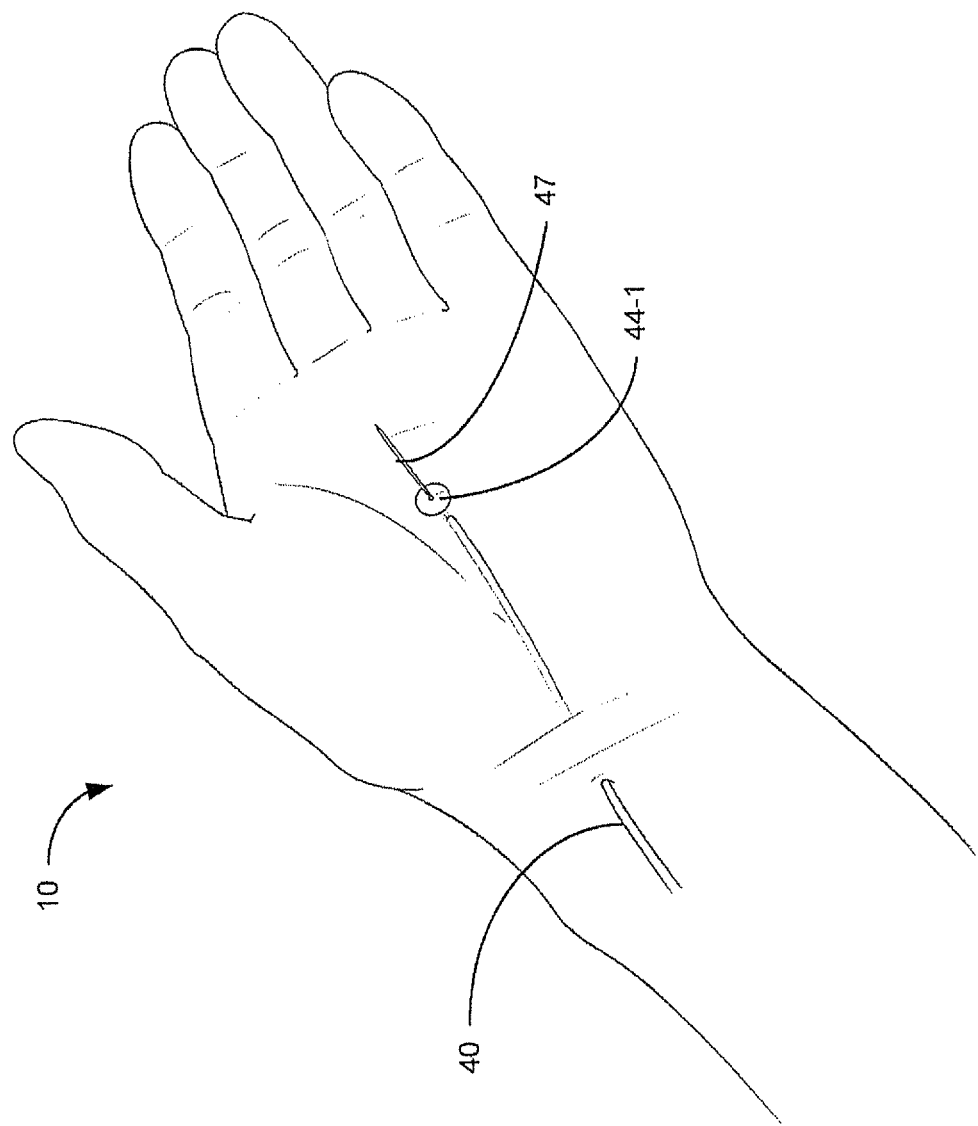

For a detailed description of a system and method for releasing the TCL to decompress the median nerve, reference is first made to FIGS. 5-8D. FIG. 5 illustrates placement of an introducer 35 into the carpal tunnel area 5 of FIG. 2. FIG. 6A depicts introduction of an elongated body 40 through the introducer 35 into the carpal tunnel area 5 of FIG. 2. FIG. 6B illustrates an internal cutting wire 47 or other cutting member 45 being introduced through the elongated body 40.

As can be understood from FIGS. 5-68, the system 100 may include an introducer 35 and an elongated body 40 including a blunt tip 42 and a cutting member 45. In some embodiments, the introducer 35 may be a 2 cm introducer needle (16-18 gauge) that may be inserted through a needle stick access. In some embodiments, the introducer 35 may be a 14 gauge introducer needle. It can be appreciated that the introducer 35 may be used in various embodiments described herein but is not required to be present throughout the procedure.

The elongated body 40 may be a supple metal wire or a similar sized cannula or other hollow-type body. In some embodiments, the elongated body may be an abrasive material, such as an abrasive suture. The elongated body 40 may also include cutting member 45. The elongated body 40 may have a blunt ball point tip or blunt probe 42 to prevent nerve irritation or nerve or tendon damage as it is passed through the carpal tunnel parallel to the nerve and flexor tendons from proximal to distal. The distal end 43 of the elongated body 40 may naturally assume a curled shape such that when it is passed through the tunnel into the palm, the tip 42 trajectory is upwards towards the palm skin.

In one embodiment, FIG. 6A-1 depicts three differently-sized examples of the elongated body 40 and the blunt ball point tip 42. In one particular embodiment, the elongated body 40 may have a contoured portion 900 that extends proximally from the blunt ball point tipe 42 until transitioning into a generally straight portion 905 that continues proximally to generally form the rest of the elongated body 40. The contoured portion may be generally curved so as to be contoured to the 3.5 centimeter proximal-distal length of the average carpal tunnel.

In addition as indicated by arrow A in FIG. 6A-1, some embodiments of the blunt ball point tip 42 may include serrated edges, ribs, ridges 910 or other tactile features along the dorsal surface of the blunt ball 42 that, when displaced against certain tissue within the wrist, the tactile features 910 provide a vibration or other tactile sensation through the elongated body 40 to the hand of an operator to indicate to the operator of the proper placement of the elongate body 40 within the carpal tunnel. For example, the transverse ribs 910 on the dorsal surface of the blunt ball 42 may provide tactile indications to the user when the transverse ribs 910 rub along the texture of the ligament 20 when the elongated body 40 is moved distally within the wrist. Thus, such a rib-equipped ball end elongated body 40 can be used to identify the location of the target ligament 20.

In one embodiment, the elongate bodies 40 depicted in FIG. 6A-1 are probes with ball-ends 42, wherein the probe is inserted into the wrist to clear the way through the wrist before the elongate body 40 or cutting device 47 of FIG. 6B are inserted into the wrist to make possible severing the ligament 20. The ball-end probes depicted in FIG. 6A-1 may have an electrode capability such that it can be used to identify the location of nerves. Such ball-end probes 42 may be provided as part of a surgical kit including the introducer 35, elongate body 42 and cutting device 47 illustrated in FIG. 6B. Such a surgical kit may be sterile packaged and include instructions for using the kit in the context of a surgery, such as, for example, a carpel tunnel surgical procedure.

Figure 2:
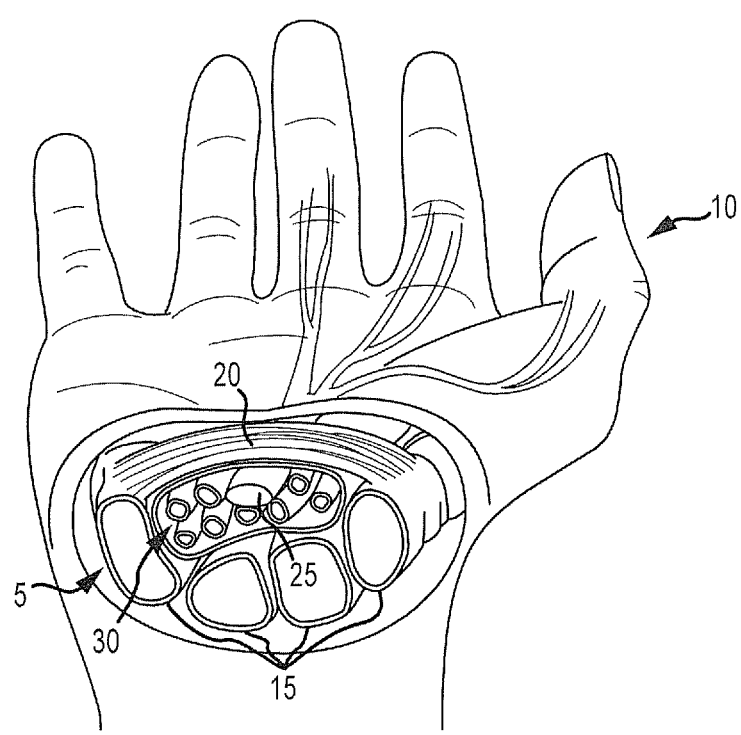
FIG. 2 illustrates a compressed carpal tunnel area of a wrist and palm of a hand.

FIG. 6A-2 depicts another embodiment of the elongated body 40 of FIG. 6A, wherein the elongate body includes a hamate bone landmark indicator 41 along the surface of the elongated body. The hamate bone 41-1 is a landmark within the carpal tunnel that includes a ledge that may be detected by the interaction between the hamate bone ledge and the indicator 41, which may be in the form of a circumferentially extending ring or ridge 41 on the circumferential surface of the elongated body 40. Thus, the indicator 41 on the elongated body 40 may be used to indicate to a physician that the elongated body is properly located within the carpal tunnel. To aid in locating the hamate bone 41-1, the elongated body 40 may include a small transverse circumferential ridge 41 on the outer circumferential surface of the elongated body that approximates anatomically the arch of the ledge of the hamate bone 41-1 in height, size, shape, etc. When the ridge 41 comes into contact with the hamate bone 41-1, a tactical feedback is provided along the elongated body 40 to the user of the body to indicate that the hamate bone has been reached by the elongate body 40.

In one embodiment, the elongate body 40 depicted in FIG. 6A-2 is a probe with the hamate bone indicator 41, wherein the probe is inserted into the wrist to clear the way through the wrist before the elongate body 40 or cutting device 47 of FIG. 6B are inserted into the wrist to make possible severing the ligament 20. The indicator ridge equipped probe depicted in FIG. 6A-2 may have an electrode capability such that it can be used to identify the location of nerves. Such indicator ridge equipped probes may be provided as part of a surgical kit including the introducer 35, elongate body 42 and cutting device 47 illustrated in FIG. 6B. Such a surgical kit may be sterile packaged and include instructions for using the kit in the context of a surgery, such as, for example, a carpel tunnel surgical procedure.

The elongated body 40 may have neuro monitoring features, such as a supple metal probe, that may be used in conjunction with neuro monitoring systems or nerve detection systems (see, for example, FIG. 18 or FIGS. 20A-20F) to help guide the elongated body 40 through the carpal tunnel area without harming nearby nerves and such that the body 40 is properly positioned under the TCL. In some embodiments, the neuro monitoring system may be the system offered by Cadwell Laboratories, Inc., Kennewick, Wash., Biotronic, Ann Arbor, Mich. or Medtronic, Minneapolis, Minn. The supple metal probe, such as the blunt probe tip 42, is also attached to a nerve monitor to assist the surgeon in navigation under the TCL. It can be appreciated that the probe may also be a separate instrument from the elongated body. The surgeon can identify median nerve irritation and accordingly alter the course of the body 40 with hand movements or remove the body 40 and start over again.

In various embodiments the body 40 may be partially coated with a non-conductive material such that only a portion of the diameter of the body 40 is exposed for nerve stimulation.

Figure 3:
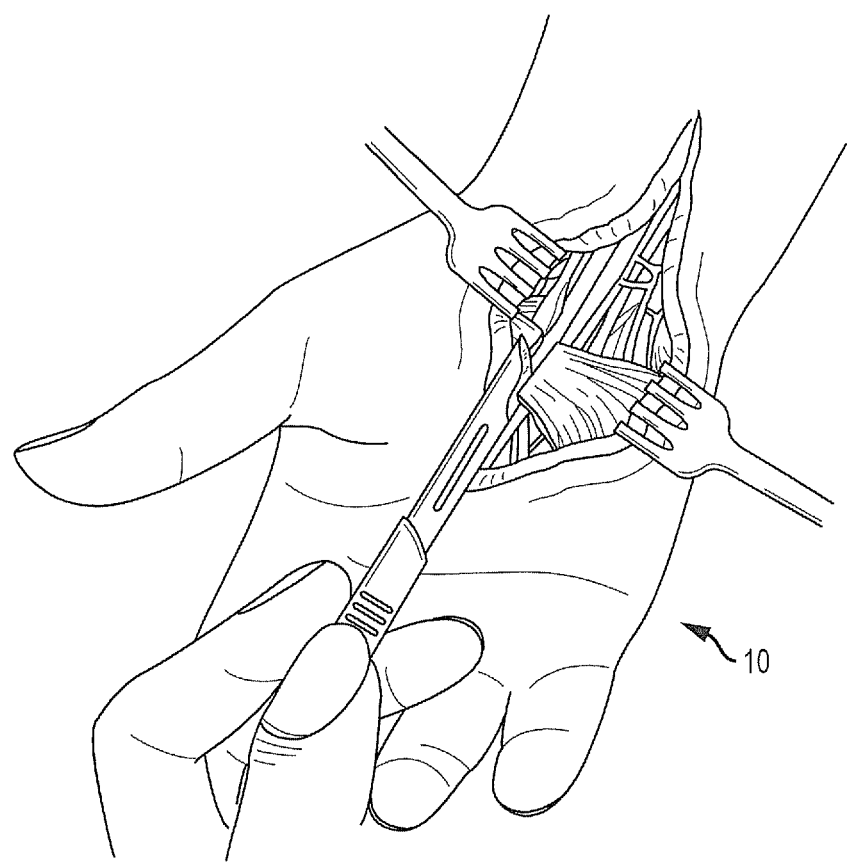
FIG. 3 depicts an open release surgical procedure being performed on the compressed carpal tunnel area of FIG. 2.

As indicated in FIG. 6A-3, the elongated body 40 may also have a Doppler probe 42-1 located at the distal tip 42 of the elongated body. The Doppler probe 42-1 may be integrated with or into other features of the elongated body 40, such as the blunt ball point tip 42 described above. In general, the Doppler probe 42-1 may aid in identifying structures within the hand 10 during the compressed nerves release treatment. For example, the Doppler probe 42-1 may identify the palmer arch artery 42-2 within the palm of the hand 10 to warn the user that the elongated body 40 is approaching the artery. The Doppler probe 42-1 may provide one or more electrical signals through the elongated body 40 to a Doppler monitoring system that provides the feedback to the user of the probe. Use of the Doppler probe 42-1 may aid in prevention of injury to the hand 10 during the release procedure.

In one embodiment, the elongate body 40 depicted in FIG. 6A-3 is a probe with the Doppler probe 42-1, wherein the probe is inserted into the wrist to clear the way through the wrist before the elongate body 40 or cutting device 47 of FIG. 6B are inserted into the wrist to make possible severing the ligament 20. The Doppler probe equipped probe depicted in FIG. 6A-2 may have an electrode capability such that it can be used to identify the location of nerves. Such Doppler probe equipped probes may be provided as part of a surgical kit including the introducer 35, elongate body 42 and cutting device 47 illustrated in FIG. 6B. Such a surgical kit may be sterile packaged and include instructions for using the kit in the context of a surgery, such as, for example, a carpel tunnel surgical procedure. Such a surgical kit may also include any or all of the other probes discussed above with respect to FIGS. 6A-1 and 6A-2.

For a more detailed discussion of the cutting member 45 of the elongated body, reference is now made to FIGS. 6C-6H, which illustrate various embodiments of the cutting member 45. In some embodiments, the cutting member may be an abrasive suture material 255, such as discussed below with respect to FIG. 15L, or an internal cutting wire 47, such as discussed below with respect to FIGS. 6C-6H. It can be appreciated that the elongated body 40 may include the cutting member 45 or the cutting member 45 may be a separate cutting instrument that is passed or inserted over or through the elongated body to a site below the TCL. That is, and as discussed in more detail below, in some embodiments, the cutting member 45 may be integral with the elongated body 40 and the elongated body is operably attached to at least one handle member, while in some embodiments, the cutting member 45 may be displaceable with respect to the body while the body remains in a fixed location or is in a stationary position, and in still other embodiments, the cutting member 45 may be separate from and displaceable with respect to the body such that the cutting member 45 is operably attached to the handle members.

Figure 6C:
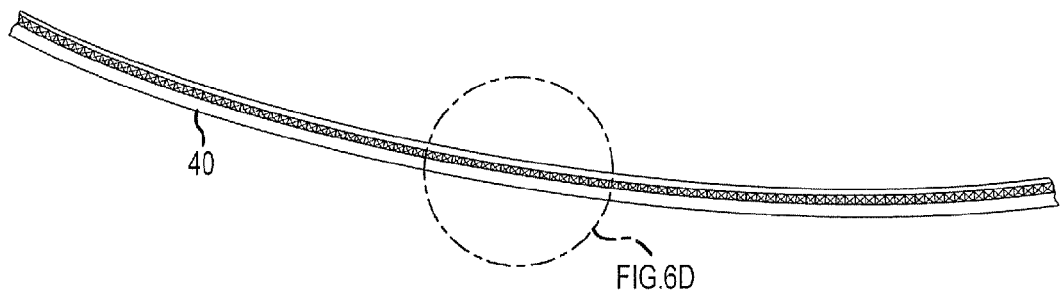
FIG. 6C depicts one embodiment of the elongated body of FIG. 6A, wherein a cutting member is also shown.
Figure 6D:
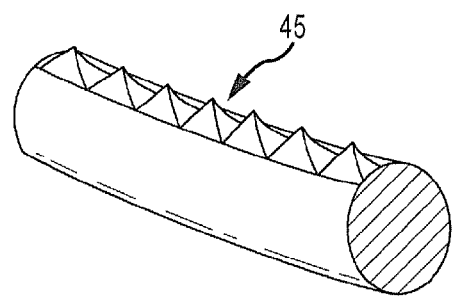
FIG. 6D is an enlarged view of a segment of the elongated body of FIG. 6C.

As can be understood from FIGS. 6C and 6D, the cutting member 45 may be coated with non-conductive smooth material on three sides with the exposed metal surface having multiple shark teeth, single tooth, abrasive surface, or long sharp surface that is electrified. If the cutting member comes in contact with the nerve, it will be detected by the nerve monitor. If there is nerve stimulation, the surgeon can adjust or alternatively re-pass the elongated body 40. The cutting member may then be used to saw or cut through the ligament.

In some embodiments, the cutting member 45 may be a round, triangular shaped or other configuration such that surgeon can recognize the directional surface that cuts and accordingly hold the elongated body such that the surface of the cutting member is in contact with the TCL.

Figure 6E:
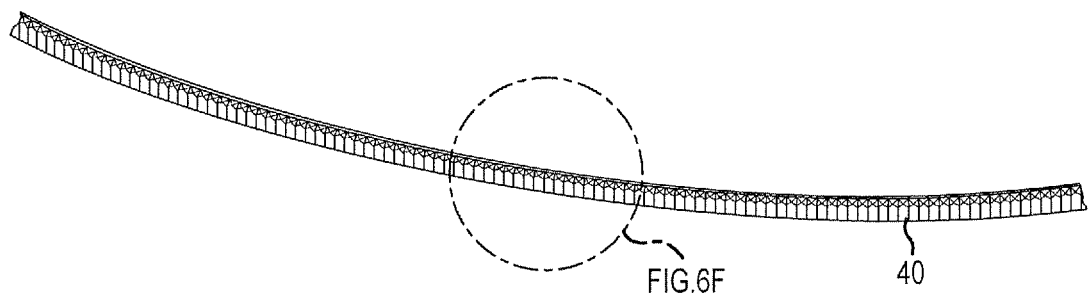
FIG. 6E depicts another embodiment of the elongated body of FIG. 6A, wherein a cutting member is also shown.
Figure 6F:
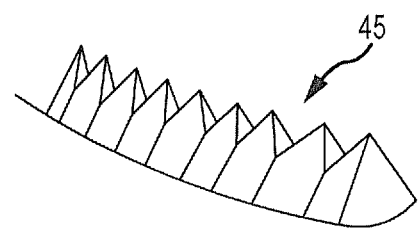
FIG. 6F is an enlarged view of a segment of the elongated body of FIG. 6E.

As shown in FIGS. 6E and 6F, in one embodiment, there is no coating on the elongated body and the cutting member has exposed teeth placed along a substantial length of the elongated body such that the entire TCL could be released through a single unidirectional pull of the elongated body.

Figure 6G:
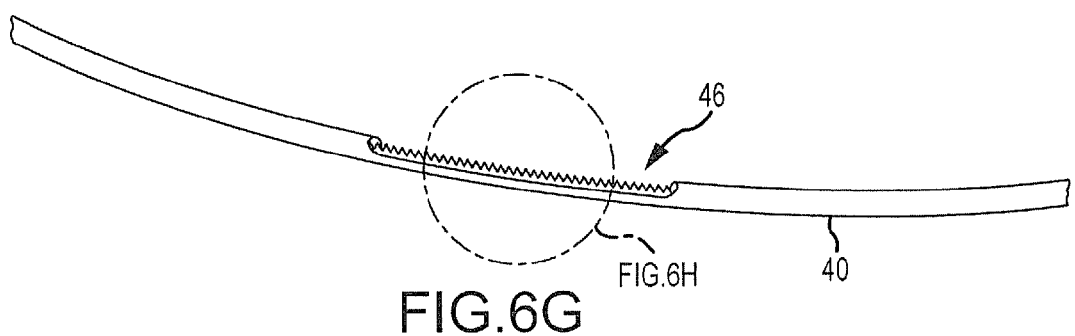
FIG. 6G depicts still another embodiment of the elongated body of FIG. 6A wherein a cutting member is also shown.
Figure 6H:
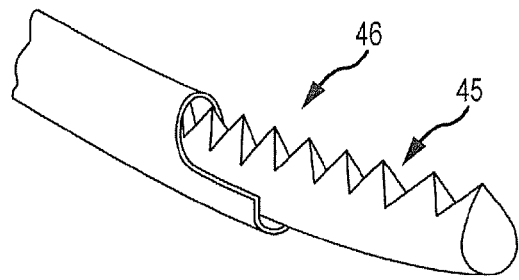
FIG. 6H is an enlarged view of a segment of the elongated body of FIG. 6G.

As can be understood from FIGS. 6G and 6H, the cutting member 45 may be exposed through the body 40 via only a small window 46 where the body 40 is not coated with a non conductive material. The size of this small window 46 corresponds with the proximal/distal length of the TCL being cut/released. By exposing a smaller cutting surface, the risk of nerve irritation or damage is reduced.

As can be understood from FIGS. 6C-6H and 16A-H (and others), in some embodiments where the cutting member is not a part of the body 40, the body may have a window cut out on one dorsal surface. The window is the same length or smaller then the proximal to distal length of the TCL. The window is positioned under the TCL. A cutting member with a single tooth, multiple teeth, sharp or abraded surface or other element for cutting is passed through the body that cuts only at or near the site of the window.

As discussed in more detail below and with reference to, for example, FIGS. 15A-15L and FIGS. 19A-19E-2 (and others), in some embodiments, the cutting member 45 (which may be an abrasive suture or other abrasive material 255) may be separate from and displaceable with respect to the body such that the cutting member 45 is operably attached to a handle member while the body 40 is at or below, but does not exit, the exit point of the hand 10. In some embodiments, the elongated body may be an abrasive material and may be operably connected to handle members (see FIGS. 12A-12D).

As can be understood from FIG. 6B, once the elongated body 40 has been introduced under the TCL and extended to an appropriate exit point 51 in the palm, a stylet or internal cutting or piercing wire 47 may be advanced to the distal end 43 of the elongated body 40. This cutting wire 47 may exit a port 44 in the ball point tip 42 and pierce the skin on the palm for access to the distal end 43 of the elongated body 40. In addition, as shown in FIG. 6B-1, a plastic grommet 44-1 or covering may be adhered to via an adhesive, sutured to, or press fit into the skin of the palm 10 at the location of the pierce. The grommet 44-1 may prevent inadvertent cutting or tearing of the skin during the procedure. A similar grommet 44-1 may also be similarly located on the skin at the insertion site. The surgical kit may include two or more such grommets 44.

In other embodiments, the ball tip 42 can emit a light that can be identified in the subcutaneous tissues and a small stab wound made to retrieve the probe 42 and deliver the cutting wire 47 or cutting member 45 to the surface.

The surgeon may grasp the distal end 43 of the elongated body 40 and, together with the proximal end of the elongated body, both ends of the elongated body may be operably connected to handle members. In some embodiments, the surgeon may instead grasp the distal end of the cutting member 45 or cutting wire 47 that has extended through the exit point of the hand and both the distal end of the cutting member 45 or wire 47 and the proximal end of the elongated body may be operably connected to handle members. In still other embodiments, the distal end of the cutting member 45 or the elongated body 40 may not exit the palm at the exit point but may be operably attached to a second elongated body introduced into the carpal tunnel region. The second elongated body may be used to withdraw the distal end of the first elongated body through the wrist entry point such that both the proximal and distal ends of the first elongated body may be operably connected to a handle member(s). In some embodiments, both the distal and proximal ends of the cutting member 45 or wire 47 may be operably connected to handle members 50.

For a more detailed discussion of the handle members, reference is now made to FIGS. 7A-8D and 21A-21G, which depict various embodiments of the handle members 50 of the system 100. As can be understood from FIGS. 7A-8D, the elongated body 40 may be exposed at both its proximal and distal ends. The elongated body 40 is placed underneath the TCL such that the ligament can be cut through a back and forth sawing action by the cutting member 45. In embodiments where the cutting member is a separate instrument, the distal and proximal ends of the separate cutting instrument may be operably connected to the handle members and the sawing or cutting motion happens as described below. That is, although FIGS. 7A-8D show handle members attached to the body 40, in other embodiments, the handle members 50 may be operably attached to the cutting member 45 or internal cutting wire 47. This sawing/cutting action is achieved by pulling the elongated body or the cutting member back and forth.

Figure 7A:
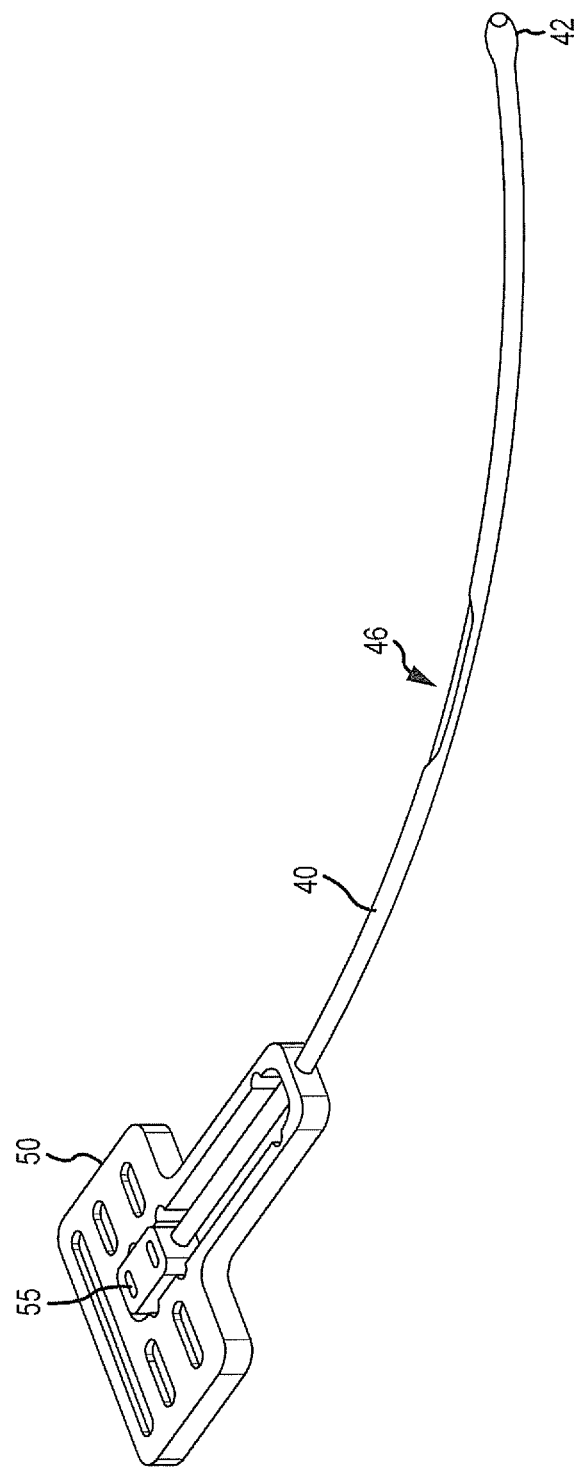
FIG. 7A depicts another embodiment of the release system, wherein an elongated body is shown connected to one embodiment of a handle member, and the hand and the introducer are not shown for clarity purposes.
Figure 7B:
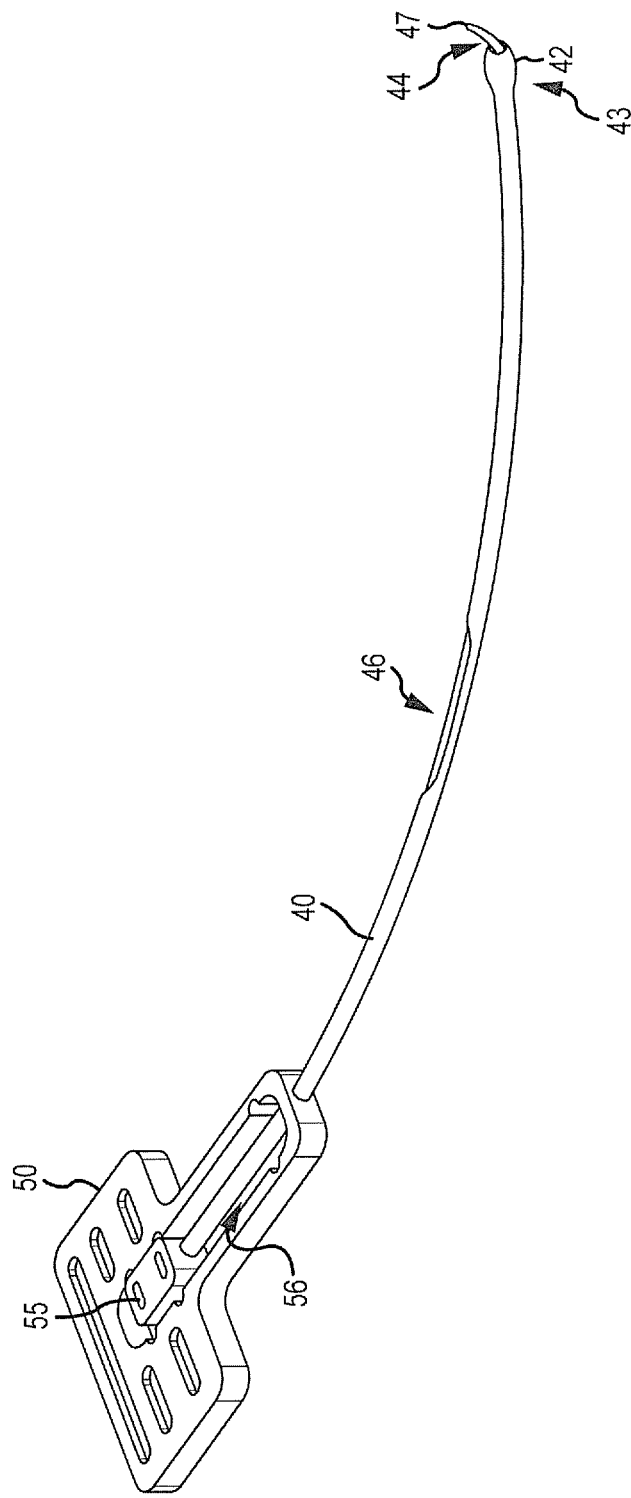
FIG. 7B depicts the elongated body of FIG. 7A, wherein one embodiment of the internal cutting wire of FIG. 6B is introduced through the elongated body.
Figure 7C:
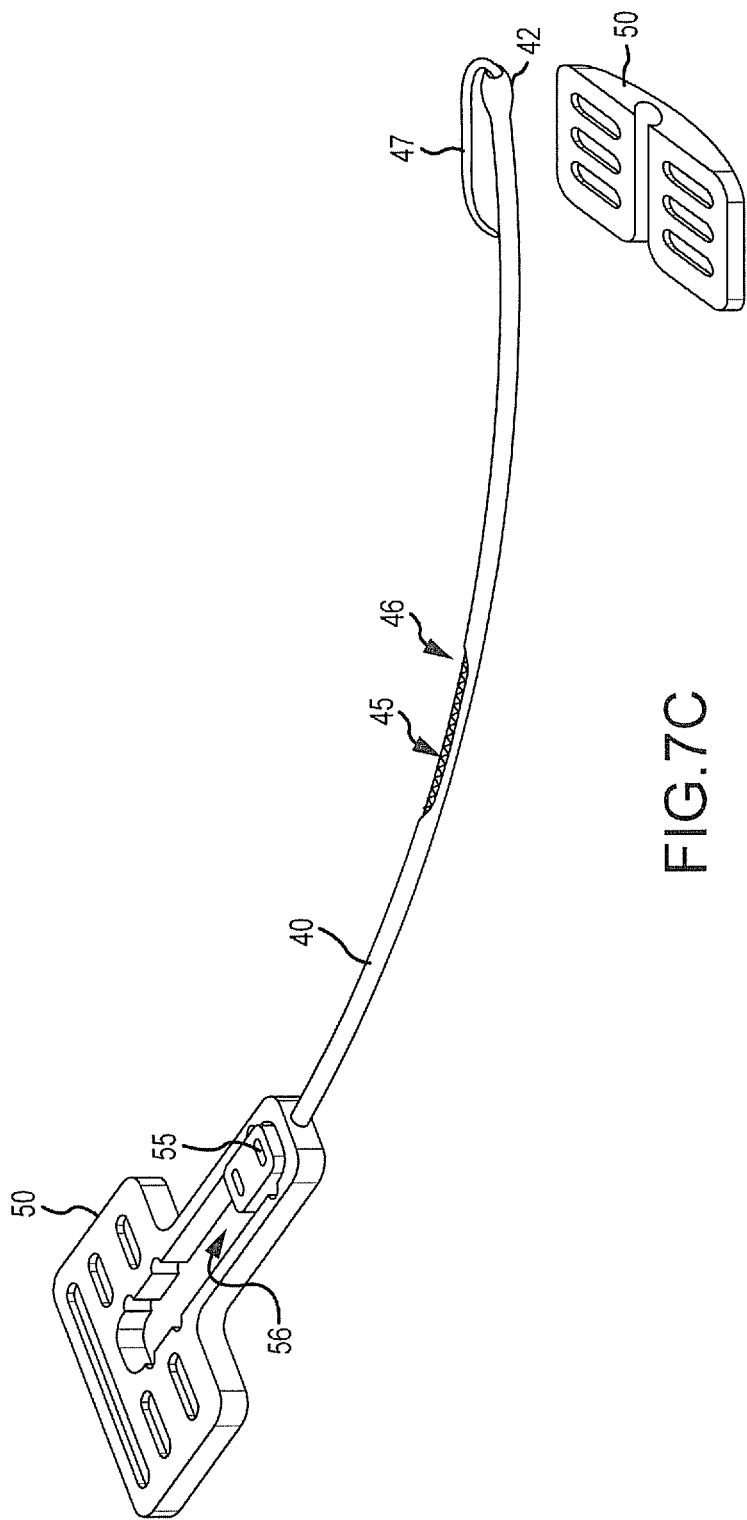
FIG. 7C depicts the elongated body of FIG. 7A, wherein a cutting member is shown.
Figure 7D:
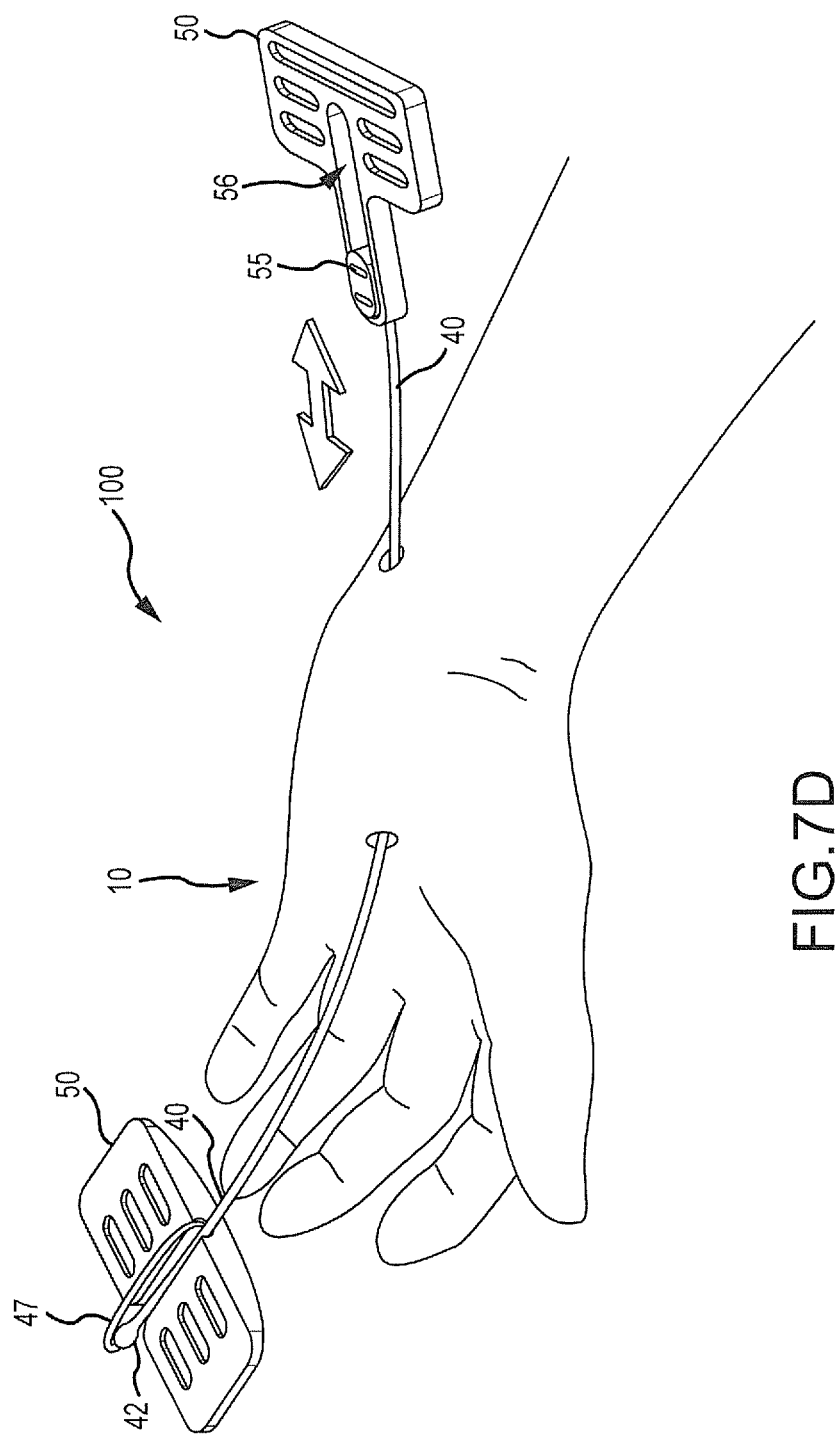
FIG. 7D illustrates the elongated body and handle members of FIG. 7C wherein the hand is shown.

As shown in FIGS. 7A-7D, in one embodiment, the handle members 50 may be grip handles with an actuator 55. As can be understood from FIGS. 7A-7C (the hand is not shown for clarity), a first grip handle member 50 includes the actuator 55 in a channel 56, and the actuator 55 may be displaced relative to the grip handle 50, thereby extending the internal cutting wire 47 and exposing the cutting member 45 in the window 46. As shown in FIGS. 7C and 7D, the elongated body 40 and internal cutting wire 47 are operably connected to a second handle member 50. As indicated in FIG. 7D (which shows the system in the hand), the actuator 55 is displaced relative to the first handle member within the channel 56, thereby inducing a cutting, sawing or other motion to release the TCL to decompress the median nerve.

As illustrated in FIGS. 8A-8D, in one embodiment, the handle member 50 may be a trigger grip handle that first extends the external cutting wire 47 such that the cutting member 45 is exposed within the window 46 and then the internal cutting wire 47 is pulled back and forth through finger/hand actuated trigger grips while the body remains in location. Because the cutting member 45 is properly placed under the TCL, the back and forth movement of the cutting member will release the TCL thereby decompressing the median nerve.

As can be understood from FIGS. 21A and 21C-G, the elongated body 40 may be exposed at both its proximal and distal ends. The elongated body 40 is placed underneath the TCL such that the ligament can be cut through a back and forth sawing action by the cutting member 45. As can be understood from FIG. 21B, in embodiments where the cutting member 45 is a separate instrument, the distal and proximal ends of the separate cutting instrument may be operably connected to the handle members 50 and the sawing or cutting motion happens as described herein. That is, although FIGS. 21A and 21C-G show handle members attached to the body 40, in other embodiments, as shown in FIG. 21B (and others), the handle members 50 may be operably attached to the cutting member 45. This sawing/cutting action is achieved by displacing the cutting member. In still other embodiments where the cutting member 45 is a separate instrument, for example FIGS. 17A-17H, a proximal end of the elongated body 40 may be operably attached to a handle member 50 and a distal end of the cutting member 45 may be operably attached to a second handle member 50.

Figure 21A:
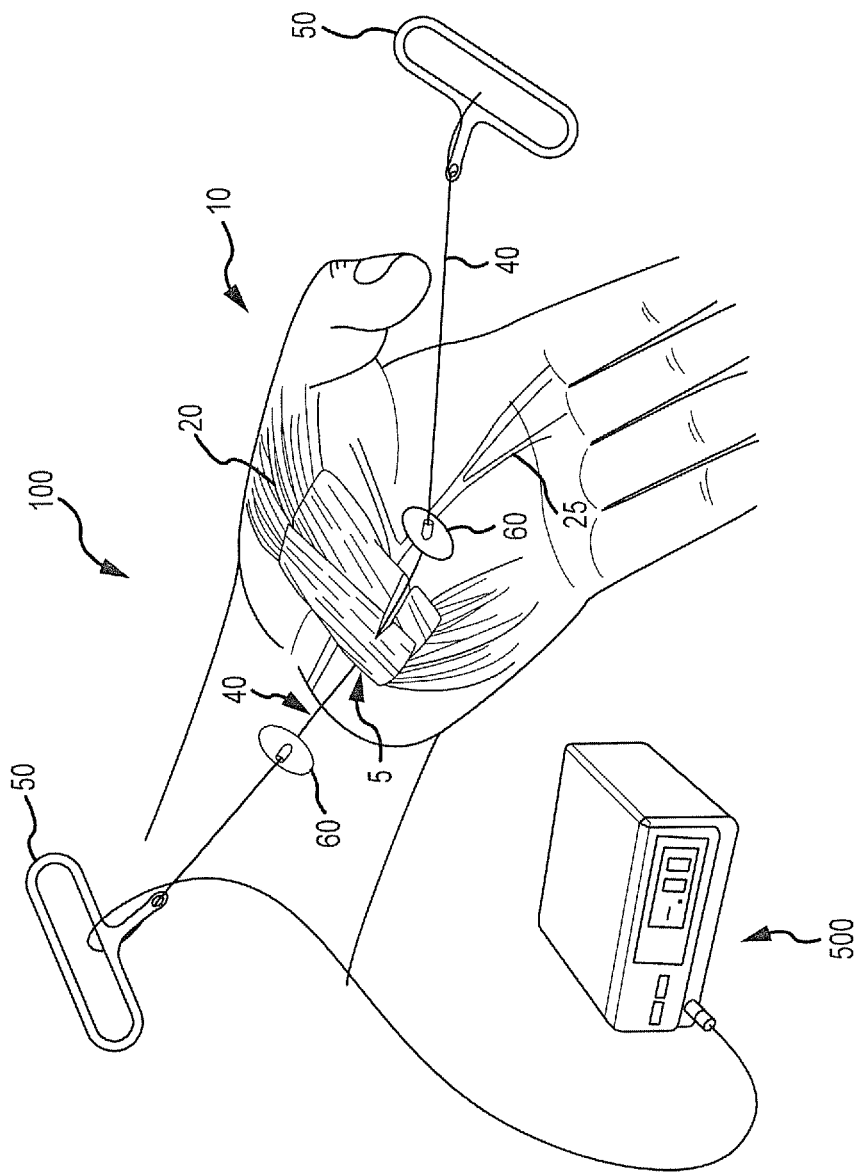
FIGS. 21A-21G illustrate various additional embodiments of a handle member which may be used with a release system according to the present disclosure.
Figure 21B:
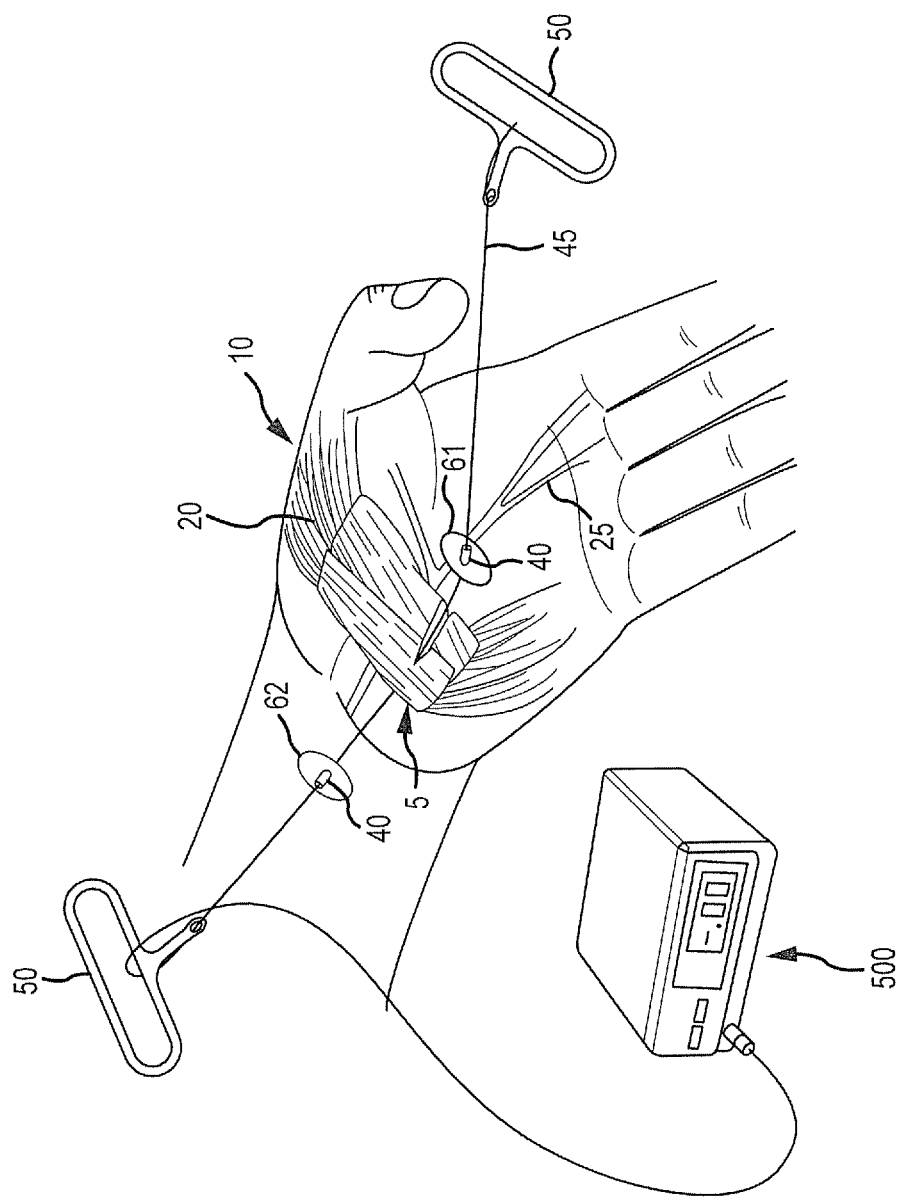

FIGS. 21A and 21B illustrate embodiments of the system including handle members 50 and a neuro-monitoring or nerve detection system 500. As can be understood from FIG. 21A, the system 100 may also include short hollow metal tubes 60 that can be placed onto the proximal and distal portions of the hand and positioned through the skin surface to prevent skin laceration from the elongated body 40 as the cutting member is displaced to saw or cut through the TCL. As can be understood from FIG. 21B, in some embodiments, the cutting member 45 may be separate from and displaceable with respect to the body 40 such that the cutting member 45 is operably attached to the handle members while the body 40 is affixed, for example by an adhesive attachment 61, 62 of the distal and proximal ends of the body 40 to the entry and exit points of the hand 10.

As shown in FIGS. 21A and 21B, the handle members 50 may be elongated oval shaped handles which may provide feedback to the surgeon's fingers or fine motor skills during the sawing or cutting motion as described herein.

Figure 21C:
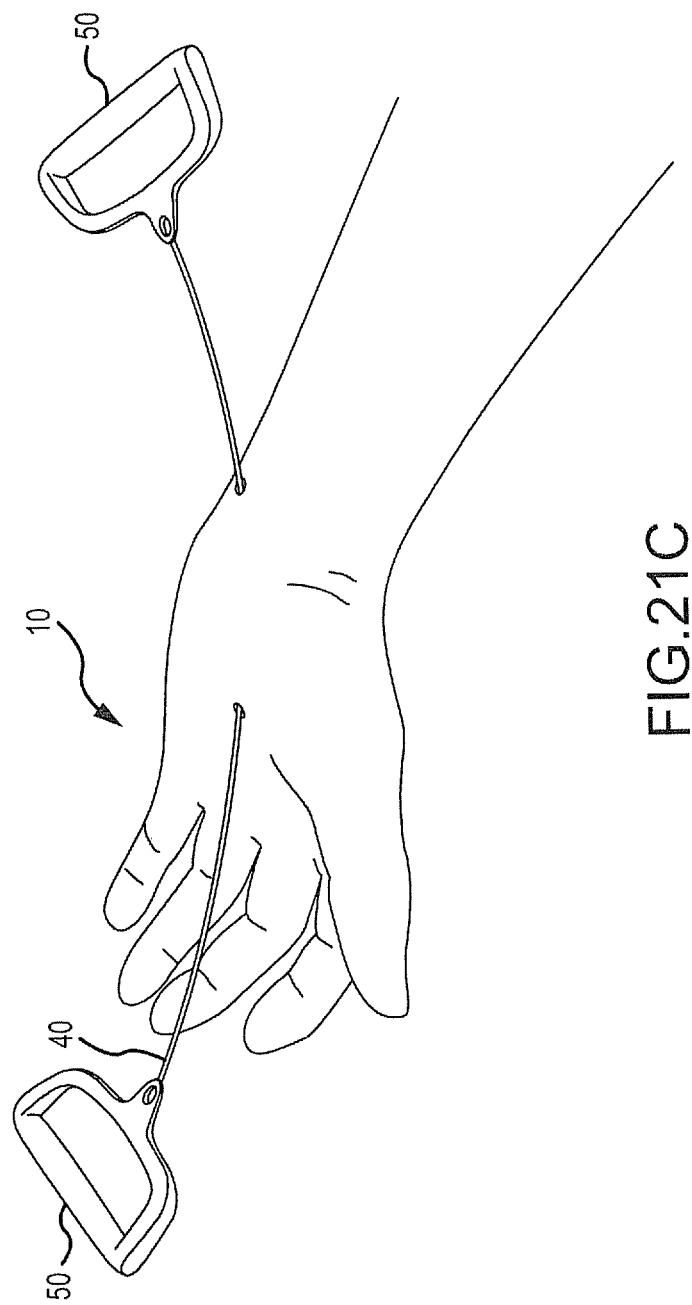

As indicated in FIG. 21C, in one embodiment, the handle members 50 may be D shaped handles which may also provide feedback to the surgeon's fingers/fine motor skills during the sawing/cutting motion.

Figure 21D:
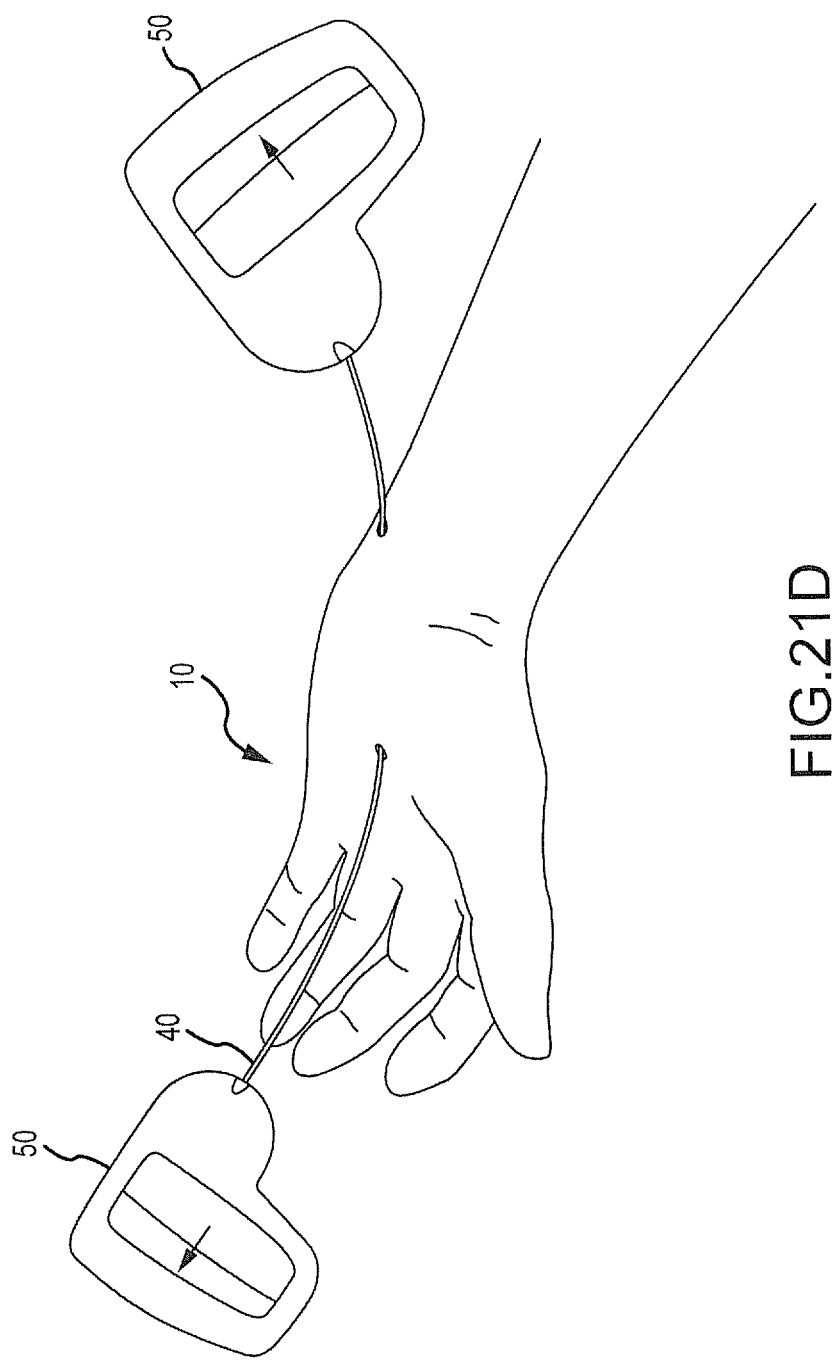

As illustrated in FIG. 21D, in one embodiment, the handle members 50 may be trigger grip handles that pull the elongated body 40 back and forth through finger/hand actuated trigger grips. In another embodiment, the trigger grip handles may pull the cutting member 45 back and forth through finger/hand actuated trigger grips while the body 40 remains in location.

Figure 21E:
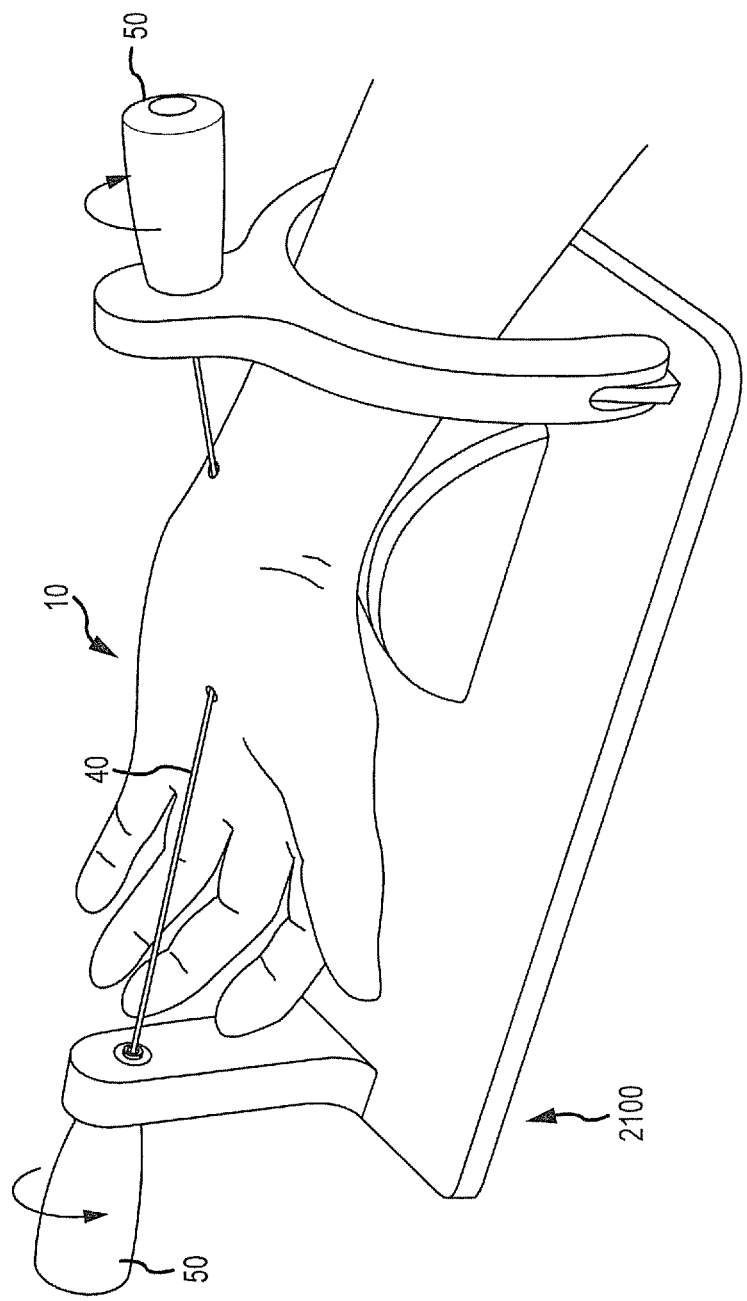

As indicated in FIG. 21E, in one embodiment, the handle members 50 may be rotating knobs that are anchored on a hand stabilization system 2100. The knobs facilitate a controlled back and forth movement of the elongated body. The hand stabilization system 2100 may be a sterile hand immobilizer that rigidly fixates the hand such that sawing, flossing or single pull through maneuvers by the surgeon do not move the wrist and inadvertently reposition the wire or cutting member under the TCL, once it has been safely positioned. See FIGS. 17A-18 for additional embodiments and discussion related to hand immobilization or stabilization systems.

Figure 21F:
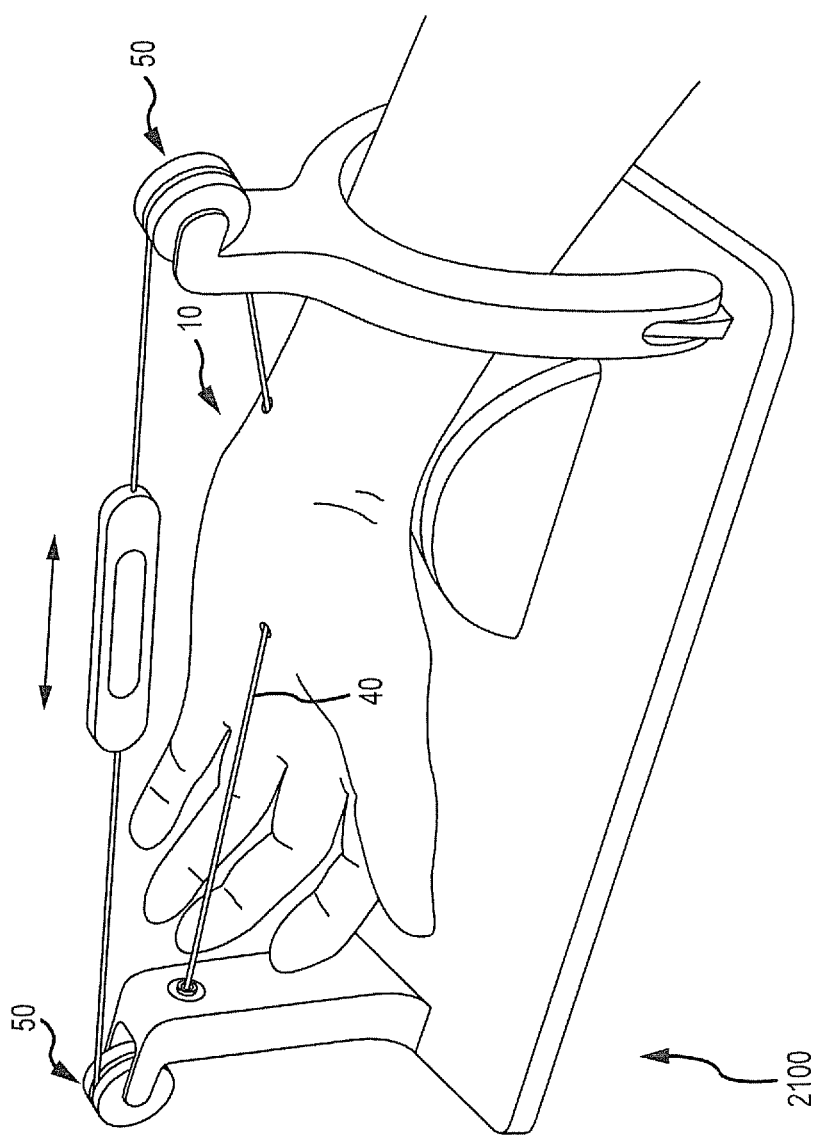

As can be understood from FIG. 21F, in one embodiment, the handle members 50 may be a rotating wire belt for the elongated body 40 and further utilizing a hand stabilization system 2100.

Figure 21G:
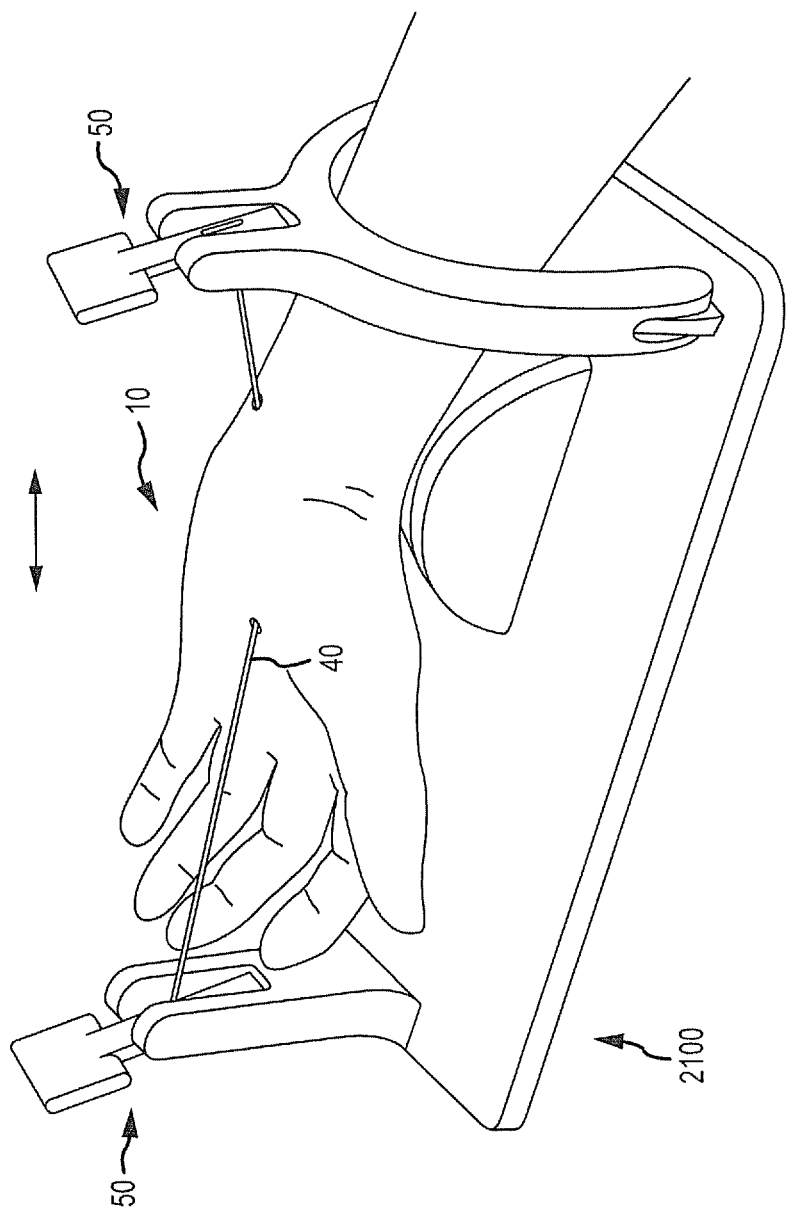

As shown in FIG. 21G, in one embodiment, the handle members 50 may be hand levers that utilize a hand stabilization system 300 and facilitate back and forth movement of the elongated body 40.

For a more detailed discussion of the embodiments where the elongated body 40 may not exit at the exit point of the hand, reference is now made to FIGS. 9A-13B, which depict various embodiments of the system in which the distal end of the elongated body does not exit the palm of the hand.

Figure 9A:
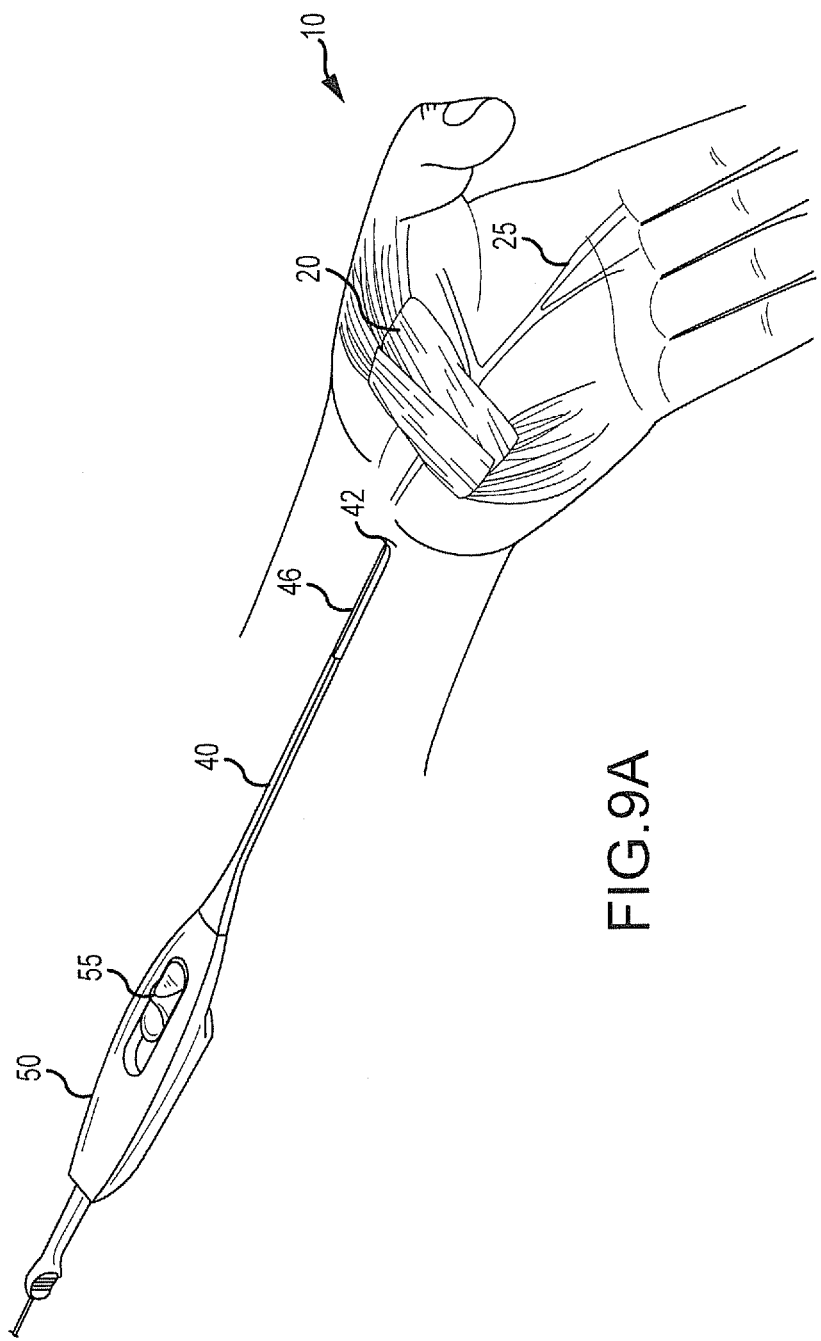
FIG. 9A depicts another embodiment of the release system of FIG. 6B wherein an additional introducer is not shown for clarity purposes.
Figure 9B:
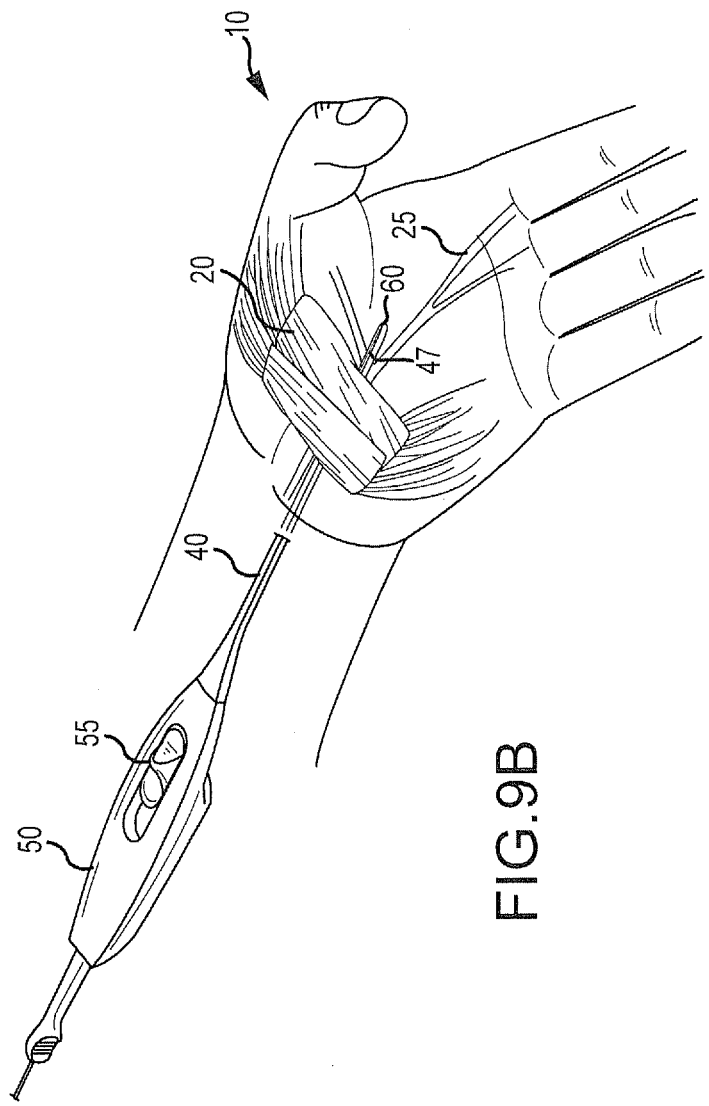
FIG. 9B illustrates placement of the embodiment of FIG. 9A into the carpal tunnel area of FIG. 2.
Figure 9C:
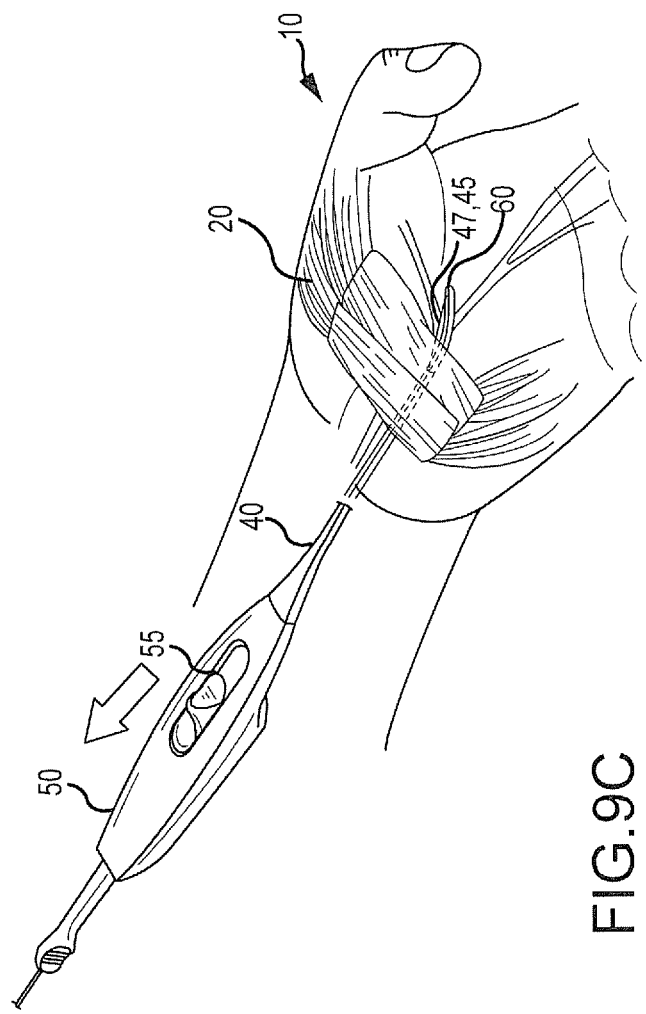
FIG. 9C illustrates the embodiment of FIG. 9B wherein a cutting member or internal cutting wire is exposed.
Figure 9D:
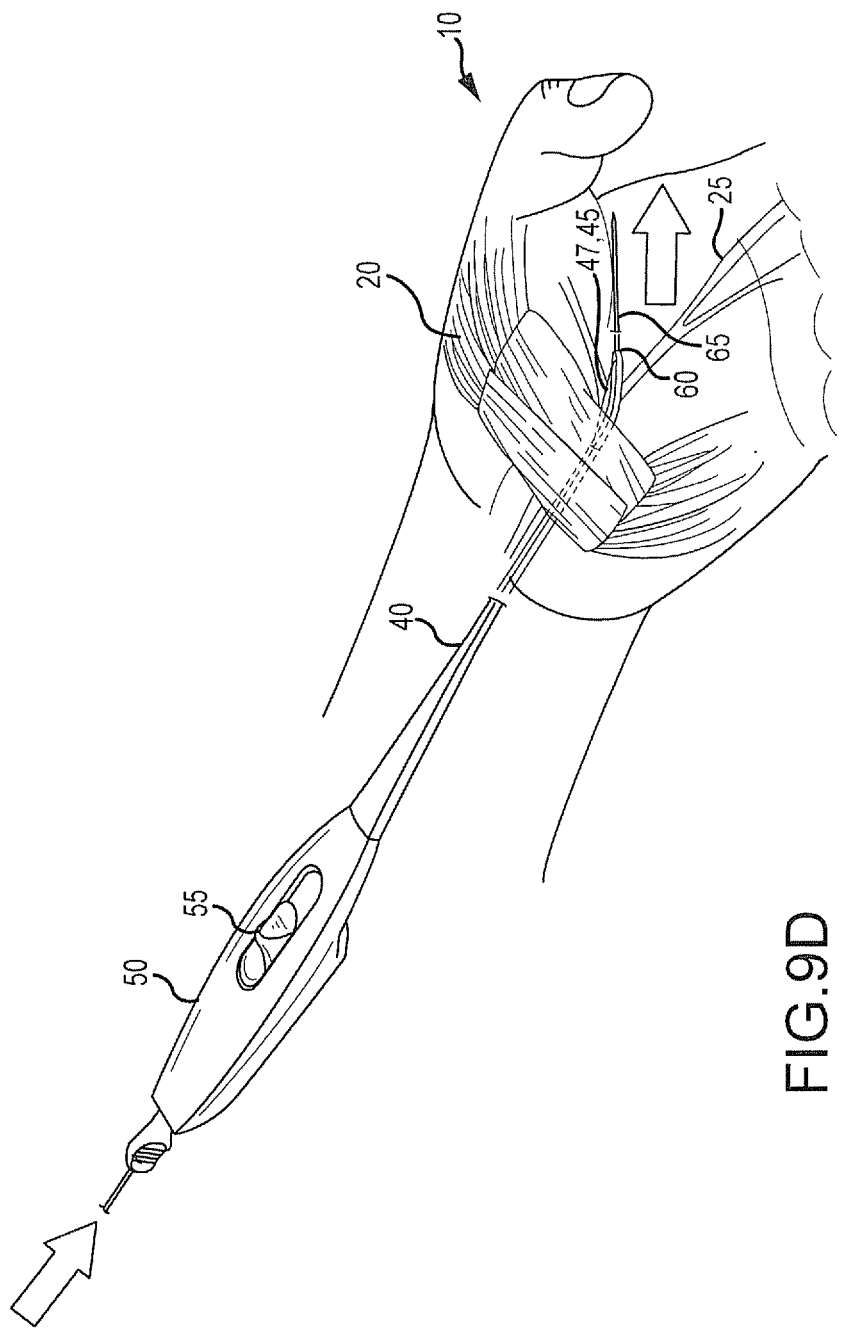
FIG. 9D depicts the embodiment of FIG. 9B wherein a securing member is also shown.

As can be understood from FIGS. 9A-9E, the handle member 50 may be a flat introducer with an actuator 55. As indicated in FIGS. 9A-9B, the elongated body 40 is inserted via an introducer (see, for example, FIG. 5) and the actuator 55 is in a first position. As shown in FIGS. 9C-9E-1, the elongated body 40 may be flexible such that after insertion under the TCL, it may curl at least slightly at its most distal tip 60. The actuator 55 is displaced relative to the handle member and the internal cutting wire 47 or cutting member 45 extends from the window 46, thereby forming a "bow" shape, as can be understood from FIG. 9E-1. A distal end of the external cutting wire 47 or cutting member 45 may extend through the exit point of the hand and may be held in place by a securing member 65, as illustrated in FIG. 9D. The securing member 65 may be a pin, a needle, a wire, an adhesive or other appropriate securing member, or a combination thereof. In one embodiment, the securing member 65 may be coupled to the cutting wire 47 or cutting member 45 after the cutting wire 47 or cutting member 45 has exited the exit point in the hand 10. In some embodiments, the securing member 65 may be coupled to the internal cutting wire 47 or cutting member 45 within the elongated body 40 (see e.g. FIGS. 15C-15F). Once the distal end of the cutting wire or cutting member is secured at the palm of the hand by the securing member 65 (or a combination of securing members), the actuator 55 is moved between the first and second positions thereby raising and lowering the "bow" (see FIG. 9E-1) created by the internal cutting wire 47 or cutting member 45 and the elongated body 40 is moved in a sawing, cutting or other motion, thereby releasing the TCL and decompressing the median nerve.

Figure 10D:
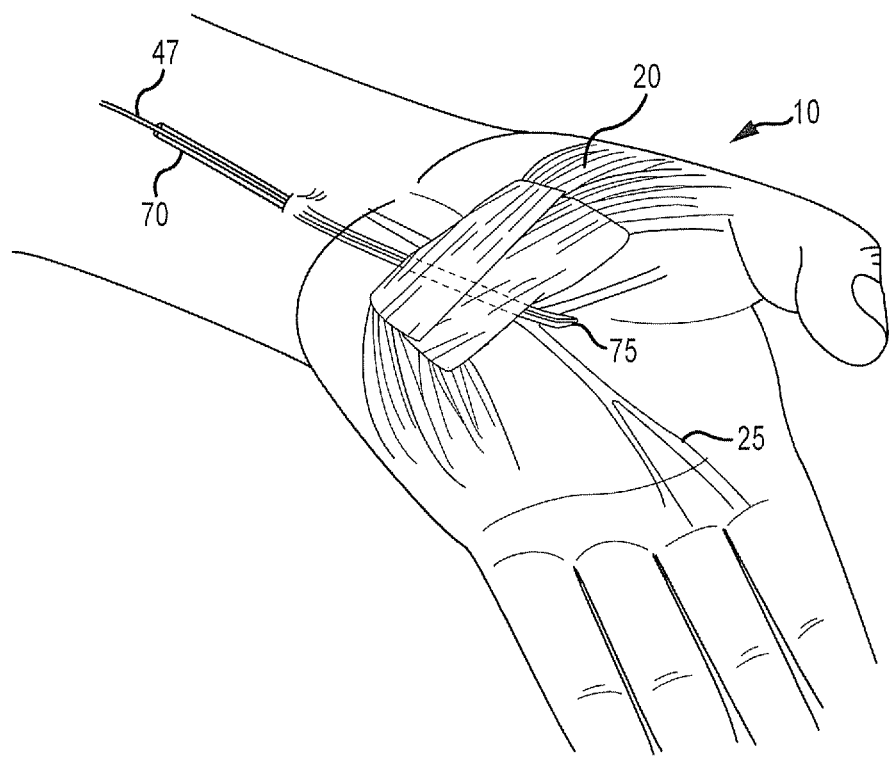
FIG. 10D illustrates placement of the embodiment of FIG. 10A under the TCL.
Figure 10E:
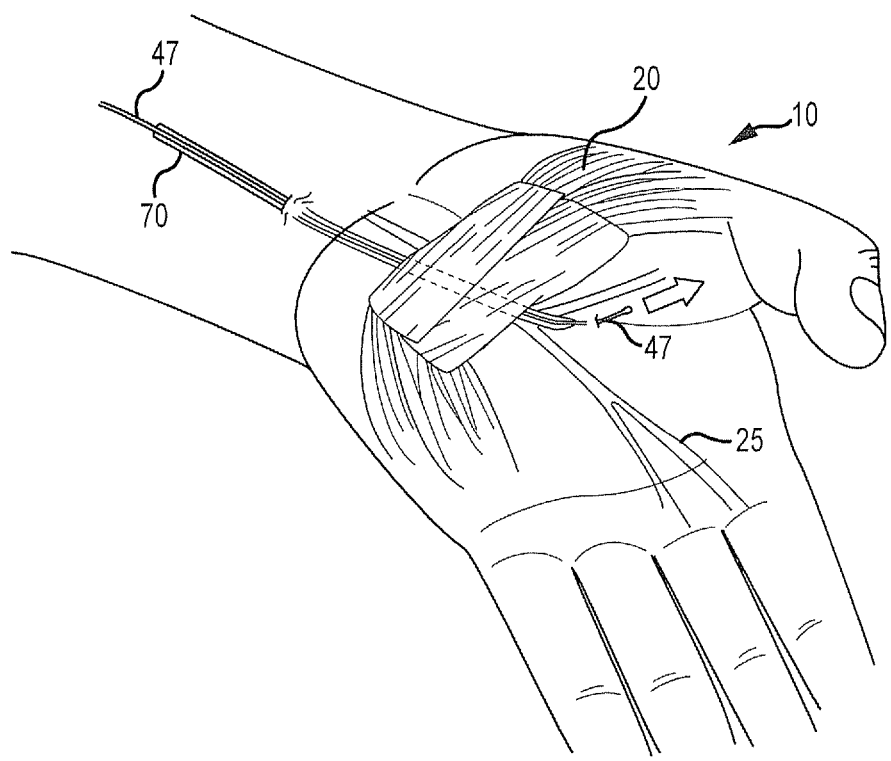
FIG. 10E depicts the embodiment of FIG. 10A wherein the cutting wire is shown exiting the palm of the hand.
Figure 10F:
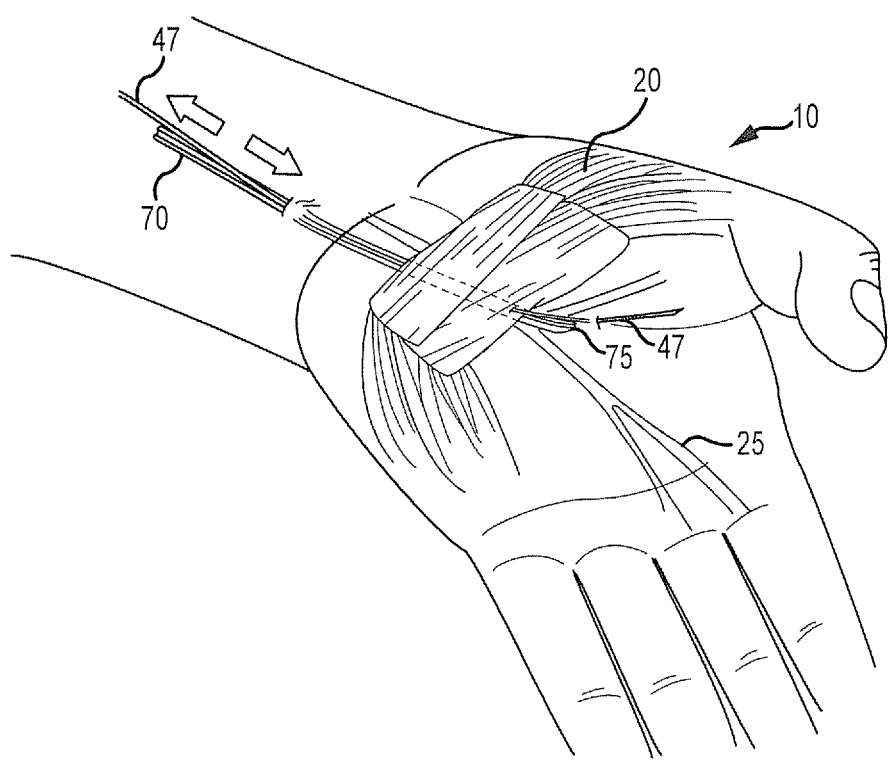
FIG. 10F depicts the system of FIG. 10A wherein a cutting member (not shown) is used to release the TCL.

As can be understood from FIGS. 10A-10F and 11A-11C, the internal cutting wire 47 may be received by a sled member 70. As shown in FIGS. 10A-10C and 11A-11C, the sled member 70 may have a variable length and includes a channel 77 that is configured to receive the internal cutting wire 47. In some embodiments, the sled member may be configured to receive the elongated body 40 which may be an abrasive material or abrasive suture as described in other embodiments. In some embodiments, the sled member may be configured to receive a cutting member 45 as described herein. The distal end 75 of the sled member 70, which may be rounded (FIG. 11A-11C) or slightly pointed (FIGS. 10A-10C), is at a slight slope or incline relative to the proximal end 80 of the sled member 70 thereby creating an upslope trajectory to facilitate exit of the cutting wire 47 from the palm of the hand once the sled member is properly positioned under the TCL (see FIG. 10D). As shown in FIG. 10B, the sled member 70 may also include a retaining member 75, such as a groove snap, to retain the cutting wire 47 in the channel 77 of the sled member 70. As indicated in FIGS. 10E and 10F, the internal cutting wire 47 may then be extended from the distal end of the sled member and exit the palm of the hand at the exit point, and secured by a securing member 65 or other appropriate device (e.g. a handle member). The cutting wire 47 is now properly positioned beneath the TCL and is moved in a sawing, cutting or other motion, thereby releasing the TCL and decompressing the median nerve.

Figure 12A:
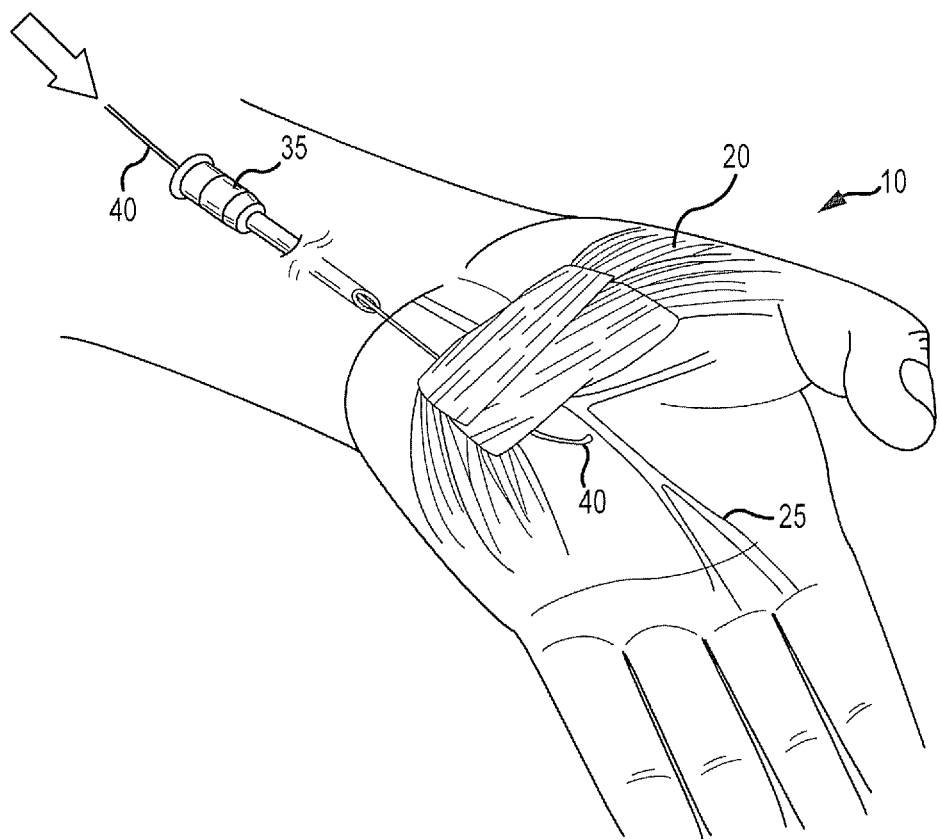
FIG. 12A illustrates still another embodiment of the system, wherein a first elongated body is being introduced under the TCL.
Figure 12B:
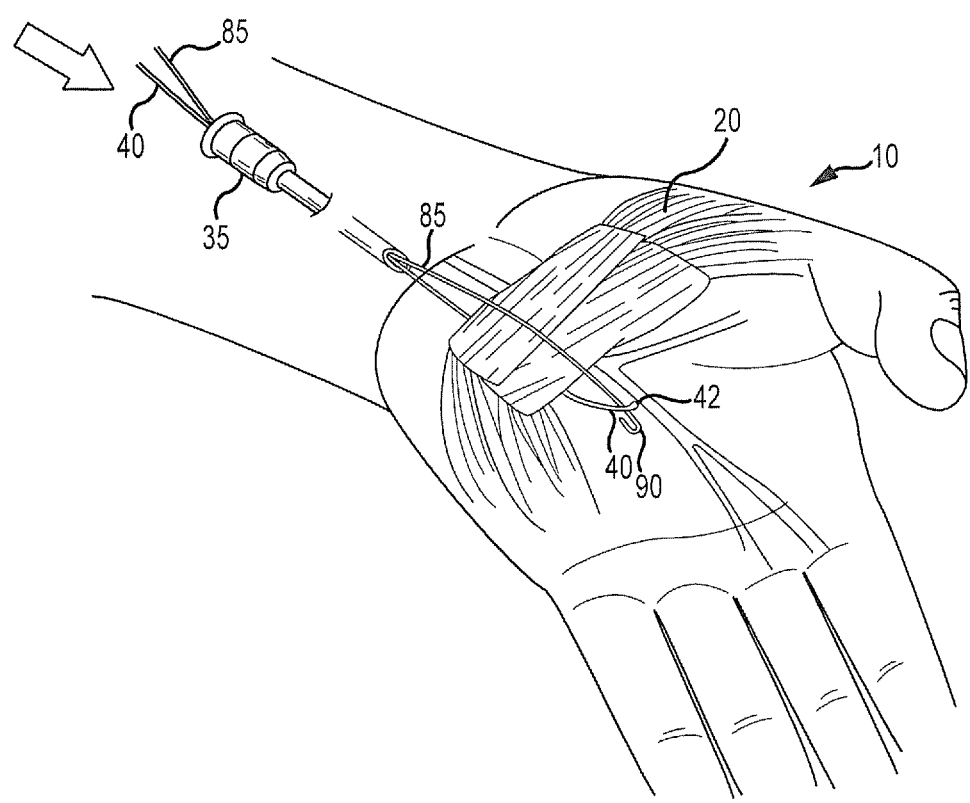
FIG. 12B depicts the system of FIG. 12A wherein a second elongated body with a hook member is introduced to the subcutaneous tissue above the TCL.

As can be understood from FIGS. 12A-12D, the elongated body 40 may be introduced through an introducer 35 into the carpal tunnel region and into its proper position beneath the TCL but without exiting the hand 10 (FIG. 12A). As indicated in FIG. 12B, a second elongated body 85 having a hook end 90 is introduced through the introducer 35 into the subcutaneous tissue above the TCL. The hook end 90 of the second elongated body 85 is advanced towards the distal end 43 of the elongated body 40, such as the ball point tip 42 of the elongated body 40, and coupled to the distal end 43 of the elongated body 40. In some embodiments, the first elongated body 40 and/or the second elongated body 85 may be formed of an abrasive material such as abrasive sutures and introduced to the carpal tunnel region via a sled member 70 as discussed above with reference to FIGS. 10A-11C.

Figure 12C:
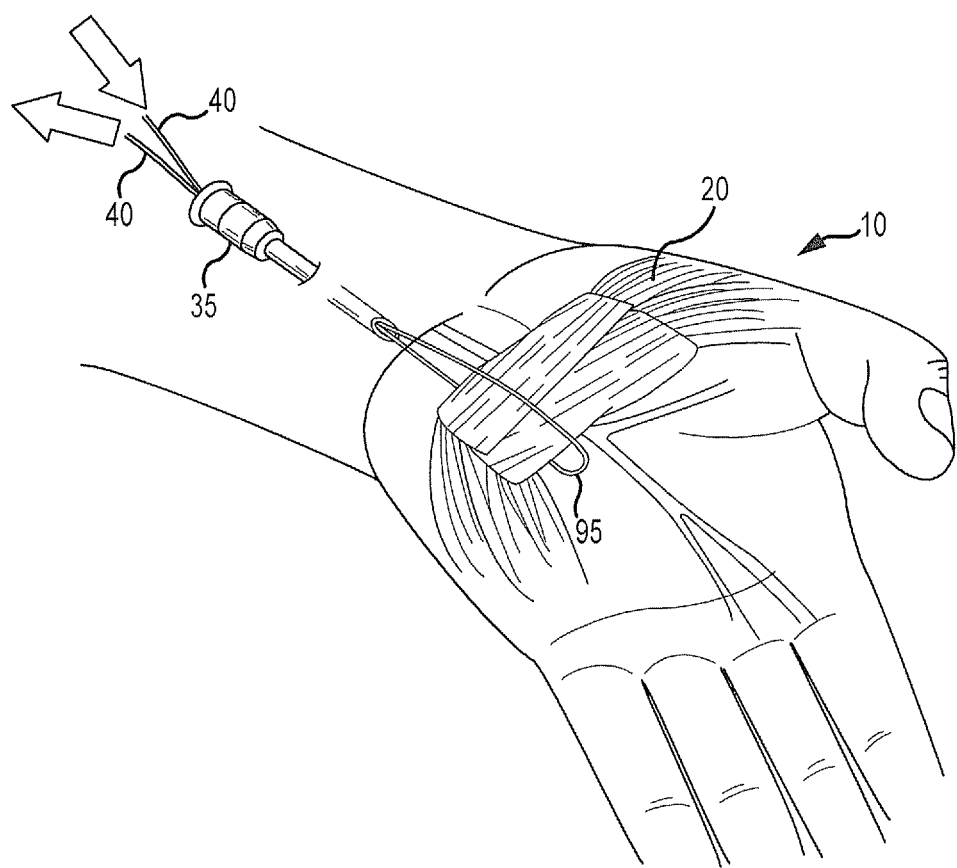
FIG. 12C illustrates the system of FIG. 12B wherein the first elongated body has formed a loop structure about the TCL.
Figure 12D:
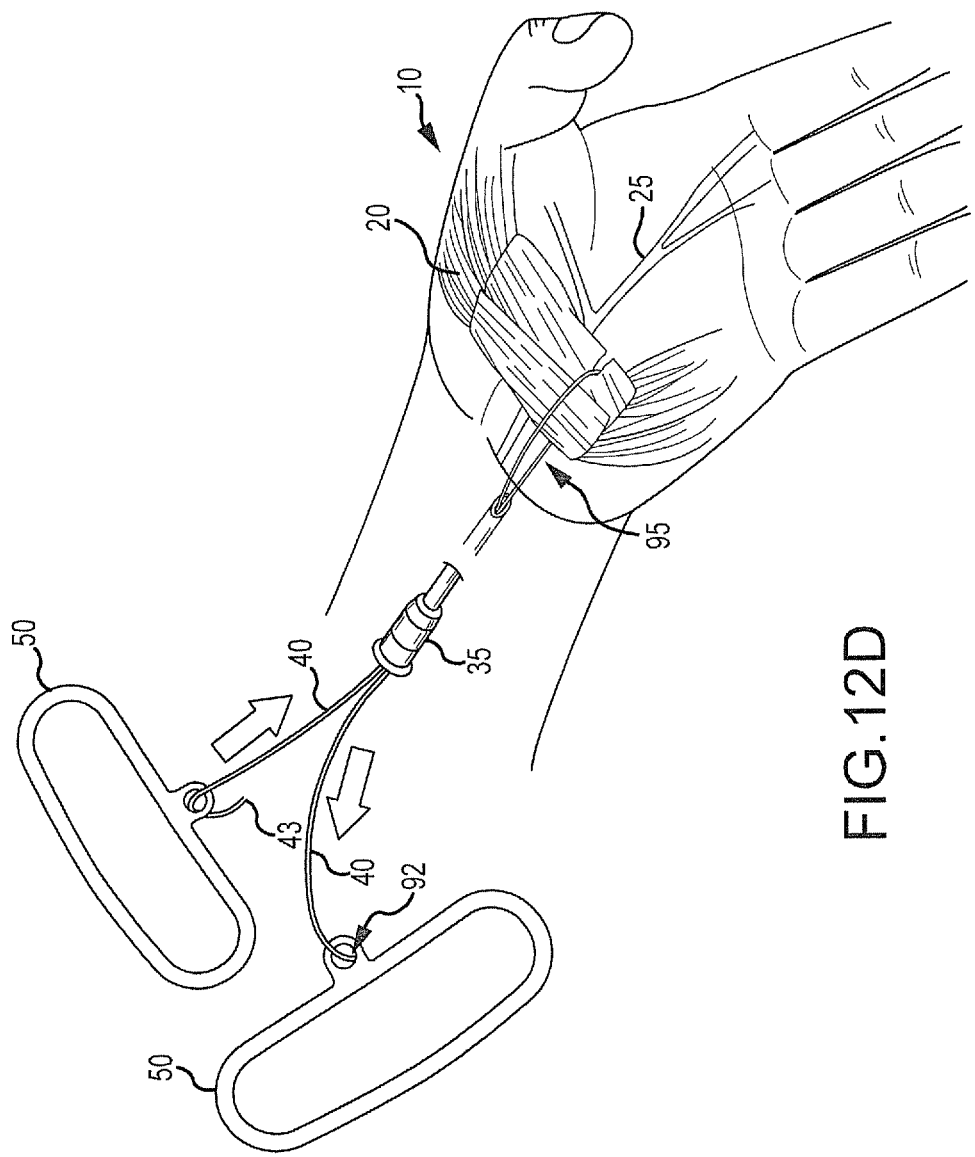
FIG. 12D illustrates the system of FIG. 12C wherein a proximal end and a distal end of the first elongated body is operably connected to a handle member and the TCL is being released.

As can be understood from FIG. 12C, the second elongated body 85 is withdrawn through the introducer, thereby pulling the first elongated body 40 through the subcutaneous space above the TCL and creating a loop structure 95. A cutting member may be exposed within the loop structure to facilitate release of the TCL. As shown in FIG. 12D, a proximal end 92, and a distal end 43 of the elongated body 40 is coupled to a handle member 50 and each handle member 50 is displaced in the opposite direction relative to the other to create a sawing or cutting motion as the loop structure 95 releases the TCL thereby decompressing the median nerve.

Figure 13A:
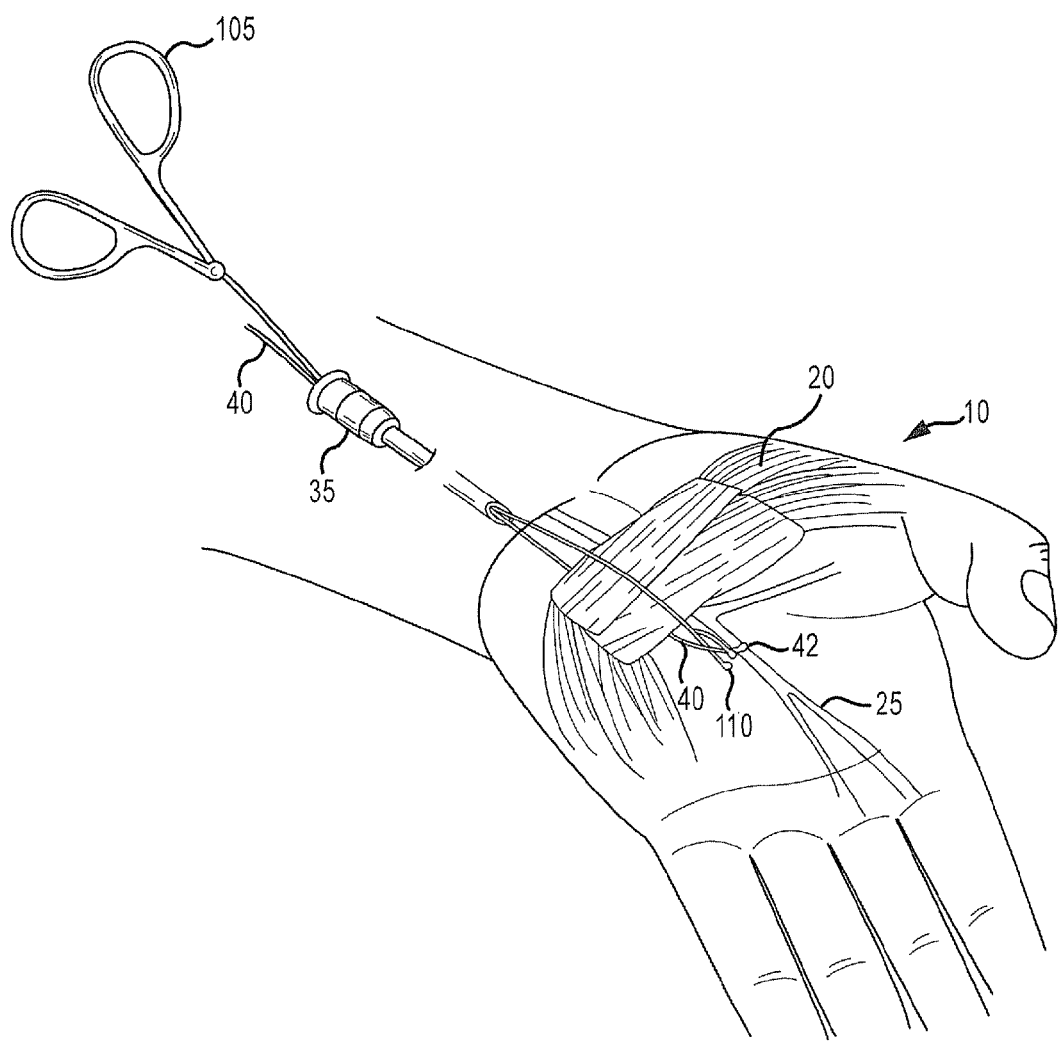
FIG. 13A illustrates still another embodiment of the system, wherein both an elongated body and a forceps device have been introduced into the carpal tunnel area/subcutaneous tissue of FIG. 2.
Figure 13B:
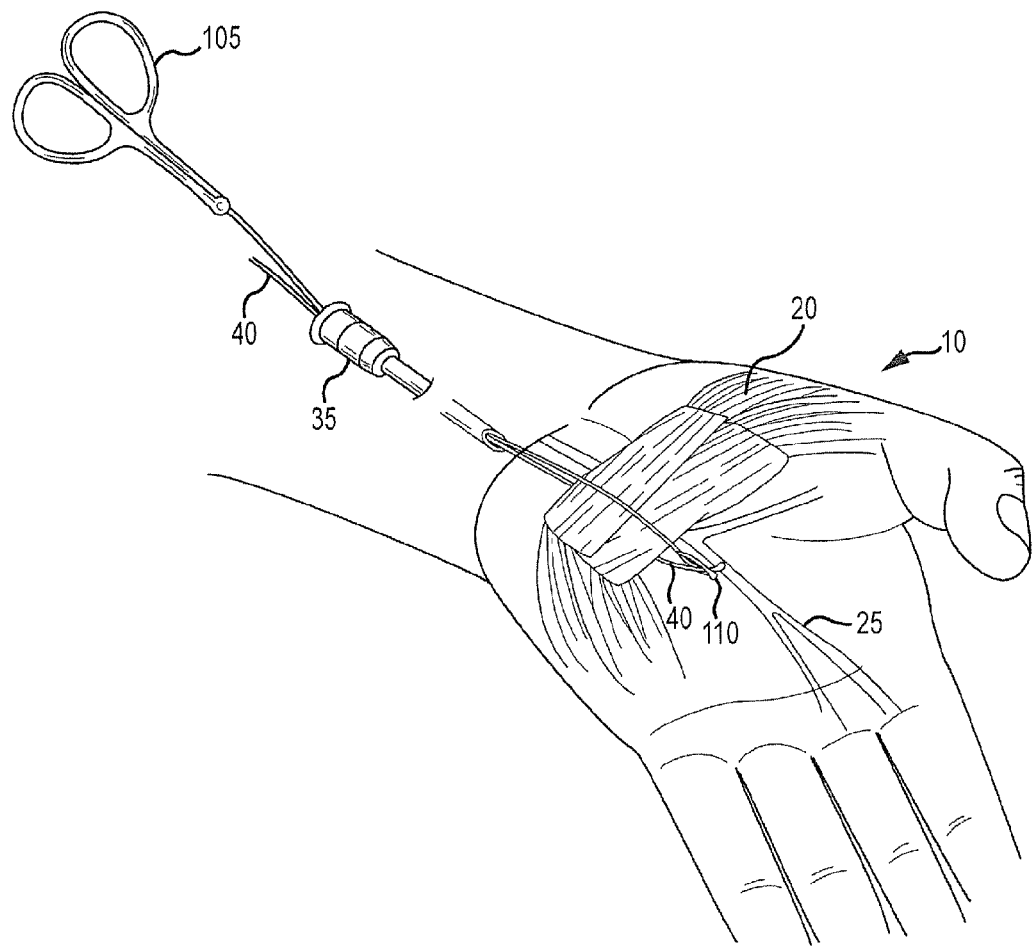
FIG. 13B is the same view as FIG. 13A except the forceps device has fully engaged the elongated body.

As can be understood from FIGS. 13A-13B, the elongated body 40 may be introduced through an introducer 35 into the carpal tunnel region and into its proper position beneath the TCL but without exiting the hand 10. In some embodiments, the elongated body may be an abrasive material, such as an abrasive suture. As shown in FIG. 13A, a forceps device 105 may also be introduced through the introducer 35 into the subcutaneous tissue above the TCL. As indicated in FIG. 13B, the distal end 110 of the forceps 105 is coupled to the ball point tip 42 of the elongated body 40 to securely hold the elongated body 40 about the TCL. The forceps device 105 may be withdrawn subcutaneously, thereby pulling the elongated body 40 into the subcutaneous space above the TCL and creating a loop structure, as described above with reference to FIGS. 12C and 12D. A cutting member 45 may be exposed at the loop of the loop structure. The proximal and distal ends of the elongated body 40 may be attached to a handle member (such as those depicted in FIG. 7A-8D or 21A-21G) and the elongated body may be displaced in a sawing or cutting motion. The sawing or cutting motion releases the TCL thereby decompressing the median nerve.

Figure 14A:
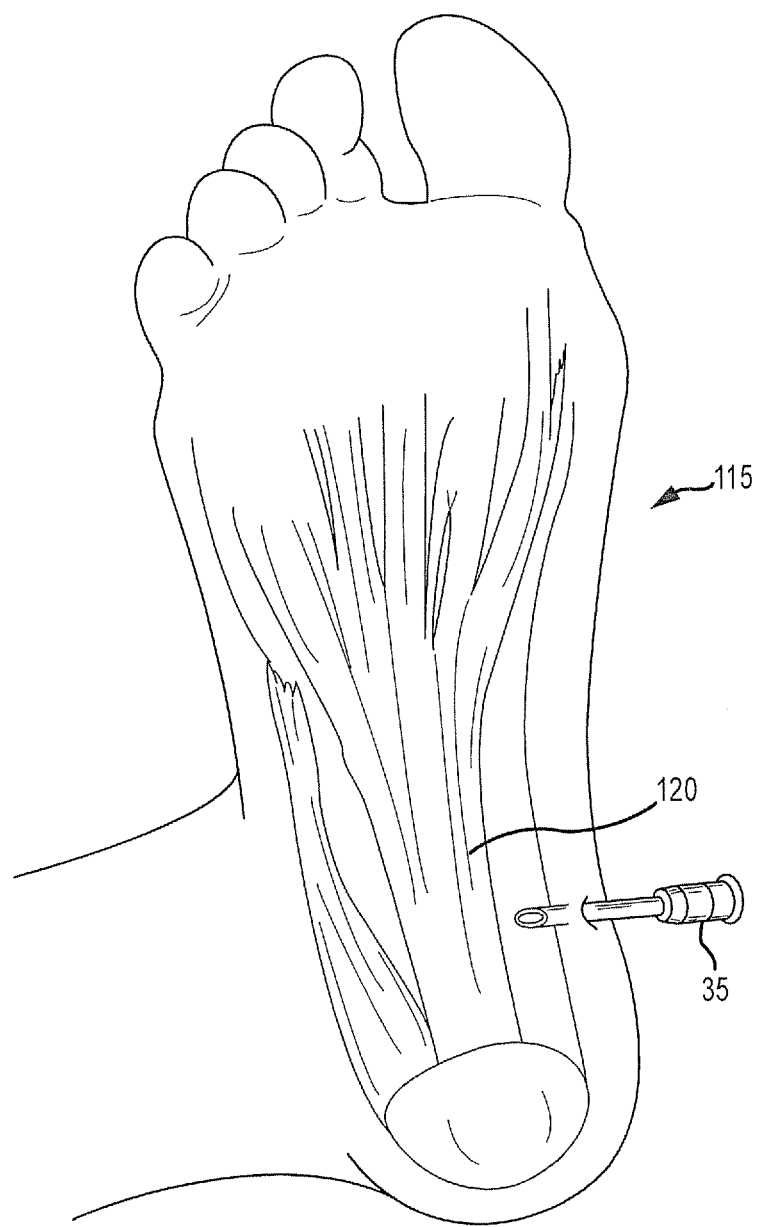
FIG. 14A illustrates an embodiment of the release system for treatment of plantar fasciitis, showing placement of an introducer into a foot.
Figure 14B:
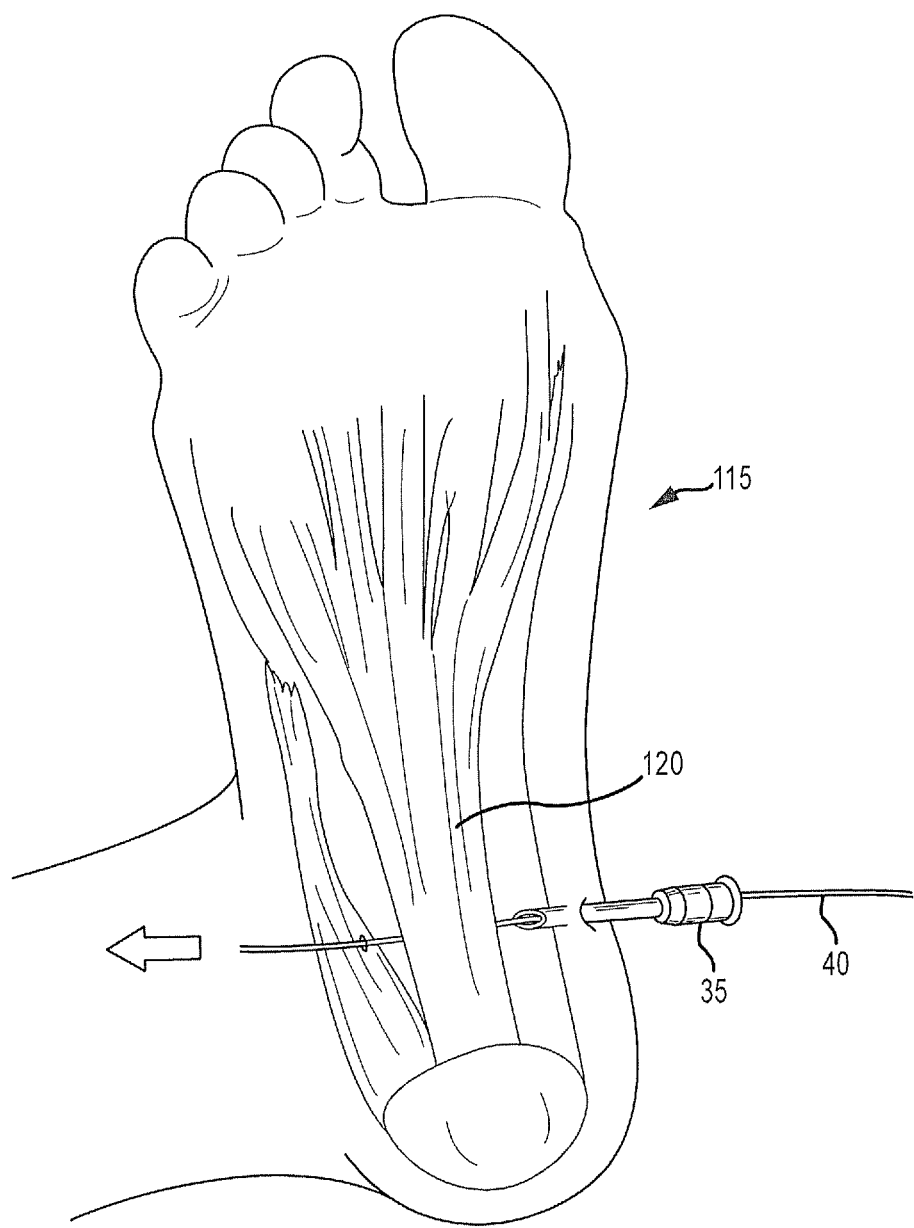
FIG. 14B depicts introduction of an elongated body through the introducer under a plantar fascia of the foot.
Figure 14C:
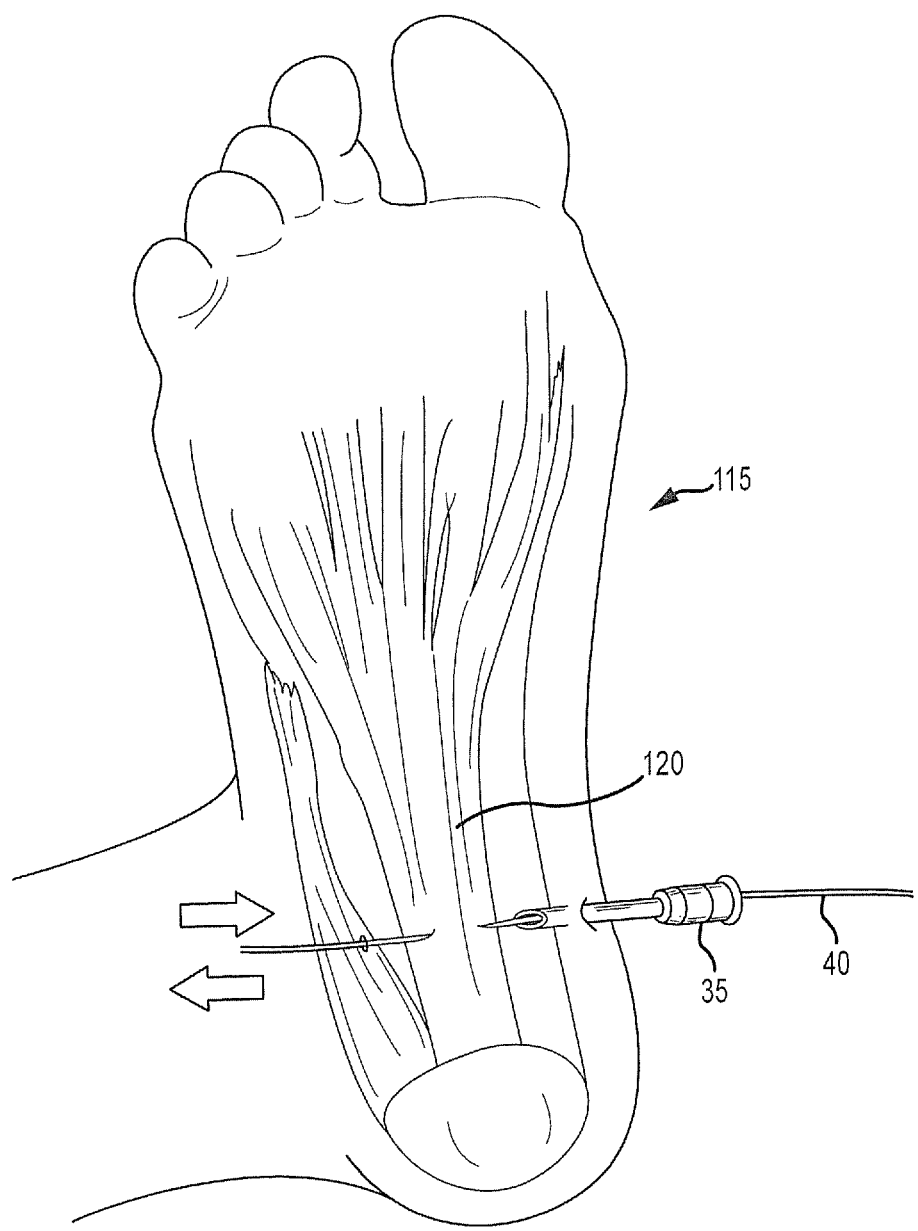
FIG. 14C depicts the elongated body releasing the plantar fascia.

For a discussion of an embodiment that may be used to treat plantar fasciitis through plantar fascia release, reference is now made to FIGS. 14A-14C. As can be understood from FIGS. 14A-14B, an elongated body 40 may be introduced through an introducer 35 into the foot 115 and underneath the plantar fascia 120. The distal end and proximal end of the elongated body 40 may be coupled to handle member(s) (such as those depicted in FIG. 7A-8D or 21A-21G or elsewhere in this disclosure). The distal and proximal ends of the elongated body 40 may be displaced in a cutting or sawing motion thereby releasing the plantar fascia (FIG. 14C) and decreasing the inflammation. It can be appreciated that other embodiments disclosed herein in the context of treatments for carpal tunnel syndrome may be adapted to treat plantar fasciitis without departing from the spirit and scope of the disclosure.

For a discussion of another embodiment of a system where the elongated body is not required to exit the exit point of the hand, reference is now made to FIGS. 15A to 15L which depict a complete system in which the distal end of the elongated body does not exit the palm of the hand.

FIG. 15A illustrates one embodiments of a release system. As can be understood from FIG. 15A, in one embodiment, the complete system 200 includes a deployment or delivery instrument 205, a return shaft device 210 and a handle member 50. The system 200 may also include nerve stimulation equipment or a nerve detection device 500 as described herein.

Figure 15B:
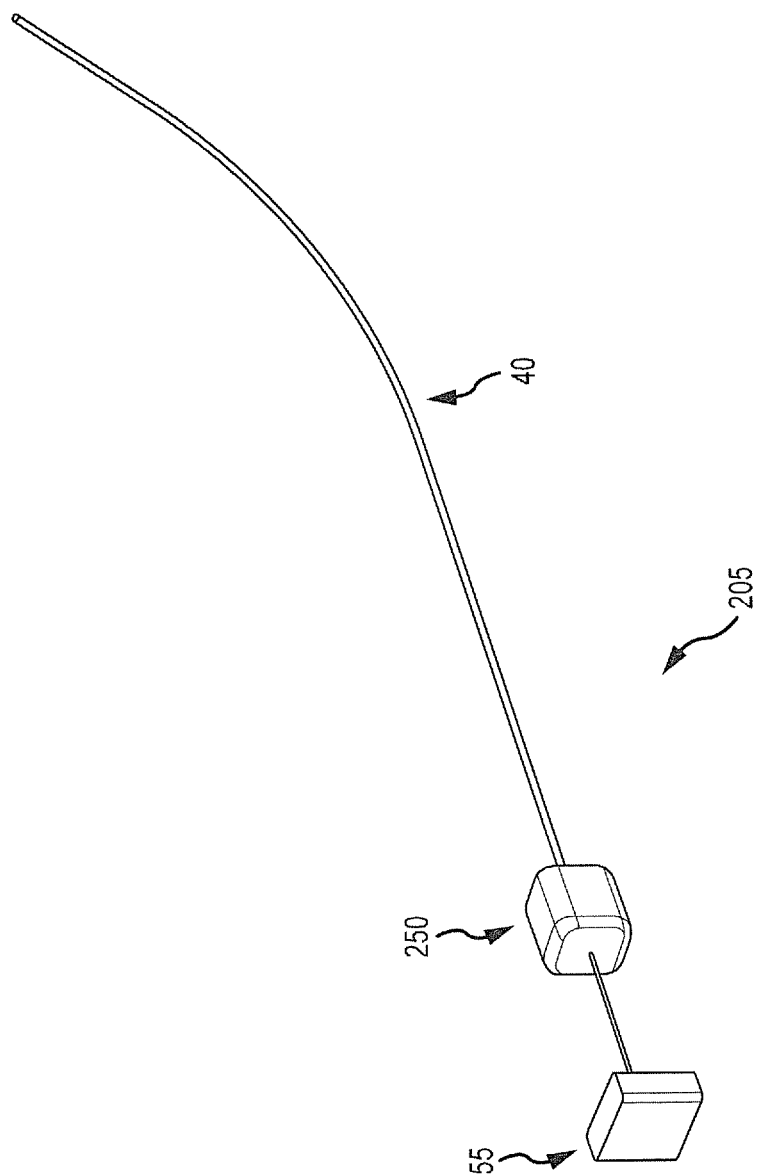
FIG. 15B depicts the delivery or deployment instrument of FIG. 15A.

FIG. 15B illustrates the deployment or delivery instrument 205 wherein an elongated body 40 is shown. FIG. 15C illustrates the deployment or delivery instrument 205 wherein the elongated body 40 is shown transparent such that a piston 220 and a cutting member delivery device 222 may be seen. As shown in FIGS. 15B-15O, and with reference to FIGS. 15D-15F, the deployment or delivery instrument 205 may include an elongated body 40, a deployment device handle member 50a, an actuator 55 and a cutting member delivery device 222. The elongated body 40 may also be configured to receive a piston 220 therein. The actuator 55 and elongated body 40 may be similar to the same elements as described elsewhere in this disclosure. The cutting member delivery device 222 may be a needle, pin or other appropriate device that can deliver an abrasive suture 255 through the deployment or delivery instrument 205. The deployment device handle member 50a may be similar to one of the handle members 50 as described elsewhere in this disclosure. The cutting member delivery device 222 may be coupled to an abrasive suture, wire or other abrasive material 255 (see FIG. 15L).

Figure 15E:
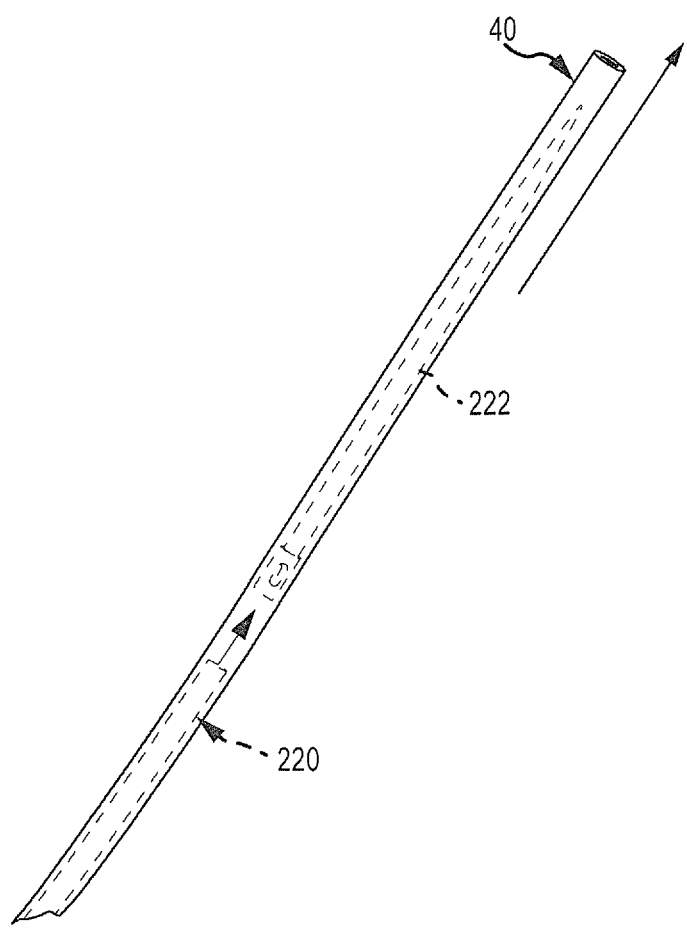
FIG. 15E is an enlarged view of a distal end of the delivery or deployment instrument of FIG. 15D.
Figure 15F:
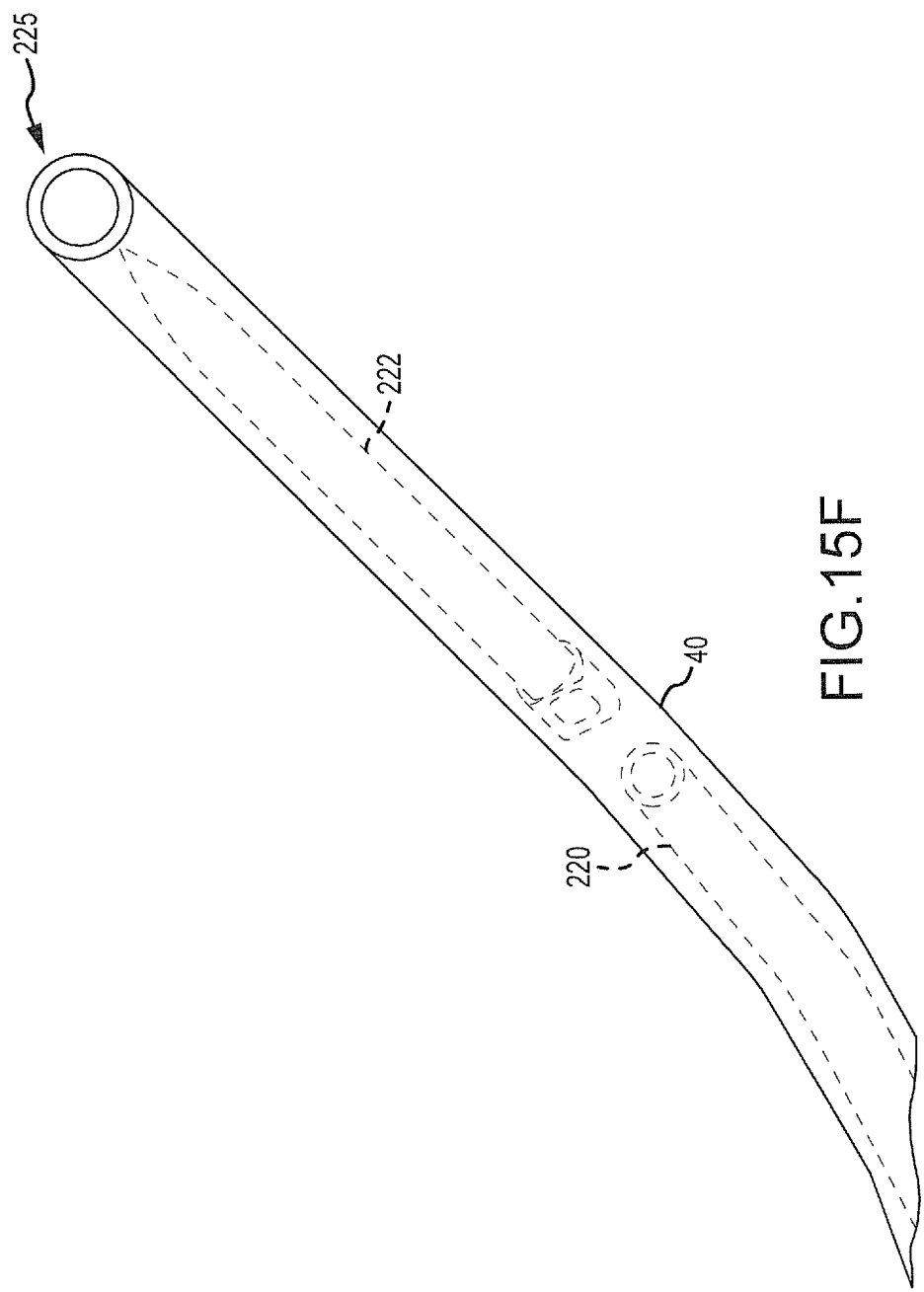
FIG. 15F is still another enlarged view of the distal end of the delivery or deployment instrument of FIG. 15D.

FIG. 15D illustrates deployment of the cutting member delivery device 222. FIG. 15E is an enlarged view of a distal end 225 of the elongated body 40 wherein the cutting member delivery device 222 and piston 220 are shown prior to engagement of the piston 220 with the cutting member delivery device 222. FIG. 15F is an enlarged view of FIG. 15E. As can be understood from FIGS. 15D-15F, as the actuator 55 is displaced towards the handle member 50a, the piston 220 extends through the elongated body 40 into engagement with (but not coupling with) the cutting member delivery device 222, thereby pushing the cutting member delivery device 222 beyond the distal end 225 of the elongated member 40 to the exit point in the palm and outside of the palm of the hand. The suture 255 may be passed through the piston 220. Once the cutting member delivery device 222 has exited the palm, the deployment handle 50a is retrieved or withdrawn from the device.

Figure 15H:
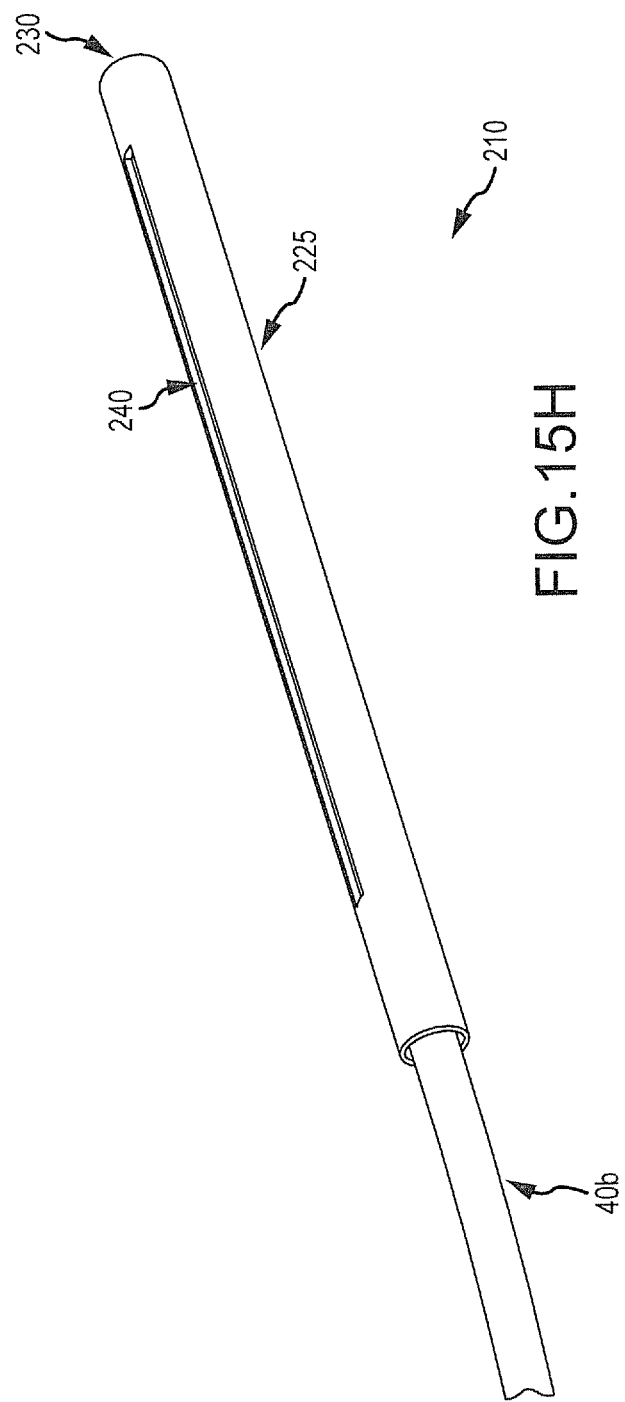
FIG. 15H depicts an enlarged view of a distal end of the return shaft member of FIG. 15G.
Figure 15J:
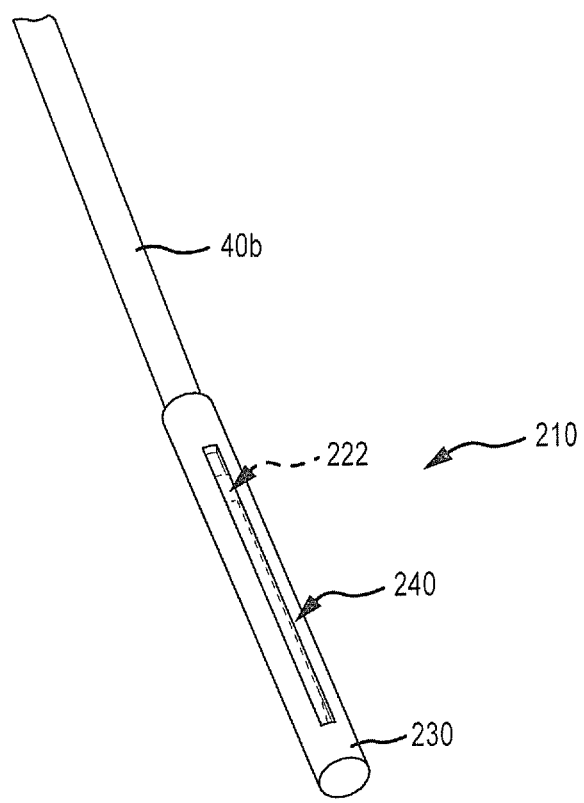
FIG. 15J is a top side view of the return shaft member of FIG. 15H.

FIG. 15G illustrates the return shaft device 210. FIG. 15H illustrates an enlarged view of a distal end 230 of the device 210 wherein a device pocket 225 is shown. FIG. 15I depicts an enlarged view of the distal end 230 of the device 210 wherein the device pocket 225 is transparent such that the cutting member delivery device 222 can be seen. FIG. 15J is a top plan view of FIG. 15H. As can be understood from FIGS. 15G-15J, the return shaft device 210 may include a handle member 50b, an elongated body 40b and a cutting member delivery device pocket 225 at a distal end 230 of the device 210 (FIG. 15G). The handle member 50b and the elongated body 40b may be as described above. As shown in FIGS. 15H and 15J, the device pocket 225 is generally cylindrical in shape and includes an axial opening 240 defined therein. The opening 240 is configured to receive the cutting member delivery device 222 and may extend less than the length of the device pocket 225. The opening 240 may be configured to receive securing devices of various dimensions and the dimensions of the opening 240 can be adapted accordingly. As shown in FIG. 15I the distal end 245 and the proximal end 250 of the device 222 are placed into the opening 240, thereby securing the device 222 within the chamber. The abrasive suture material 255 may be outside of the opening 240. In some embodiments, the distal end 245 may be placed in the opening 240 first. In some embodiments, the proximal end 250 may be placed in the opening 240 first. In other embodiments, both the proximal and distal ends 250, 245 may be placed in the opening simultaneously.

With reference to FIGS. 15D-F, once the device 222 has been delivered outside the palm, the handle 50a is retrieved or withdrawn from the hand. The device 210 is introduced when the device 222 is outside the palm. The device 222 is received in the device 210 at the opening 240 and the suture 255 trails outside of the opening 240. As can be understood from FIG. 15J, the return shaft 210 is then navigated back through the puncture in the palm, navigated above the TCL and out through the original puncture site near the wrist, thereby "wrapping" the suture 255 around the TCL.

Figure 15K:
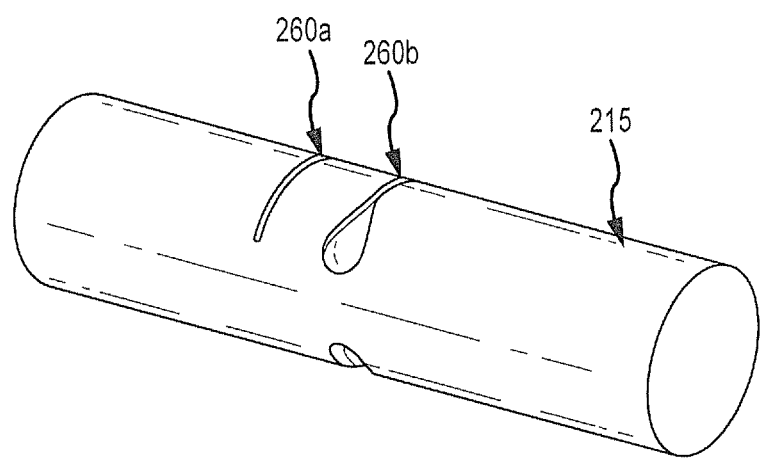
FIG. 15K depicts the handle member of FIG. 15A.
Figure 15L:
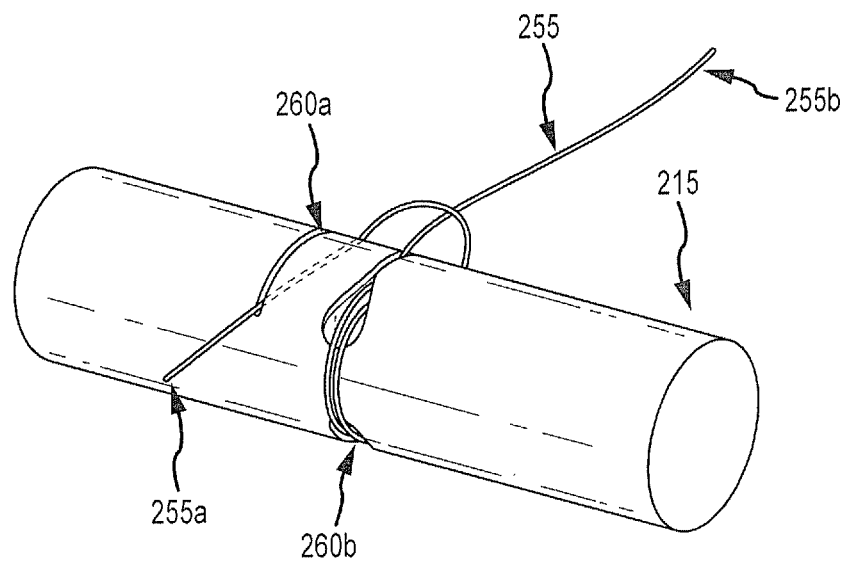
FIG. 15L is the same view as FIG. 15K except an abrasive suture material is also shown positioned on the handle member.

FIG. 15K depicts a suture handle member 215. FIG. 15L illustrates a method of wrapping the suture 255 about the handle member 215. As can be understood from FIGS. 15K-15L, the suture handle member 215 may be a solid cylindrical shape and may include two suture receiving slits 260. A first suture receiving slit 260a is configured to receive a first end 255a of the suture 255 and the suture is then wrapped around the handle through a second suture receiving slit 260b.

With reference to FIGS. 15K-15L, in use, once the return shaft device 210 has exited the puncture site in the wrist, the suture material 255 is cut so there are two suture lines (the proximal and distal ends of the suture 255a, 255b). Each of the suture lines 255 may be attached to a suture handle member 215 as described above. The surgeon now has both ends 255a, 255b of the suture wrapped around a respective handle 215 and can saw, cut, floss or otherwise release the TCL, thereby decompressing the median nerve. At completion of the procedure, the suture 255 is cut and removed.

For a discussion of another embodiment of a system where the elongated body and the introducer do not exit the exit point of the hand, reference is now made to FIGS. 16A to 16H, which depict a release system in which neither the distal end of the elongated body nor the introducer exit the exit point in the palm of the hand.

Figure 16A:
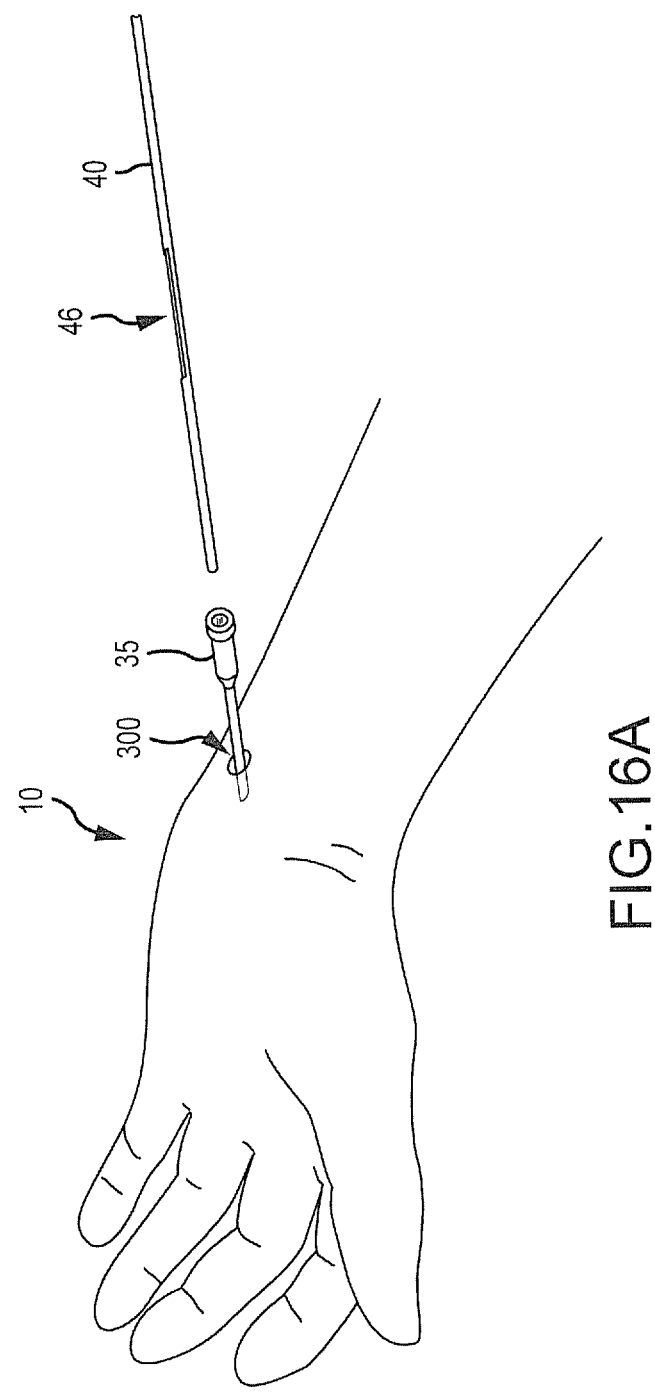
FIG. 16A depicts still another embodiment of a release system including an introducer and an elongated body.
Figure 16B:
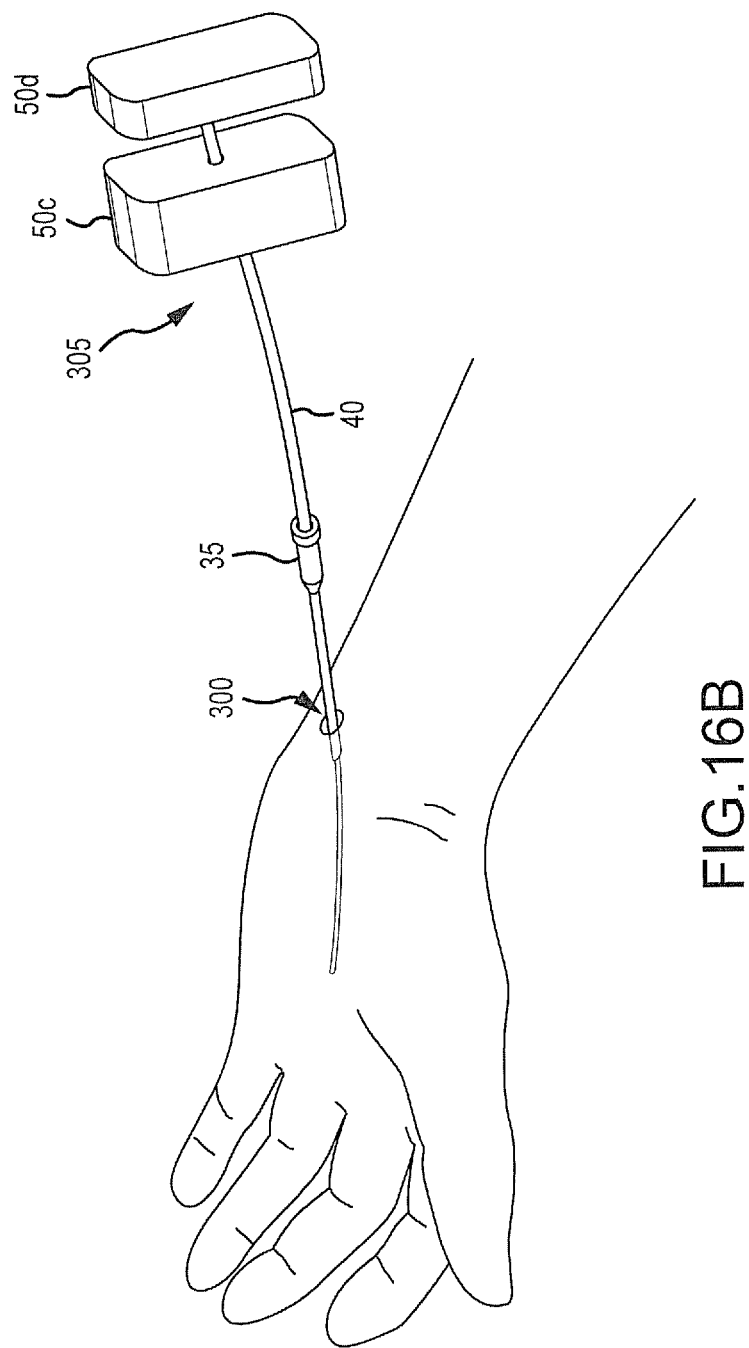
FIG. 16B depicts the release system of FIG. 16A, wherein handle members are shown operably connected to the elongated body and the elongated body is introduced into the carpal tunnel region of FIG. 2.

As can be understood from FIG. 16A, an introducer 35 is introduced at an entry point 300 in the palm of the hand 10. The introducer 35 may be a 10-12 GA introducer needle. As shown in FIGS. 16A and 16B, an elongated body 40 including handle members 50c, 50d at a proximal end 305 of the body 40 and a window 46 is introduced into the palm of the hand through the introducer 35 and guided under the TCL by a neuro-monitoring system (not shown). In some embodiments, the handle member 50d may be an actuator 55.

Figure 16C:
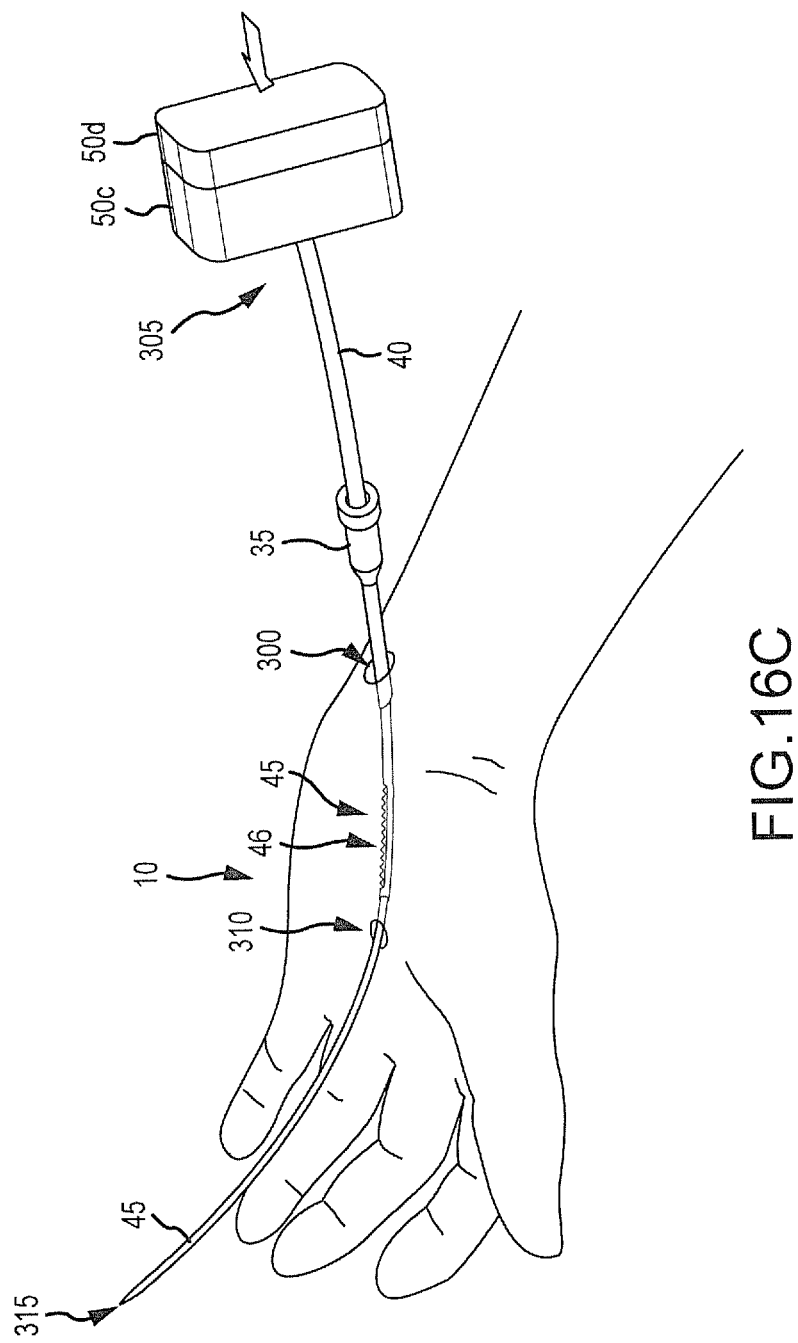
FIG. 16C is the same view as FIG. 16B, except a cutting member is shown exiting the palm of the hand.

As indicated in FIG. 16C, the handle members 50c, 50d at a proximal end 305 of the elongated body 40 are snapped together or otherwise coupled together, thereby extending the cutting member 45 through an exit point 310 in the palm of the hand 10. In some embodiments, the cutting member 45 may include a piercing member 315, such as a needle or a pin to pierce the skin at the exit point 310 in the palm of the hand 10. Coupling the handle members 50c, 50d also exposes the cutting member 45 in the window 46 of the elongated body 40.

Figure 16D:
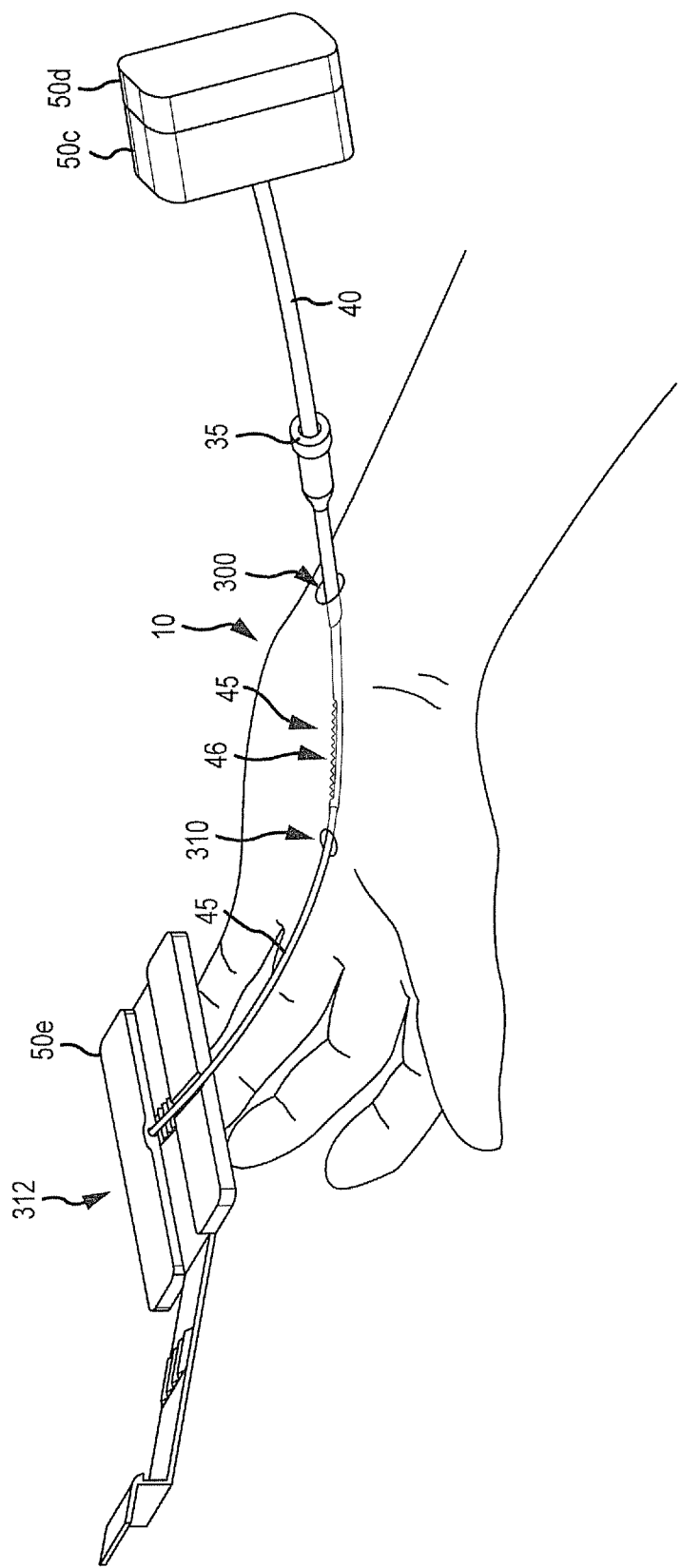
FIG. 16D is the same view as FIG. 16O, except the cutting member is shown operably connected to a handle member.
Figure 16E:
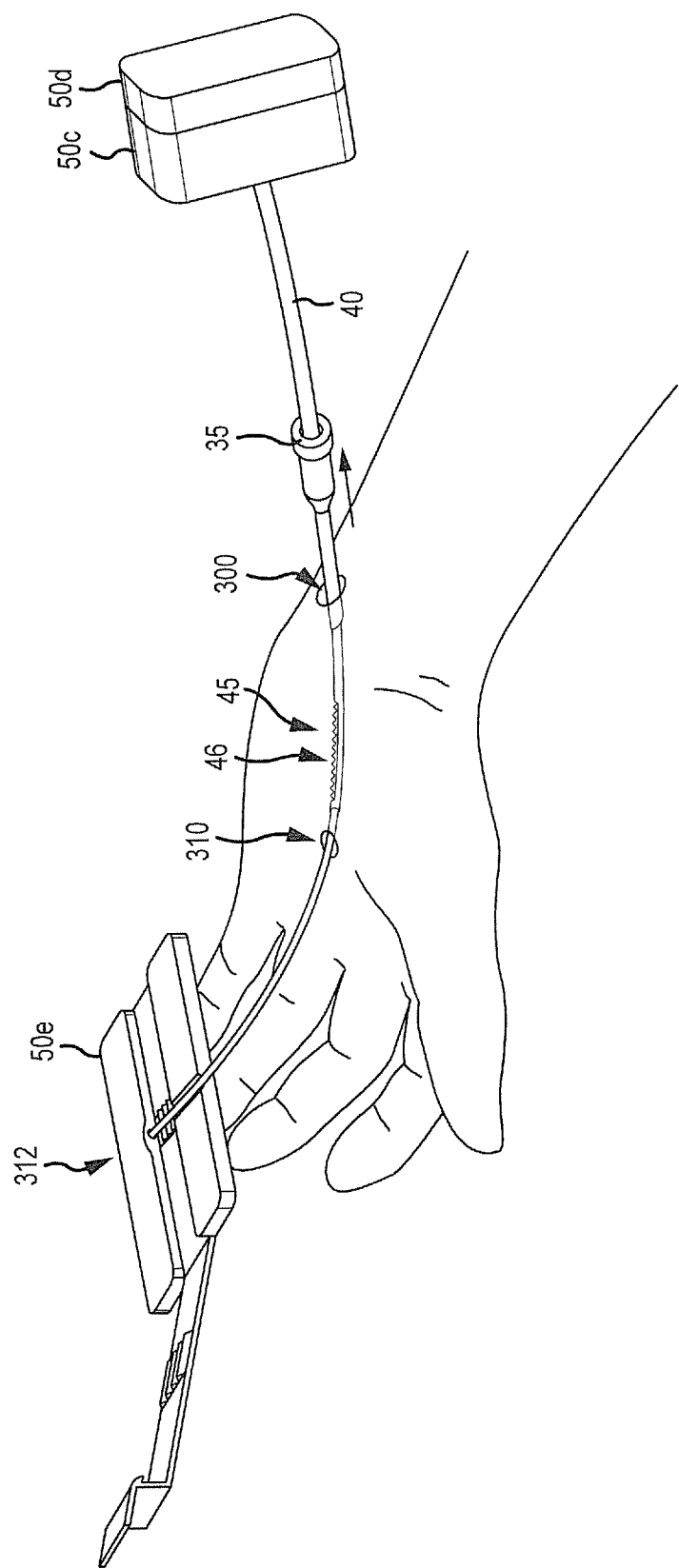
FIG. 16E is the same view as FIG. 16O, except the introducer is being withdrawn from an entry site in the palm of the hand.

As shown in FIG. 16D, the piercing member 315 of the cutting member 45 is received in the handle member 50e and the elongated body 40 does not exit the exit point 310 of the hand 10. As indicated in FIG. 16E, the introducer 35 is withdrawn from the entry point 300 of the palm of the hand 10.

Figure 16F:
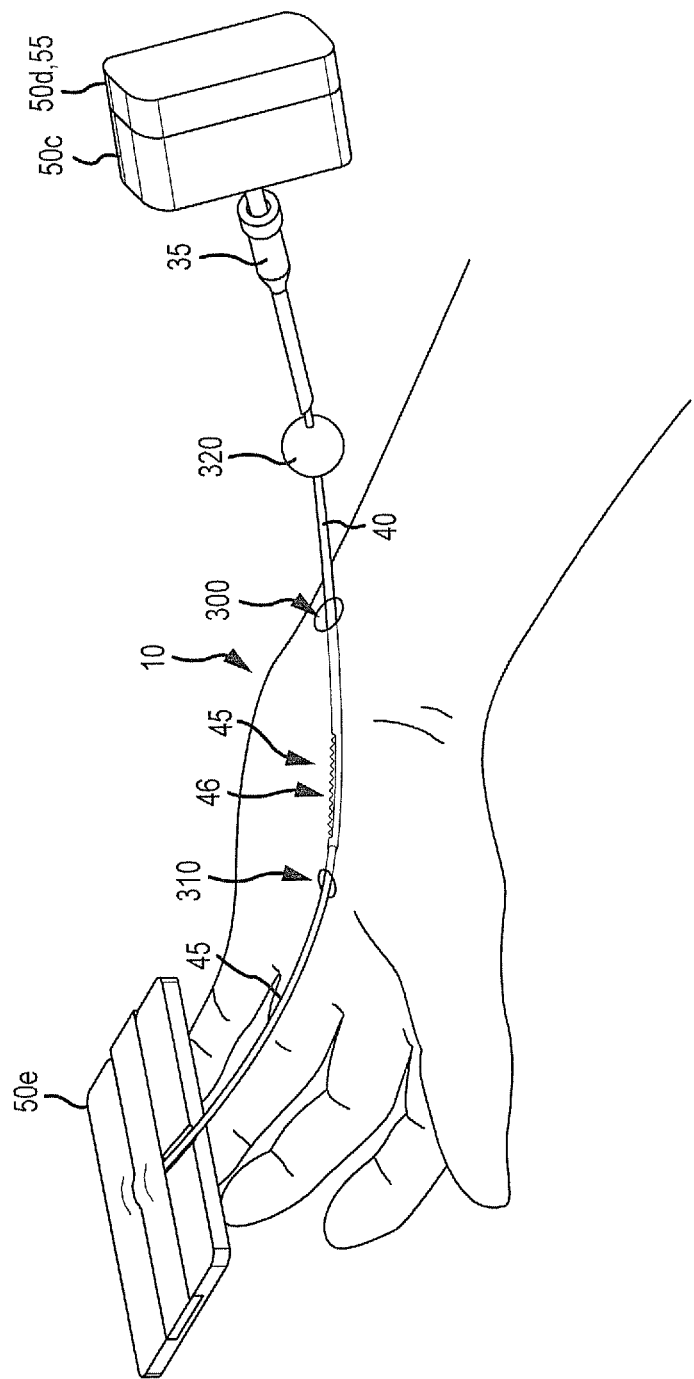
FIG. 16F is the same view as FIG. 16E, except the withdrawn introducer is being held in place by a motion limiting feature.

As can be understood from FIGS. 16F-16H, the handle member 50e is closed about the distal end 312 of the cutting member 45 thereby securing the cutting member 45 within the handle member 50e. The surgeon may now grasp the handle members 50 and can saw, cut, floss or otherwise release the TCL, thereby decompressing the median nerve.

As shown in FIGS. 16F-16H, a motion limiting feature 320 is operably connected to the elongated body 40 and operates to hold the introducer 35 in place such that during the TCL release procedure, the introducer 35 will not further puncture the hand. As indicated in FIGS. 16G and 16H, the motion limiting feature also prevents the distal end of the elongated body 40 from exiting the palm of the hand. Upon completion of the procedure, the handle member 50e may be removed, the cutting member 45 may be retracted and the release system may be removed. In other embodiments, the cutting member 45 may be simply "clipped off" and the system removed.

For a discussion of another embodiment of a system where the elongated body and the introducer do not exit the exit point of the hand, reference is now made to FIGS. 17A to 17H, which depict a release system in which neither the distal end of the elongated body nor the introducer exit the exit point in the palm of the hand.

Figure 17A:
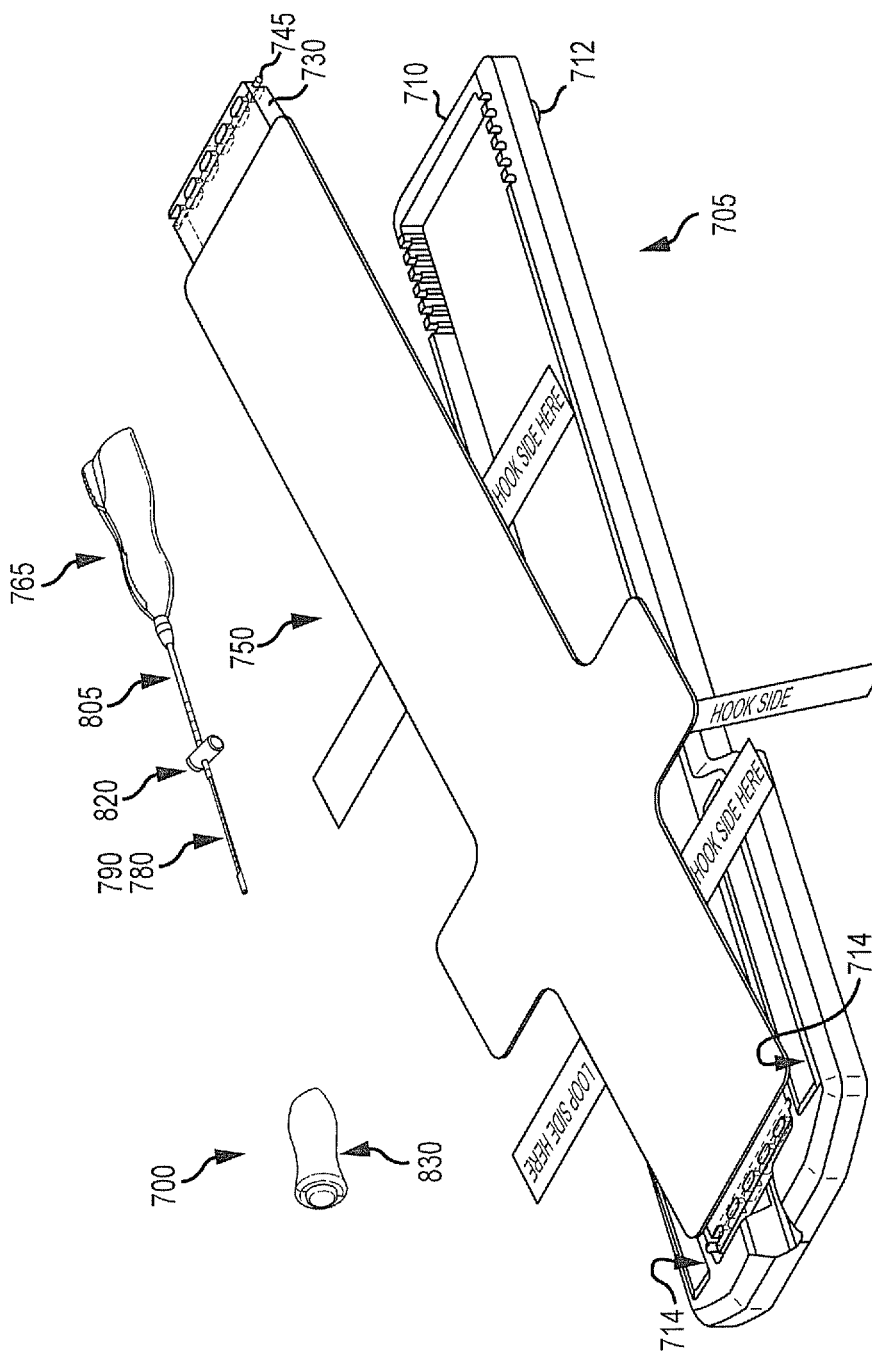
FIG. 17A depicts another embodiment of a release system including a handboard assembly and handle members.

As can be understood from FIG. 17A, which is an isometric view of the system 700, in one embodiment, the release system 700 may include handle members 50 (also referred to as a proximal handle assembly 765 and a distal handle assembly 830), an introducer 35 (also referred to as an introducer assembly 805), and a motion limiting feature 320 (also referred to as a shaft lock assembly 820). In some embodiments, the proximal handle assembly 765 may also include an elongated body 40 with a window 46 (also referred to as a probe wire assembly 780) and a cutting member 45 (portions of a cutting wire assembly 790). In some embodiments, the system 700 may include a hand immobilization device, such as a handboard assembly 705 and a drape assembly 750. In some embodiments, the handboard assembly 705 may also include at least one cavity 714 configured to receive a nerve detection system or a neuro monitoring system 500.

Figures 1, 17B:
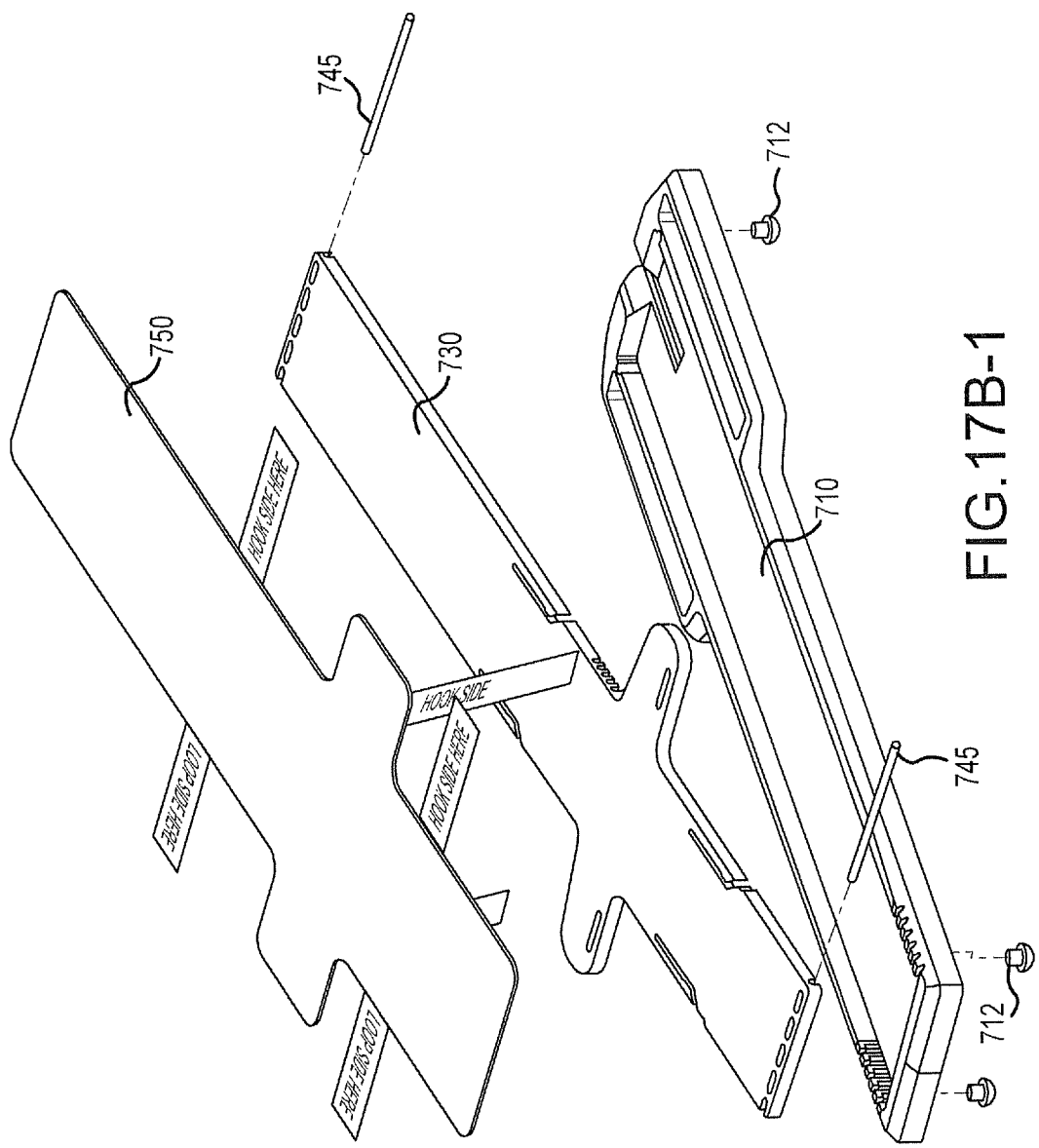
Figures 2, 17B:
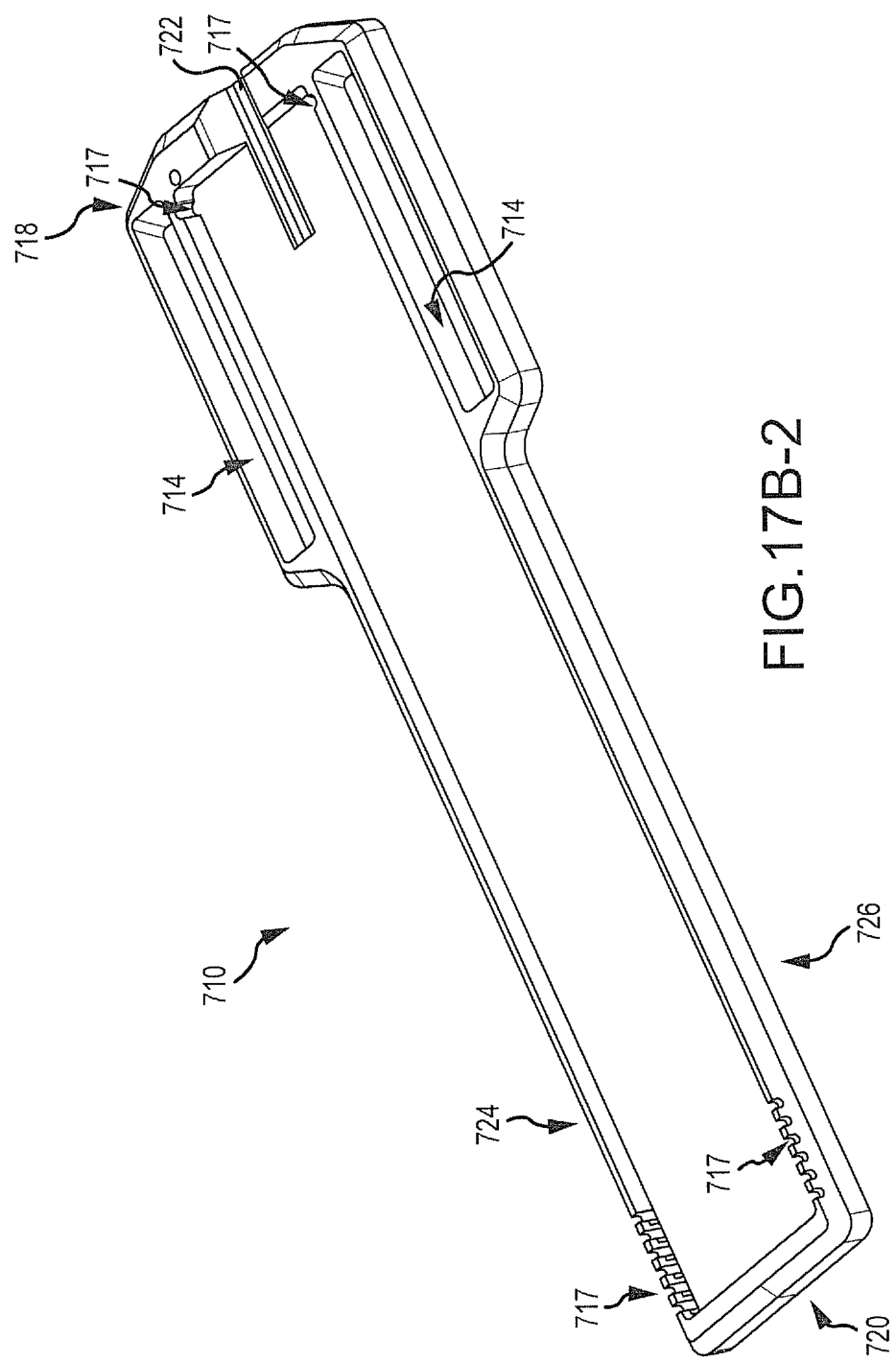
Figures 3, 17B:
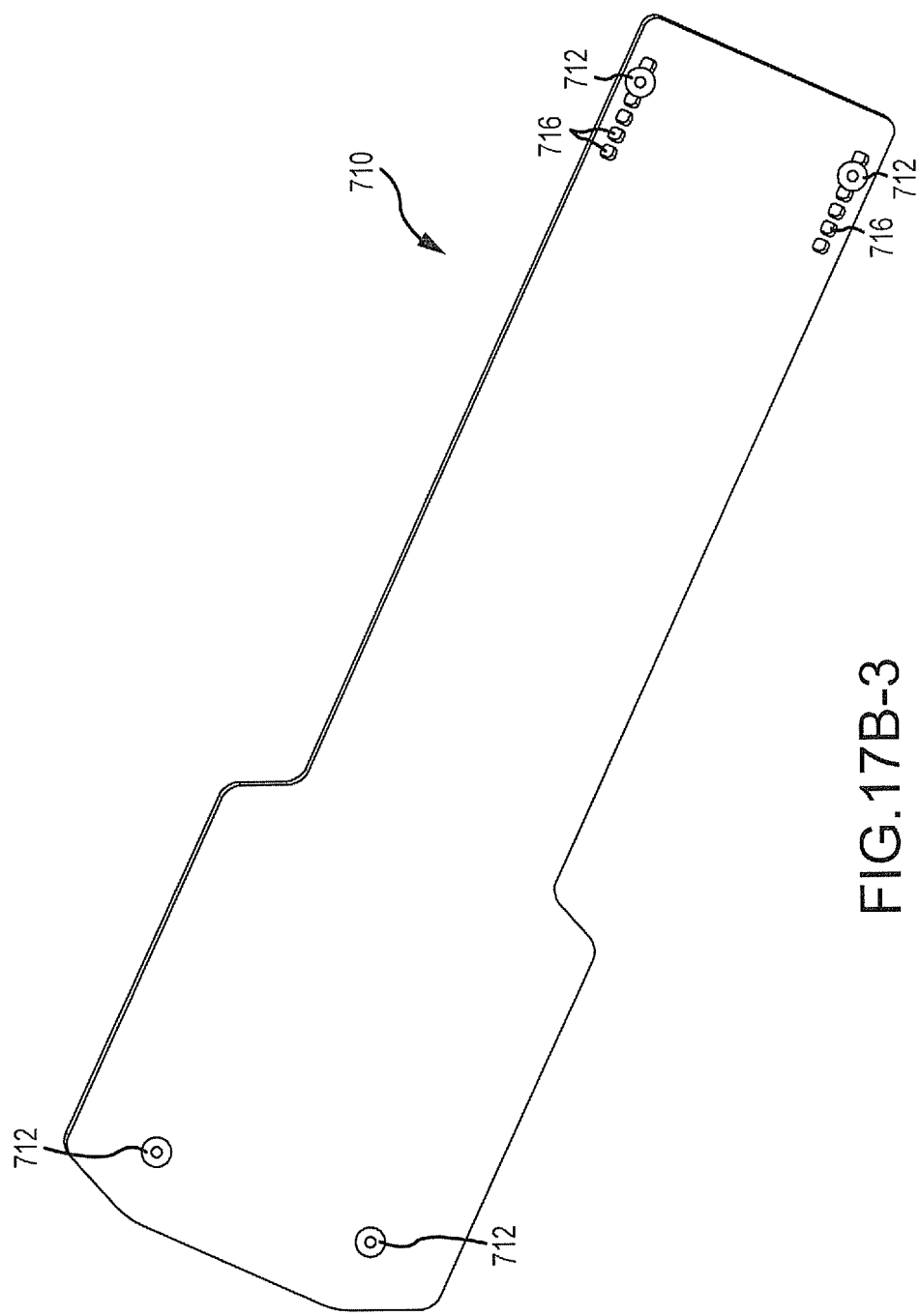
Figures 4, 17B:
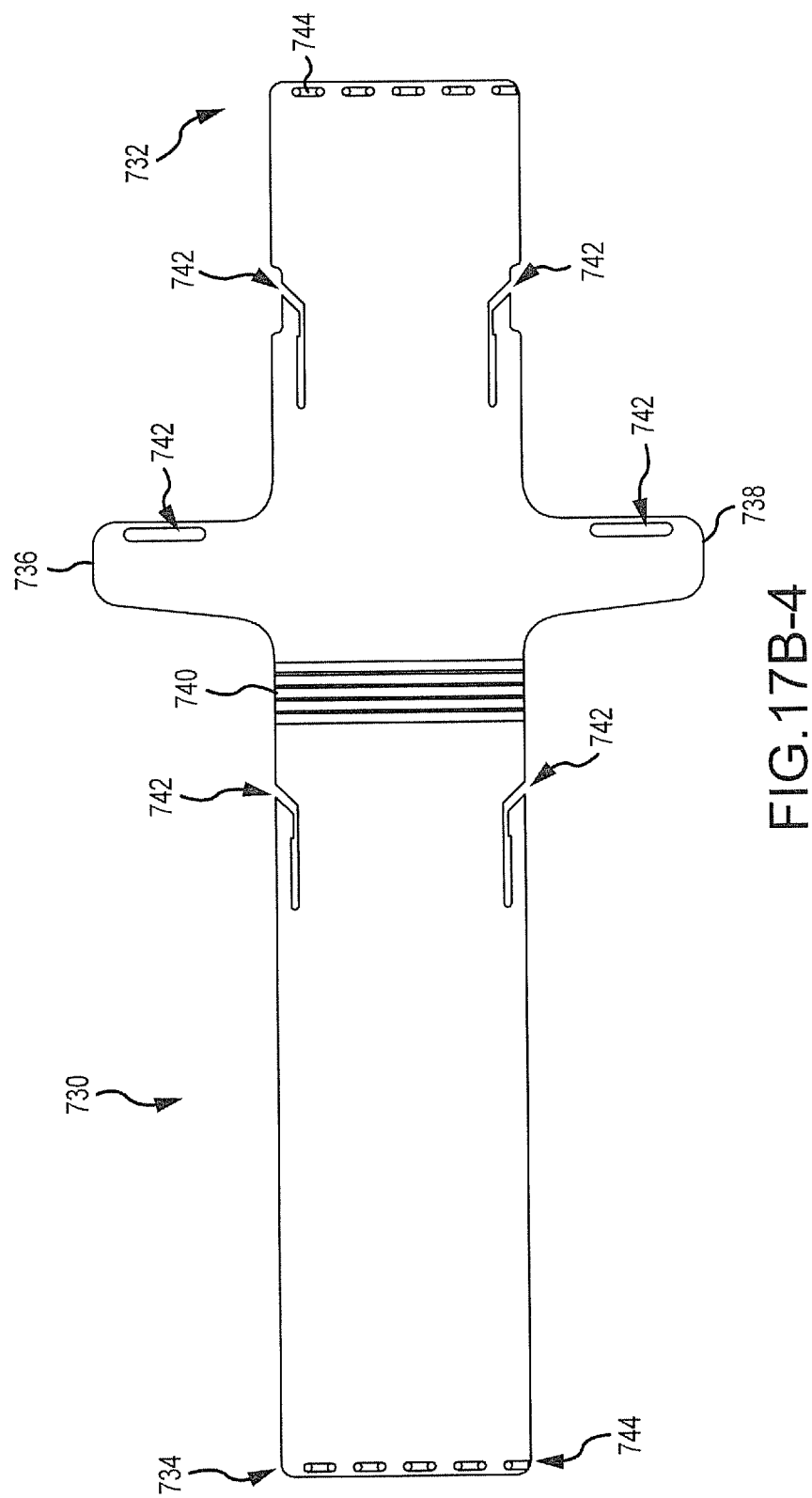
Figures 5, 17B:
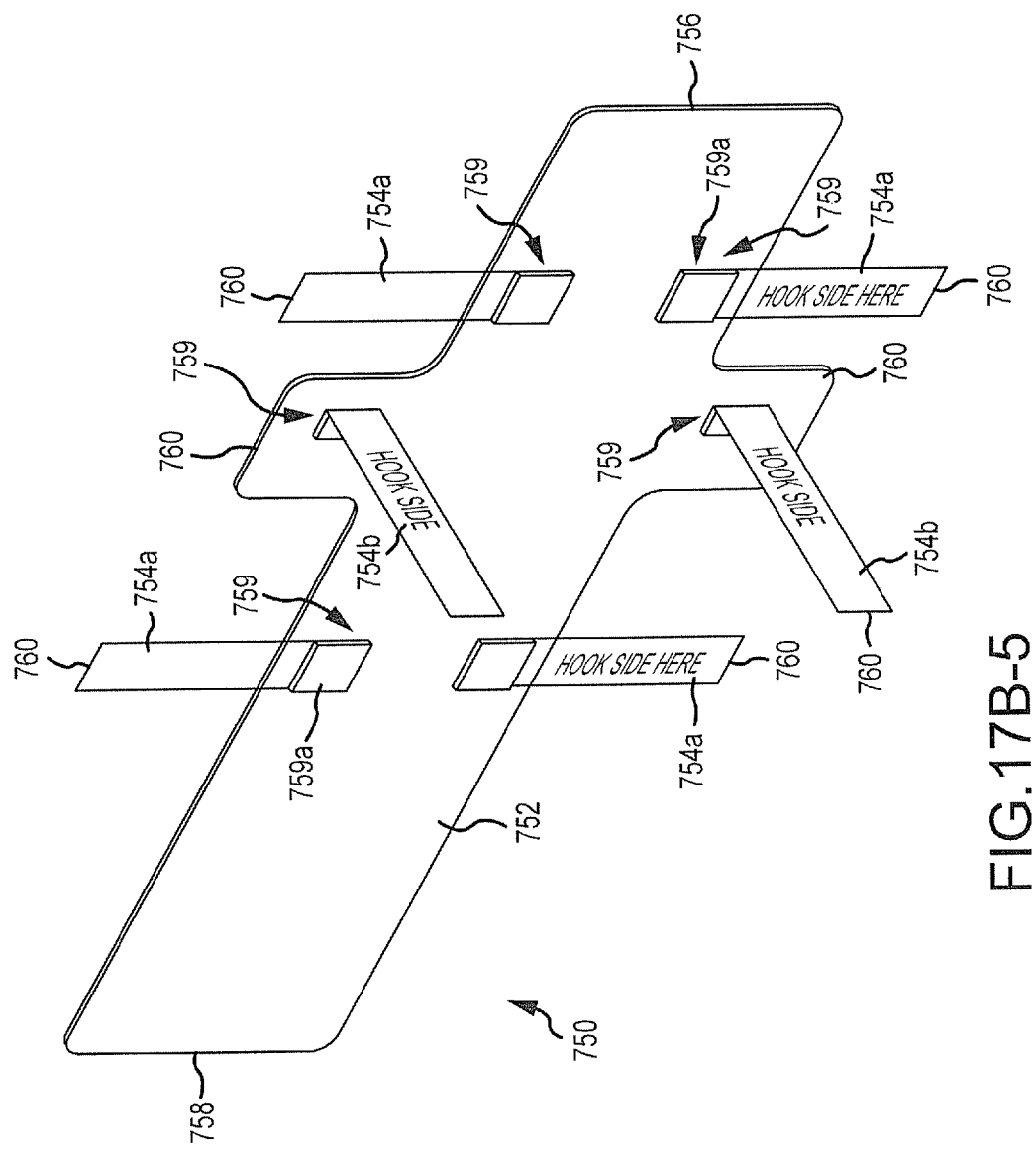

As shown in FIG. 17B-1, the handboard assembly 705 includes a baseplate chassis 710, a handboard flexboard 730 and a drape assembly 750. The handboard assembly 705 is configured to receive a patient's hand and to hold the hand steady during a release procedure. The baseplate chassis 710, the handboard flexboard 730 and the drape assembly 750 may be manufactured as separate pieces and operably connected as indicated in FIG. 17A (or as indicated in a different embodiment, shown in FIG. 18A). The baseplate chassis 710 may be made of steel or steel alloy or other appropriate material. The handboard flexboard 730 may be made of polypropylene or other appropriate material. The drape assembly 750 may be made of SMS (spunbound-meltdown-spunbound) material (a synthetic blown fabric) or other appropriate material (e.g. other non-woven materials) and the tabs 754 may be nylon Velcro straps or other appropriate material.

As indicated in FIGS. 17B-2 and 17B-3, which show top and bottom isometric views of the baseplate chassis 710, the chassis 710 has a first end 718 and a second end 720 and is generally rectangular in shape. The chassis 710 may also include pin slots 717, a first cavity 714 configured to receive a nerve detection system or neuro-monitoring device 500, a second cavity 722, a plurality of feet 712 and a plurality of openings 716 configured to selectively receive a foot 712. The second cavity 722 is configured to receive or at least not hinder the movement of the distal handle of the release system when the system is in use.

As shown in FIG. 17B-2, in one embodiment, the first end 718 of the chassis 710 includes two first cavities 714 configured to receive a nerve detection system 500. In other embodiments, there may be a single first cavity or more than two cavities. In some embodiments, the chassis 710 may not include a cavity 714.

As indicated in FIG. 17B-2, the chassis 710 also includes pin slots 717 configured to removably receive the ends of the handboard pin 745 once the handboard pin 745 has been assembled with the flexboard 730 (see discussion below with respect to FIG. 17B-4). The second end 720 of the chassis 710 includes six pin slots 717 on each of the left and right sides 724, 726 of the chassis 710. The first end 718 of the chassis 710 includes one pin slot 717 on each of the left and right sides 724, 726 of the chassis 710. The handboard pin 745 may be selectively positioned in any of the pin slots 717 as needed for proper positioning of the hand during a release procedure. In other embodiments, the chassis 710 may include greater than seven slots 717 on each side or fewer than seven slots 717 on each side. In some embodiments, the slots 717 may be located in other positions about the chassis 710, such as closer to the middle of the respective sides of the chassis 710. Further, additional embodiments may include other mechanisms for adjusting the position of the components of the handboard. These mechanisms are discussed below with reference to FIGS. 17B-7A through 17B-11B.

As shown in FIG. 17B-3, the feet 712 are generally mushroom-shaped and may be made of rubber or other appropriate material. The feet 712 are removably coupled to the chassis 710. When operably connected to the baseplate chassis 710, the feet 712 are configured to hinder or reduce movement of the chassis 710 while the release system is in use. In one embodiment, four feet 712 may be used. In other embodiments, less than four feet or more than four feet may be used. In some embodiments, the feet 712 may be a different shape such as rectangular or oval or other appropriate shape. In some embodiments, the feet 712 may be integrally formed with the chassis 710.

As indicated in FIG. 17B-3, the second end 720 of the chassis 710 includes six openings 716 on each of the left and right sides 724, 726 of the chassis 710. The first end 718 of the chassis 710 includes one opening 716 on each of the left and right sides 724, 726 of the chassis 710. A foot 712 may be selectively positioned in any of the openings 716 as needed for balancing of the chassis 710 or to hinder or reduce movement of the chassis 710 during use. In other embodiments, the chassis 710 may include greater than seven openings 716 on each side or fewer than seven openings 716 on each side. In some embodiments, the openings 716 may be located in other positions about the chassis 710, such as down a center line of the chassis 710. In some embodiments, the chassis 710 may not include openings 716 such as where the feet 712 are integrally formed with the chassis 710.

Figure 4:
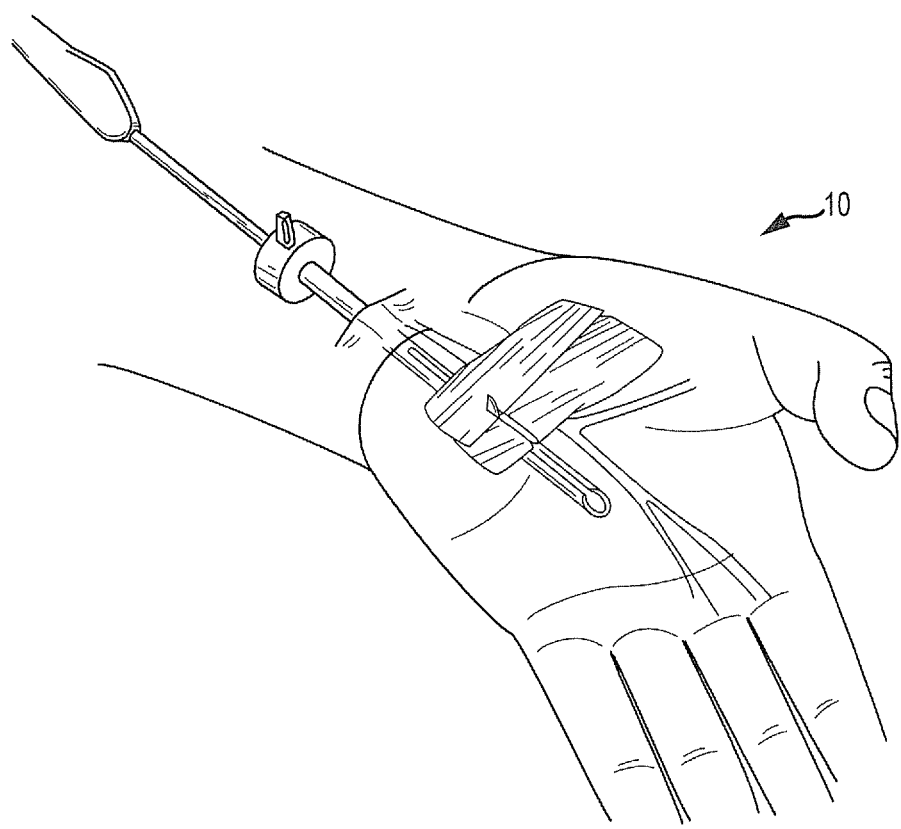
FIG. 4 depicts an endoscopic release surgical procedure being performed on the compressed carpal tunnel area of FIG. 2.

As shown in FIG. 17B-4, which is a bottom elevation view of the handboard flexboard 730, the flexboard 730 is generally rectangular in shape and includes a first end 732 and a second end 734, which generally correspond in width to and generally align with the ends 718, 720 of the chassis 710. The flexboard 730 additionally includes arms 736, 738 extending from opposite sides of the flexboard 730, a flex strip 740, drape slots 742 and pin openings 744.

As can be understood with reference to FIG. 17B-1, the arms 736, 738 extending from the flexboard 730 also include drape slots 742 and thus are configured to accept a portion of the drape assembly 750. As shown in FIG. 17B-4, the flexboard 730 also includes drape slots 742 configured to receive a portion of the drape assembly 750.

As shown in FIG. 17B-4, the flex strip 740 extends transversely across the flexboard 730 and is configured to allow the flexboard 730 to angle or arc or bend when the flexboard 730 is coupled to the chassis 710. This bend encourages proper placement and alignment of a patient's hand during the TCL release procedure (i.e. the patient's hand moves from flexion to extension).

As indicated in FIG. 17B-4, and with reference to FIGS. 17A, 17B-1 and 17B-2, the pin openings 744 are configured to receive a handboard pin 745. Once the handboard pin 745 is inserted, the flexboard 730 may be removably attached to the chassis 710 in any of the pin slots 717 as needed for proper positioning of the hand during a release procedure.

Figures 6, 17B:
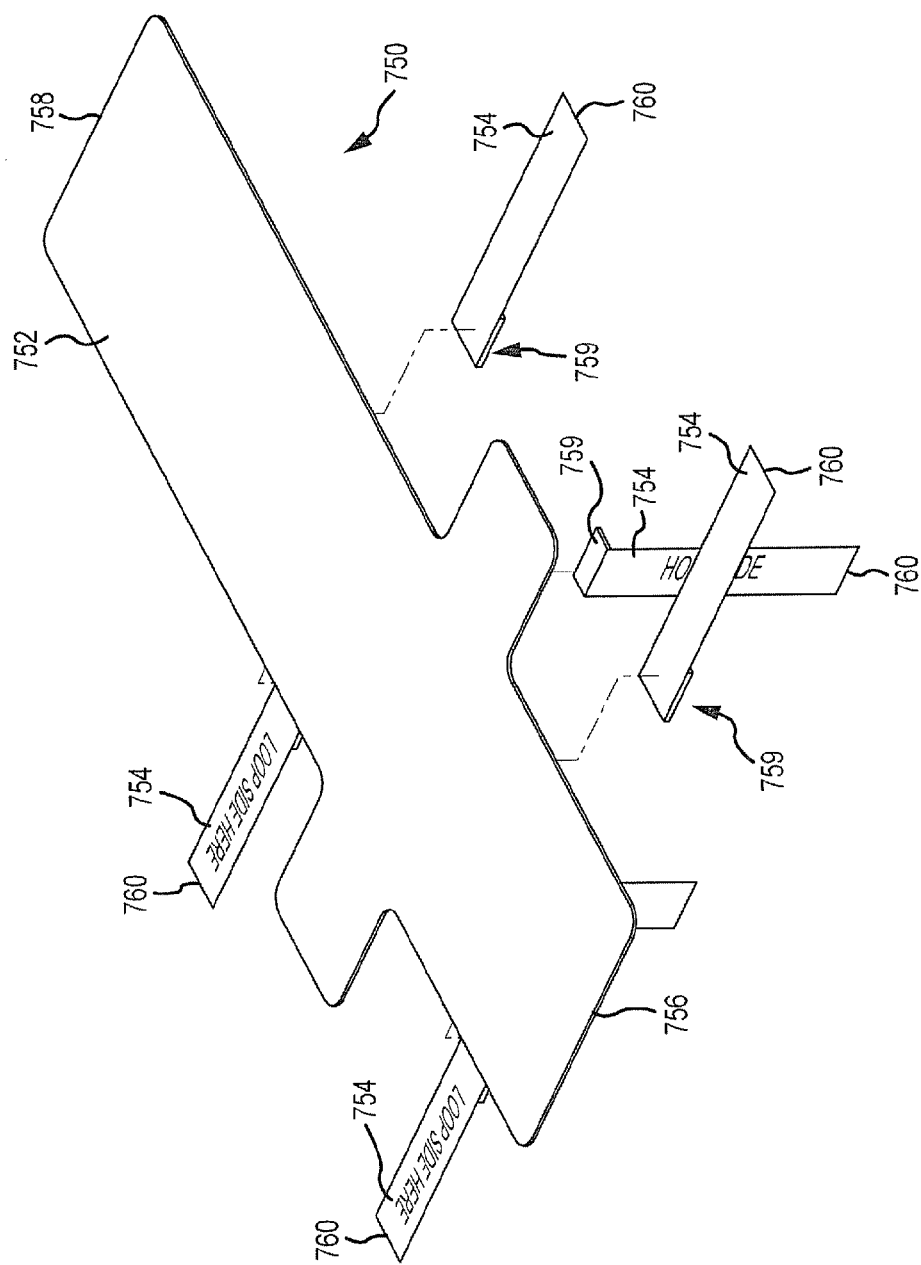
Figures 12A, 12B, 17B:
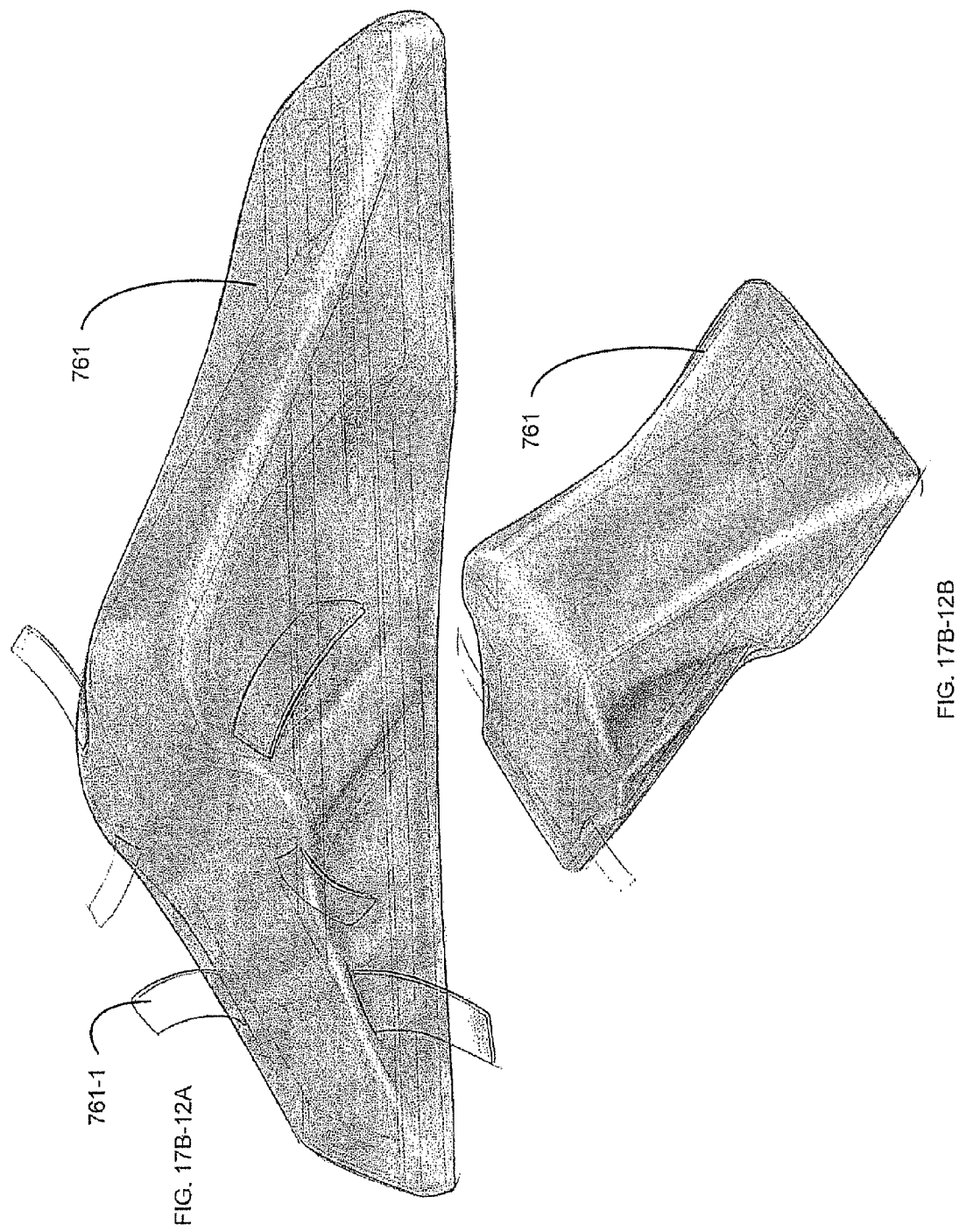

FIGS. 17B-5 and 17B-6 depict a bottom isometric view and an exploded view from a top elevation perspective of the drape assembly 750. As can be understood from FIGS. 17B-5 and 17B-6, in one embodiment, the drape assembly 750 includes a drape body 752 and tabs 754. The drape body 752 includes a first end 756, a second end 758 and arms 760. The drape body 752 is generally rectangular in shape, with generally rectangularly shaped arms 760, and the width of the drape body 752 at each end 756, 758 generally corresponds to the width of the flexboard 730 and the chassis 705. The drape body 752 may be made of SMS material and the tabs 754 may be nylon Velcro straps.

FIGS. 17B-7A through 17B-11B depict several alternate adjustment mechanisms for adjusting the position of the handboard for proper placement of a hand on the handboard 705. The adjustment mechanisms may be used with the pin adjustment system described above, or may be used in lieu of the pin adjustment system. In general, any known or hereafter mechanism for incrementally adjusting the placement of the flexboard 730 within the handboard assembly 705 is contemplated and may be integrated into the handboard. The following are merely examples of the many adjustment mechanisms that may be used.

FIGS. 17B-7A and 17B-7B depict a balloon adjustment mechanism for the handboard assembly 705. More particularly, a series of air-filled sacs, or balloons 705-1, may be located on the baseplate chassis 710 at the second end 720, adjacent to one end of the flexboard 730. To adjust the position of the flexboard 730, one or more of the balloons 705-1 may be inflated or deflated with air or other gas. Increasing inflation of the balloons 705-1 causes the flexboard 730 to slide along the baseplate chassis 710 so as to increase the height of the flexboard, and decreasing inflation of the balloons 705-1 allows the flexboard 730 to slide along the baseplate chassis 710 in an opposite direction so as to decrease the height of the flexboard, the resulting operation brought about by inflation/deflation of the balloons being similar to the pin adjustment mechanism described above to adjust the position of a hand of a patient upon the handboard.

Figure 8A:
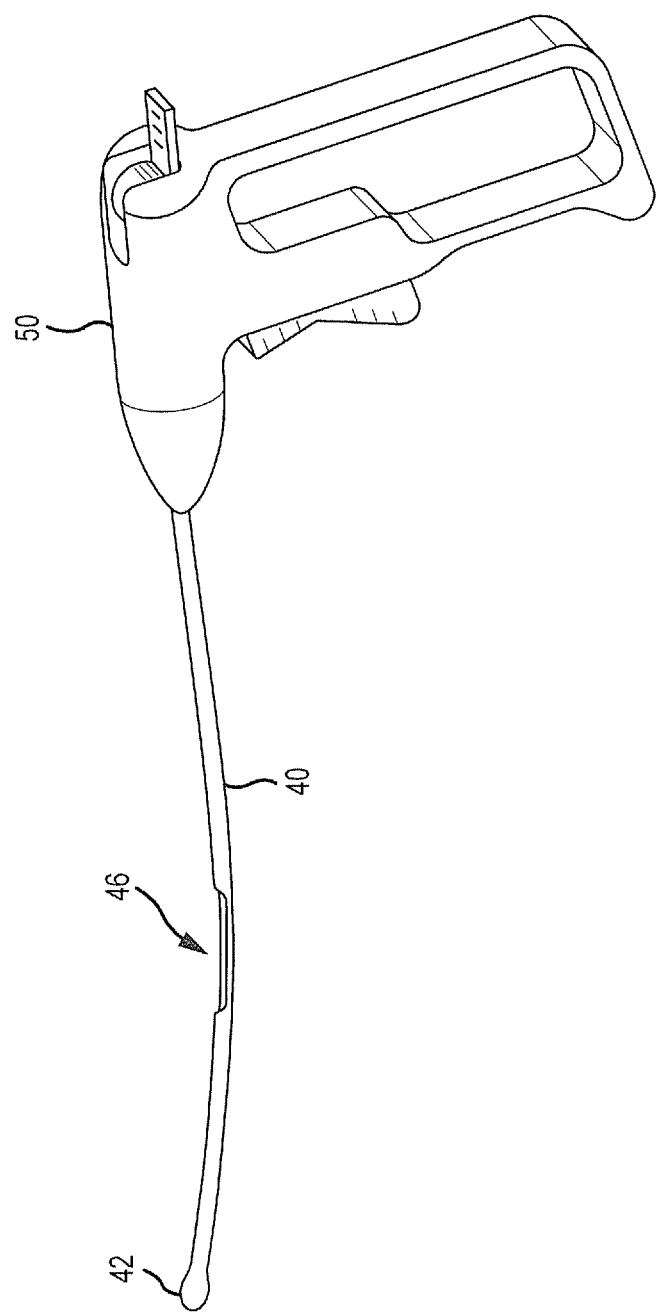
FIG. 8A depicts another embodiment of the release system, wherein an elongated body is shown connected to one embodiment of a handle member and the hand and the introducer are not shown for clarity purposes.
Figure 8B:
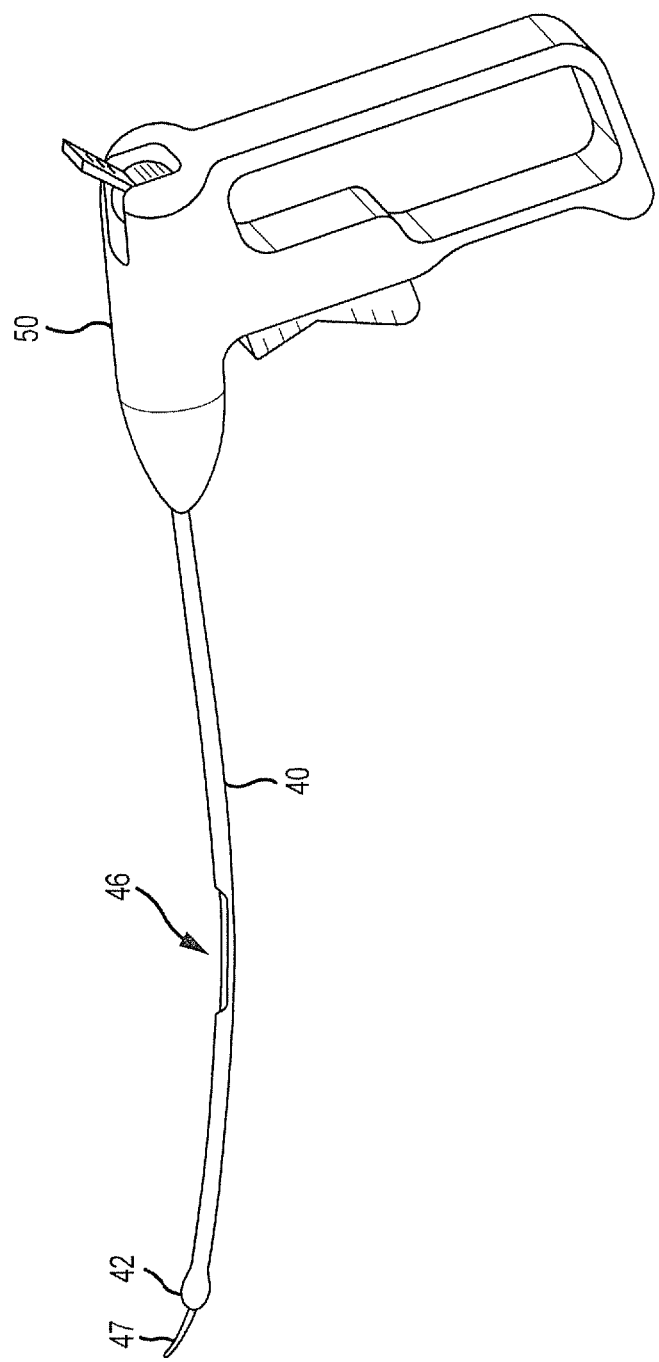
FIG. 8B depicts the elongated body of FIG. 8A wherein one embodiment of the internal cutting wire of FIG. 6B is introduced through the elongated body.
Figure 8C:
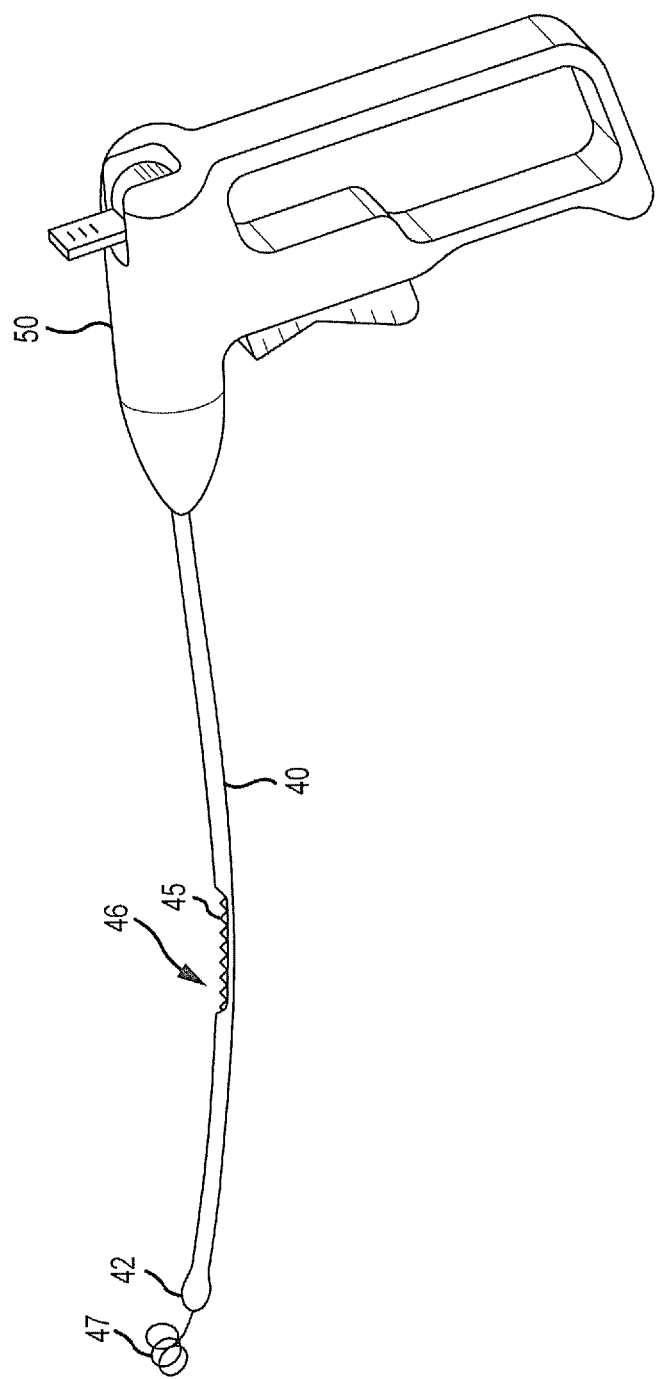
FIG. 8C depicts the elongated body of FIG. 8A, wherein a cutting member is shown.
Figure 8D:
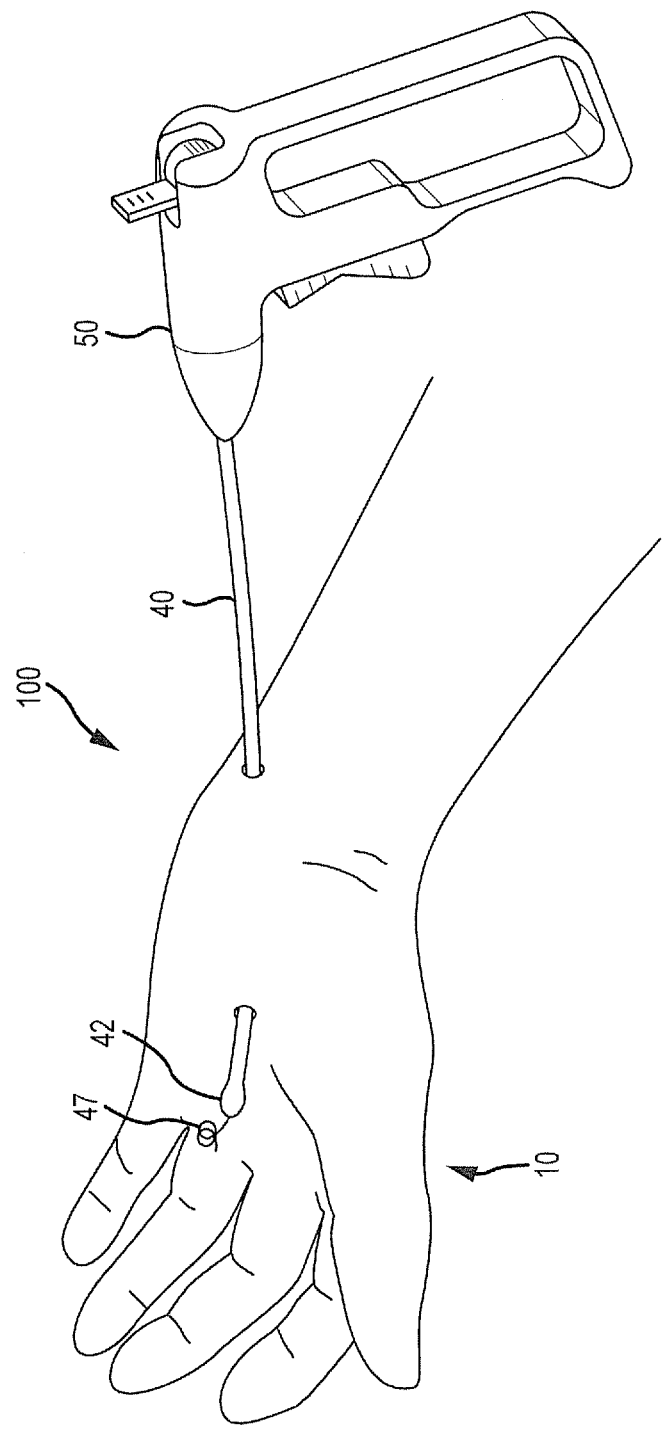
FIG. 8D illustrates the elongated body and internal cutting wire of FIG. 8B wherein the hand is shown.

In another embodiment, shown in FIGS. 17B-8A through 17B-8C, a ratchet adjustment mechanism is utilized on the handboard assembly 705. The ratchet assembly 705-2 is located on the baseplate chassis 710 adjacent to one end of the flexboard 730. The ratchet mechanism may include a series of teeth 705-3 disposed along the surface of the baseplate chassis 710 that align with one or more pawls 705-4 on the flexboard 730. In general, the one or more pawls 705-4 engage the teeth 705-3 of the ratchet system to hold the flexboard 730 in position. To adjust the placement of the flexboard 730, the pawl 705-4 may engage any of the teeth 705-3 as desired.

In yet another embodiment of the handboard 705, shown in FIGS. 17B-9A and 17B-9B, a rack-and-pinion adjustment mechanism is utilized to adjust the position of the handboard. The rack-and-pinion assembly 705-5 is located on the baseplate chassis 710 adjacent to one end of the flexboard 730. The rack-and-pinion mechanism 705-5 may include a linear rack 705-6 with a series of teeth disposed along the linear rack. The linear rack 705-6 engages a pinion 705-7 device on one end of the flexboard 730. To adjust the position of the flexboard 730, the pinion device 705-7 may be rotated to cause the pinion to engage the teeth to slide along the rack 705-6 until the flexboard is in the desired position.

In yet another embodiment of the handboard, shown in FIGS. 17B-10A and 17B-10B, a scissor adjustment mechanism 705-8 is utilized on the handboard assembly 705. Similar to the above structures, the scissor assembly 705-8 is located on the baseplate chassis 710 adjacent to one end of the flexboard 730. The scissor mechanism 705-8 may include linked, folding supports that engage one end of the flexboard 730. To adjust the position of the flexboard 730, the scissor device 705-8 may be extended or withdrawn to slide along the baseplate chassis 710 into a desired position.

In still another embodiment of the handboard, shown in FIGS. 17B-11A and 17B-11B, a screw adjustment mechanism 705-9 is utilized on the handboard assembly 705. Similar to the above structures, the screw assembly 705-9 is located on the baseplate chassis 710 adjacent to one end of the flexboard 730. The screw mechanism 705-9 may include a screw device 705-10 positioned longitudinally along the base of the baseplate chassis 710. The thread of the screw device 705-10 engages a tab at one end of the flexboard 730 such that, when the screw is rotated, the tab and flexboard slide along the baseplate chassis 710 into a desired position.

As shown in FIGS. 17B-5 and 17B-6, the tabs 754 are generally rectangular in shape and include a drape end 759 and a flexboard end 760. The drape end 759 of the tabs 754 may be different. That is, tabs 754a may include a slightly raised, hollow box 759a at the drape end 759. This slightly raised, hollow box 759a is the attachment surface of the tab 754a. Tabs 754b may include a lip 759b at the drape end 759. The lip 759b is the attachment surface of the tab 754b. The tabs 754 may be operably connected to the drape body 752 by velcro or other adhesive, such as glue or tape or by other appropriate attachment features. In some embodiments, the tabs 754 may also include a reference or other informative direction to assist the user in assembling the release system (i.e. connecting the disposable drape body to the flexboard) and/or for securing the patient's hand to the handboard assembly 705.

The handboard 705 may also include a drape glove 761 that fits over the handboard assembly and acts to keep the assembly sterilized during use. The drape glove 761 is shown in FIGS. 17B-12A and 17B-12B. In one embodiment, the drape glove 761 includes adhesive tape 761-1 to affix the drape glove to the handboard assembly 705.

Figures 13, 17B:
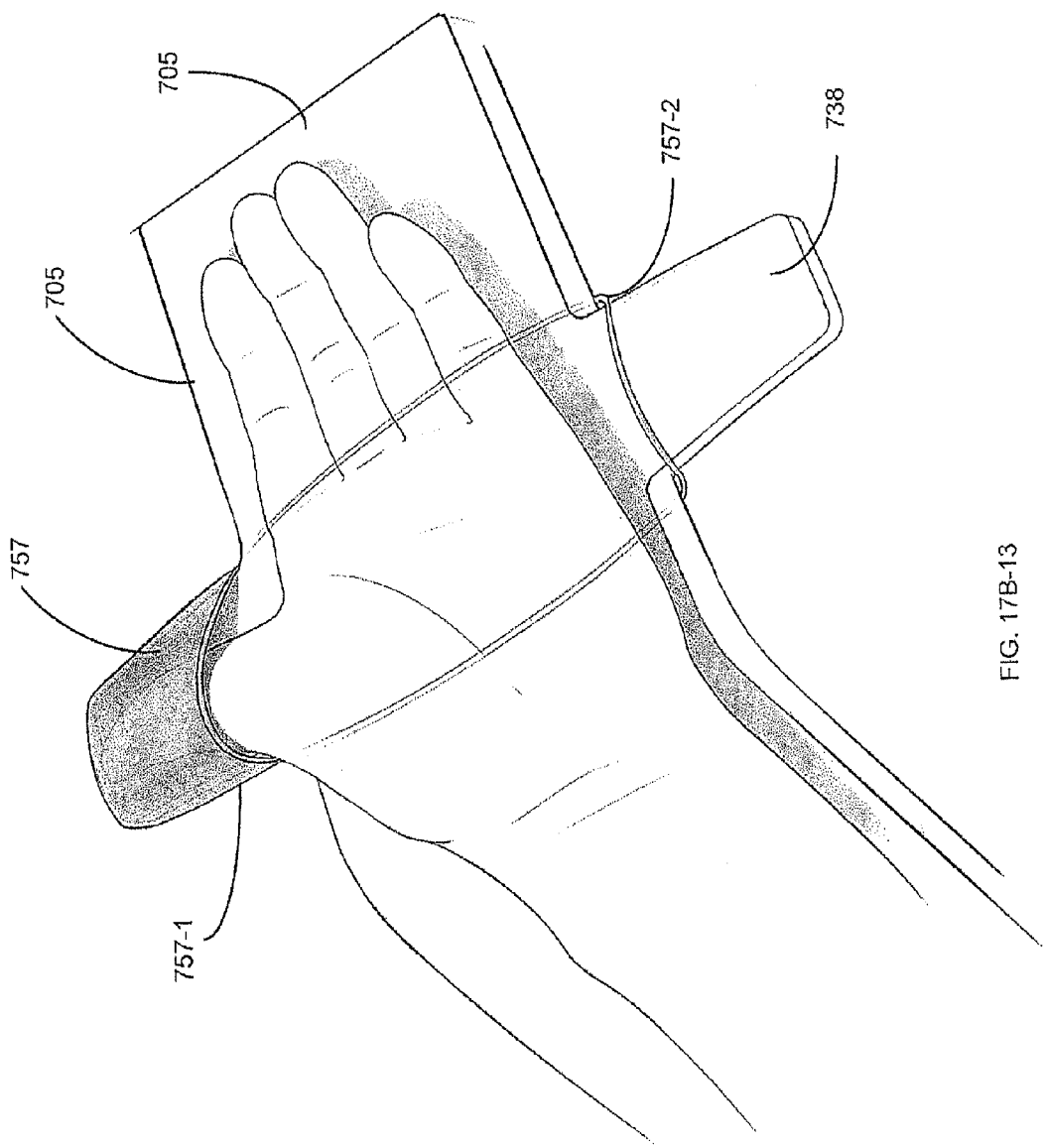

Another embodiment of the handboard assembly 705 includes a thumb girdle 757 that secures the thumb of a patient to the handboard assembly. As shown in FIG. 17B-13, the thumb girdle 757 includes a sock 757-1 that fits over one arm of the flexboard 730 and the thumb of a patient. In addition, a flexible tie string 757-2 or other lacing device is attached to the sock 757-1 that loops around the opposite arm 738 of the flexboard 730 to secure the thumb to the handboard assembly. In this position, the thumb is abducted to place the transverse carpal ligament in tension to allow for ease of cutting.

In use, the handboard assembly 705 is assembled by placing the feet 712 in the desired openings 716 of the chassis 710 and the tabs 754 are operably connected to the drape body 752 and the drape body 752 is operably attached to the flexboard 730 by via the tabs 754 which are received in their respective drape slots 742. Any or all of these steps may have been previously completed by the manufacturer. The tabs 754 may also be used to secure the patient's hand to the handboard assembly 705. The handboard pins 745 are also inserted into their respective openings 744 and the flexboard 730 with drape assembly 750 may now be operably and removably attached to the chassis 710. In one embodiment, the ends 734, 720 are attached first to allow the user to determine the desired angle at which to bend the flexboard 730 at the flex strip 740. The angle or arc is determined based on the desired flexion of the hand. Once the desired angle is found, the other end 732 of the flexboard 730, with drape assembly 750 attached, may now be operably and removably attached to the slots 717 at the end 718 of the chassis 710.

Figures 1, 17C:
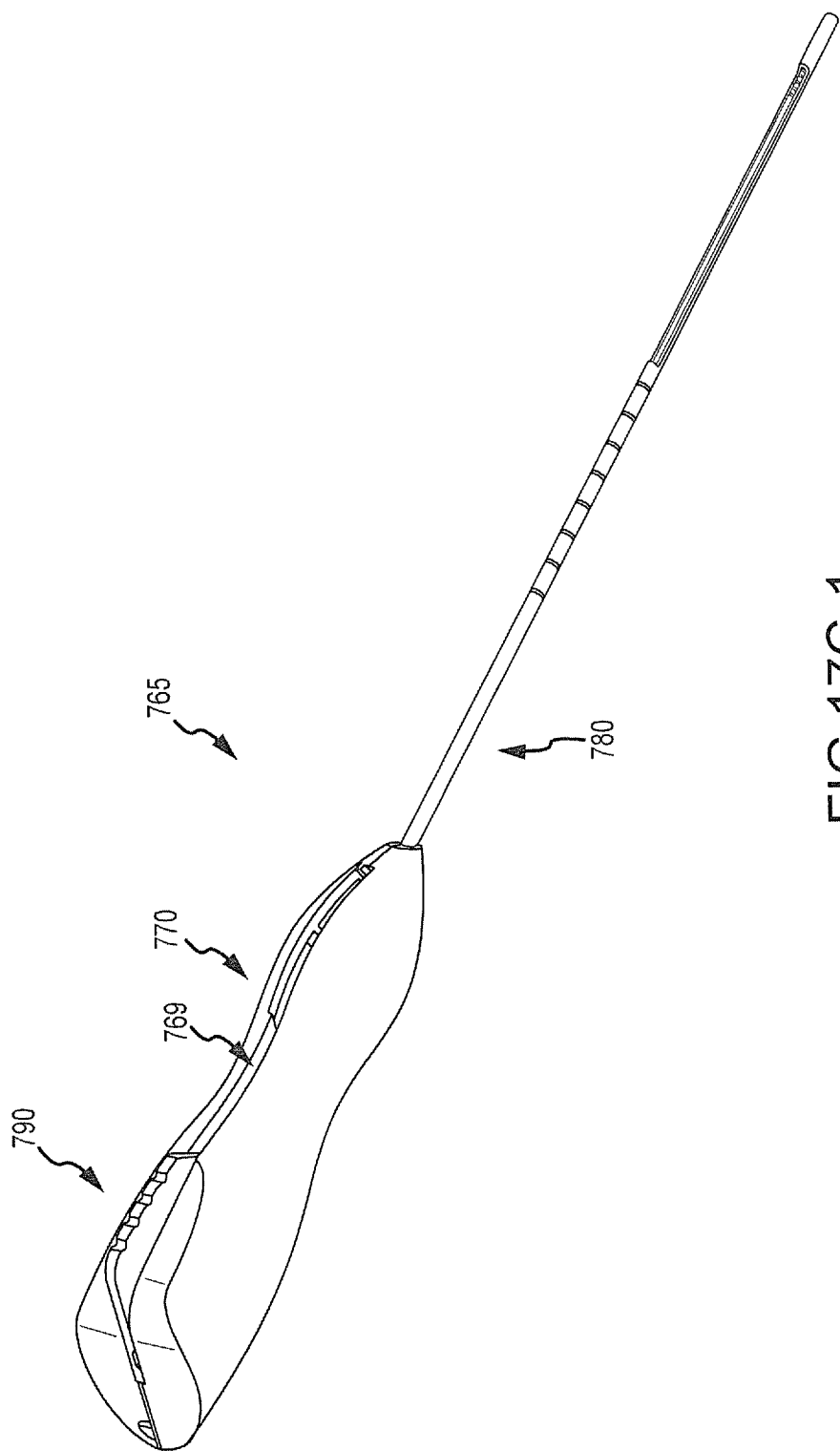
Figures 3, 17C:
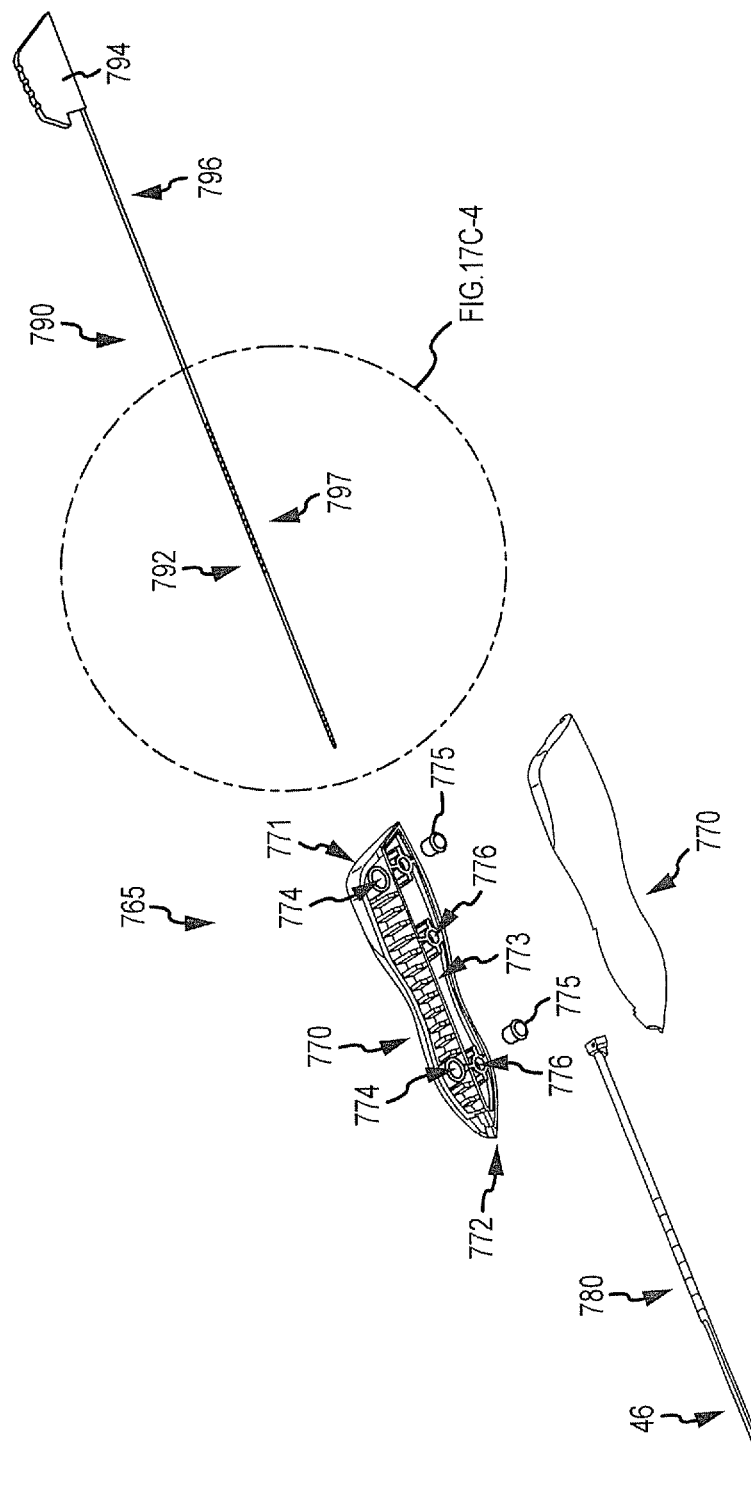
Figures 4, 17C:
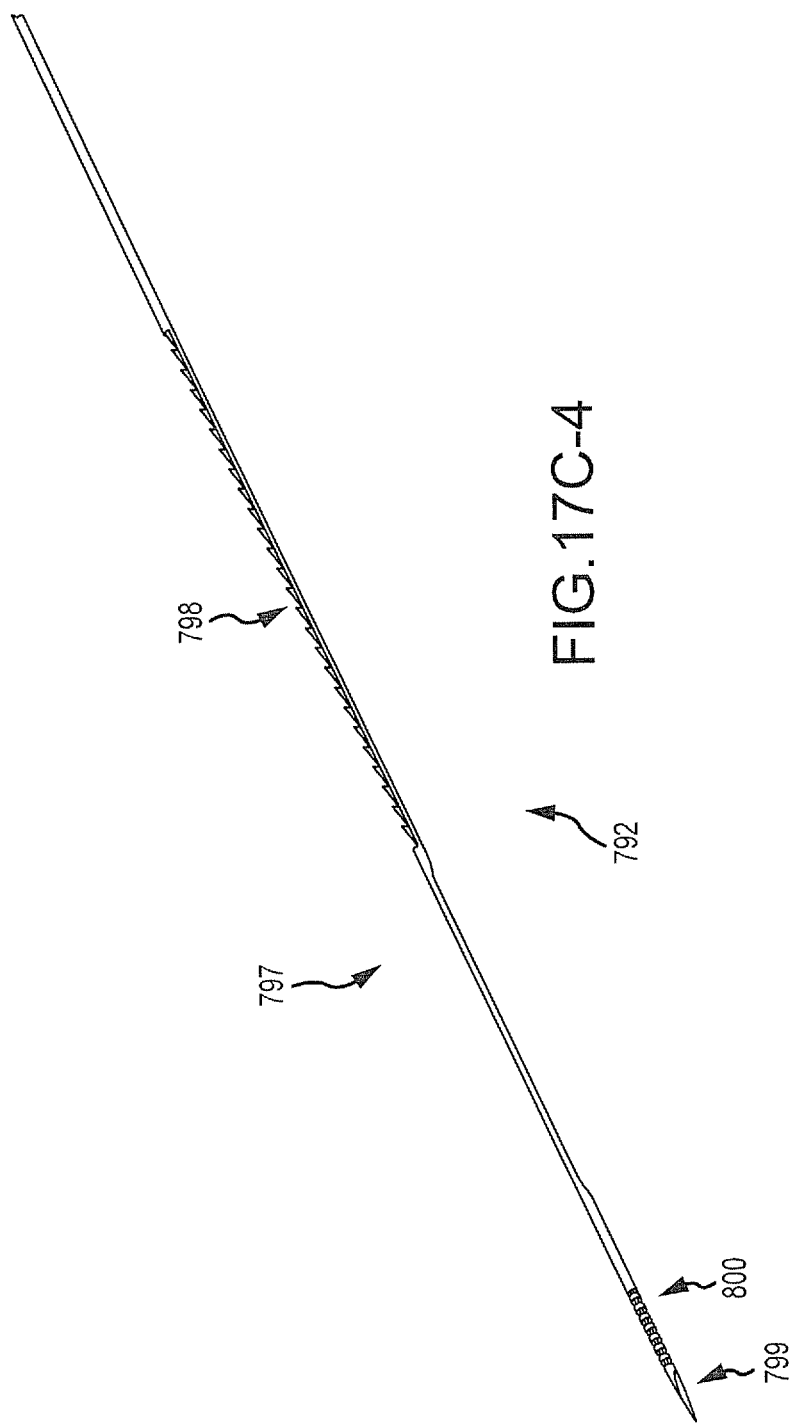
Figures 5, 17C:
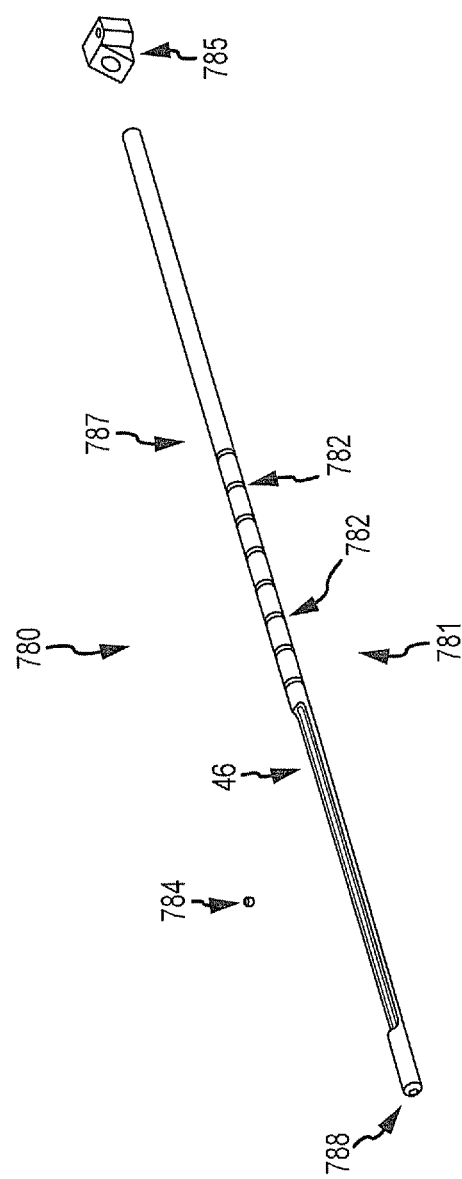

As can be understood from FIG. 17C-1, which depicts the proximal handle assembly 765 in a non-deployed state, the handle assembly 765 includes a handle 770 having a slider channel 769, a probe wire assembly 780 and a cutting wire assembly 790. The handle may be made of polycarbonate or other appropriate material. As shown in FIGS. 17C-2 and 17C-3, which depict a partially exploded view of each side of the proximal handle assembly 765, the handle 770 includes a slider end 771, a probe end 772, a saw wire channel 773 extending axially through the handle 770, ball detent openings 774, ball detents 775, female fastening members 776 and male fastening members 777. Female fastening members 776 are configured to receive male fastening members 777, thereby joining each side of the handle 770. Additional fastening members (not shown) such as screws or pins may be used to further secure the female and male fastening members 776, 777. In some embodiments, the handle assembly 765 may also include wiring (nerve wire assembly 850 and see 550 on FIG. 18) configured to electrically couple components of the handle assembly 765, such as the probe wire assembly 780, with a neuro-monitoring or nerve detection device 500.

As indicated in FIGS. 17C-2 and 17C-3, the cutting wire assembly 790 includes a needle saw wire 792 and a needle saw wire slider 794. The saw wire 792 and saw wire slider 794 may be made of steel, a steel alloy or other appropriate material. The needle saw wire 792 includes a slider end 796 and a distal end 797. The slider end 796 of the needle saw wire 792 is coupled to the slider 794 by laser welding or other appropriate method. The needle saw wire slider 794 provides a gripping or pushing surface by which the user can extend and retract the needle saw wire 792 from a non-deployed to or from a deployed state. The saw wire channel 773 extending axially through the handle 770 is configured to receive the saw wire 792 as it extends through the handle as the slider 794 transitions from a non-deployed state (see FIG. 17C-1) to a deployed state (see FIG. 17H) and back to a non-deployed state.

As can be seen in FIG. 17C-2, the slider 794 includes an opening 795 configured to receive the ball detents 775. As indicated in FIGS. 17C-2 and 17C-3, the ball detent openings 774 are configured to receive ball detents 775. The ball detents 775 extend into the slider channel 769 of the handle 770 to hinder or restrict movement of the needle saw wire slider 794 once it is positioned in a non-deployed state (FIG. 17C-1) or fully deployed state (FIG. 17H).

As shown in FIG. 17C-4, which is an enlarged view of the distal end 797 of the needle saw wire 792, the needle saw wire 792 includes a tissue cutting member 798, such as a plurality of teeth 798, a penetration tip or piercing member 799 and threads or ridges 800. In some embodiments, the cutting member 798 may be another cutting or abrasive surface or may be the saw wire itself. With reference to FIG. 17C-1, the saw wire 792 is configured to be received in the probe assembly 780 and the teeth 798 are configured to be exposed in the window 46 of the probe assembly 780 once the window 46 is properly positioned for a release procedure. In some embodiments, the teeth 798 may be unidirectional. In other embodiments, the teeth may have a shape as disclosed elsewhere herein. The piercing member 799 is configured to puncture the skin in the palm of the hand during a release procedure and, as described in more detail below, is received by the distal handle. The threads 800 secure the needle saw wire 792 in the distal handle during a procedure.

As indicated in FIG. 17C-5, which illustrates an exploded view of the probe wire assembly, the probe wire assembly 780 includes an elongated body 781 having a window 46 and threads 782, a bump pin 784 and an elongated body mount 785. The elongated body 781 is received in the body mount 785. The mount 785 and the body 781 are coupled by any appropriate method, such as welding. The bump pin 784 is received in the elongated body 781 at approximately the window 46 and hinders or restricts forward movement of the needle 799 and teeth 798 of the needle saw wire assembly 790 when the slider 794 is in a non-deployed position. The threads 782 of the elongated body 781 are configured to receive a motion limiting feature 820, such as a shaft lock assembly 820, as described in more detail below. The elongated body 781 may be coated with a non-conductive coating, such as Parylene C or other appropriate material.

Figures 1, 17D:
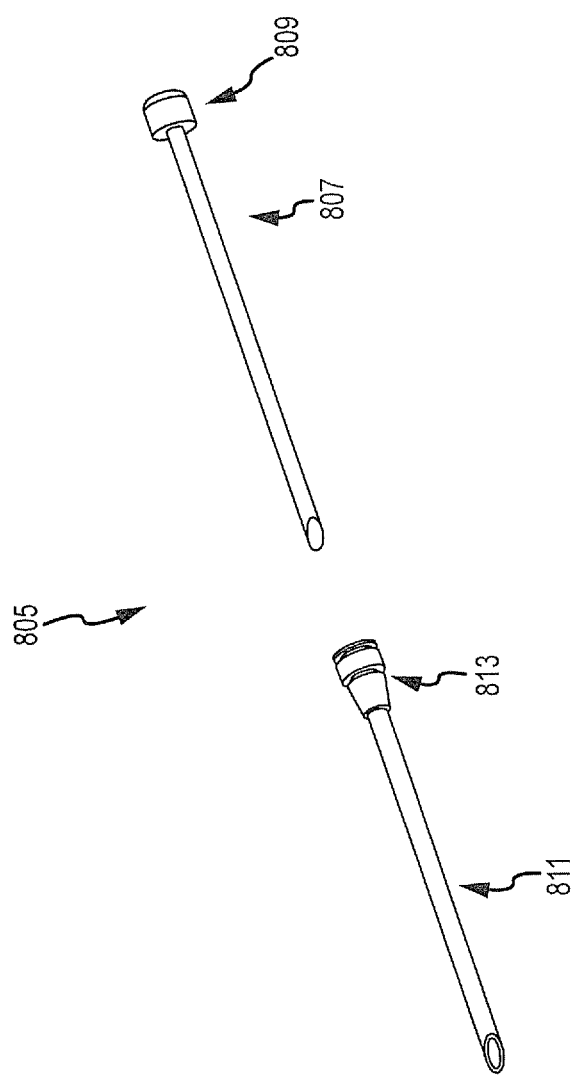
Figures 2, 17D:
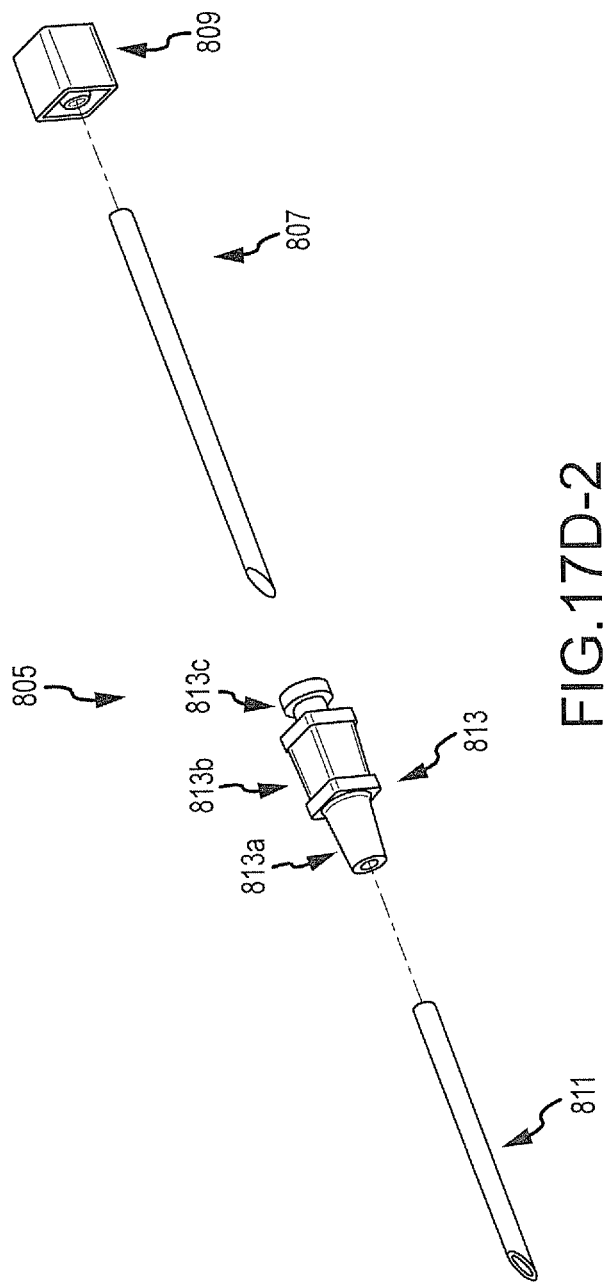
Figures 2, 3, 17E:
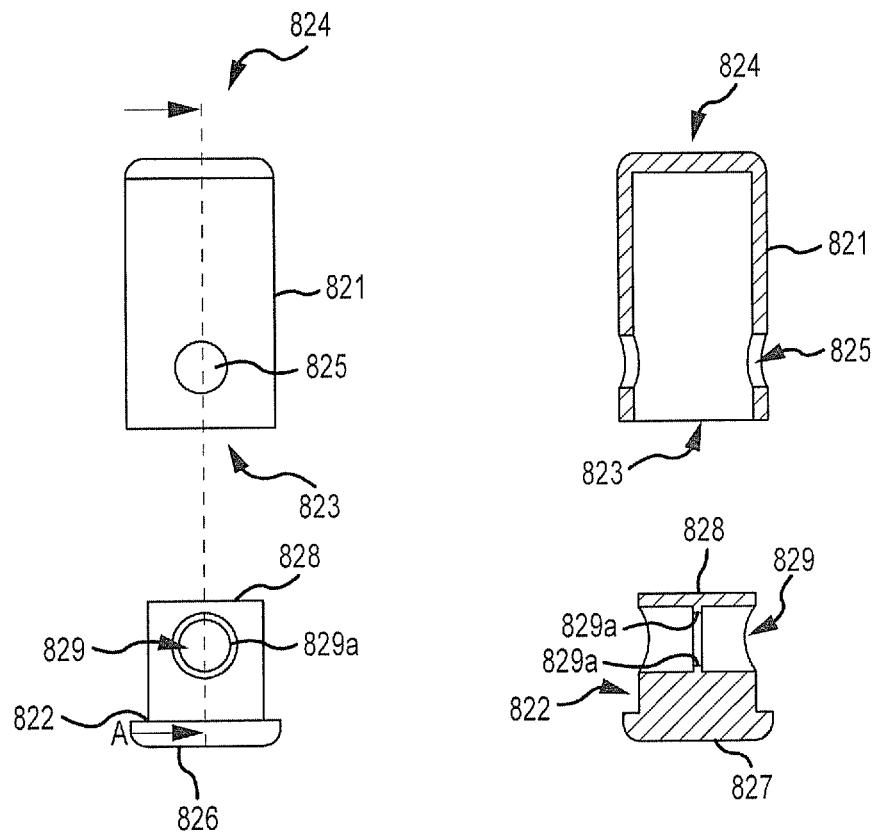
Figures 1, 17E:
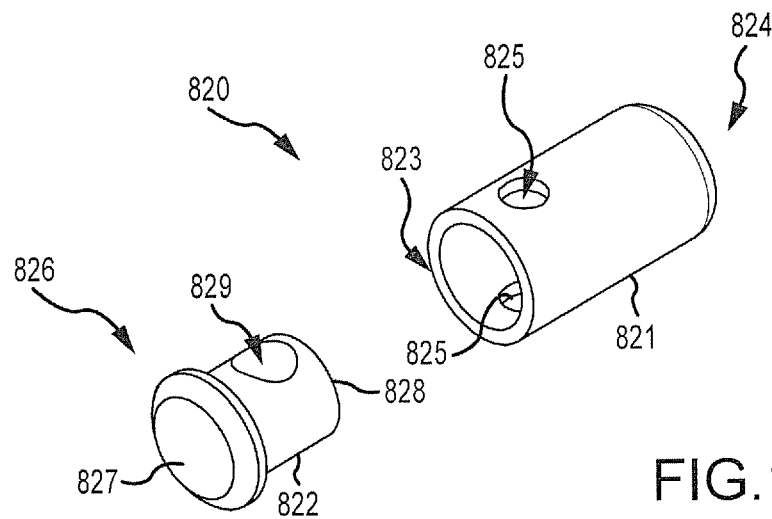

With reference to FIG. 17A and as shown in FIGS. 17D and 17E, the system may also include an introducer assembly 805 and a motion limiting feature 820. As indicated in FIGS. 17D-1 and 17D-2, which illustrate two different embodiments of an introducer assembly, the introducer assembly 805 may include an introducer stylet 807, a stylet hub 809, an introducer needle 811 and a needle hub 813. As shown in FIG. 17D-1 and with reference to FIG. 17A, the stylet 807 and the needle 811 are hollow, elongated bodies configured to receive the probe wire assembly 780 and the cutting wire assembly 790. The needle 811 and needle hub 813 are also configured to receive the stylet 807 and stylet hub 809. The introducer stylet 807 and stylet hub 809 may be integrally formed (see FIG. 17D-1) or formed separately and subsequently coupled (see FIG. 17D-2). In one embodiment, the stylet hub 809 may be generally rounded and the needle hub 813 may be generally cylindrical (see FIG. 17D-1). In other embodiments, the stylet hub 809 may be generally rectangular and the needle hub 813 may include cylindrical 813a, rectangular 813b and disc 813c shaped portions (see FIG. 17D-2). In other embodiments, it can be appreciated that the hubs 809, 813 may be any other appropriate shape or combination of shapes. The components of the introducer assembly 805 may be made of stainless steel or a steel alloy or other appropriate material.

As shown in FIGS. 17E-1 to 17E-3, which show an isometric, side elevation and cross sectional elevation of the motion limiting feature, respectively, and with reference to FIG. 17A, the system 700 may also include a motion limiting feature 820, such as a shaft lock assembly 820. In one embodiment, the shaft lock assembly 820 includes a shaft lock 821, a shaft lock inner portion 822 and a spring (not shown). The components of the shaft lock assembly may be made of stainless steel or a steel alloy or other appropriate material. The spring may be a McMaster PN#9001T22. The shaft lock 821 is generally cylindrical and includes an open proximal end 823, a closed distal end 824 and an opening 825 configured to receive the probe wire assembly 780 or the introducer needle 811 as detailed herein. The shaft lock inner portion 822 is generally mushroom shaped and includes a disc shaped proximal portion 826 with a closed end 827, a cylindrical body with an open end 828 and a probe wire assembly opening 829 located in the body and configured to receive the probe wire assembly 780 as detailed above. The lock 821, inner portion 822 and spring are assembled together (the spring is received in the lock 821 and then the inner portion 822 is received in the lock 821) and introduced to the probe wire assembly 780 or the introducer needle 811. The inner portion is depressed, thereby engaging the spring and aligning the openings 825, 829 such that the probe wire assembly 780 or the introducer needle 811 can be engaged. A lip 829a in the inner portion 822 engages the assembly 780 or needle 811 and together with the spring, maintains the shaft lock assembly 820 in the desired position. To release the shaft lock assembly 820, the inner portion 822 is again depressed, thereby aligning the openings 825, 829, and the assembly 820 is removed from the probe wire assembly 780 or the needle 811.

Figures 1, 17F:
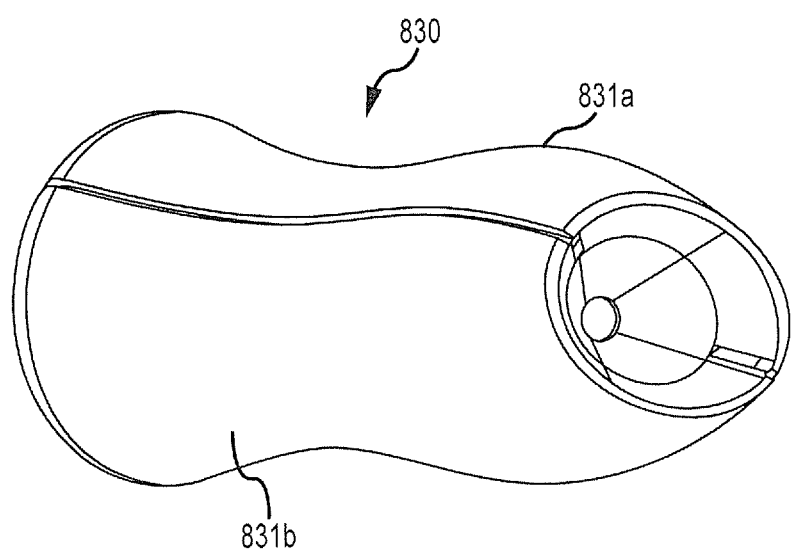
Figures 2, 17F:
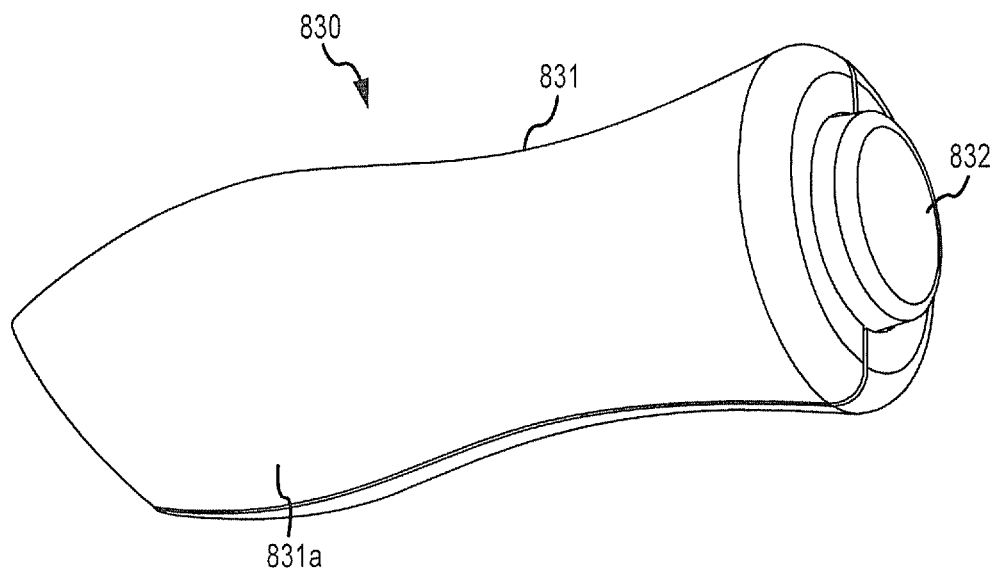
Figures 3, 17F:
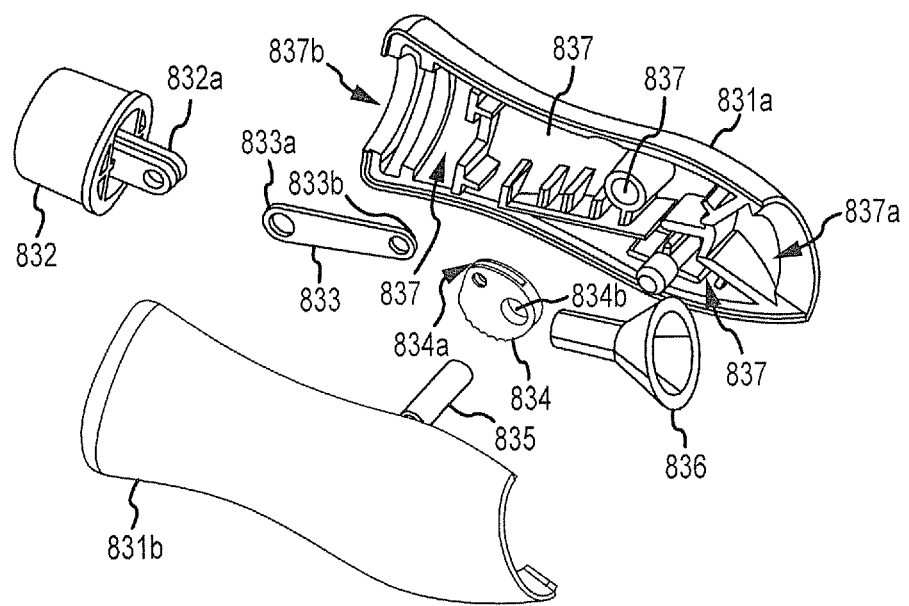
Figures 4, 17F:
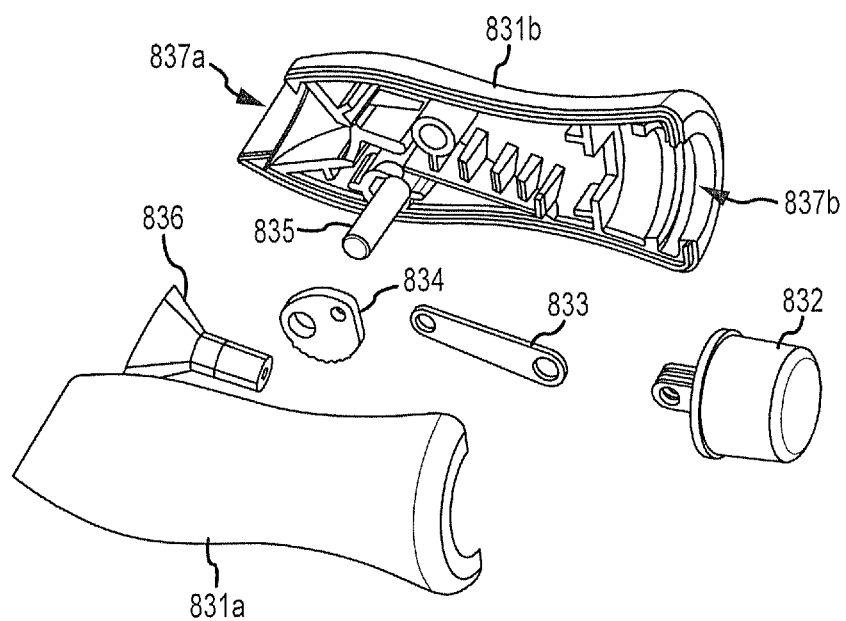

FIGS. 17F-1 to 17F-4 depict front and back isometric views and exploded views of those isometric views of the distal handle assembly 830. As indicated in FIGS. 17F-1 and 17F-2, and with reference to FIG. 17A, the distal handle assembly 830 includes a handle 831 which is generally cylindrical in shape and may include some contouring. The handle may be made of polycarbonate or other appropriate material. As shown in FIGS. 17F-3 and 17F-4, and with reference to FIGS. 17F-1 and 17F-2, the distal handle assembly 830 also includes a rear button 832, a linkage arm 833, a lock cam 834 configured to receive the needle saw wire 792, a cam pin 835 and a funnel 836 configured to receive the distal end 797 of the needle saw wire 792.

As indicated in FIG. 17F-3, a first side 831a of the handle 831 also includes internal cavities 837 configured to receive the components of the assembly 830 described above and similarly, and as indicated in FIG. 17F-4, a second side 831b of the handle 831 also includes internal cavities 837 configured to receive the components of the assembly 830 described above such that the sides 831a and 831b may be joined or coupled together to form the handle 831. In other embodiments, the handle 831 is formed as a single piece.

As assembled, prongs 832a of the button 832 receive a button end 833a of the linkage arm 833, a cam end 833b of the arm 833 is received by an arm end 834a of the cam 834. The cam 834 also includes a cam pin opening 834b configured to receive the cam pin 835. The funnel 836 is received in a cavity 837a and the button is received in a cavity 837b. As discussed in more detail below, in use, the needle wire 792 of the needle wire assembly 790 enters the handle 831 through the funnel 836 and engages the cam lock 834, thereby locking the needle in place. To release, the button 832 is depressed, thereby engaging the linking arm 833 and rotating the cam lock 834 to release the needle wire 792.

Figures 1, 17G:
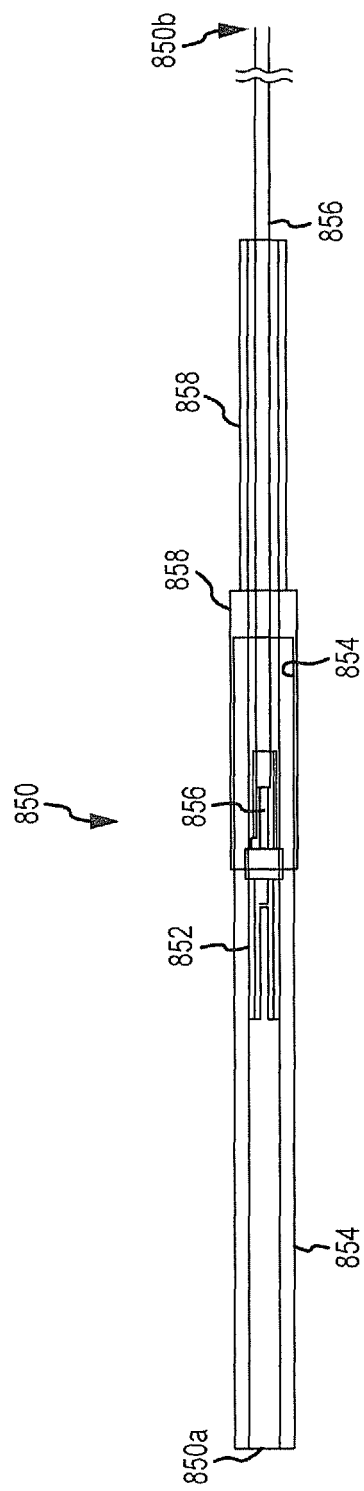
Figures 2, 17G:
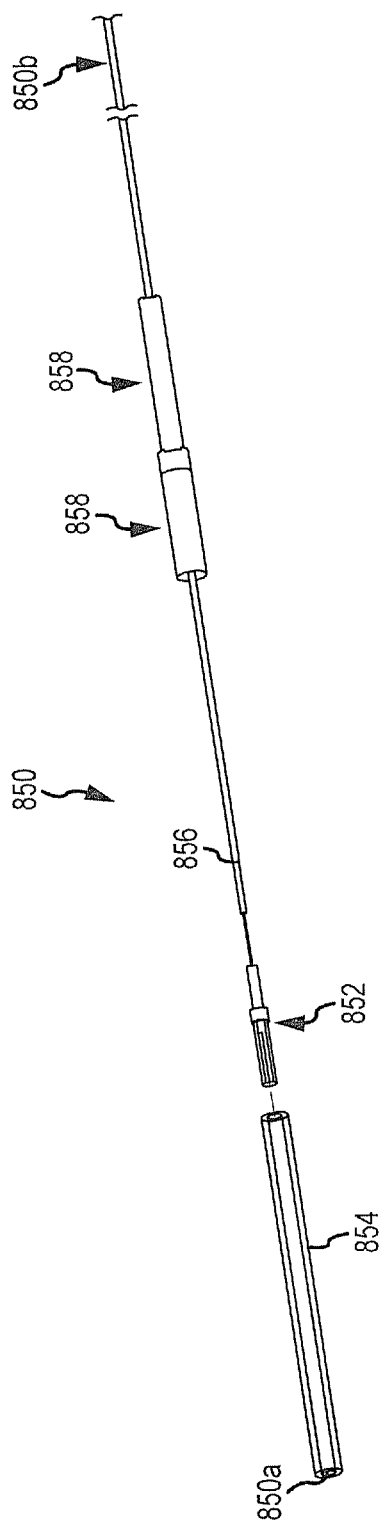
Figure 17H:
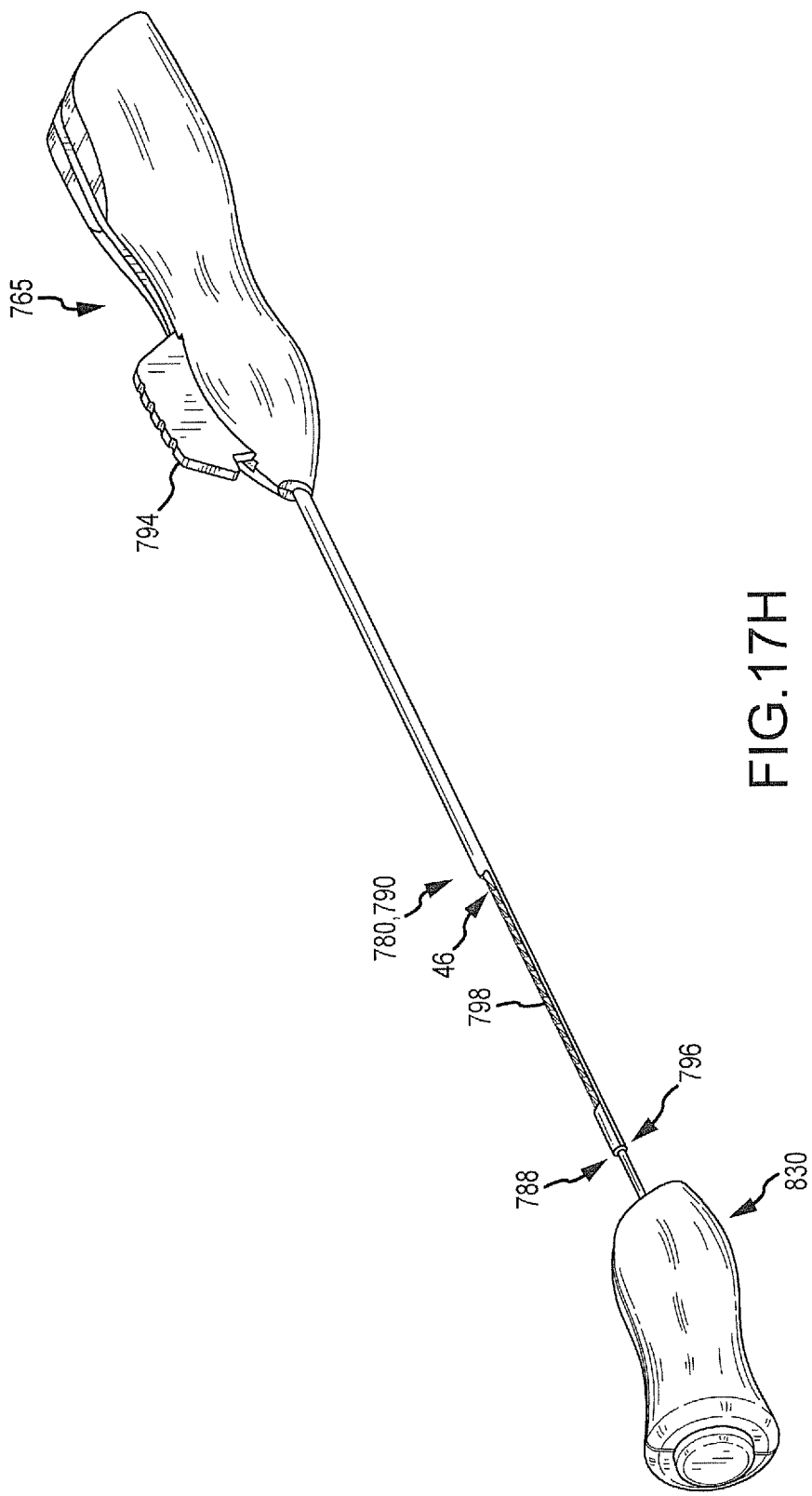
FIG. 17H illustrates the proximal handle assembly and the distal handle assembly of FIG. 17A operably connected for a release procedure, wherein the hand is not shown for clarity.

FIGS. 17G-1 and 17G-2 show an isometric and exploded view of a portion of a nerve wire assembly 850. With reference to FIG. 17A and as can be understood from FIGS. 17G-1 and 17G-2, the nerve wire assembly 850 may be used with a nerve detection system 500 to aid the user in navigating the elongated body 781 in the carpal tunnel region without damaging or contacting nearby anatomical structures, such as nerves, non-target ligaments, etc. The nerve wire assembly 850 may include a female crimp pin 852, a sheath 854, a wire 856 and a shrink wrap 858. In one embodiment, the crimp pin 852 may be a RS232 female contact pin with insulation support, the sheath 854 may be FDA rated polyurethane tubing ⅛"OD ¹⁄₁₆"ID, McMaster PN:5195T616, the wire 856 may be 22 AWG stranded wire with FDA rated insulation and the shrink wrap 858 may be FDA rated heat shrink with adhesive on ID. In some embodiments, the shrink wrap 858 may be a coating on the nerve wire assembly 850 rather than a separate, physical component of the assembly 850. As assembled, the crimp pin 852 is crimped onto the wire 856, the sheath 854 slides over the crimp pin and wire, ensuring that the connector slit is visible, yet covers the connector completely. Then, shrink the shrink wrap 858 over the sheath, pin and wire. In one embodiment, in use, the distal end 850a of the assembly 850 receives a contact portion (not shown) of a nerve detection device 500 and the proximal end 850b of the assembly 850 is received in the proximal handle 770 such that the needle in the proximal handle assembly is electrified and the user is notified when the needle is close to a nerve.

FIG. 17H illustrates the proximal handle assembly 765 and the distal handle assembly 830 operably connected for a release procedure, wherein the hand is not shown for clarity. As can be understood from FIG. 17H, the needle end 799 of the needle wire assembly 790 punctures the palm and a distal end 797 of the assembly 790 is received in the distal handle assembly 830 (see FIG. 17H, with reference to FIGS. 17F-3 and F-4). The threads 800 and needle end 799 at the distal end 797 of the assembly 790 engage the internal components 836, 834 of the distal handle assembly 830, thereby securing the needle wire assembly 790 and the proximal handle assembly 765 together (see FIG. 17H). Once the distal end of the needle wire assembly 790 is secured in the distal handle assembly 830 and the shaft lock assembly 805 has been secured to prevent the introducer assembly 805 and elongated body 781 from exiting the palm, the user (surgeon) may use a sawing, cutting or other motion to release the TCL, thereby decompressing the median nerve. (see, for example, FIGS. 9E and 9E-1 showing partial release of the TCL or FIGS. 16G and 16H). When the procedure is complete, the button 832 of the distal handle 831 is depressed, thereby disengaging the distal end 797, including the needle end 799, of the needle wire assembly 790 from the distal handle assembly 830.

In use, the system 700 may be used as an incisionless technique for releasing the TCL to decompress the median nerve to treat carpal tunnel syndrome. In other embodiments, the system 700 may be used as an incisionless technique for releasing another ligament or anatomical structure to decompress a nerve or other anatomical structure, such as the plantar fascia ligament to treat plantar fasciitis or to decompress the ulnar nerve to treat cubital tunnel syndrome or Guyon's canal syndrome. With cubital tunnel syndrome, the ulnar nerve is compressed by a bone (the humerus bone). The system could shave down this bone to relieve compression on the nerve. Guyon's canal syndrome is compression of the ulnar nerve. This compression can be caused by a cyst or an ulnar ligament, e.g. volnar radio-ulnar ligament.

As can be understood from FIGS. 17D-1 and 17D-2, and with reference to FIG. 5, the introducer stylet 807 and stylet hub 809 are received in the introducer needle 811 and needle hub 813 of the introducer assembly 805. As can be understood with reference to FIG. 17A, the shaft lock assembly 820 may be placed on the assembly 805. The inner portion 822 of the shaft lock assembly 820 is depressed, thereby engaging the spring and aligning the openings 825, 829 such that the needle 811 can be engaged. A lip 829a in the inner portion 822 engages the needle 811 and together with the spring, maintains the shaft lock assembly 820 in the desired position on needle 811 such that it does not hinder entry of the assembly 805 into the wrist. The stylet 807 punctures the skin, provides access to the carpal tunnel and prevents coring out of tissue when the introducer assembly 805 is inserted into the deep wrist two to three centimeters proximal to the wrist skin crease and just medial to the palmar longus. Once the introducer assembly 805 is positioned in the deep wrist, the stylet 807 and stylet hub 809 are withdrawn from the introducer needle 811 and needle hub 813 and the needle 811 and hub 813 and shaft lock assembly 820 remain in place.

As can be understood from FIGS. 17C-1 to 17C-5, the needle wire assembly 790 is received in the handle 770 and the probe wire assembly 780, thereby resulting in the proximal handle assembly 765. In some embodiments, and with reference to FIG. 18, the proximal handle assembly 765 may also be electrically coupled to a neuro-monitoring device 500 via a nerve wire assembly 850 (see the wire 550 of FIG. 18). The nerve wire assembly 850 supplies electrical current to the probe wire assembly 780 such that during insertion of the elongated body 781 into the carpal tunnel, such that contact between the elongated body and a nerve will elicit patient response, e.g. sensory and/or motor. This patient response aids the surgeon in locating the nerve to support safe positioning of the device. As indicated in FIG. 17A, the proximal handle assembly 765 may then be inserted into the introducer assembly 805 and the shaft lock assembly 820 transitions from the introducer assembly 805 to the proximal handle assembly 765. The inner portion 822 of the shaft lock assembly 820 is depressed, thereby engaging the spring and aligning the openings 825, 829 such that the lock assembly 820 can be removed from the needle 811 and a thread 782 of the probe wire assembly 780 can be engaged. A lip 829a in the inner portion 822 engages the thread 782 and together with the spring, maintains the shaft lock assembly 820 in the desired position on the elongated body 781 of the probe wire assembly 780. With reference to FIG. 6A, the elongated body 781 of the probe wire assembly 781 is then passed through the carpal tunnel parallel to the nerve and flexor tendons proximal to distal. As shown in FIG. 17C-5, the elongated body 781 has a ball tip or blunt probe at a distal end 788 similar to nerve stimulators to prevent impaling the nerve or tendons. Once the assembly 765 has been properly positioned relative to the TCL, with the aid of a nerve detection device 500, the slider 794 may be advanced from a non-deployed position (see FIG. 17A) to a deployed position (see FIG. 17H), thereby exposing the cutting surface or teeth 798 of the needle wire assembly 790 in the window 46. The needle end 799 of the needle wire assembly 790 punctures the palm and a distal portion of the assembly 790 is received in the distal handle assembly 830 (see FIG. 17H, with reference to FIGS. 17F-3 and F-4). The threads 800 and needle end 799 at the distal end of the assembly 790 engage the internal components 836, 834 of the distal handle assembly 830, thereby securing the needle wire assembly 790 and the proximal handle assembly 765 together. (see FIG. 17H). The shaft lock assembly 805 is repositioned as needed on the thread 782 of the elongated body 781 such that the introducer assembly 805 and the elongated body 781 do not exit the palm. The distal end of the needle wire assembly 790 is secured in the distal handle assembly 830 and the shaft lock assembly 820 is secured to prevent the introducer needle 811 and elongated body 781 from exiting the palm. This reduces the opening or puncture made in the patient's palm. The user (surgeon) may use a sawing, cutting or other motion to release the TCL, thereby decompressing the median nerve (see, for example, FIGS. 9E and 9E-1 showing partial release of the TCL and FIGS. 16G and 16H). When the procedure is complete, the button 832 of the distal handle 831 is depressed, thereby disengaging the distal end 797, including the needle end 799, of the needle wire assembly 790 from the distal handle assembly 830. The distal handle 831 may be placed to the side or discarded. The slider 794 of the proximal handle assembly 765 is retracted from the deployed state into the non-deployed state, thereby withdrawing the cutting member 798 of the needle wire assembly 790 from the window 46. The shaft lock assembly 820 is disengaged from the elongated body 781 and re-engaged with the introducer needle 811. The proximal handle assembly 765 is withdrawn from the introducer needle 811 and hub 813. The introducer needle 811 and hub 813 are withdrawn from the wrist.

In some embodiments, the hand may be immobilized in a hand immobilizer system, such as the handboard assembly 705, thereby reducing the chance of movement of the hand out of its position under the TCL, thereby increasing control of the device during the release procedure. The handboard assembly 705 is assembled as described above to place the hand into a proper position to conduct the procedure. The hand may be initially secured by the tabs 754 and may be further secured by additional straps to further immobilize the hand.

Figure 18:
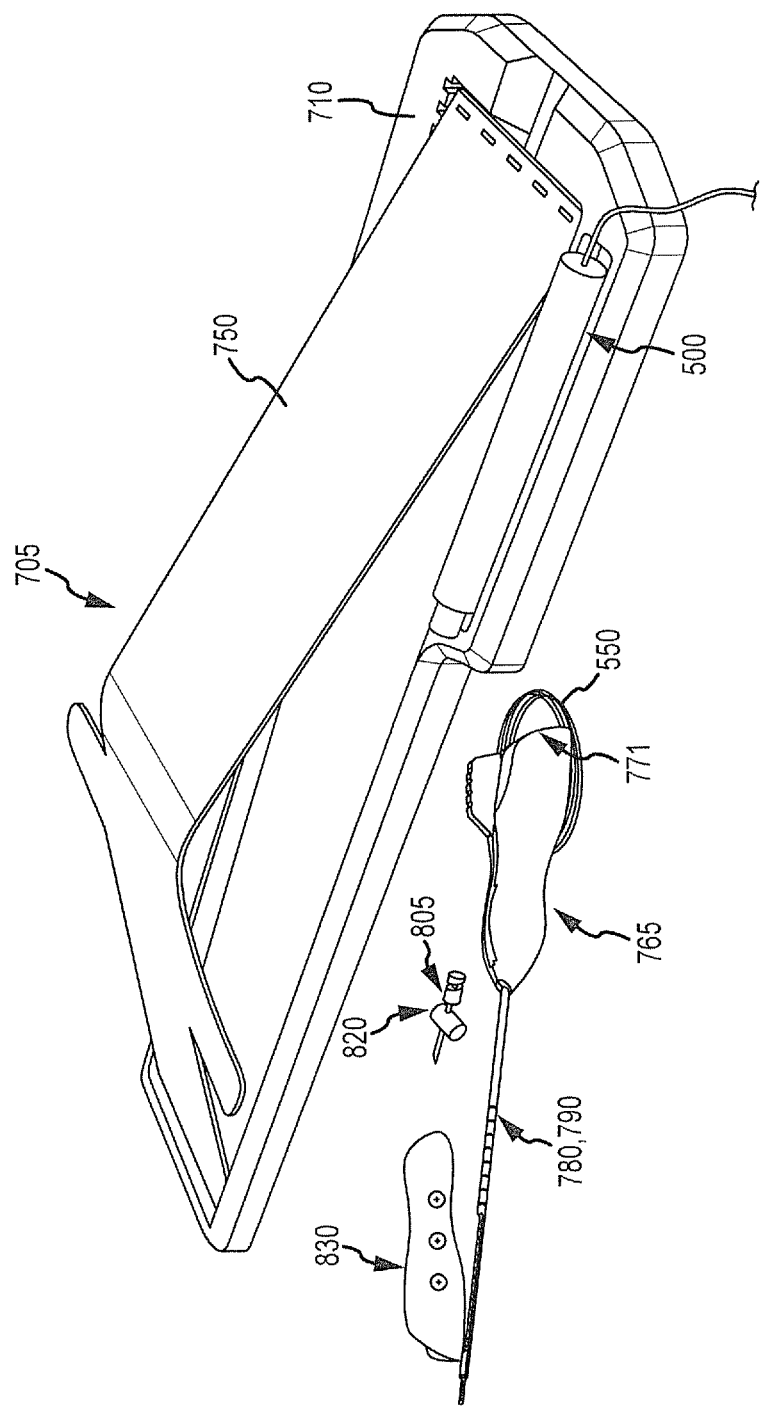
FIG. 18 depicts still another embodiment of a release system including a hardboard assembly and handle members, wherein a nerve detection system and a different embodiment of a distal handle are also shown.

For a discussion of another embodiment of a system where the elongated body and the introducer do not exit the exit port of the hand, reference is now made to FIG. 18, which depicts a release system in which neither the distal end of the elongated body nor the introducer exit the exit point in the palm of the hand.

FIG. 18 illustrates an embodiment with many similar features as described above with reference to FIGS. 17A-17H. In general, the handboard assembly 705, the nerve detection/stimulator wiring assembly, the introducer assembly 805, shaft lock assembly 820, proximal handle assembly 765 and distal handle assembly 830 are as described above with respect to FIGS. 17A-17H. As can be understood from FIG. 18, the handboard assembly 705 includes comparable elements except only one nerve detection system cavity 714 is shown and the drape assembly 750 does not include tabs. In addition, a nerve detection system 500 is illustrated. FIG. 18 also illustrates a wire 550 at the proximal end 771 of the proximal handle assembly 765 which may be used with the nerve detection system. The distal handle assembly 830 illustrates a different embodiment of the handle, wherein the shape is similar to the proximal handle and the proximal end with the release button has a slope. The fastening members (e.g. screws) that join the two sides of the handle can also be seen. The embodiment of the system as depicted in FIG. 18 operates as described above with respect to FIGS. 17A-17H.

As discussed above, the cutting member 45 may extend from or about the window 46 to release the TCL. For a discussion of some embodiments of a cutting member 45 that may be used according to the present disclosure, reference is now made to FIGS. 19A-19E, which illustrate various additional embodiments of a cutting member 45.

Figure 19A:
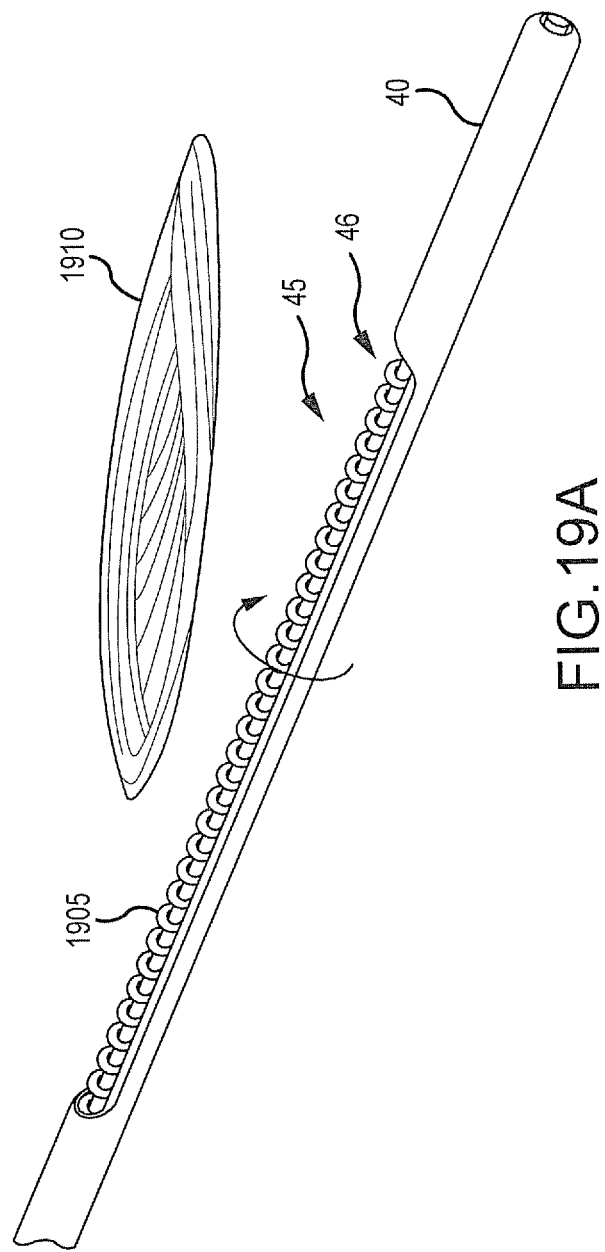

As shown in FIG. 19A, in one embodiment, the cutting member 45 may be a rotating cutting wire or other rotating abrasive surface. This embodiment of the cutting member 45 is inserted into the elongated body 40 and advanced such that it is exposed in the window 46 once the window is properly positioned under the ligament. The cutting member 45 is rotated like a screw. The rotation of the cutting member 45 within the elongated body 40 can be accomplished by either manual or mechanical energy. The rotating blades or threads 1905 of the cutting member 45 release a ligament 1910, such as the TCL, plantar fascia or other anatomical structure, to relieve compression of a nerve, such as the median nerve, or other nerve in need of decompression, such as the ulnar nerve.

Figure 19B:
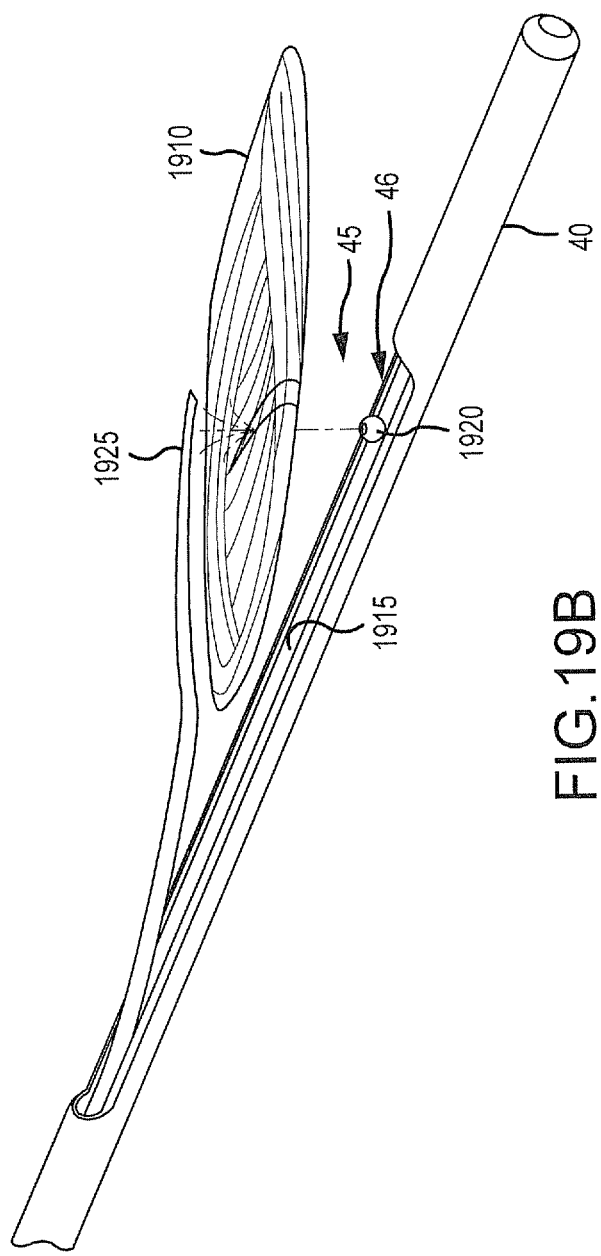

As can be understood from FIG. 19B, in one embodiment, the cutting member 45 is a hydraulic cutting wire or water jet. The cutting member 45 may include a water delivery body 1915 having a water jet 1920, and a protective shield 1925. In use, the elongated body 40 is positioned dorsal to (underneath) the ligament and the water delivery body 1915 including a water jet 1920 and the protective shield 1925 are advanced to the window 46 of the elongated body 40. The water jet 1920 is activated (via delivery of water or other appropriate liquid, via the water delivery tube, which may have a water inlet system at a proximal end of the elongated body) and produces a high velocity stream of water that cuts the TCL through a precise and controlled release. It can be appreciated that in other embodiments, the water delivery body 1915, water jet 1920 and/or the protective shield 1925 may be integrated with the elongated body 40 rather than being separate or individual pieces.

Figure 19C:
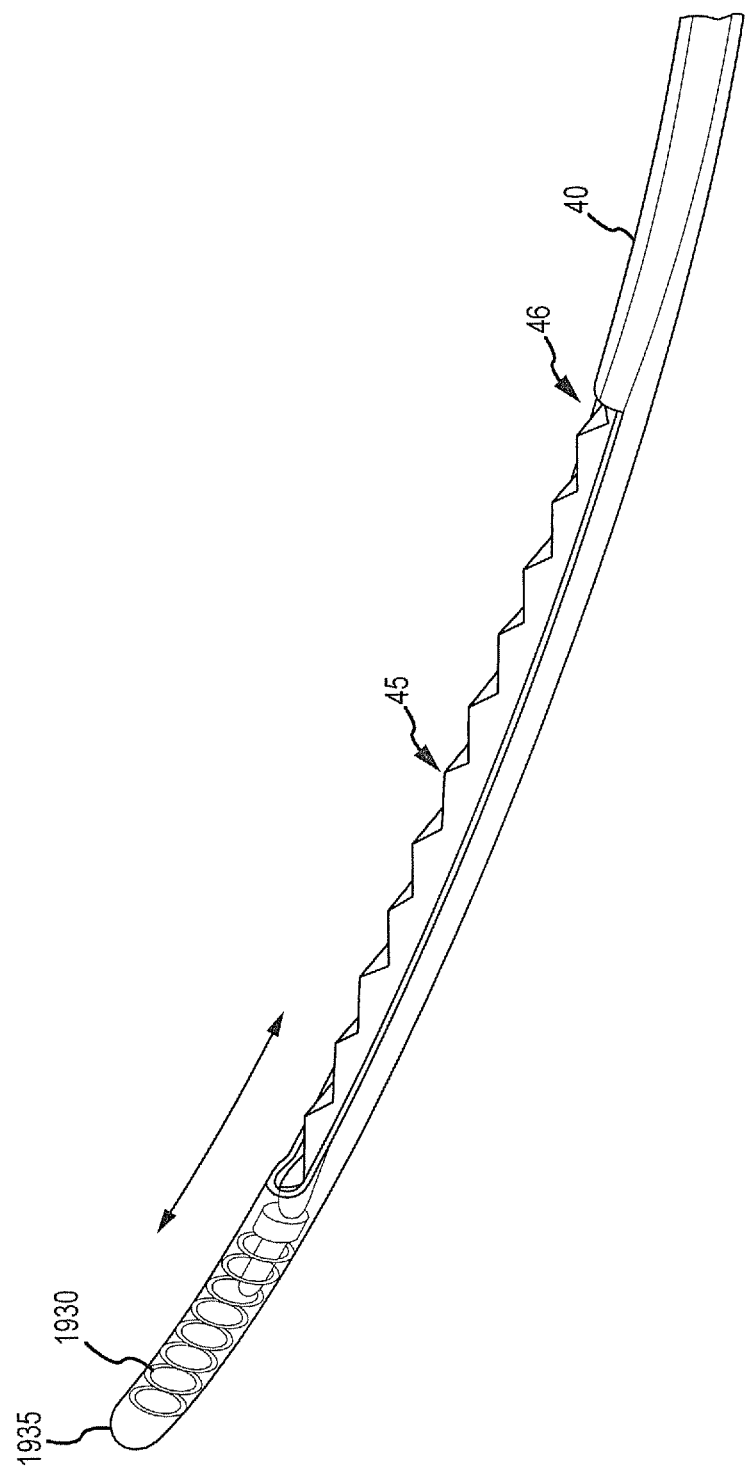

As shown in FIG. 19C, in one embodiment, the cutting member 45 may be a spring assisted-reciprocating cutting member. The cutting member may be a wire or other abrasive material. In this embodiment, the elongated body 40 includes a spring feature 1930 in the distal end 1935 of the body 40. In use, the elongated body 40 is positioned dorsal to (underneath) the ligament and as the cutting member 45 is advanced distally, the cutting member 45 engages the spring feature 1930, thereby causing a reciprocating cutting motion in the proximal direction to release the TCL. This spring feature 1930 is included in the elongated body 40 and is compatible with a number of different embodiments of the cutting member 45 as disclosed herein.

Figures 3, 19D:
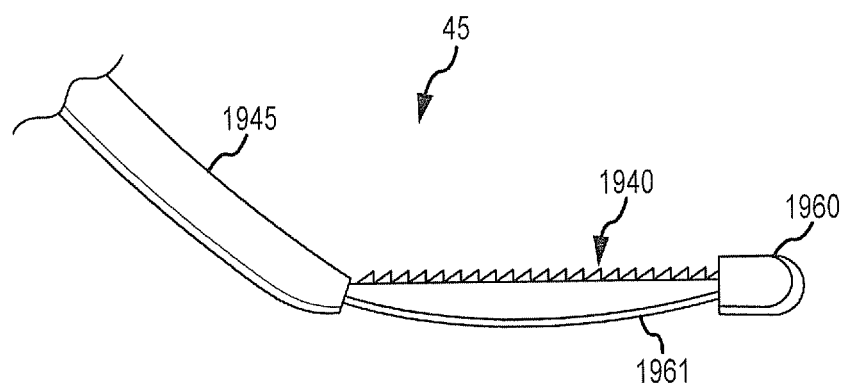

As can be understood from FIGS. 19D-1 to 19D-3, in one embodiment, the cutting member 45 may be a circular cutting wire 45. The cutting member 45 may be a stand-alone cutting member 45 or may be inserted into the elongated body 45 and the teeth 1940 may be exposed in the window 46. As shown in FIG. 19D-1, the cutting member 45 may include a body 1945 having a proximal end 1946 and a distal end 1947. The proximal end 1946 includes a handle feature 1950 and an actuation mechanism 1955. As indicated in FIGS. 19D-2 and 19D-3, the actuation mechanism 1955 releases a cap 1960 at the distal end 1947 of the body 1945 via a linking bar 1961, thereby exposing the teeth 1940 or other abrasive surface of the cutting member 45. That is, as actuation mechanism 1955b is retracted proximally, the cap 1960 is extended distally and actuation mechanism 1955a is extended distally, thereby creating a reciprocating or circular-like sawing or cutting motion such that the teeth 1940, which may form a "bow" shape, and which may be exposed in the window 46 (not shown), can release the TCL.

As shown in FIGS. 19E-1 and 19E-2, in one embodiment, the cutting member 45 may be a cutting wire 1965 utilizing RF energy. An RF energy device (not shown) may be operably attached to the cutting wire 1965 and the device may be located at a proximal end of the elongated body 40. As shown in FIG. 19E-1, once the elongated body is properly positioned, the cutting wire 1965 is advanced through the elongated body 40 to the window 46. As shown in FIG. 19E-2, the cutting wire 1965 is advanced through the window 46. The RF energy device provides RF energy to the cutting wire 1965 in a controlled and directed manner in order to release the ligament 1910.

For a discussion of various embodiments of a nerve detection system or neuro monitoring system 500, reference is now made to FIGS. 20A-20F, which illustrate various embodiments of a nerve detection system that may be used with a release system as disclosed herein. In embodiments which utilize a nerve detection system, the nerve detection system helps to enable the release system to be a "closed release system" or an incisionless system because the user can safely navigate the release system within the carpal tunnel region and surrounding areas without making an incision.

As discussed above, the elongated body 40 may have neuro monitoring features, such as a supple metal probe, that may be used in conjunction with neuro monitoring systems or nerve detection systems 500 to help guide the elongated body 40 through the carpal tunnel area without harming nearby nerves and such that the body 40 is properly positioned under the TCL. In some embodiments, the neuro monitoring system 500 may be the system offered by Cadwell Laboratories, Inc., Kennewick, Wash., Biotronic, Ann Arbor, Mich. or Medtronic, Minneapolis, Minn. (such as the Vari-Stim III Nerve Locator). The supple metal probe, such as the blunt probe tip 42, is also attached to a nerve monitor to assist the surgeon in navigation under the TCL. It can be appreciated that the probe may also be a separate instrument from the elongated body. The surgeon can identify median nerve irritation and accordingly alter the course of the body 40 with hand movements or remove the body 40 and start over again.

Figure 20A:
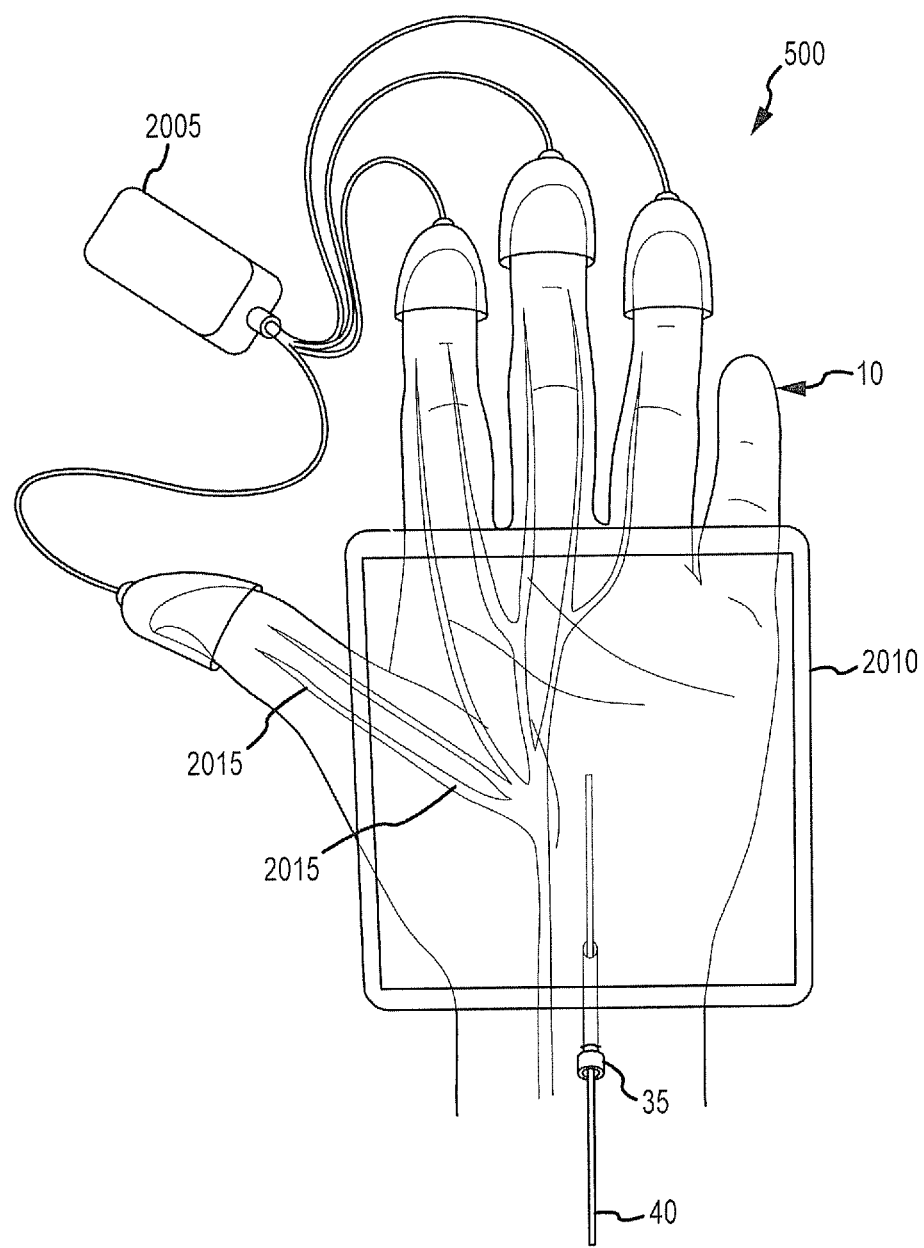

As shown in FIG. 20A, in one embodiment, the nerve detection system 500 is a nerve locating device. This device 500 is a nerve locating system that is placed external to the patient's hand 10 and includes a nerve stimulator 2005 and a visualization device 2010, which may be a screen, monitor or other appropriate device. Stimulation is applied by the stimulator 2005 to the nerves 2015 and the device 500 detects magnetic fields from the nerves 2015 and translates them into a lighted mapping of the nerve location, which is shown on the visualization device 2010. That is, the nerves 2015 are stimulated using an external electrical current such as a surface electrode which creates an increased electrical signal in the nerves. The device then detects the signal and enables a visual mapping of the nerves. An elongated body 40 of a release system as disclosed herein may be inserted through an introducer 35 and deployed at a safe distance from the nerves as determined by looking at the nerve location on the visualization device 2010.

Figures 1, 20B:
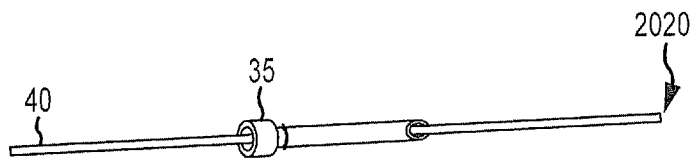
Figures 2, 20B:
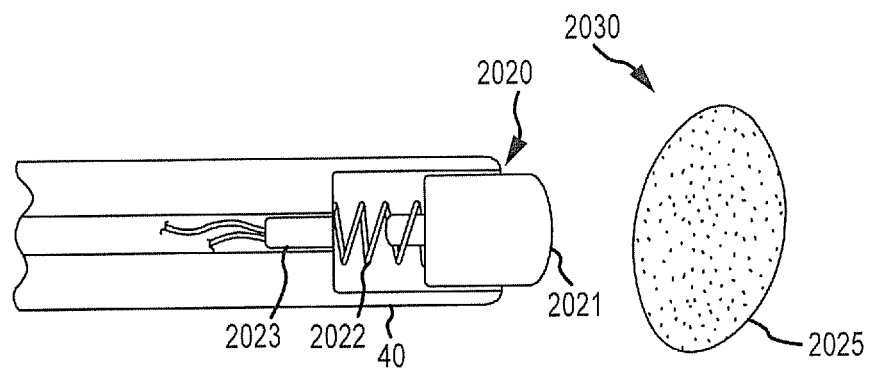
Figures 3, 20B:
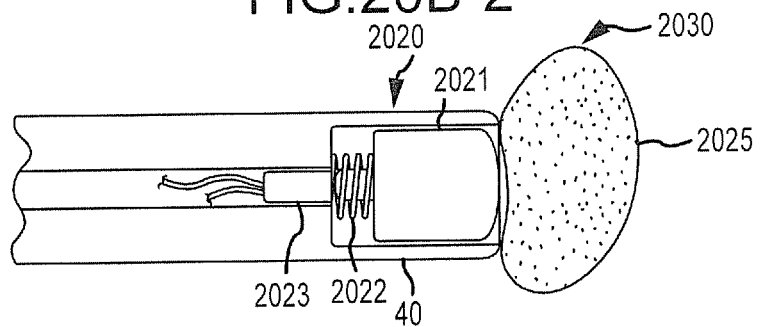
Figure 20C:
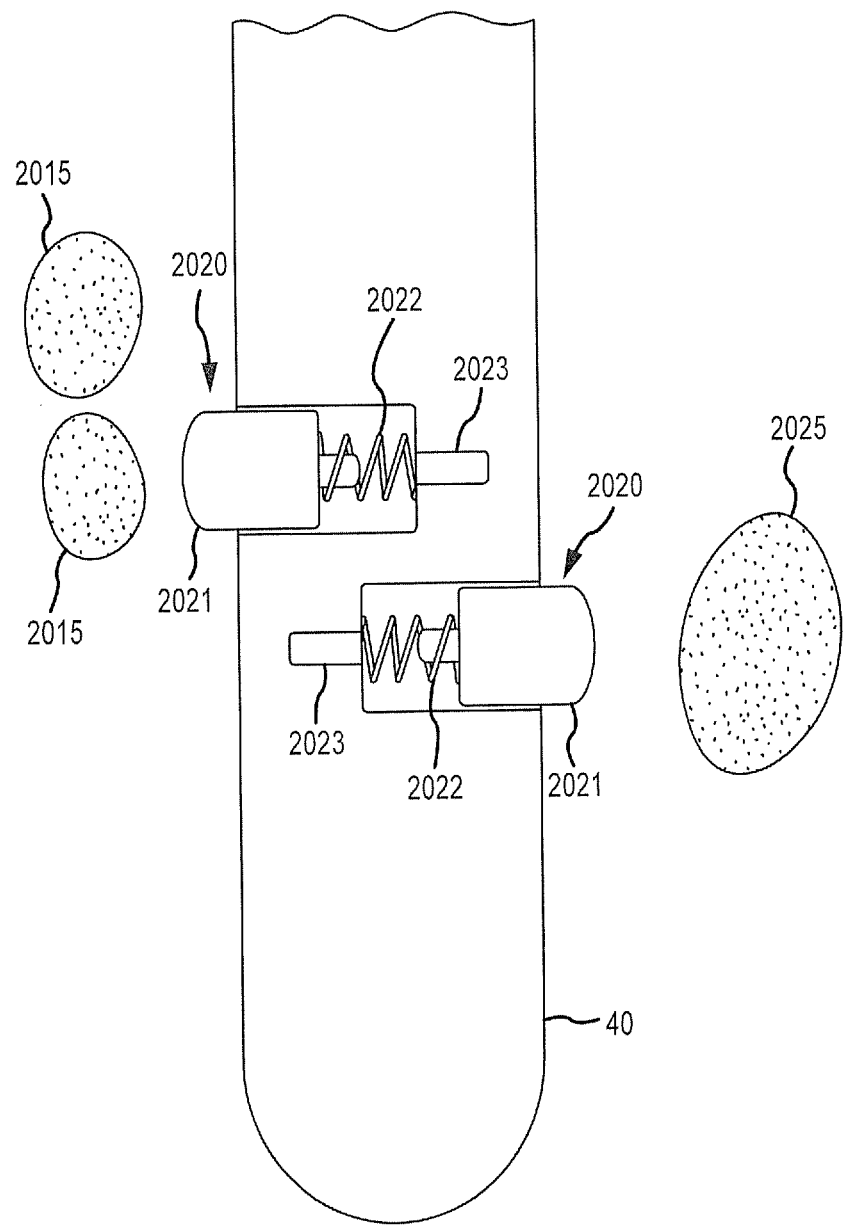

As indicated in FIGS. 20B-1 to 20C, in some embodiments, the nerve detection system 500 is or includes a durometer or other similar hardness tester 2020. The durometer 2020 may include a pin 2021, a spring 2022 and a force sensor 2023. The durometer 2020 measures variations in material hardness and, accordingly, can detect or identify the differences in hardness of anatomical structures 2030, such as nerves 2015, ligaments 2025, tendons, bones, or etc. As shown in FIGS. 20B-2 and 20B-3, the durometer 2020 may be operably connected to or axially extend from a distal end of the elongated body 40. As shown in FIG. 20C, a plurality of durometers 2020 may be operably connected or extend transversely from a distal end of the elongated body 40.

One or more durometers 2020 may be operably connected to the elongated body 40 and can detect if the body 40 comes in contact with a nerve 2015 or other anatomical structure 2030. As shown in FIG. 20B-2, in a non-compressed (precontact) state, the spring 2022 is in an expanded state. As indicated in FIG. 20B-3, if the pin 2021 comes into contact with an anatomical structure 2030, the pin 2021 will compress the spring 2022, which compression is measured by the force sensor 2023. Because anatomical structures have varying degrees of hardness (e.g. bones are harder than nerves), the durometer 2020 will help to detect if the elongated body 40 of the release system is being (or will be) inserted too close to a nerve. In such a case, the elongated body 40 may be redirected or reinserted.

As shown in FIG. 20D, in one embodiment, the nerve detection system 500 may be an electromagnetic sensor 2035. The sensor 2035 is operably connected to the elongated body and can detect proximity to the nerves 2015. A nerve conveys information in the form of electrochemical impulses (known as nerve impulses or action potentials) carried by the individual neurons that make up the nerve. The detection by the sensor 2035 is accomplished by sensing differences in electromagnetic fields emanating from the nerves and may offer a warning, e.g. a signal, that contact with a nerve is imminent. This detection allows the surgeon to reposition the elongated body 40 without coming in contact with the nerve.

Figure 20E:
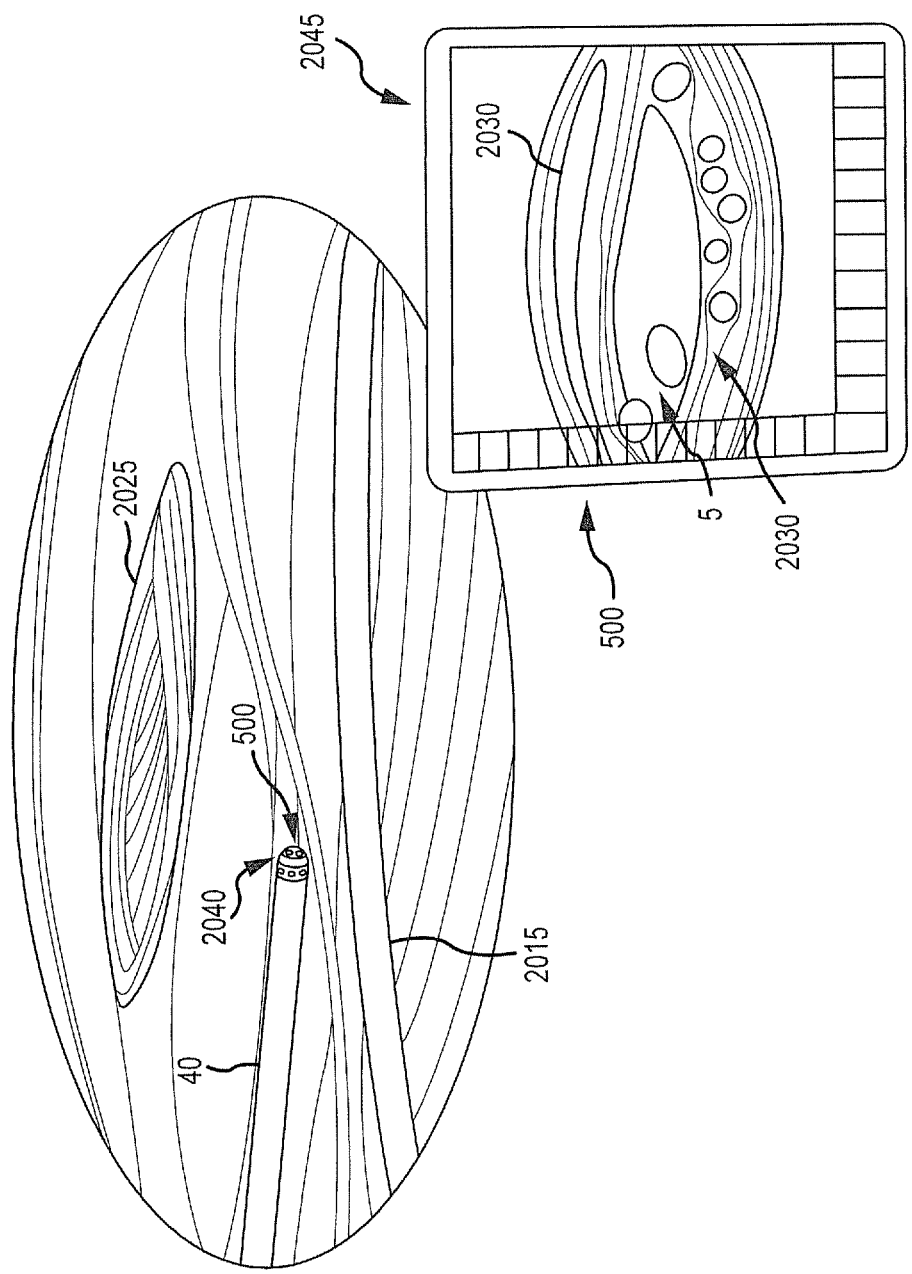

As indicated in FIG. 20E, in one embodiment, the nerve detection system 500 may be an ultrasound probe 2040 and associated visualization device 2045, which may be a screen, monitor or other appropriate device. The probe 2040 is integrated with the elongated body 40 of the release system to enable ultrasound imaging within the carpal tunnel 5 and hand. The probe 2040 operates like a traditional ultrasound transducer but is sized to be compatible with the elongated body 40 and the release system. As the surgeon is advancing the system within the carpal tunnel, the ultrasound probe 2040 will transmit images to the visualization device 2045 and the surgeon can advance or alter the course of advancement of the elongated body 40 in order to avoid contact and/or injury of neural and vascular structures.

Figure 20F:
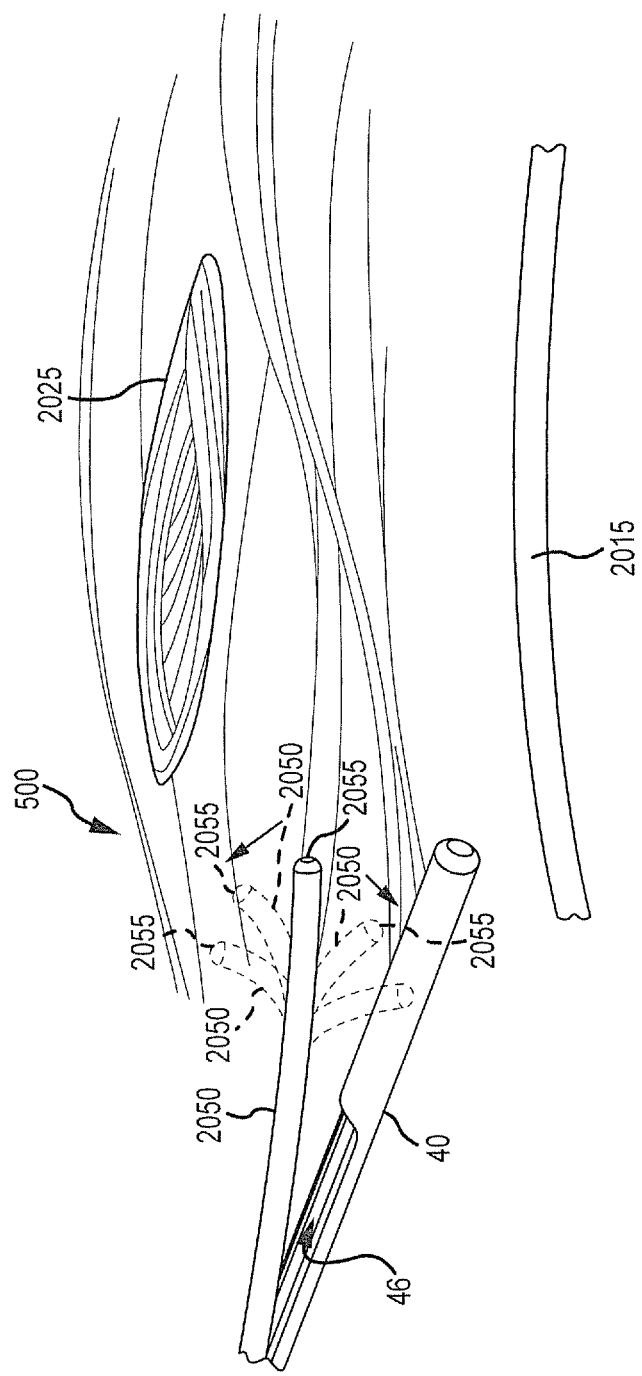

As shown in FIG. 20F, in one embodiment, the nerve detection system 500 may be a catheter 2050 with nerve stimulation contact points 2055. The catheter 2050 may be a steerable catheter that is advanced through the elongated body 40. In one embodiment, the catheter 2050 is advanced through the elongated body 40 while the cutting member 45 is not assembled within the elongated body 40. The catheter 2050 can be directionalized and advanced toward suspected nerve location(s) in order to identify the location(s) and direct the elongated body 40 away from such location. The catheter 2050 exits through the window 46 of the elongated body 40 and the catheter 2050 may be removed once the elongated body 40 is properly positioned in the carpal tunnel area as described elsewhere herein.

The embodiment shown in FIGS. 22A-1 and 22A-2 includes a trigger grip handle 2200 connected to the tubular body 40 at the proximal end. The cutting member 45 of the release system is located at least partially within the tubular body 40. In addition, through an actuator 2202 or trigger on the handle 2200, the cutting member 45 and tubular body 40 may be longitudinally displaced from a non-deployed to a deployed position, thereby causing the cutting member 45 to distally extend from the distal end 42 of the tubular body 40, exposing the cutting member 45 for use in releasing the TCL. Various actuators 2202 and related movement of the tubular body 40 and cutting member 45 are described below with reference to FIGS. 22B-1 through 22K-2. In general, any of the features of the embodiments described below may be combined in any combination for a release system. Further, in use, the tubular body 40 is introduced into the carpal tunnel with the cutting member 45 in the non-deployed position to prevent damage to the tissue of the hand. Upon proper placement of the tubular body within the tunnel, the cutting member 45 is placed into the deployed position such that the TCL may be cut.

As described above, a nerve detector 2201 may be integrated into the release device. In the embodiment shown in FIGS. 22A-1 and 22A-2, the nerve detector 2201 includes one or more conductors on the distal end 42 of the tubular body 40. The nerve detectors operate in a similar manner as described above and may be uni-polar or bi-polar. In other embodiments, the nerve detector 2201 is located on the distal end of the cutting member 45. In yet other embodiments, nerve detectors 2201 are located on both the tubular body 40 and the cutting member 45 and may be in communication to provide the user of the release system an indication of an encountered nerve. The indication of the encountered nerve may be in the form of a visual and/or audio indication that increases in intensity as the proximity to the nerve increases.

In one embodiment of the trigger release device, shown in FIGS. 22B-1 and 22B-2, a trigger grip handle 2204 includes an actuator trigger 2206 that may be pressed by the fingers of a user of the device. When the user presses the actuator 2206, the tubular body 40 is longitudinally displaced or retracted toward the handle 2204. In one example, the trigger 2206 is mechanically connected to the tubular body 40 such that longitudinal movement of the trigger by the fingers of the user results in a corresponding longitudinal movement of the tubular body. In addition, the retraction of the tubular body 40 causes the cutting member 45 located within the tubular body to pass through the distal end 42 of the tubular body to expose a cutting surface of the cutting member, placing the cutting member in a deployed position for cutting the TCL. Upon cutting of the TCL, the trigger 2206 may be released to return the tubular body 40 over the cutting member 45 and placing the cutting member in a non-deployed position. In one embodiment, the cutting member 45 may include a point 2208 at the distal end of the cutting member for piercing the palm of the hand, for the procedures explained above regarding cutting the TCL.

In another embodiment of the trigger release device shown in FIGS. 22C-1 and 22C-2, the release device includes the above-described trigger 2206 and a thumb actuator 2212 located on the top surface of the handle 2210 near the thumb of the operator of the device. Pressing the thumb actuator 2212 causes the cutting member 45 to longitudinally displace away from the handle (i.e., displace distally), and pressing the trigger 2206 causes the tubular body 40 to displace in the opposite direction (i.e., proximally). The thumb actuator 2212 may actuate a spring device that displaces the cutting member 45 in a similar manner as described above. The trigger actuator 2206 may operate as described above to longitudinally displace the tubular body 40 toward the handle. Thus, the combined movement of the tubular body 40 and the cutting member 45 in opposite directions in relation to the handle 2210 act to place the cutting member in the deployed position for cutting.

In some embodiments, such as those shown in FIGS. 22D-1 through 22E-2, a rotatable actuator 2216 may be employed on the handle 2214. For example, in the embodiment shown in FIGS. 22D-1 and 22D-2, the handle 2214 includes the thumb rotation actuator 2216 that is rotatable by the thumb of the user and is in communication with the tubular body 40 or the cutting member 45. In one embodiment, rotation of the thumb rotation actuator 2216 causes the tubular body 40 to retract toward the handle. In another embodiment, rotation of the thumb rotation actuator 2216 causes the cutting member 45 to be longitudinally displaced away from the handle. A trigger actuator 2206, similar to those described above, may also be used in conjunction with the rotatable actuator 2216 to longitudinally displace either the tubular body 40 or the cutting member 45 to expose the cutting member during the procedure.

In one embodiment, the thumb rotation actuator 2216 may be in communication to the tubular body 40 and/or the cutting member 45 through a screw device such that rotation of the rotation actuator causes the tubular body and/or cutting member to also rotate in addition to the longitudinal displacement. In other embodiments, the tubular body 40 and/or the cutting member 45 do not rotate when longitudinally displaced.

FIGS. 22E-1 and 22E-2 depict a similar release device as that described above with a rotatable actuator shown in FIGS. 22D-1 and 22D-2. However, in this embodiment, the rotation actuator is located at the junction of the tubular body 40 and the handle 2218. Rotation of the rotation actuator 2220 may result in the same longitudinal displacement of the tubular body 40 and/or cutting member 45 as described above. In an additional embodiment, actuation of the rotation actuator 2220 may occur by the pressing of the trigger 2206 of the handle 2218. In other words, in this embodiment, the trigger actuator 2206 controls both longitudinal displacements of the tubular body 40 and the cutting member 45 by actuating the rotation actuator 2220 and the trigger actuator simultaneously.

In another embodiment, shown in FIGS. 22F-1 and 22F-2, the cutting member 45 is longitudinally displaced away from the handle 2222 when the trigger actuator 2206 is pressed. This longitudinal displacement orients a cutting surface 2224 of the cutting member 45 within a window 46 of the tubular body 40, similar to the embodiment described above with reference to FIGS. 8A-8C. In a similar embodiment, the tubular body 40 may be retracted by actuation of the trigger 2206 to orient the cutting surface 2224 within the window 46 of the tubular body. Upon release of the trigger 2206, the cutting member 45 may return to a non-deployed position within the tubular body 40 for safe removal of the tool from the hand. The distal tip of the cutting member 45 and the distal end 42 of the tubular body 40 may include electrodes 2201 for sensing the nerves. The distal region of the cutting member 45 can be caused to distally project out of and retract into the distal end 42 of the tubular body 40 via actuation of the trigger actuator 2206.

In a similar embodiment, shown in FIGS. 22G-1 and 22G-2, longitudinal displacement of the cutting member 45 is activated by the trigger 2206 of the handle 2222 to expose a cutting tooth 2228 through a window 2226 in the tubular member. In this embodiment, the window 2226 may be smaller than in previously described embodiments. The cutting tooth 2228 is biased by a spring device within the cutting member 45 such that when the cutting tooth is aligned with the window 2226, the cutting tooth is forced through the window. In this deployed position, the cutting tooth 2228 may be used to cut the TCL. In addition, the cutting tooth 2228 may include a concave surface on the proximal edge of the tooth such that, as the cutting member 45 is retracted into the non-deployed position, the concave surface of the cutting tooth 2228 may engage the edge of the window 2226 to counter the spring bias on the cutting tooth and return the cutting tooth to within the tubular body 40. In this position, the tubular body 40 may be removed from the patient without further cutting of the tissue of the hand. In another embodiment, the trigger 2206 longitudinally displaces the tubular body 40 into the deployed position. In yet another embodiment, both the tubular body 40 and the cutting member 45 are longitudinally displaced by the trigger 2206. The distal tip of the cutting member 45 and the distal end 42 of the tubular body 40 may include electrodes 2201 for sensing the nerves. The distal region of the cutting member 45 can be caused to distally project out of and retract into the distal end 42 of the tubular body 40 via actuation of the trigger actuator 2206.

In another embodiment, shown in FIGS. 22H-1 and 22H-2, the trigger 2206 of the handle 2224 activates to open a hinged flap or flaps 2230 on the tubular body 40. The opening of the flap or flaps 2230 reveals the cutting member 45 for the sawing action, as described above. In one embodiment, the tubular body 40 includes a single flap 2230 that rotatably opens in a clockwise or counter-clockwise direction. In other embodiments, the tubular body 40 includes a plurality of flaps 2230 that open to expose the cutting member 45. In addition, the flaps 2230 may be configured to provide a physical barrier between the cutting member 45 and the tissues of the hand that are not intended to be cut. For example, the flap 2230 upon opening may press against a nerve or other tissue near the cutting member 45 to provide a physical barrier between the cutting member 45 and the nerve prevent damage to the nerve. The flap 2230 may also physically move certain tissue near the cutting area away from the TCL for further protection when opened.

In one embodiment as depicted in FIGS. 22I-1 through 22I-5, the tubular body 40 may be rotatable about its longitudinal axis relative to the cutting member 45 and/or the cutting member 45 may be rotatable about its longitudinal axis relative to the tubular body 40 so as to expose the cutting features 2225 of the cutting member within a window 2224 of the tubular body 40. For example, as can be understood from FIGS. 22I-1 and 22I-2, the window 2224 may be oriented relative to the cutting features 2225 of the cutting member 45 such that the cutting features 2225 are hidden from exposure to tissue by the cylindrical wall of the tubular body 40. Such a condition is depicted in FIG. 22I-4, which is a longitudinal cross section of the tubular body 40 and cutting member 45 with the cutting features 2225 oriented opposite the window 2224 so as to hide the cutting features within the tubular body.

As indicated by the rotational arrows in FIG. 22I-1, the thumb knob 2216 or similar actuation feature may be rotated to cause rotation of the tubular body 40 about the cutting member 45 and/or cause rotation of the cutting member within the tubular body. Such rotation occurs until the window 2224 is positioned such that the cutting features 2225 are exposed within the window 2224, thereby allowing the cutting features to be used for cutting tissue. Such a condition is depicted in FIG. 22I-5, which is a longitudinal cross section of the tubular body 40 and cutting member 45 with the cutting features 2225 aligned with the window 2224 so as to deploy the cutting features for the cutting of the tissue. When the cutting is complete, the rotation can be reversed to return the cutting features to the non-deployed state depicted in FIG. 22I-3. As shown in FIG. 22I-4, the distal end 42 of the tubular body 40 may have an electrode 2201 for sensing nerves.

In the embodiment shown in FIGS. 22J-1 and 22J-2, depression of the trigger 2206 of the handle 2232 operates to pull the cutting member 45 toward the handle. However, in this embodiment, the distal end of cutting member 45 is attached to the distal end 42 of the tubular body 40. In addition, the tubular body 40 is flexible at the distal end 42 and includes a window exposing the cutting member 45 within the window. When tension is created on the cutting member 45 by the depression of the trigger 2206, the distal end 42 of the tubular body bends laterally, creating a bowstring effect (as seen in FIG. 22J-2) with the cutting member 45 such that the cutting member may be used to cut the TCL. Release of the trigger 2206 returns the cutting member 45 and tubular body 40 to the non-deployed state with the cutting member within the tubular body.

In the embodiment shown in FIGS. 22K-1 and 22K-2, the tubular body 40 and the cutting member 45 may have different contours in the deployed position. More particularly, the cutting member 45 may be flexible such that when the cutting member is in the non-deployed position within the tubular body 40, the cutting member has the shape of the tubular body. As described above, the tubular body 40 may have a contour or curvature shape to aid in positioning the release device within the carpal tunnel. Similar to the embodiments described above, the handle 2236 may include a trigger 2206 to longitudinally displace the cutting member 45 and/or tubular body 40 into a deployed position. However, in this embodiment, the cutting member 45 has an alternate shape or curvature than the tubular body 40 in the deployed position. For example, the cutting member 45 may have a shape or contour that curves in an alternate direction than the curvature of the tubular body 40. The alternate curvature of the cutting member 45 may aid in cutting tissue within the hand of the patient. Upon return to the non-deployed position, the flexible cutting member 45 is housed within the tubular body 40 for removal from the patient's hand.

As can be understood from FIGS. 22K-1 and 22K-2, in one embodiment the tubular body 40 is bowed upward while the cutting member 45 is bowed downward. In other words, cutting member and tubular body are oppositely bowed when the cutting member is fully distally extended from the distal end 42 of the tubular body. An electrode 2201 for sensing nerves may be located at the distal end of the tubular body.

In one method of use for the embodiment depicted in FIGS. 22K-1 and 22K-2, the tubular body can be inserted into the wrist with the cutting member just slightly extending from the distal end of the tubular body, the pointed tip of the cutting member acting as a piercing feature but the cutting member not being so extending from the tubular body distal end that the cutting member is oriented differently from the tubular body. In such a configuration the tubular body and slightly protruding piercing feature can be distally advanced through the wrist until the piercing feature penetrates the palm. A handle can then be attached to the distal end of the cutting member similar to as described above with FIG. 17H. The cutting member can then be fully extended from the tubular body as shown in bottom picture of FIG. 22K-1. As a result, the cutting member will bow upward to create a configuration that enhances the TCL severing capability of the cutting member.

Figure 23:
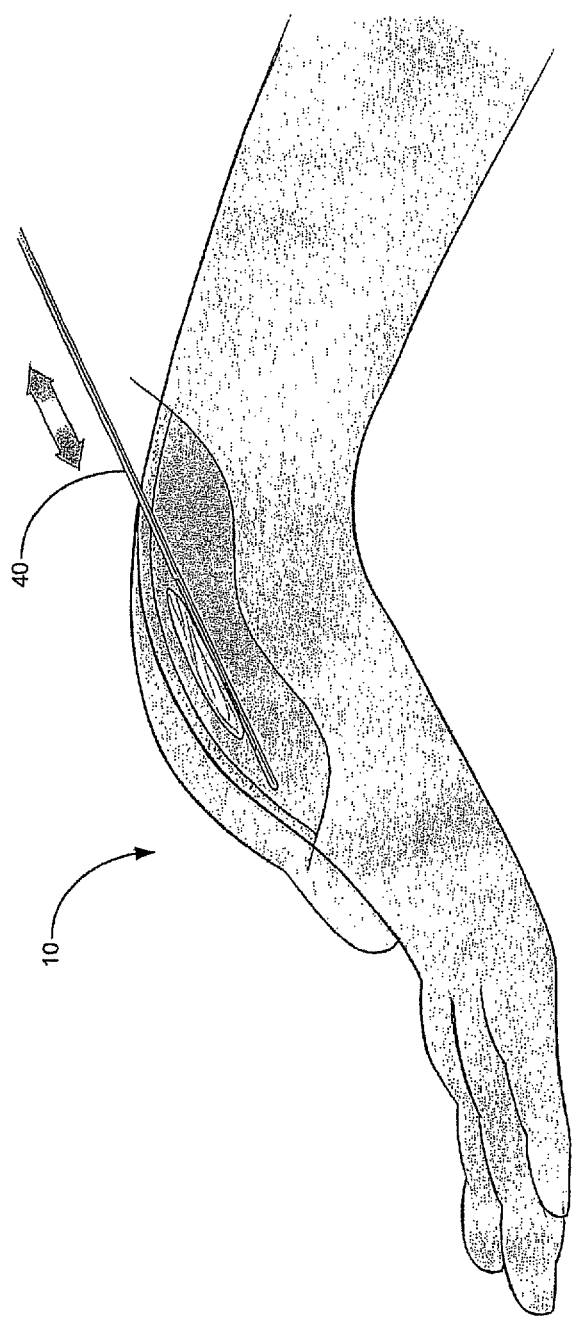

FIG. 23 depicts a side-view of an embodiment of the release system conducted with a single puncture through the wrist of a patient. In this embodiment, no puncture is made in the palm of the patient's hand, thereby reducing the number of cuts in the skin needed for the procedure. Any of the above described embodiments may be configured as single-puncture devices for releasing the TCL to reduce the recovery time needed for the procedure.

Figure 24E:
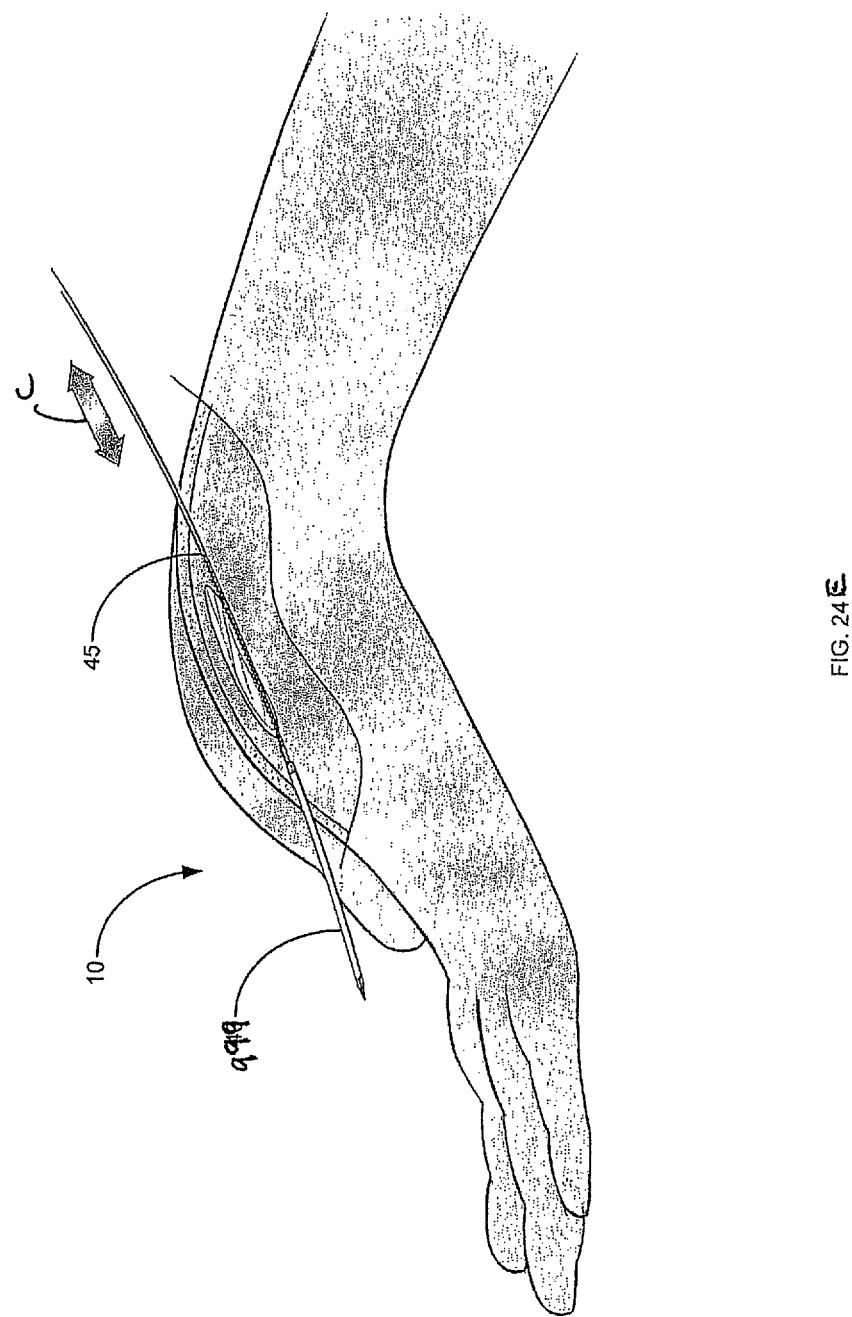

FIGS. 24A-24E depict an embodiment of the release system 10 with a braided suture 45 or other cutting member 45 distally terminating in a needle 999 or other penetrating element, the penetrating element 999 being pushed through the wrist tissue via a tubular body in the form of a push rod 45. As shown in FIG. 24A, which is a distal/proximal cross sectional elevation of a patient's wrist, a proximal end of the penetrating element 999 is coupled to the distal end of the cutting member 45. As indicated by arrow A in FIG. 24A, the tubular body 40 is used to push the penetrating element 999 through the patient's wrist, the distal end of the tubular body abutting against the proximal end of the penetrating element in a coupled arrangement.

As indicated in FIGS. 24B and 24C, which are longitudinal cross sectional elevations of the penetrating element 999 and the distal end of the tubular body 40 coupled thereto, in one embodiment, the coupled arrangement between the penetrating element and the tubular body may take the form of a male-female coupling arrangement. For example, as shown in FIG. 24B, the male-female coupling arrangement between the penetrating element and the tubular body may have a male portion 3333 on the proximal end of the penetrating element 999 and a female portion 3334 on the distal end of the tubular body 40. Alternatively, as shown in FIG. 24C, the male-female coupling arrangement between the penetrating element and the tubular body may have a female portion 3335 on the proximal end of the penetrating element 999 and a male portion 3336 on the distal end of the tubular body 40.

As indicated by arrow B in FIG. 24D, which is the same view as FIG. 24A, once the penetrating element 999 as been driven through the skin of the palm, the tubular body 40 can be proximally withdrawn from the wrist and from about the penetrating element. As shown by arrow C in FIG. 24E, which is the same view as FIG. 24D, the cutting member 45 can then be displaced proximal-distal to sever the TCL. Handles can be coupled to the proximal and distal ends of the cutting member 45 as described above with respect to previously described embodiments.

In use, the systems and methods disclosed herein may be used as an incisionless technique for releasing the TCL to decompress the median nerve. In one embodiment, a 14 gauge or similar sized needle introducer is inserted into the deep wrist three or four centimeters proximal to the wrist skin crease and just medial to the palmar longus. An elongated body is then passed through the carpal tunnel parallel to the nerve and flexor tendons proximal to distal. The elongated body has a ball tip or blunt probe similar to nerve stimulators to prevent impaling the nerve or tendons. The distal end of the body (or other associated device, e.g. the sled member) may assume a curled shape such that when it is passed through the ligament towards or into the palm, the tip trajectory is upwards towards the palm skin. A probe is attached to a nerve monitor to assist the surgeon in navigation under the TCL. The surgeon can identify median nerve irritation and accordingly alter the course of the elongated body with hand movements or remove the elongated body and start over again. In various embodiments the elongated body can be at least partially coated with a non-conductive material such that only a portion of the diameter of the body is exposed for nerve stimulation. The elongated body is passed under the TCL to approximately the palm skin between the third and fourth fingers on the medial side of the nerve. The palm skin may be pierced by a sharp wire or stylet inserted through the elongated body (or alternative cutting instrument), the sharp wire extending beyond the blunt tip or probe tip of the elongated body once the probe is identified underneath the skin surface. Alternatively, the ball tip can emit a light that can be identified in the subcutaneous tissues and a small stab wound made to retrieve the probe and deliver it to the surface. Accordingly, the surgeon has passed the elongated body under the carpal tunnel ligament on the ulnar/medial side of the nerve using intraoperative nerve studies to safely navigate through two needle puncture sites. The surgeon may use an embodiment of the elongated body that includes a cutting member or the surgeon may pass other cutting wires or instruments over or through the elongated body for the purpose of cutting the carpal tunnel ligament using a flossing, sawing, cutting or single pull through movement. In some embodiments, the hand may be immobilized in a hand immobilizer system, thereby reducing the chance of movement of the elongated body out of its position under the TCL.

Some or all of the various components, e.g., the introducer, elongated body, cutting member, proximal handle assembly, distal handle assembly, etc., may be provided in the form of a packaged kit provided in one or more sterilized, sealed packages from the manufacturer along with instructions provided with the kit or on a website. Some or all of the various components of the kit may be disposable. The instructions provided with the kit or on a website may be assembly instructions related to some or all of the various components of the kit and/or instructions for use of some or all of the components in a release procedure. In one embodiment, a kit for releasing a ligament may include an introducer including a stylet needle, a stylet hub, an introducer needle and an introducer hub. A first handle assembly including: a first handle member, an elongated body including a blunt tip, a window, and a distal end and a proximal end and a cutting member including a piercing member at a distal end of the cutting member may also included. The kit may also include a second handle configured to receive a distal end of the cutting member of the first handle assembly. The kit may also include a motion limiting feature configured to removably couple with the elongated body and/or a handboard assembly, the handboard assembly comprising a baseplate chassis, a flexboard and a drape assembly. At least some components of the kit may be disposable.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification and examples provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A system for releasing a ligament, the system comprising:
   a tubular body comprising:
      a proximal end,
      a distal end opposite the proximal end,
      a tubular wall defining a lumen extending longitudinally through the tubular body and comprising an inner diameter and an outer diameter, and
      a window extending through the tubular wall;
   an inner body extending through the lumen of the tubular body and comprising:
      a proximal end,
      a distal end opposite the proximal end,
      a tissue penetration tip at the distal end of the inner body, and
      a tissue cutting portion located between the distal end and the proximal end of the inner body; and
   a proximal handle coupled to the proximal end of the tubular body and comprising a first rotatable actuator coupled to the inner body and configured to rotationally displace the inner body relative to the tubular body to rotationally transition the tissue cutting portion between a non-deployed state and a deployed state, wherein in the non-deployed state the tissue cutting portion is hidden from the window, and in the deployed state the tissue cutting portion is exposed at the window and remains confined within a boundary defined by the outer diameter of the tubular wall of the tubular body.

2. The system of claim 1, wherein the tissue cutting portion includes a plurality of teeth or an abrasive surface.

3. The system of claim 1, wherein the inner body is also longitudinally displaceable relative to the tubular body.

4. The system of claim 3, further comprising a second actuator near the proximal handle that causes the inner body to be longitudinally displaced relative to the tubular body to transition the tissue cutting portion between the non-deployed state and the deployed state.

5. The system of claim 1, wherein the tissue cutting portion comprises a cutting tooth that protrudes through the window in the deployed state.

6. The system of claim 1, wherein the tissue cutting portion of the inner body forms a bow-like arrangement with the tubular body when the cutting portion is in the deployed state.

7. The system of claim 1, wherein the tissue penetration tip at the distal end of the inner body moves from a recessed state to a tissue penetration state when the tubular body is longitudinally displaced relative to the inner body.

8. The system of claim 1, further comprising at least one of: a nerve sensing system electrically coupled to the tubular body or inner body; or an ultrasound probe operably coupled to the tubular body.

9. The system of claim 1 or 2, wherein the tissue cutting portion is defined along a segment length of a longitudinal axis of the inner body, the longitudinal axis extending from the proximal end to the distal end of the inner body.

10. The system of claim 9, wherein the plurality of teeth extend radially outward from a center point of the longitudinal axis of the inner body.

11. The system of claim 10, wherein the plurality of teeth are aligned in a saw tooth orientation.

12. The system of claim 10, wherein, in the deployed state a cutting stroke occurs by displacement of the system along the longitudinal axis.

13. They system of claim 1, wherein, in the non-deployed state the tubular body completely covers the tissue cutting portion.

14. The system of claim 2, wherein each of the teeth in the plurality of teeth is a saw tooth.

15. The system of claim 2, wherein in the non-deployed state the plurality of teeth are rotationally displaced from exposure in the window so that each tooth in the plurality of teeth is covered by the tubular body.

16. The system of claim 1, wherein the rotational displacement of the inner body relative to the tubular body is configured to provide no longitudinal displacement of the inner body relative to the tubular body.

17. A system for releasing a ligament, the system comprising:
   a tubular body comprising:
      a proximal end,
      a distal end opposite the proximal end,
      a tubular wall located between the proximal end and the distal end of the tubular body, the tubular wall defining a lumen extending longitudinally through the tubular wall and comprising an inner diameter and an outer diameter, and
      a window defined in the tubular wall;
   an inner body extending through the lumen of the tubular body and comprising:
      a proximal end,
      a distal end opposite the proximal end,
      a tissue penetration tip at the distal end of the inner body, and
      a tissue cutting portion located between the distal end and the proximal end of the inner body; and
   a proximal handle coupled to the proximal end of the tubular body and comprising a first actuator coupled to the inner body, the first actuator configured such that actuation of the actuator causes the inner body to axially rotationally displace relative to the tubular body to transition the tissue cutting portion between a non-deployed state and a deployed state, wherein in the non-deployed state the tissue cutting portion is hidden from the window, and in the deployed state the tissue cutting portion is exposed at the window and remains confined to a boundary defined by the outer diameter of the tubular wall of the tubular body;
   wherein the tissue cutting portion includes a plurality of teeth that extend radially outward from the inner body.

18. The system of claim 17, wherein actuation of the actuator comprises rotational displacement of the actuator.

19. The system of claim 17, wherein the inner body is also longitudinally displaceable relative to the tubular body.

20. The system of claim 19, further comprising a second actuator near the proximal handle that causes the inner body to be longitudinally displaced relative to the tubular body.

21. The system of claim 20, wherein the longitudinal displacement at least contributes to transitioning the tissue cutting portion between the non-deployed state and the deployed state.

22. The system of claim 19, wherein the tissue penetration tip at the distal end of the inner body moves from a recessed state to a tissue penetration state when the inner body is longitudinally displaced relative to the tubular body.

23. The system of claim 17, wherein the tissue cutting portion comprises a cutting tooth that protrudes through the window in the deployed state.

24. The system of claim 17, wherein the tissue cutting portion of the inner body forms a bow-like arrangement with the tubular body when the tissue cutting portion is in the deployed state.

25. The system of claim 17, further comprising at least one of: a nerve sensing system electrically coupled to the tubular body or inner body; or an ultrasound probe operably coupled to the tubular body.

26. A system for releasing a ligament, the system comprising:
   a tubular body comprising:
      a proximal end,
      a distal end opposite the proximal end,
      a tubular wall defining a lumen extending longitudinally through the tubular body, and comprising an inner diameter and an outer diameter, and
      a window extending through the tubular wall;
   an inner body extending through the lumen and comprising:
      a proximal end,
      a distal end opposite the proximal end,
      a tissue penetrating tip at the distal end of the inner body, and
      a tissue cutting portion located between the distal end and the proximal end of the inner body;
   a proximal handle coupled to the proximal end of the tubular body and comprising a first rotatable actuator coupled to the inner body and configured to rotationally displace the inner body relative to the tubular body to transition the tissue cutting portion between a non-deployed state and a deployed state, wherein in the non-deployed state the tissue cutting portion is hidden from the window, and in the deployed state the tissue cutting portion is exposed at the window and remains confined to a boundary defined by the outer diameter of the tubular wall of the tubular body.

27. The system of claim 26, wherein the tissue cutting portion includes a plurality of saw teeth that are hidden within the tubular body so as to be enclosed by the wall of the tubular body when the inner body is in the non-deployed state.

28. The system of claim 27, wherein the tissue cutting portion is defined along a segment length of a longitudinal axis, the longitudinal axis extending from the proximal end to the distal end of the inner body.

29. The system of claim 28, wherein the plurality of saw teeth extend radially outward from a center point of the longitudinal axis of the inner body.

30. The system of claim 29, wherein, in the deployed state a cutting stroke occurs by displacement of the system along the longitudinal axis.

31. The system of claim 26, wherein the inner body is also longitudinally displaceable relative to the tubular body.

32. The system of claim 31, further comprising a second actuator near the proximal handle that causes the inner body to be longitudinally displaced relative to the tubular body to transition the tissue cutting portion between the non-deployed state and the deployed state.

* * * * *